(12) United States Patent
Li et al.

(10) Patent No.: US 11,492,624 B2
(45) Date of Patent: Nov. 8, 2022

(54) RNAI AGENTS AND COMPOSITIONS FOR INHIBITING EXPRESSION OF ASIALOGLYCOPROTEIN RECEPTOR 1

(71) Applicant: Arrowhead Pharmaceuticals, Inc., Pasadena, CA (US)

(72) Inventors: Zhen Li, Westfield, NJ (US); Tao Pei, Middleton, WI (US); Rui Zhu, San Diego, CA (US); Bruce D. Given, Charleston, SC (US); Stacey Melquist, Pasadena, CA (US)

(73) Assignee: Arrowheads Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 16/756,440

(22) PCT Filed: Oct. 16, 2018

(86) PCT No.: PCT/US2018/056077
§ 371 (c)(1),
(2) Date: Apr. 15, 2020

(87) PCT Pub. No.: WO2019/079294
PCT Pub. Date: Apr. 25, 2019

(65) Prior Publication Data
US 2020/0283777 A1 Sep. 10, 2020

Related U.S. Application Data

(60) Provisional application No. 62/635,277, filed on Feb. 26, 2018, provisional application No. 62/608,606, filed on Dec. 21, 2017, provisional application No. 62/573,206, filed on Oct. 17, 2017.

(51) Int. Cl.
*C12N 15/113* (2010.01)
*A61K 9/00* (2006.01)
*C12Q 1/68* (2018.01)

(52) U.S. Cl.
CPC ........ *C12N 15/1138* (2013.01); *A61K 9/0019* (2013.01); *C12N 2310/11* (2013.01); *C12N 2310/14* (2013.01); *C12N 2310/321* (2013.01); *C12N 2310/322* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,885,968 A | 3/1999 | Biessen et al. | |
| 2019/0256849 A1* | 8/2019 | Li | C07H 21/04 |
| 2019/0309306 A1* | 10/2019 | Ollmann | C12N 15/1138 |
| 2020/0263179 A1* | 8/2020 | Melquist | A61P 43/00 |

FOREIGN PATENT DOCUMENTS

| | | |
|---|---|---|
| WO | 2000053722 A2 | 9/2000 |
| WO | 2008022309 A2 | 2/2008 |
| WO | 2011104169 A1 | 9/2011 |
| WO | 2012083185 A2 | 6/2012 |
| WO | 2013032829 A1 | 3/2013 |
| WO | 2013158141 A1 | 10/2013 |
| WO | 2017156012 A1 | 9/2017 |
| WO | 2018039647 A1 | 3/2018 |
| WO | 2018044350 A1 | 3/2018 |

OTHER PUBLICATIONS

Snead et al., Molecular Therapy Nucleic Acids vol. 2:e103, 7 pages, 2013.*
2013 ACC/AHA Guideline on the Assessment of Cardiovascular Risk: A report of the American College of Cardiology/American Heart Association Task Force on Practice Guidelines.
Baenziger et al.; "Galactose and N-Acetylgalactosamine-Specific Endocytosis of Glycopeptides by Isolated Rat Hepatocytes"; Cell; vol. 22; pp. 611-620; (1980).
Biessen et al.; "Synthesis of Cluster Galactosides with High Affinity for the Hepatic Asialoglycoprotein Receptor"; J. Med. Chem.; 38; 1538-1546; 1995.
Connolly et al.; "Binding and Endocytosis of Cluster Blycosides by Rabbit Hepatocytes"; The Journal of Biological Chemistry; vol. 257, No. 2; 939-945; 1982.
Czauderna et al.; "Structural variations and stabilizing modifications of synthetic siRNAs in mammalian cells"; Nucleic Acids Research; vol. 31, No. 11; 2705-2716; 2003.
Iobst et al.; "Selective Sugar Binding to the Carbohydrate Recognition Domains of the Rat Hepatic and Macrophage Asialoglycoprotein Receptors"; The Journal of Biological Chemistry; vol. 271, No. 12; 6686-6693; 1996.
Nioi et al; "Variant ASGR1 Associated with a Reduced Risk of Coronary Artery Disease"; N Engl J Med; 374: 2131-2141; 2016.
Rana et al.; "The role of non-HDL cholesterol in risk stratification for coronary artery disease"; Curr. Atheroscler. Rep.; vol. 14:130-134; 2012.
Zhang G et al.; "High Levels of Foreign Gene Expression in Hepatocytes after Tail Vein Injections of Naked Plasmid DNA"; Human Gene Therapy; vol. 10; 1735-1737; 1999.
GenBank NM_001671.4; 2011.

* cited by examiner

*Primary Examiner* — Sean McGarry
(74) *Attorney, Agent, or Firm* — Robert M. Teigen; Paul VanderVelde; Meibo Chen

(57) ABSTRACT

Described herein are compositions and methods for inhibition of Asialoglycoprotein receptor 1 (ASGR1) gene expression. RNA interference (RNAi) agents, e.g., double stranded RNAi agents, and RNAi agent-targeting ligand conjugates for inhibiting the expression of an ASGR1 gene are described. Pharmaceutical compositions comprising one or more ASGR1 RNAi agents, optionally with one or more additional therapeutics, are also described. The ASGR1 RNAi agents can be used in methods of treatment of various diseases and conditions, such as cardiometabolic diseases related to elevated non-HDL cholesterol (non-HDL-C) levels, elevated LDL cholesterol (LDL-C) levels, elevated total cholesterol levels, and/or elevated triglyceride (TG) levels.

21 Claims, 21 Drawing Sheets

Specification includes a Sequence Listing.

RNAI AGENTS AND COMPOSITIONS FOR INHIBITING EXPRESSION OF ASIALOGLYCOPROTEIN RECEPTOR 1

CROSS REFERENCE TO RELATED APPLICATIONS

This application is a U.S. National Phase Application under 35 U.S.C. § 371 of International Patent Application No. PCT/US18/56077 which claims priority from U.S. Provisional Patent Application Ser. No. 62/635,277, filed on Feb. 26, 2018, U.S. Provisional Patent Application Ser. No. 62/608,606, filed on Dec. 21, 2017, and U.S. Provisional Patent Application Ser. No. 62/573,206, filed on Oct. 17, 2017, the contents of each of which are incorporated herein by reference in their entirety.

SEQUENCE LISTING

This application contains a Sequence Listing which has been submitted in ASCII format and is hereby incorporated by reference in its entirety. The ASCII copy is named 30653-WO1_SEQLIST.txt and is 226 kb in size.

FIELD OF THE INVENTION

The present disclosure relates to RNA interference (RNAi) agents, e.g., double stranded RNAi agents, for inhibition of asialoglycoprotein receptor 1 (ASGR1) gene expression, compositions that include ASGR1 RNAi agents, and methods of use thereof.

BACKGROUND

Asialoglycoprotein receptor 1 (ASGR1, also known as ASGPR, ASGPR1, HL-1, and CLEC4H1), was previously known as the Ashwell-Morell receptor. ASGR1 is a transmembrane protein that plays a primary physiological role of binding, internalization, and clearance from the circulation of desialylated glycoproteins. ASGR1 is predominantly expressed in the liver by the Asialoglycoprotein receptor 1 gene (ASGR1 gene).

Genome-wide association studies for variants that affect non-HDL cholesterol levels and risk of coronary artery disease and myocardial infarction have identified a sequence variant in ASGR1. The del12 ASGR1 sequence variant, which results in haploinsufficiency of ASGR1, has been reported to be associated with reduced non-HDL cholesterol, and reduced risk for coronary artery disease and myocardial infarction (Nioi, Sigurdsson et al., N. Engl. J. Med. 2016, 374, 2131-41). As predicted by ~50% reduction of ASGR1 levels in del12 carriers, there was an increase of alkaline phosphatase (ALP or ALKP) and vitamin $B_{12}$ levels, as both these proteins are substrates for the asialoglycoprotein receptor. Reducing ASGR1 protein has thus emerged as a promising target for the treatment of cardiovascular diseases. Therapeutics that are able to target the ASGR1 gene and reduce ASGR1 protein levels represent a novel way of treating cardiovascular disease, including coronary artery disease.

SUMMARY

There exists a need for novel ASGR1-specific RNA interference (RNAi) agents (also herein termed RNAi agent, RNAi trigger, or trigger), e.g., double stranded RNAi agents, that are able to selectively and efficiently inhibit the expression of an ASGR1 gene. Further, there exists a need for compositions of novel ASGR1-specific RNAi agents for the treatment (including preventative treatment) of diseases associated with, among other things, elevated non-HDL cholesterol (non-HDL-C) levels, elevated LDL cholesterol (LDL-C) levels, elevated total cholesterol levels, and/or elevated triglyceride (TG) levels.

In general, the present disclosure features novel ASGR1 gene-specific RNAi agents, compositions that include the ASGR1 gene-specific RNAi agents, and methods for inhibiting expression of an ASGR1 gene in vivo and/or in vitro using the ASGR1 gene-specific RNAi agents and compositions that include ASGR1 gene-specific RNAi agents described herein. Further described herein are methods of treatment of diseases or disorders that are mediated at least in part by ASGR1 gene expression, the methods including administration to a subject one or more of the ASGR1 RNAi agents disclosed herein.

The ASGR1 gene-specific RNAi agents described herein are able to selectively and efficiently decrease expression of an ASGR1 gene. The described herein ASGR1 RNAi agents are thereby capable of reducing non-HDL cholesterol levels, and/or LDL cholesterol levels, and/or total cholesterol levels, and/or triglyceride levels, in a subject, e.g., a human or animal subject. The ASGR1 RNAi agents described herein can also impact other endogenous factors associated with atherosclerosis and/or vascular disease. For example, the described ASGR1 RNAi agents can be used in methods for therapeutic treatment and/or prevention of symptoms and diseases associated with abnormal serum lipoprotein levels, including but not limited to obesity, metabolic syndrome, hyperlipidemia, hypertriglyceridemia, hypercholesterolemia, abnormal lipid and/or cholesterol metabolism, atherosclerosis, diabetes, cardiovascular disease, coronary artery disease, myocardial infarction, peripheral vascular disease, cerebrovascular disease, and other metabolic-related disorders and diseases. In some embodiments, the methods disclosed herein include the administration of one or more ASGR1 RNAi agents to a subject. The one or more ASGR1 RNAi agents described herein may be administered to a subject by any suitable methods known in the art, such as subcutaneous injection or intravenous administration.

In one aspect, the disclosure features compositions comprising one or more ASGR1 RNAi agents that are able to selectively and efficiently decrease or inhibit expression of an ASGR1 gene. In some embodiments, the disclosed herein compositions comprising one or more ASGR1 RNAi agents are able to reduce the level of ASGR1 protein in the subject. In some embodiments, the disclosed herein compositions comprising one or more ASGR1 RNAi agents are able to reduce the level of ASGR1 mRNA in the subject. The compositions comprising one or more ASGR1 RNAi agents can be administered to a subject, such as a human or animal subject, for the treatment and/or prevention of symptoms and diseases associated with elevated non-HDL-C levels, and/or elevated LDL-C levels, and/or elevated total cholesterol levels, and/or elevated TG levels.

An ASGR1 RNAi agent described herein includes a sense strand (also referred to as a passenger strand), and an antisense strand (also referred to as a guide strand). The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. In some embodiments, the sense and antisense strands are independently 21 to 26 nucleotides in length. In some embodiments, the sense and antisense strands are independently 21 to 24 nucleotides in length. In some embodiments, the sense and antisense strands are both 21 nucleotides in length. In some embodiments, the sense and/or antisense strands are independently 16, 17, 18, 19, 20, 21, 22, 23, 24, 25, 26, 27, 28, 29, or 30 nucleotides in length. The sense and antisense strands can be either the same length or different lengths. The RNAi agents described herein, upon delivery to a cell expressing ASGR1, inhibit the expression of one or more ASGR1 genes in vivo or in vitro.

A sense strand of the ASGR1 RNAi agents described herein includes at least 16 consecutive nucleotides that have at least 85% identity to a core stretch sequence (also referred to herein as a "core stretch" or "core sequence") of the same number of nucleotides in an ASGR1 mRNA. In some embodiments, the sense strand core stretch having at least 85% identity to a sequence in an ASGR1 mRNA is 16, 17, 18, 19, 20, 21, 22, or 23 nucleotides in length. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of an ASGR1 RNAi agent includes at least 16 consecutive nucleotides that have at least 85% complementarity to a core stretch of the same number of nucleotides in an ASGR1 mRNA and to a core stretch of the same number of nucleotides in the corresponding sense strand. In some embodiments, the antisense strand core nucleotide stretch having at least 85% complementarity to a sequence in an ASGR1 mRNA or the corresponding sense strand is 16, 17, 18, 19, 20, 21, 22, or 23 nucleotides in length. In some embodiments, this antisense strand core stretch is 17 nucleotides in length. In some embodiments, this antisense strand core stretch is 19 nucleotides in length.

In some embodiments, the ASGR1 RNAi agents disclosed herein are designed to target the portion of an ASGR1 gene having the sequence of any of the sequences disclosed in Table 1.

Examples of ASGR1 RNAi agent sense strands and antisense strands that can be included in the ASGR1 RNAi agents disclosed herein are provided in Tables 2, 3, and 4. Examples of ASGR1 RNAi agent duplexes are provided in Table 5. Examples of 19-nucleotide core stretch sequences that consist of or are included in the sense strands and antisense strands of ASGR1 RNAi agents disclosed herein, are provided in Table 2.

In another aspect, the disclosure features methods for delivering ASGR1 RNAi agents to liver cells in a subject, such as a mammal, in vivo. Also described herein are compositions for use in such methods. The one or more ASG1 RNAi agents can be delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors, or Dynamic Polyconjugates™ (DPCs) (see, for example WO 2000/053722, WO 2008/0022309, WO 2011/104169, and WO 2012/083185, each of which is incorporated herein by reference).

In some embodiments, an ASGR1 RNAi agent is delivered to target cells or tissues by covalently linking or conjugating the RNAi agent to a targeting group. In some embodiments, the targeting group includes, consists of, or consists essentially of an antibody, such as a monoclonal antibody. (See, e.g., International Patent Application Publication No. WO 2018/039647, which is incorporated by reference herein in its entirety). In some embodiments, the targeting group consists of, consists essentially of, or comprises as an asialoglycoprotein receptor ligand (i.e., a ligand that includes a compound having affinity for the asialoglycoprotein receptor). In some embodiments, an asialoglycoprotein receptor ligand includes, consists of, or consists essentially of a galactose or galactose derivative cluster. In some embodiments, an ASGR1 RNAi agent is linked to a targeting ligand comprising the galactose derivative N-acetyl-galactosamine. In some embodiments, a galactose derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer. In some embodiments, the ASGR1 RNAi agents that are conjugated to targeting ligands that include N-acetyl-galactosamine are selectively internalized by liver cells, and hepatocytes in particular, either through receptor-mediated endocytosis or by other means. Examples of targeting groups useful for delivering RNAi agents are disclosed, for example, in International Patent Application Publication Nos. WO 2018/044350 and WO 2017/156012 to Arrowhead Pharmaceuticals, Inc., which are incorporated by reference herein in their entirety.

A targeting group can be linked to the 3' or 5' end of a sense strand or an antisense strand of an ASGR1 RNAi agent. In some embodiments, a targeting group is linked to the 3' or 5' end of the sense strand. In some embodiments, a targeting group is linked internally to a nucleotide on the sense strand and/or the antisense strand of the RNAi agent. In some embodiments, a targeting group is linked to the 5' end of the sense strand. In some embodiments, a targeting group is linked to the RNAi agent via a linker.

A targeting group, with or without a linker, can be linked to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In some embodiments, described herein are compositions that include one or more ASGR1 RNAi agents having the duplex structures disclosed in Table 5.

In a further aspect, described herein are pharmaceutical compositions that include one or more described ASGR1 RNAi agent(s), optionally combined with one or more additional (i.e., second, third, etc.) therapeutics. An additional therapeutic can be another ASGR1 RNAi agent (e.g., an ASGR1 RNAi agent which targets a different sequence within an ASGR1 gene). An additional therapeutic can also be a small molecule drug, antibody, antibody fragment, peptide, and/or aptamer. The ASGR1 RNAi agents, with or without the one or more additional therapeutics, can be combined with one or more excipients to form pharmaceutical compositions. The described ASGR1 RNAi agent(s) can be optionally combined with one or more additional therapeutics in a single dosage form (i.e., a cocktail included in a single injection). In some embodiments, the pharmaceutical compositions that include one or more described ASGR1 RNAi agent(s), optionally combined with one or more additional (i.e., second, third, etc.) therapeutics, can be formulated in a pharmaceutically acceptable carrier or diluent. In some embodiments, these compositions can be administered to a subject, such as a mammal. In some embodiments, the mammal is a human.

In some embodiments, the described ASGR1 RNAi agent (s) may be administered separately from one or more optional additional therapeutics. In some embodiments, the described ASGR1 RNAi agent(s) are administered to a subject in need thereof via subcutaneous injection, and the one or more optional additional therapeutics are administered orally, which together provide for a treatment regimen for diseases and conditions associated with elevated non-HDL-C levels, and/or elevated LDL-C levels, and/or elevated total cholesterol levels, and/or elevated TG levels. In some embodiments, the described ASGR1 RNAi agent(s) are administered to a subject in need thereof via subcutaneous injection, and the one or more optional additional therapeutics are administered via a separate subcutaneous injection.

In some embodiments, described herein are compositions that include a combination or cocktail of at least two ASGR1 RNAi agents having different nucleotide sequences. In some embodiments, the two or more different ASGR1 RNAi agents are each separately and independently linked to targeting groups. In some embodiments, the two or more different ASGR1 RNAi agents are each separately and independently linked to targeting groups that include or consist of targeting ligands that include one or more moieties that target an asialoglycoprotein receptor. In some embodiments, the two or more different ASGR1 RNAi agents are each linked to targeting groups that include or consist of targeting ligands that include one or more galactose derivatives. In some embodiments, the two or more different ASGR1 RNAi agents are each linked to targeting groups that include or consist of targeting ligands that include one or more N-acetyl-galactosamines. In some embodiments, when two or more RNAi agents are included in a composition, each of the RNAi agents is independently linked to the same targeting group. In some embodiments, when two or more RNAi agents are included in a composition, each of the RNAi agents is independently linked to a different targeting group, such as targeting groups having different chemical structures.

In some embodiments, targeting groups are linked to the ASGR1 RNAi agents without the use of an additional linker. In some embodiments, the targeting group is designed having a linker readily present to facilitate the linkage to an ASGR1 RNAi agent. In some embodiments, when two or more RNAi agents are included in a composition, the two or more RNAi agents may be linked to their respective targeting groups using the same linkers. In some embodiments, when two or more RNAi agents are included in a composition, the two or more RNAi agents are linked to their respective targeting groups using different linkers.

In another aspect, the disclosure features methods of treatment (including prevention or preventative treatment) of diseases or symptoms caused by or attributable to elevated non-HDL-C levels, and/or elevated LDL-C levels, and/or elevated total cholesterol levels, and/or elevated TG levels, wherein the methods include administering an ASGR1 RNAi agent having an antisense strand comprising the sequence of any of the sequences in Tables 2 or 3.

In some embodiments, disclosed herein are methods of inhibiting expression of an ASGR1 gene, wherein the methods include administering to a cell an ASGR1 RNAi agent that includes an antisense strand comprising the sequence of any of the sequences in Tables 2 or 3.

In some embodiments, disclosed herein are methods of treatment or prevention of diseases or symptoms caused by elevated non-HDL-C levels, and/or elevated LDL-C levels, and/or elevated total cholesterol levels, and/or elevated TG levels, wherein the methods include administering an ASGR1 RNAi agent having a sense strand comprising the sequence of any of the sequences in Tables 2 or 4.

In some embodiments, disclosed herein are methods of inhibiting expression of an ASGR1 gene, wherein the methods include administering an ASGR1 RNAi agent having a sense strand comprising the sequence of any of the sequences in Tables 2 or 4.

In some embodiments, disclosed herein are methods of inhibiting expression of an ASGR1 gene, wherein the methods include administering to a subject a therapeutically effective amount of an ASGR1 RNAi agent that includes a sense strand comprising the sequence of any of the sequences in Table 4, and an antisense strand comprising the sequence of any of the sequences in Table 3.

In some embodiments, disclosed herein are methods of inhibiting expression of an ASGR1 gene, wherein the methods include administering an ASGR1 RNAi agent that includes a sense strand consisting of the nucleobase sequence of any of the sequences in Table 4, and the antisense strand consisting of the nucleobase sequence of any of the sequences in Table 3. In other embodiments, disclosed herein are methods of inhibiting expression of an ASGR1 gene, wherein the methods include administering an ASGR1 RNAi agent that includes a sense strand consisting of the modified sequence of any of the modified sequences in Table 4, and an antisense strand consisting of the modified sequence of any of the modified sequences in Table 3.

In some embodiments, disclosed herein are methods for inhibiting expression of an ASGR1 gene in a cell, wherein the methods include administering one or more ASGR1 RNAi agents having the duplex structure of any of the duplexes in Table 5.

In a further aspect, the disclosure features methods of treatment (including preventative or prophylactic treatment) of diseases or symptoms caused by elevated non-HDL-C levels, and/or elevated LDL-C levels, and/or elevated total cholesterol levels, and/or elevated TG levels, wherein the methods include administering an ASGR1 RNAi agent that has an antisense strand that is at least partially complementary to the portion of an ASGR1 mRNA having any one of the sequences listed in Table 1.

In some embodiments, disclosed herein are methods for inhibiting expression of an ASGR1 gene in a cell, wherein the methods include administering an ASGR1 RNAi agent that has an antisense strand that is at least partially complementary to the portion of an ASGR1 mRNA having any one of the sequences listed in Table 1.

In some embodiments, disclosed herein are methods of treatment or prevention of diseases or symptoms caused by elevated non-HDL-C levels, and/or elevated LDL-C levels, and/or elevated total cholesterol levels, and/or elevated TG levels, wherein the methods include administering an ASGR1 RNAi agent having an antisense strand that includes the sequence of any of the sequences in Tables 2 or 3, and a sense strand that includes any of the sequences in Tables 2 or 4 that is at least partially complementary to the antisense strand.

In some embodiments, disclosed herein are methods of treatment or prevention of diseases or symptoms caused by elevated non-HDL-C levels, and/or elevated LDL-C levels, and/or elevated total cholesterol levels, and/or elevated TG levels, wherein the methods include administering an ASGR1 RNAi agent having a sense strand that includes any of the sequences in Tables 2 or 4, and an antisense strand that includes the sequence of any of the sequences in Tables 2 or 3 that is at least partially complementary to the sense strand.

In some embodiments, disclosed herein are methods of inhibiting expression of an ASGR1 gene, wherein the methods include administering an ASGR1 RNAi agent that includes an antisense strand comprising the sequence of any of the sequences in Tables 2 or 3, and a sense strand that includes any of the sequences in Tables 2 or 4 that is at least partially complementary to the antisense strand.

In some embodiments, disclosed herein are methods of inhibiting expression of an ASGR1 gene, wherein the methods include administering an ASGR1 RNAi agent that includes a sense strand that comprises any of the sequences in Tables 2 or 4, and an antisense strand that includes the sequence of any of the sequences in Tables 2 or 3 that is at least partially complementary to the sense strand.

In some embodiments, disclosed herein are compositions for inhibiting expression of an ASGR1 gene in a cell, the composition comprising any of the ASGR1 RNAi agents described herein.

In some embodiments, disclosed herein are compositions for delivering an ASGR1 RNAi agent to a liver cell in vivo, wherein the composition includes an ASGR1 RNAi agent conjugated or linked to a targeting group. In some embodiments, the targeting group is an asialoglycoprotein receptor ligand. In some embodiments, compositions for delivering an ASGR1 RNAi agent to a liver cell in vivo are described, wherein the compositions include an ASGR1 RNAi agent linked to a targeting ligand that comprises N-acetyl-galactosamine.

In some embodiments, one or more of the described ASGR1 RNAi agents are administered to a subject, such as a mammal, in a pharmaceutically acceptable carrier or diluent. In some embodiments, the mammal is a human.

The use of ASGR1 RNAi agents provide methods for therapeutic and/or prophylactic treatment of diseases/disorders which are associated with elevated non-HDL-C, levels, and/or elevated LDL-C levels, and/or elevated total cholesterol levels, and/or elevated TG levels, and/or enhanced or elevated ASGR1 expression. The described ASGR1 RNAi agents can mediate RNA interference to inhibit the expression of one or more genes necessary for production of ASGR1 protein. ASGR1 RNAi agents can also be used to treat or prevent various diseases or disorders associated with abnormal serum lipoprotein levels, including but not limited to obesity, metabolic syndrome, hyperlipidemia, hypertriglyceridemia, hypercholesterolemia, abnormal lipid and/or cholesterol metabolism, atherosclerosis, diabetes, cardiovascular disease, coronary artery disease, myocardial infarction, peripheral vascular disease, cerebrovascular disease and other metabolic-related disorders and diseases. The described herein ASGR1 RNAi agents may also impact other endogenous factors associated with atherosclerosis and/or vascular disease. Further, compositions for delivery of ASGR1 RNAi agents to liver cells in vivo are described.

The pharmaceutical compositions comprising one or more ASGR1 RNAi agents can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

The described ASGR1 RNAi agents and/or compositions that include ASGR1 RNAi agents can be used in methods for therapeutic treatment of diseases or conditions caused by elevated non-HDL-C levels, and/or elevated LDL-C levels, and/or elevated total cholesterol levels, and/or elevated TG levels. Such methods include administration of an ASGR1 RNAi agent as described herein to a subject, e.g., a human or animal subject.

In some embodiments, the ASGR1 RNAi agents described herein can include one or more targeting groups having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

In some embodiments, the ASGR1 RNAi agents described herein include one targeting group at the 5' end of the sense strand having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UACUCCUUGGUCAUGAUAGGU (SEQ ID NO:3). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') UACUCCUUGGUCAUGAUAGGU (SEQ ID NO:3), wherein all or substantially all of the nucleotides are modified nucleotides. In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UACUCCUUGGU-CAUGAUAGGU (SEQ ID NO:3), wherein SEQ ID NO:3 is located at positions 1-21 (5'→3') of the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') usAfscUfcCfuUfgGfuCfaUfgA-fuAfgsGfsu (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1M showing all internucleoside linkages). In some embodiments, an ASGR1 RNAi agent disclosed herein includes an antisense strand that consists of, consists essentially of, or comprises the nucleotide sequence (5'→3') usAfscUfcCfuUfgGfuCfaUfgAfuAfgsGfsu (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') usAfscUfcCfU$_{UNA}$UfgGfuCfaUfgAfuAfgsGfsu (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; U$_{UNA}$ represents a 2',3'-seco-uridine (see, e.g., Table 6); and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1M showing all internucleoside linkages). In some embodiments, an ASGR1 RNAi agent disclosed herein includes an antisense strand that consists of, consists essentially of, or comprises the nucleotide sequence (5'→3') usAfscUfcCfU$_{UNA}$UfgGfuCfaUfgAfuAfgsGfsu (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; U$_{UNA}$ represents a 2',3'-seco-uridine (see, e.g., Table 6); and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCCG (SEQ ID NO:6). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUCUUUCUUCCG (SEQ ID NO:6), wherein all or substantially all of the nucleotides are modified nucleotides. In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCCG (SEQ ID NO:6), wherein SEQ ID NO:6 is located at positions 1-21 (5'→3') of the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') asGfscGfaCfuucauCfuUfuCfuUfcsCfsg (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1M showing all internucleoside linkages). In some embodiments, an ASGR1 RNAi agent disclosed herein includes an antisense strand that consists of, consists essentially of, or comprises the nucleotide sequence (5'→3') asGfscGfaCfuucauCfuUfuCfuUfcsCfsg (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCGU (SEQ ID NO:8). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUCUUUCUUCGU (SEQ ID NO:8), wherein all or substantially all of the nucleotides are modified nucleotides. In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCGU (SEQ ID NO:8), wherein SEQ ID NO:8 is located at positions 1-21 (5'→3') of the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') asGfscGfaCfuucauCfuUfuCfuUfcsGfsu (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ASGR1 RNAi agent disclosed herein includes an antisense strand that consists of, consists essentially of, or comprises the nucleotide sequence (5'→3') asGfscGfaCfuucauCfuUfuCfuUfcsGfsu (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') asGfscsgacuucauCfuUfuCfuUfcGfsu (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ASGR1 RNAi agent disclosed herein includes an antisense strand that consists of, consists essentially of, or comprises the nucleotide sequence (5'→3') asGfscsgacuucauCfuUfuCfuUfcGfsu (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') ACUUCAUCUUUCUUCCCACGC (SEQ ID NO:11). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') ACUUCAUCUUUCUUCCCACGC (SEQ ID NO:11), wherein all or substantially all of the nucleotides are modified nucleotides. In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') ACUUCAUCUUUC-UUCCCACGC (SEQ ID NO:11), wherein SEQ ID NO:11 is located at positions 1-21 (5'→3') of the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') asCfsusUfcAfuCfuU-fuCfuUfcCfcAfcGfsc (SEQ ID NO:10), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ASGR1 RNAi agent disclosed herein includes an antisense strand that consists of, consists essentially of, or comprises the nucleotide sequence (5'→3') asCfsusUfcAfuCfuU-fuCfuUfcCfcAfcGfsc (SEQ ID NO:10), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UGAAAUAAAUUAAAGGAGAGG (SEQ ID NO:27). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') UGAAAUAAAUUAAAGGAGAGG (SEQ ID NO:27), wherein all or substantially all of the nucleotides are modified nucleotides. In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UGAAAUAAAUUAAAGGAGAGG (SEQ ID NO:27), wherein SEQ ID NO:27 is located at positions 1-21 (5'→3') of the antisense strand.

In some embodiments, an ASGR1 RNAi agent disclosed herein includes an antisense strand that consists of, consists essentially of, or comprises a modified nucleotide sequence differing by no more than 1 nucleotide from the nucleotide sequence (5'→3') usGfsaAfaUfaAfaUfuAfaAfgGf-aGfasGfsg (SEQ ID NO:28), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ASGR1 RNAi agent disclosed herein includes an antisense strand that consists of, consists essentially of, or comprises the nucleotide sequence (5'→3') usGfsaAfaUfaAfaUfuAfaAfgGf-aGfasGfsg (SEQ ID NO:28), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UACUCCUUGGUCAUGAUAGGU (SEQ ID NO:3) and a sense strand that consists of, consists essentially of, or comprises a nucleobase sequence differing by 0 or 1 nucleobases from the nucleotide sequence (5'→3') ACCUAU-CAUGACCAAGGAIUA (SEQ ID NO:12). (I represents an inosine nucleotide.) In some embodiments, an ASGR1 RNAi agent disclosed herein includes an antisense strand that consists of, consists essentially of, or comprises a nucleotide sequence differing by no more than 1 nucleotide from the nucleotide sequence (5'→3') UACUCCUUGGU-CAUGAUAGGU (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') ACC-UAUCAUGACCAAGGAIUA (SEQ ID NO:12), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UACUCCUUGGUCAUGAUAGGU (SEQ ID NO:3) and a sense strand that consists of, consists essentially of, or comprises a nucleobase sequence differing by 0 or 1 nucleobases from the nucleotide sequence (5'→3') ACCUAU-CAUGACCAAGGAGUA (SEQ ID NO:13). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') UACUCCUUGGUCAUGAUAGGU (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') ACCUAUCAUGACCAAGGAGUA (SEQ ID NO:13), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UACUCCUUGGUCAUGAUAGGU (SEQ ID NO:3) and a sense strand that consists of, consists essentially of, or comprises a nucleobase sequence differing by 0 or 1 nucleobases from the nucleotide sequence (5'→3') ACCUAU-CAUGACCAAIGAIUA (SEQ ID NO:14). (I represents an inosine nucleotide.) In some embodiments, an ASGR1

RNAi agent disclosed herein includes an antisense strand that consists of, consists essentially of, or comprises a nucleotide sequence differing by no more than 1 nucleotide from the nucleotide sequence (5'→3') UACUCCUUGGU-CAUGAUAGGU (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') ACC-UAUCAUGACCAAIGAIUA (SEQ ID NO:14), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCCG (SEQ ID NO:6) and a sense strand that consists of, consists essentially of, or comprises a nucleobase sequence differing by 0 or 1 nucleobases from the nucleotide sequence (5'→3') CGGAAGAAAGAUGAAGUCICU (SEQ ID NO:15). (I represents an inosine nucleotide.) In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUC-UUUCUUCCG (SEQ ID NO:6), wherein all or substantially all of the nucleotides are modified nucleotides, and a sense strand that consists of, consists essentially of, or comprises a nucleotide sequence differing by no more than 1 nucleotide from the nucleotide sequence (5'→3') CGGAAGAAAGAUGAAGUCICU (SEQ ID NO:15), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCGU (SEQ ID NO:8) and a sense strand that consists of, consists essentially of, or comprises a nucleobase sequence differing by 0 or 1 nucleobases from the nucleotide sequence (5'→3') ACGAAGAAAGAUGAAGUCICU (SEQ ID NO:16). (I represents an inosine nucleotide.) In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUC-UUUCUUCGU (SEQ ID NO:8), wherein all or substantially all of the nucleotides are modified nucleotides, and a sense strand that consists of, consists essentially of, or comprises a nucleotide sequence differing by no more than 1 nucleotide from the nucleotide sequence (5'→3') ACGAAGAAAGAUGAAGUCICU (SEQ ID NO:16), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCGU (SEQ ID NO:8) and a sense strand that consists of, consists essentially of, or comprises a nucleobase sequence differing by 0 or 1 nucleobases from the nucleotide sequence (5'→3') ACGAAGAAAGAUGAAGUCGCU (SEQ ID NO:17). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUCUUUCUUCGU (SEQ ID NO:8), wherein all or substantially all of the nucleotides are modified nucleotides, and a sense strand that consists of, consists essentially of, or comprises a nucleotide sequence differing by no more than 1 nucleotide from the nucleotide sequence (5'→3') ACGAAGAAAGAUGAAGUCGCU (SEQ ID NO:17), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') ACUUCAUCUUUCUUCCCACGC (SEQ ID NO:11) and a sense strand that consists of, consists essentially of, or comprises a nucleobase sequence differing by 0 or 1 nucleobases from the nucleotide sequence (5'→3') GCGUGG-GAAGAAAGAUGAAGU (SEQ ID NO:18). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') ACUUCAUCUUUCUUCCCACGC (SEQ ID NO:11), wherein all or substantially all of the nucleotides are modified nucleotides, and a sense strand that consists of, consists essentially of, or comprises a nucleotide sequence differing by no more than 1 nucleotide from the nucleotide sequence (5'→3') GCGUGGGAAGAAAGAUGAAGU (SEQ ID NO:18), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCCG (SEQ ID NO:6) and a sense strand that consists of, consists essentially of, or comprises a nucleobase sequence differing by 0 or 1 nucleobases from the nucleotide sequence (5'→3') CGGAAGAAAGAUGAAIUCICU (SEQ ID NO:31). (I represents an inosine nucleotide.) In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUC-UUUCUUCCG (SEQ ID NO:6), wherein all or substantially all of the nucleotides are modified nucleotides, and a sense strand that consists of, consists essentially of, or comprises a nucleotide sequence differing by no more than 1 nucleotide from the nucleotide sequence (5'→3') CGGAAGAAAGAUGAAIUCICU (SEQ ID NO:31), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') AGCGACUUCAUCUUUCUUCCG (SEQ ID NO:6) and a sense strand that consists of, consists essentially of, or comprises a nucleobase sequence differing by 0 or 1 nucleobases from the nucleotide sequence (5'→3') CGGAAGAAAGAUGAAGUCGCU (SEQ ID NO:33). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') AGCGACUUCAUCUUUCUUCCG (SEQ ID NO:6), wherein all or substantially all of the nucleotides are modified nucleotides, and a sense strand that consists of, consists essentially of, or comprises a nucleotide sequence differing by no more than 1 nucleotide from the nucleotide sequence (5'→3') CGGAAGAAAGAUGAAGUCGCU (SEQ ID NO:33), wherein all or substantially all of the nucleotides are modified nucleotides.

In some embodiments, an ASGR1 RNAi agent disclosed herein includes an antisense strand that consists of, consists essentially of, or comprises a nucleobase sequence differing by 0 or 1 nucleobases from the nucleotide sequence (5'→3') UGAAAUAAAUUAAAGGAGAGG (SEQ ID NO:27) and a sense strand that consists of, consists essentially of, or comprises a nucleobase sequence differing by 0 or 1 nucleobases from the nucleotide sequence (5'→3') CCUCUCCUUUAAUUUAUUUCA (SEQ ID NO:35). In some embodiments, an ASGR1 RNAi agent disclosed herein includes an antisense strand that consists of, consists essentially of, or comprises a nucleotide sequence differing by no more than 1 nucleotide from the nucleotide sequence (5'→3') UGAAAUAAAUUAAAGGAGAGG (SEQ ID NO:27), wherein all or substantially all of the nucleotides are modified nucleotides, and a sense strand that consists of, consists essentially of, or comprises a nucleotide sequence differing by no more than 1 nucleotide from the nucleotide sequence (5'→3') CCUCUCCUUUAAUUUAUUUCA (SEQ ID NO:35), wherein all or substantially all of the nucleotides are modified nucleotides.

In some embodiments, an ASGR1 RNAi agent disclosed herein includes an antisense strand that consists of, consists essentially of, or comprises the modified nucleotide sequence (5' 4 3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfccaaggaiva (SEQ ID NO:19), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfccaaggaiva (SEQ ID NO:19), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') usAfscUfcCfU$_{UNA}$UfgGfuCfaUfgAfuAfgsGfsu (SEQ ID NO:4), and a sense strand that consists of, consists essentially of, or comprises the modified nucleotide sequence (5'→3') accuaucaUfGfAfccaaggagua (SEQ ID NO:20), wherein a, c, g, and u represent 2'-O-methyl adenosine, cytidine, guanosine, or uridine, respectively; U$_{UNA}$ represents a 2',3'-seco-uridine (see, e.g., Table 6); Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usAfscUfcCfU$_{UNA}$UfgGfuCfaUfgAfuAfgsGfsu (SEQ ID NO:4), and a sense strand that consists of, consists essentially of, or comprises the modified nucleotide sequence (5'→3') accuaucaUfGfAfccaaggagua (SEQ ID NO:20), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfcCaaggagua (SEQ ID NO:21), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfcCaaggagua (SEQ ID NO:21), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfcCaaigaiva (SEQ ID NO:22), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfcCaaigaiva (SEQ ID NO:22), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' → 3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaagucicu (SEQ ID NO:23), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaagucicu (SEQ ID NO:23), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asGfscGfaCfuucauCfuUfuCfuUfcsGfsu (SEQ ID NO:7), and a sense strand that consists of, consists essentially of, or comprises the modified nucleotide sequence (5'→3') acgaagaaAfGfAfugaagucicu (SEQ ID NO:24), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asGfscGfaCfuucauCfuUfuCfuUfcsGfsu (SEQ ID NO:7), and a sense strand that consists of, consists essentially of, or comprises the modified nucleotide sequence (5'→3') acgaagaaAfGfAfugaagucicu (SEQ ID NO:24), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asGfscsgacuucauCfuUfuCfuUfcGfsu (SEQ ID NO:9), and a sense strand that consists of, consists essentially of, or comprises the modified nucleotide sequence (5'→3') acgaagaaAfGfAfugaagucgcu (SEQ ID NO:25), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asGfscsgacuucauCfuUfuCfuUfcGfsu (SEQ ID NO:9), and a sense strand that consists of, consists essentially of, or comprises the modified nucleotide sequence (5'→3') acgaagaaAfGfAfugaagucgcu (SEQ ID NO:25), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asCfsusUfcAfuCfuUfuCfuUfcCfcAfcGfsc (SEQ ID NO:10), and a sense strand that consists of, consists essentially of, or comprises the modified nucleotide sequence (5'→3') gcgugggaAfGfAfaagaugaagu (SEQ ID NO:26), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asCfsusUfcAfuCfuUfuCfuUfcCfcAfcGfsc (SEQ ID NO:10), and a sense strand that consists of, consists essentially of, or comprises the modified nucleotide sequence (5'→3') gcgugggaAfGfAfaagaugaagu (SEQ ID NO:26), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asCfsusUfcAfuCfuUfuCfuUfcCfcAfcGfsc (SEQ ID NO:10), and a sense strand that consists of, consists essentially of, or comprises the modified nucleotide sequence (5'→3') gscgugggaAfGfAfaagaugaagu (SEQ ID NO:29), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asCfsusUfcAfuCfuUfuCfuUfcCfcAfcGfsc (SEQ ID NO:10), and a sense strand that consists of, consists essentially of, or comprises the modified nucleotide sequence (5'→3') gscgugggaAfGfAfaagaugaagu (SEQ ID NO:29), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfccaaigaiva (SEQ ID NO:30), wherein a, c, g, i, and u represent 2'-O-methyl adenosine, cytidine, guanosine, inosine or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usAfscUfcCfuUfgGfuCfaUfgAfuAfgsGfsu (SEQ ID NO:2), and a sense strand that consists of, consists essentially of, or comprises the modified nucleotide sequence (5'→3') accuaucaUfGfAfccaaigaiva (SEQ ID NO:30), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaaiucicu (SEQ ID NO:32), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaaiucicu (SEQ ID NO:32), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaagucgcu (SEQ ID NO:34), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') asGfscGfaCfuucauCfuUfuCfuUfcsCfsg (SEQ ID NO:5), and a sense strand that consists of, consists essentially of, or comprises the modified nucleotide sequence (5'→3') cggaagaaAfGfAfugaagucgcu (SEQ ID NO:34), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises the modified nucleotide sequence (5' 4 3') usGfsaAfaUfaAfaUfuAfaAfgGfaGfasGfsg (SEQ ID NO:28), and a sense strand that consists of, consists essentially of, or comprises the modified nucleotide sequence (5'→3') ccucuccuUfUfAfauuuauuuca (SEQ ID NO:36), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an ASGR1 RNAi agent disclosed herein includes an antisense strand that consists of, consists essentially of, or comprises the modified nucleotide sequence (5'→3') usGfsaAfaUfaAfaUfuAfaAfgGfaGfasGfsg (SEQ ID NO:28), and a sense strand that consists of, consists essentially of, or comprises the modified nucleotide sequence (5'→3') ccucuccuUfUfAfauuuauuuca (SEQ ID NO:36), and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that consists of, consists essentially of, or comprises a nucleotide sequence that differs by 0 or 1 nucleotides from one of the following nucleotide sequences (5'→3'):

```
                               (SEQ ID NO: 3)
     UACUCCUUGGUCAUGAUAGGU;

(SEQ ID NO: 6)
     AGCGACUUCAUCUUUCUUCCG;

(SEQ ID NO: 8)
     AGCGACUUCAUCUUUCUUCGU;

(SEQ ID NO: 11)
     ACUUCAUCUUUCUUCCCACGC;
     or (SEQ ID NO: 27)
     UGAAAUAAAUUAAAGGAGAGG;
``` wherein the ASGR1 RNAi agent further includes a sense strand that is at least partially complementary to the antisense strand; and wherein all or substantially all of the nucleotides on both the antisense strand and the sense strand are modified nucleotides.

In some embodiments, an ASGR1 RNAi agent disclosed herein includes an antisense strand that consists of, consists essentially of, or comprises a nucleotide sequence that differs by 0 or 1 nucleotides from one of the following nucleotide sequences (5'→3'):

```
                                              (SEQ ID NO: 3)
UACUCCUUGGUCAUGAUAGGU;

(SEQ ID NO: 6)
AGCGACUUCAUCUUUCUUCCG;

(SEQ ID NO: 8)
AGCGACUUCAUCUUUCUUCGU;

(SEQ ID NO: 11)
ACUUCAUCUUUCUUCCACGC;
or (SEQ ID NO: 27)
UGAAAUAAAUUAAAGGAGAGG;
``` wherein the ASGR1 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 3' and/or 5' terminal end.

In some embodiments, an ASGR1 RNAi agent disclosed herein includes an antisense strand that consists of, consists essentially of, or comprises a nucleotide sequence that differs by 0 or 1 nucleotides from one of the following nucleotide sequences (5'→3'):

```
                                              (SEQ ID NO: 3)
UACUCCUUGGUCAUGAUAGGU;

(SEQ ID NO: 6)
AGCGACUUCAUCUUUCUUCCG;

(SEQ ID NO: 8)
AGCGACUUCAUCUUUCUUCGU;

(SEQ ID NO: 11)
ACUUCAUCUUUCUUCCACGC;
or (SEQ ID NO: 27)
UGAAAUAAAUUAAAGGAGAGG;
``` wherein the ASGR1 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 3' and/or 5' terminal end; and wherein the respective antisense strand sequence is located at positions 1-21 of the antisense strand.

In some embodiments, an ASGR1 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

```
                                              (SEQ ID NO: 3)
UACUCCUUGGUCAUGAUAGGU
and
```

```
                                              (SEQ ID NO: 12)
ACCUAUCAUGACCAAGGAIUA,
wherein I represents an inosine nucleotide;

(SEQ ID NO: 3)
UACUCCUUGGUCAUGAUAGGU
and (SEQ ID NO: 13)
ACCUAUCAUGACCAAGGAGUA;

(SEQ ID NO: 3)
UACUCCUUGGUCAUGAUAGGU
and (SEQ ID NO: 14)
ACCUAUCAUGACCAAIGAIUA,
wherein I represents an inosine nucleotide;

(SEQ ID NO: 6)
AGCGACUUCAUCUUUCUUCCG
and (SEQ ID NO: 15)
CGGAAGAAAGAUGAAGUCICU,
wherein I represents an inosine nucleotide;

(SEQ ID NO: 8)
AGCGACUUCAUCUUUCUUCGU
and (SEQ ID NO: 16)
ACGAAGAAAGAUGAAGUCICU,
wherein I represents an inosine nucleotide;

(SEQ ID NO: 8)
AGCGACUUCAUCUUUCUUCGU
and (SEQ ID NO: 17)
ACGAAGAAAGAUGAAGUCGCU;

(SEQ ID NO: 11)
ACUUCAUCUUUCUUCCACGC
and (SEQ ID NO: 18)
GCGUGGGAAGAAAGAUGAAGU;

(SEQ ID NO: 6)
AGCGACUUCAUCUUUCUUCCG
and (SEQ ID NO: 31)
CGGAAGAAAGAUGAAIUCICU,
wherein I represents an inosine nucleotide;

(SEQ ID NO: 6)
AGCGACUUCAUCUUUCUUCCG
and (SEQ ID NO: 33)
CGGAAGAAAGAUGAAGUCGCU;
or (SEQ ID NO: 27)
UGAAAUAAAUUAAAGGAGAGG
and (SEQ ID NO: 35)
CCUCUCCUUUAAUUUAUUUCA;
``` wherein all or substantially all of the nucleotides on both the antisense strand and the sense strand are modified nucleotides.

In some embodiments, an ASGR1 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

```
                                           (SEQ ID NO: 3)
UACUCCUUGGUCAUGAUAGGU
and (SEQ ID NO: 12)
ACCUAUCAUGACCAAGGAIUA,
wherein I represents an inosine nucleotide;

(SEQ ID NO: 3)
UACUCCUUGGUCAUGAUAGGU
and (SEQ ID NO: 13)
ACCUAUCAUGACCAAGGAGUA;

(SEQ ID NO: 3)
UACUCCUUGGUCAUGAUAGGU
and (SEQ ID NO: 14)
ACCUAUCAUGACCAAIGAIUA,
wherein I represents an inosine nucleotide;

(SEQ ID NO: 6)
AGCGACUUCAUCUUUCUUCCG
and (SEQ ID NO: 15)
CGGAAGAAAGAUGAAGUCICU,
wherein I represents an inosine nucleotide;

(SEQ ID NO: 8)
AGCGACUUCAUCUUUCUUCGU
and (SEQ ID NO: 16)
ACGAAGAAAGAUGAAGUCICU,
wherein I represents an inosine nucleotide;

(SEQ ID NO: 8)
AGCGACUUCAUCUUUCUUCGU
and (SEQ ID NO: 17)
ACGAAGAAAGAUGAAGUCGCU;

(SEQ ID NO: 11)
ACUUCAUCUUUCUUCCCACGC
and (SEQ ID NO: 18)
GCGUGGGAAGAAAGAUGAAGU;

(SEQ ID NO: 6)
AGCGACUUCAUCUUUCUUCCG
and (SEQ ID NO: 31)
CGGAAGAAAGAUGAAIUCICU,
wherein I represents an inosine nucleotide;

(SEQ ID NO: 6)
AGCGACUUCAUCUUUCUUCCG
and (SEQ ID NO: 33)
CGGAAGAAAGAUGAAGUCGCU;
or (SEQ ID NO: 27)
UGAAAUAAAUUAAAGGAGAGG
and (SEQ ID NO: 35)
CCUCUCCUUUAAUUUAUUUCA;
``` wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 3' and/or 5' terminal end.

In some embodiments, an ASGR1 RNAi agent disclosed herein includes an antisense strand that consists of, consists essentially of, or comprises a modified nucleotide sequence that differs by 0 or 1 nucleotides from one of the following nucleotide sequences (5'→3'):

```
                                           (SEQ ID NO: 2)
usAfscUfcCfuUfgGfuCfaUfgAfuAfgsGfsu;

(SEQ ID NO: 4)
usAfscUfcCfuU_{UNA}UfgGfuCfaUfgAfuAfgsGfsu;

(SEQ ID NO: 5)
asGfscGfaCfuucauCfuUfuCfuUfcsCfsg;

(SEQ ID NO: 7)
asGfscGfaCfuucauCfuUfuCfuUfcsGfsu;

(SEQ ID NO: 9)
asGfscsgacuucauCfuUfuCfuUfcGfsu;

(SEQ ID NO: 10)
asCfsusUfcAfuCfuUfuCfuUfcCfcAfcGfsc;
or (SEQ ID NO: 28)
usGfsaAfaUfaAfaUfuAfaAfgGfaGfasGfsg
``` wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; $U_{UNA}$ represents a 2',3'-seco-uridine (see, e.g., Table 6); s represents a phosphorothioate linkage; and wherein the ASGR1 RNAi agent further includes the sense strand that is at least partially complementary to the antisense strand; and wherein all or substantially all of the nucleotides on the sense strand are modified nucleotides.

In some embodiments, an ASGR1 RNAi agent disclosed herein includes an antisense strand that consists of, consists essentially of, or comprises a modified nucleotide sequence that differs by 0 or 1 nucleotides from one of the following nucleotide sequences (5'→3'):

```
                                           (SEQ ID NO: 2)
usAfscUfcCfuUfgGfuCfaUfgAfuAfgsGfsu;

(SEQ ID NO: 4)
usAfscUfcCfuU_{UNA}UfgGfuCfaUfgAfuAfgsGfsu;

(SEQ ID NO: 5)
asGfscGfaCfuucauCfuUfuCfuUfcsCfsg;

(SEQ ID NO: 7)
asGfscGfaCfuucauCfuUfuCfuUfcsGfsu;

(SEQ ID NO: 9)
asGfscsgacuucauCfuUfuCfuUfcGfsu;

(SEQ ID NO: 10)
asCfsusUfcAfuCfuUfuCfuUfcCfcAfcGfsc;
or (SEQ ID NO: 28)
usGfsaAfaUfaAfaUfuAfaAfgGfaGfasGfsg
``` wherein the ASGR1 RNAi agent further includes the sense strand that is at least partially complementary to the antisense strand; wherein all or substantially all of the nucleotides on the sense strand are modified nucleotides; and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

```
                                         (SEQ ID NO: 2)
usAfscUfcCfuUfgGfuCfaUfgAfuAfgsGfsu
and (SEQ ID NO: 19)
accuaucaUfGfAfccaaggaiua;

(SEQ ID NO: 4)
usAfscUfcCfuU_UNA_UfgGfuCfaUfgAfuAfgsGfsu
and (SEQ ID NO: 20)
accuaucaUfGfAfccaaggagua;

(SEQ ID NO: 2)
usAfscUfcCfuUfgGfuCfaUfgAfuAfgsGfsu
and (SEQ ID NO: 21)
accuaucaUfGfAfcCaaggagua;

(SEQ ID NO: 2)
usAfscUfcCfuUfgGfuCfaUfgAfuAfgsGfsu
and (SEQ ID NO: 22)
accuaucaUfGfAfcCaaigaiua;

(SEQ ID NO: 5)
asGfscGfaCfuucauCfuUfuCfuUfcsCfsg
and (SEQ ID NO: 23)
cggaagaaAfGfAfugaagucicu;

(SEQ ID NO: 7)
asGfscGfaCfuucauCfuUfuCfuUfcsGfsu
and (SEQ ID NO: 24)
acgaagaaAfGfAfugaagucicu;

(SEQ ID NO: 9)
asGfscsgacuucauCfuUfuCfuUfcGfsu
and (SEQ ID NO: 25)
acgaagaaAfGfAfugaagucgcu;

(SEQ ID NO: 10)
asCfsusUfcAfuCfuUfuCfuUfcCfcAfcGfsc
and (SEQ ID NO: 26)
gcgugggaAfGfAfaagaugaagu;

(SEQ ID NO: 10)
asCfsusUfcAfuCfuUfuCfuUfcCfcAfcGfsc
and (SEQ ID NO: 29)
gscgugggaAfGfAfaagaugaagu;

(SEQ ID NO: 10)
asCfsusUfcAfuCfuUfuCfuUfcCfcAfcGfsc
and (SEQ ID NO: 30)
accuaucaUfGfAfccaaigaiua;

(SEQ ID NO: 5)
asGfscGfaCfuucauCfuUfuCfuUfcsCfsg
and (SEQ ID NO: 32)
cggaagaaAfGfAfugaaiucicu;

(SEQ ID NO: 5)
asGfscGfaCfuucauCfuUfuCfuUfcsCfsg
and (SEQ ID NO: 34)
cggaagaaAfGfAfugaagucgcu;
or (SEQ ID NO: 28)
usGfsaAfaUfaAfaUfuAfaAfgGfaGfasGfsg
and (SEQ ID NO: 36)
ccucuccuUfUfAfauuuauuuca;
``` wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; $U_{UNA}$ represents a 2',3'-seco-uridine (see, e.g., Table 6); and s represents a phosphorothioate linkage.

In some embodiments, an ASGR1 RNAi agent disclosed herein includes an antisense strand and a sense strand that consists of, consists essentially of, or comprises one of the following nucleotide sequence pairs (5'→3'):

```
                                         (SEQ ID NO: 2)
usAfscUfcCfuUfgGfuCfaUfgAfuAfgsGfsu
and (SEQ ID NO: 19)
accuaucaUfGfAfccaaggaiua;

(SEQ ID NO: 4)
usAfscUfcCfuU_UNA_UfgGfuCfaUfgAfuAfgsGfsu
and (SEQ ID NO: 20)
accuaucaUfGfAfccaaggagua;

(SEQ ID NO: 2)
usAfscUfcCfuUfgGfuCfaUfgAfuAfgsGfsu
and (SEQ ID NO: 21)
accuaucaUfGfAfcCaaggagua;

(SEQ ID NO: 2)
usAfscUfcCfuUfgGfuCfaUfgAfuAfgsGfsu
and (SEQ ID NO: 22)
accuaucaUfGfAfcCaaigaiua;

(SEQ ID NO: 5)
asGfscGfaCfuucauCfuUfuCfuUfcsCfsg
and (SEQ ID NO: 23)
cggaagaaAfGfAfugaagucicu;

(SEQ ID NO: 7)
asGfscGfaCfuucauCfuUfuCfuUfcsGfsu
and (SEQ ID NO: 24)
acgaagaaAfGfAfugaagucicu;
```

-continued asGfscsgacuucauCfuUfuCfuUfcGfsu (SEQ ID NO: 9)
and acgaagaaAfGfAfugaagucgcu; (SEQ ID NO: 25)

asCfsusUfcAfuCfuUfuCfuUfcCfcAfcGfsc (SEQ ID NO: 10)
and gcgugggaAfGfAfaagaugaagu; (SEQ ID NO: 26)

asCfsusUfcAfuCfuUfuCfuUfcCfcAfcGfsc (SEQ ID NO: 10)
and gscgugggaAfGfAfaagaugaagu; (SEQ ID NO: 29)

asCfsusUfcAfuCfuUfuCfuUfcCfcAfcGfsc (SEQ ID NO: 10)
and accuaucaUfGfAfccaaigaiua; (SEQ ID NO: 30)

asGfscGfaCfuucauCfuUfuCfuUfcsCfsg (SEQ ID NO: 5)
and cggaagaaAfGfAfugaaiucicu; (SEQ ID NO: 32)

asGfscGfaCfuucauCfuUfuCfuUfcsCfsg (SEQ ID NO: 5)
and cggaagaaAfGfAfugaagucgcu; (SEQ ID NO: 34)
or usGfsaAfaUfaAfaUfuAfaAfgGfaGfasGfsg (SEQ ID NO: 28)
and ccucuccuUfUfAfauuuauuuca; (SEQ ID NO: 36)

wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; $U_{UNA}$ represents a 2',3'-seco-uridine (see, e.g., Table 6); s represents a phosphorothioate linkage; and wherein the sense strand further includes inverted abasic residues at the 3' terminal end and at the 5' end of the nucleotide sequence, and the sense strand also includes a targeting ligand that is covalently linked to the 3' and/or 5' terminal end. In certain embodiments, the targeting ligand is selected from (NAG25), (NAG25)s, (NAG37), and (NAG37)s, each as defined herein in Table 6.

In some embodiments, an ASGR1 RNAi agent disclosed herein includes an antisense strand that includes a nucleobase sequence that differs by 0 or 1 nucleobases from the nucleotide sequences selected from the group consisting of (5'→3'):

UACUCCUUGGUCAUGAUAG; (SEQ ID NO: 87)

AGCGACUUCAUCUUUCUUC; (SEQ ID NO: 141)

ACUUCAUCUUUCUUCCCAC; (SEQ ID NO: 133)
or

UGAAAUAAAUUAAAGGAGA. (SEQ ID NO: 239)

In some embodiments, an ASGR1 RNAi agent disclosed herein includes an antisense strand that includes a nucleobase sequence that differs by 0 or 1 nucleobases from the nucleotide sequences selected from the group consisting of (5'→3'):

UACUCCUUGGUCAUGAUAG; (SEQ ID NO: 87)

AGCGACUUCAUCUUUCUUC; (SEQ ID NO: 141)

ACUUCAUCUUUCUUCCCAC; (SEQ ID NO: 133)
or

UGAAAUAAAUUAAAGGAGA; (SEQ ID NO: 239)

and
wherein all or substantially all of the nucleotides are modified nucleotides.

In some embodiments, an ASGR1 RNAi agent disclosed herein includes an antisense strand that includes a nucleobase sequence that differs by 0 or 1 nucleobases from the nucleotide sequences selected from the group consisting of (5'→3'):

UACUCCUUGGUCAUGAUAG; (SEQ ID NO: 87)

AGCGACUUCAUCUUUCUUC; (SEQ ID NO: 141)

ACUUCAUCUUUCUUCCCAC; (SEQ ID NO: 133)
or

UGAAAUAAAUUAAAGGAGA; (SEQ ID NO: 239)

and
wherein all or substantially all of the nucleotides are modified nucleotides, and wherein SEQ ID NO:87, SEQ ID NO:141, SEQ ID NO:133, or SEQ ID NO:239, respectively, is located at nucleotide positions 1-19 (5'→3') of the antisense strand.

In some embodiments, an ASGR1 RNAi agent disclosed herein includes an antisense strand and a sense strand that each include a nucleobase sequences that differs by 0 or 1 nucleobases from the nucleotide sequence pairs selected from the group consisting of (5'→3'):

UACUCCUUGGUCAUGAUAG (SEQ ID NO: 87)
and

CUAUCAUGACCAAGGAIUA; (SEQ ID NO: 253)

UACUCCUUGGUCAUGAUAG (SEQ ID NO: 87)
and

-continued

CUAUCAUGACCAAGGAGUA; (SEQ ID NO: 250)

UACUCCUUGGUCAUGAUAG
and (SEQ ID NO: 87)

CUAUCAUGACCAAIGAIUA; (SEQ ID NO: 257)

AGCGACUUCAUCUUUCUUC
and (SEQ ID NO: 141)

GAAGAAAGAUGAAGUCICU; (SEQ ID NO: 316)

AGCGACUUCAUCUUUCUUC
and (SEQ ID NO: 141)

GAAGAAAGAUGAAGUCGCU; (SEQ ID NO: 312)

ACUUCAUCUUUCUUCCCAC
and (SEQ ID NO: 133)

GUGGGAAGAAAGAUGAAGU; (SEQ ID NO: 304)

AGCGACUUCAUCUUUCUUC
and (SEQ ID NO: 141)

GAAGAAAGAUGAAIUCICU; (SEQ ID NO: 852)

AGCGACUUCAUCUUUCUUC
and (SEQ ID NO: 141)

GAAGAAAGAUGAAGUCGCU; (SEQ ID NO: 312)

UGAAAUAAAUUAAAGGAGA
and (SEQ ID NO: 239)

UCUCCUUUAAUUUAUUUCA; (SEQ ID NO: 414)

wherein I represents an inosine nucleotide.

In some embodiments, an ASGR1 RNAi agent disclosed herein includes an antisense strand and a sense strand that each include a nucleobase sequences that differs by 0 or 1 nucleobases from the nucleotide sequence pairs selected from the group consisting of (5'→3'):

UACUCCUUGGUCAUGAUAG
and (SEQ ID NO: 87)

CUAUCAUGACCAAGGAIUA; (SEQ ID NO: 253)

UACUCCUUGGUCAUGAUAG
and (SEQ ID NO: 87)

CUAUCAUGACCAAGGAGUA; (SEQ ID NO: 250)

UACUCCUUGGUCAUGAUAG
and (SEQ ID NO: 87)

-continued

CUAUCAUGACCAAIGAIUA; (SEQ ID NO: 257)

AGCGACUUCAUCUUUCUUC
and (SEQ ID NO: 141)

GAAGAAAGAUGAAGUCICU; (SEQ ID NO: 316)

AGCGACUUCAUCUUUCUUC
and (SEQ ID NO: 141)

GAAGAAAGAUGAAGUCGCU; (SEQ ID NO: 312)

ACUUCAUCUUUCUUCCCAC
and (SEQ ID NO: 133)

GUGGGAAGAAAGAUGAAGU; (SEQ ID NO: 304)

AGCGACUUCAUCUUUCUUC
and (SEQ ID NO: 141)

GAAGAAAGAUGAAIUCICU; (SEQ ID NO: 852)

AGCGACUUCAUCUUUCUUC
and (SEQ ID NO: 141)

GAAGAAAGAUGAAGUCGCU; (SEQ ID NO: 312)

UGAAAUAAAUUAAAGGAGA
and (SEQ ID NO: 239)

UCUCCUUUAAUUUAUUUCA; (SEQ ID NO: 414)

wherein I represents an inosine nucleotide, and wherein all or substantially all of the nucleotides are modified nucleotides.

In some embodiments, the compositions described herein comprising one or more ASGR1 RNAi agents are packaged in a kit, container, pack, dispenser, pre-filled syringes, or vials. In some embodiments, the compositions described herein are administered parenterally.

Other objects, features, aspects, and advantages of the invention will be apparent from the following detailed description, accompanying figures, and from the claims.

BRIEF DESCRIPTION OF THE DRAWINGS

FIG. 1A discloses SEQ ID NOs: 10 and 631.

The following abbreviations are used in FIGS. 1A to 1M: a, c, g, i, and u are 2'-O-methyl modified nucleotides; Af, Cf, Gf, and Uf are 2'-fluoro modified nucleotides; p is a phosphodiester linkage; s is a phosphorothioate linkage; invAb is an inverted abasic residue (see, e.g., Table 6); C is a cytidine ribonucleotide; $U_{UNA}$ is a 2',3'-seco-uridine (see, e.g., Table 6); and (NAG37)s and (NAG37)p are the respective tridentate N-acetyl-galactosamine targeting ligands having the structure depicted in Table 6.

Figures 1A, 1B, 1C:
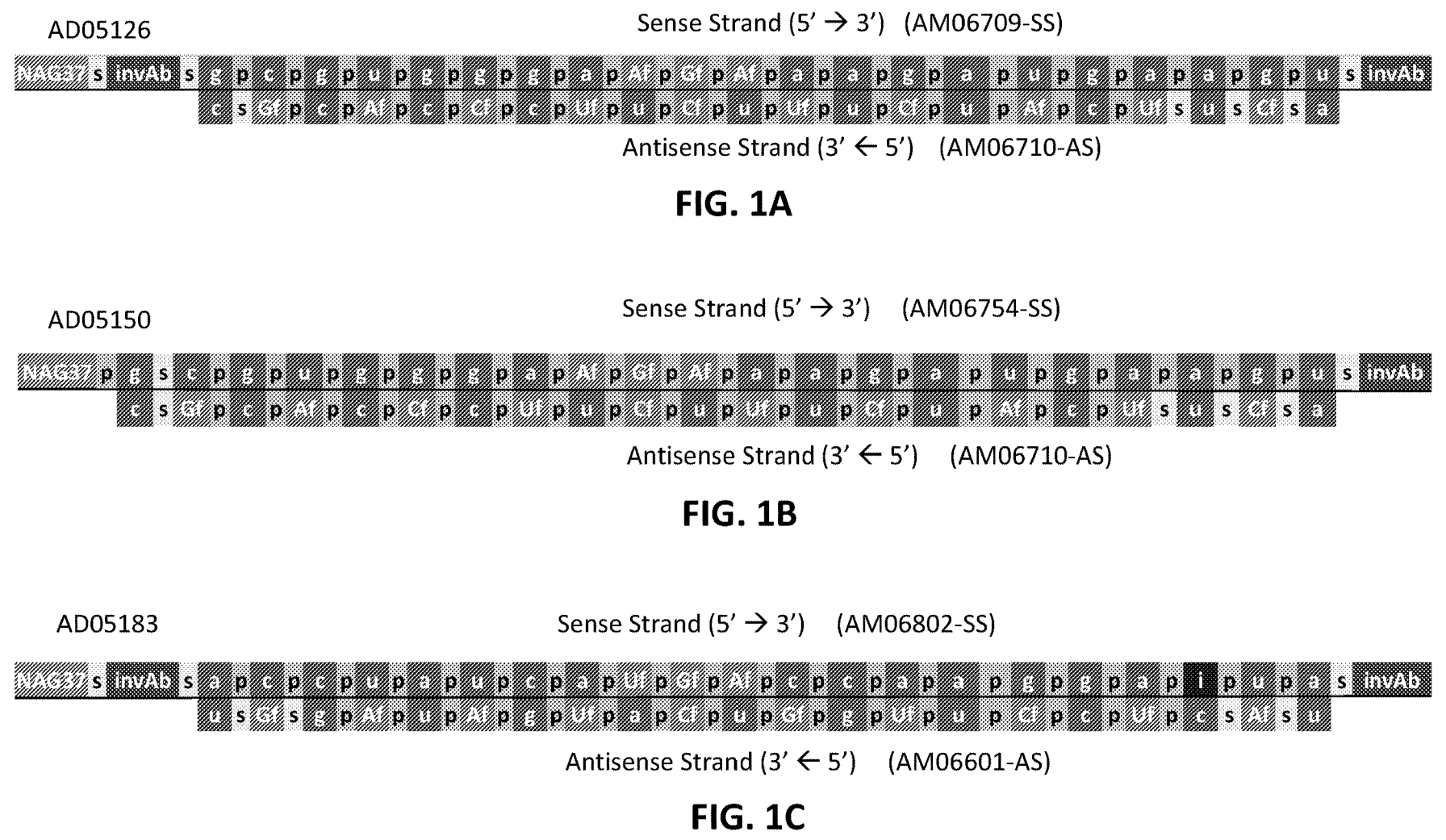

FIG. 1B. Schematic diagram of the modified sense and antisense strands of ASGR1 RNAi agent AD05150 (see Tables 3-5), conjugated to an N-acetyl-galactosamine tridentate ligand having the structure of (NAG37)s (see Table 6). FIG. 1B discloses SEQ ID NOs: 10 and 632.

FIG. 1C. Schematic diagram of the modified sense and antisense strands of ASGR1 RNAi agent AD05183 (see Tables 3-5), conjugated to an N-acetyl-galactosamine tridentate ligand having the structure of (NAG37)s (see Table 6). FIG. 1C discloses SEQ ID NOs: 2 and 636.

Figures 1D, 1E, 1F:
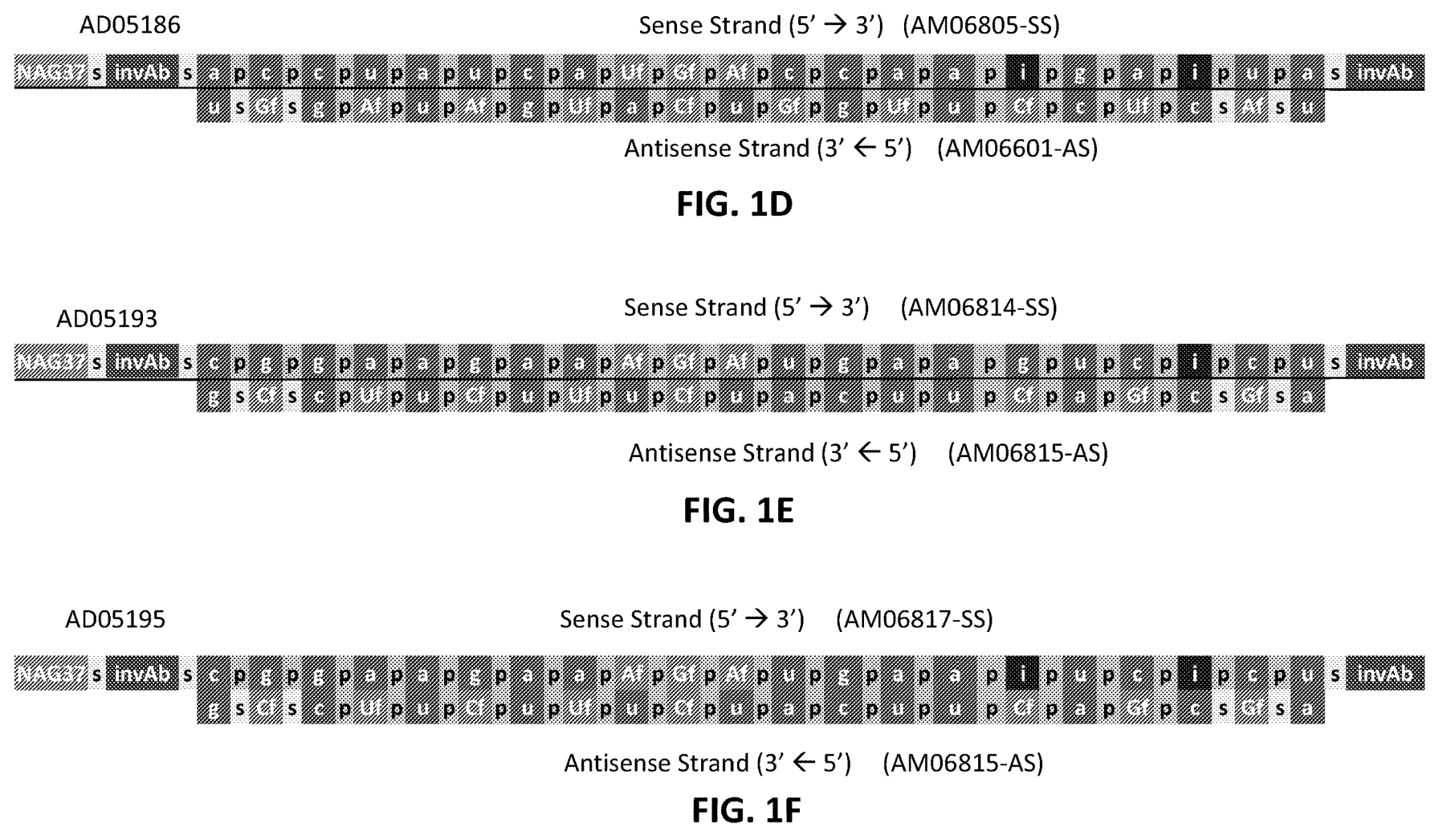

FIG. 1D. Schematic diagram of the modified sense and antisense strands of ASGR1RNAi agent AD05186 (see Tables 3-5), conjugated to an N-acetyl-galactosamine tridentate ligand having the structure of (NAG37)s (see Table 6). FIG. 1D discloses SEQ ID NOs: 2 and 639.

FIG. 1E. Schematic diagram of the modified sense and antisense strands of ASGR1 RNAi agent AD05193 (see Tables 3-5), conjugated to an N-acetyl-galactosamine tridentate ligand having the structure of (NAG37)s (see Table 6). FIG. 1E discloses SEQ ID NOs: 5 and 645.

FIG. 1F. Schematic diagram of the modified sense and antisense strands of ASGR1 RNAi agent AD05195 (see Tables 3-5), conjugated to an N-acetyl-galactosamine tridentate ligand having the structure of (NAG37)s (see Table 6). FIG. 1F discloses SEQ ID NOs: 5 and 647.

Figure 1G:
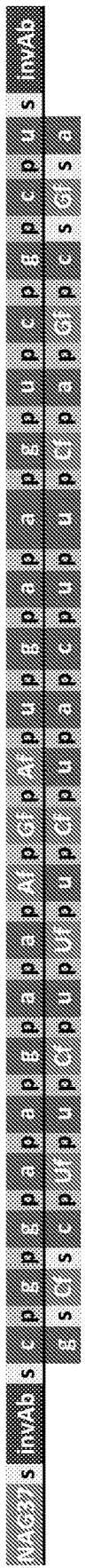
FIG. 1A. Schematic diagram of the modified sense and antisense strands of ASGR1 RNAi agent AD05126 (see Tables 3-5), conjugated to an N-acetyl-galactosamine tridentate ligand having the structure of (NAG37)s (see Table 6).

FIG. 1G. Schematic diagram of the modified sense and antisense strands of ASGR1 RNAi agent AD05196 (see Tables 3-5), conjugated to an N-acetyl-galactosamine tridentate ligand having the structure of (NAG37)s (see Table 6). FIG. 1G discloses SEQ ID NOs: 5 and 648.

Figure 1H:

FIG. 1H. Schematic diagram of the modified sense and antisense strands of ASGR1 RNAi agent AD05206 (see Tables 3-5), conjugated to an N-acetyl-galactosamine tridentate ligand having the structure of (NAG37)s (see Table 6). FIG. 1H discloses SEQ ID NOs: 28 and 658.

Figure 1I:

FIG. 1I. Schematic diagram of the modified sense and antisense strands of ASGR1 RNAi agent AD05209 (see Tables 3-5), conjugated to an N-acetyl-galactosamine tridentate ligand having the structure of (NAG37)s (see Table 6). FIG. 1I discloses SEQ ID NOs: 4 and 602.

Figure 1J:
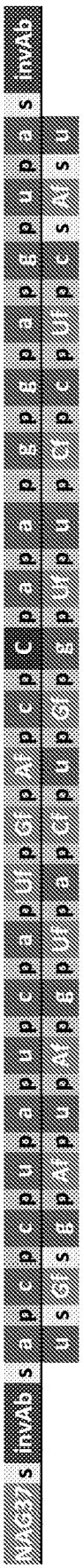

FIG. 1J. Schematic diagram of the modified sense and antisense strands of ASGR1 RNAi agent AD05256 (see Tables 3-5), conjugated to an N-acetyl-galactosamine tridentate ligand having the structure of (NAG37)s (see Table 6). FIG. 1J discloses SEQ ID NOs: 2 and 674.

Figure 1K:

FIG. 1K. Schematic diagram of the modified sense and antisense strands of ASGR1 RNAi agent AD05374 (see Tables 3-5), conjugated to an N-acetyl-galactosamine tridentate ligand having the structure of (NAG37)s (see Table 6). FIG. 1K discloses SEQ ID NOs: 2 and 700.

Figure 1L:
Figure 2A:
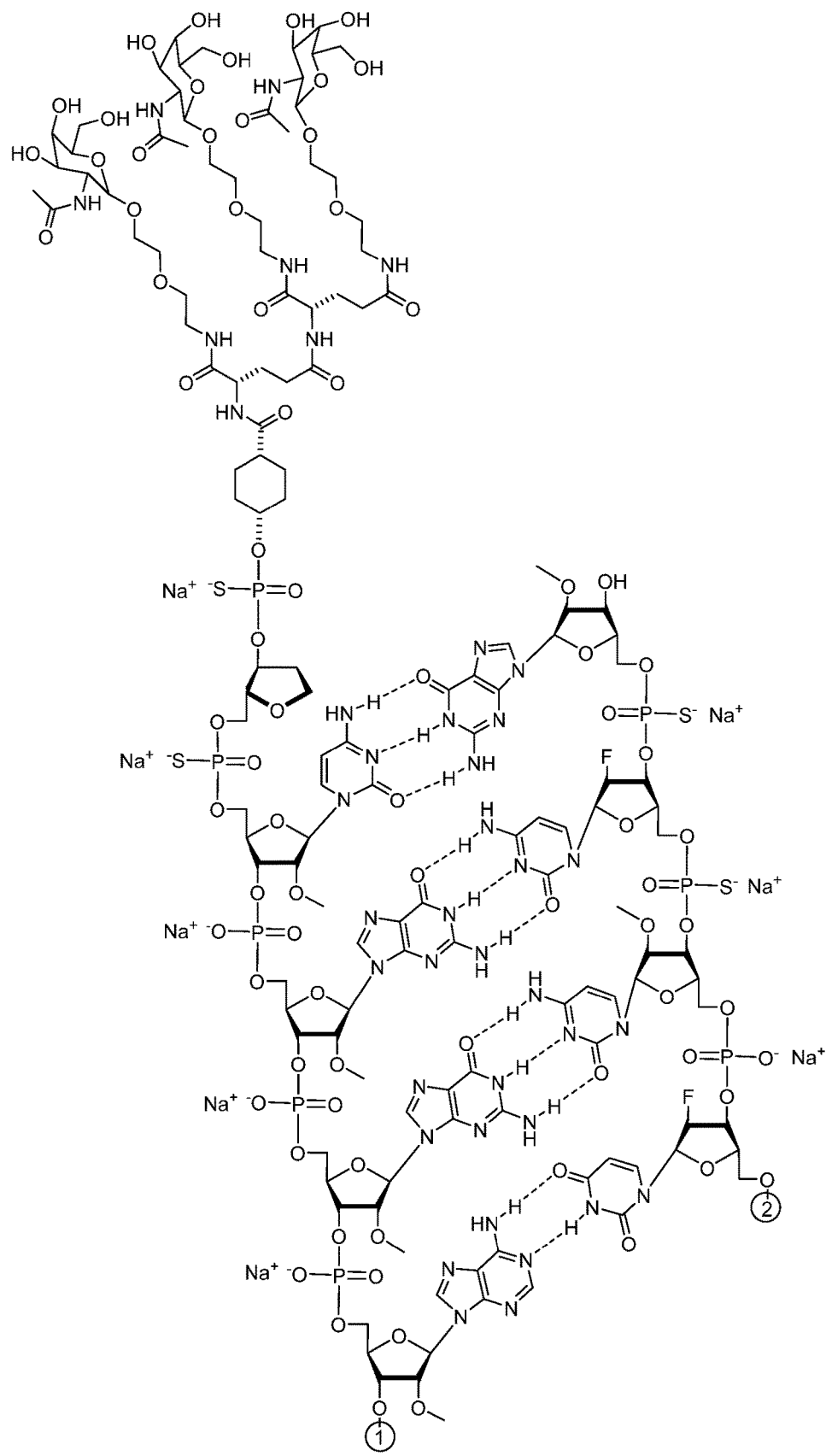
Figure 2B:
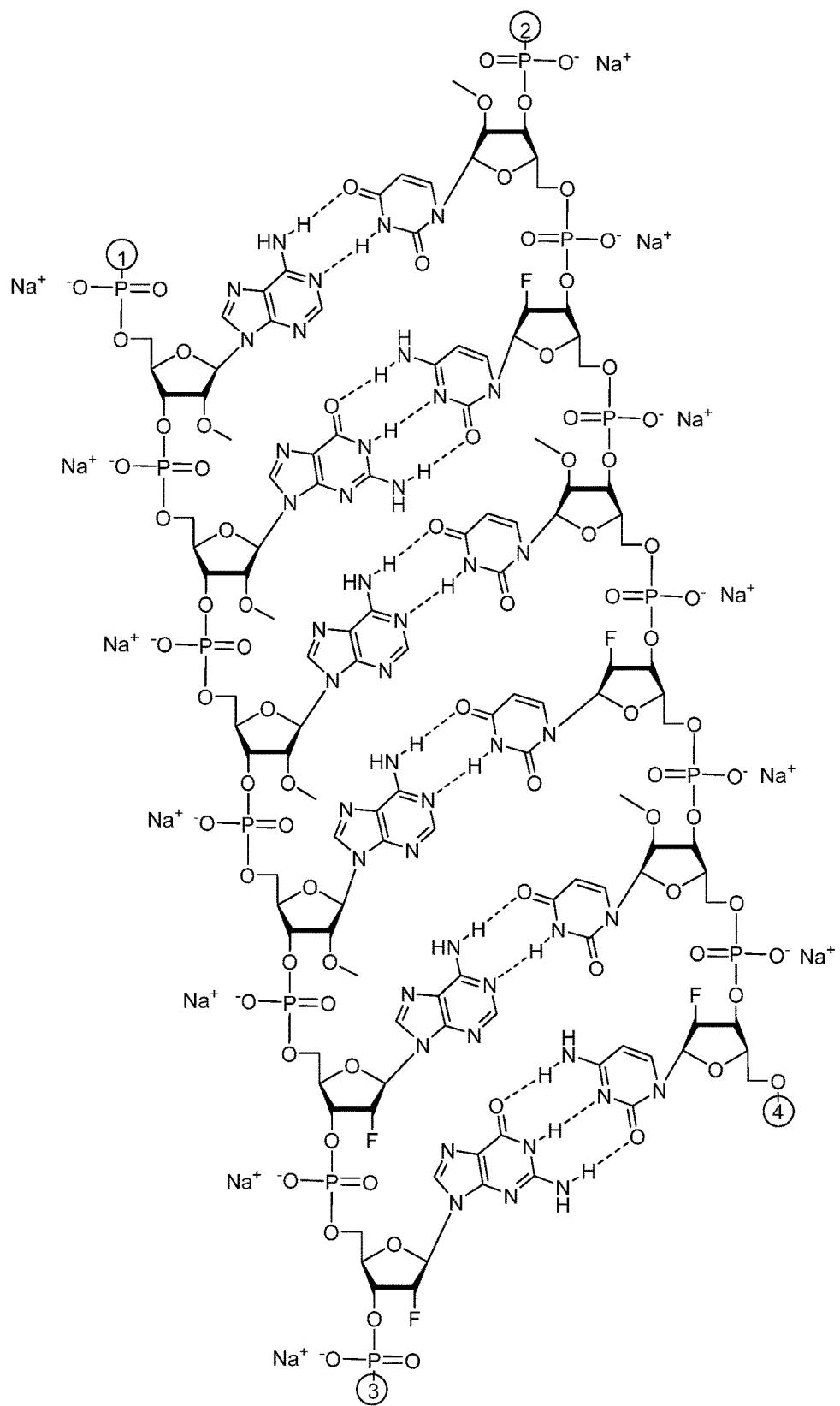
Figure 2C:
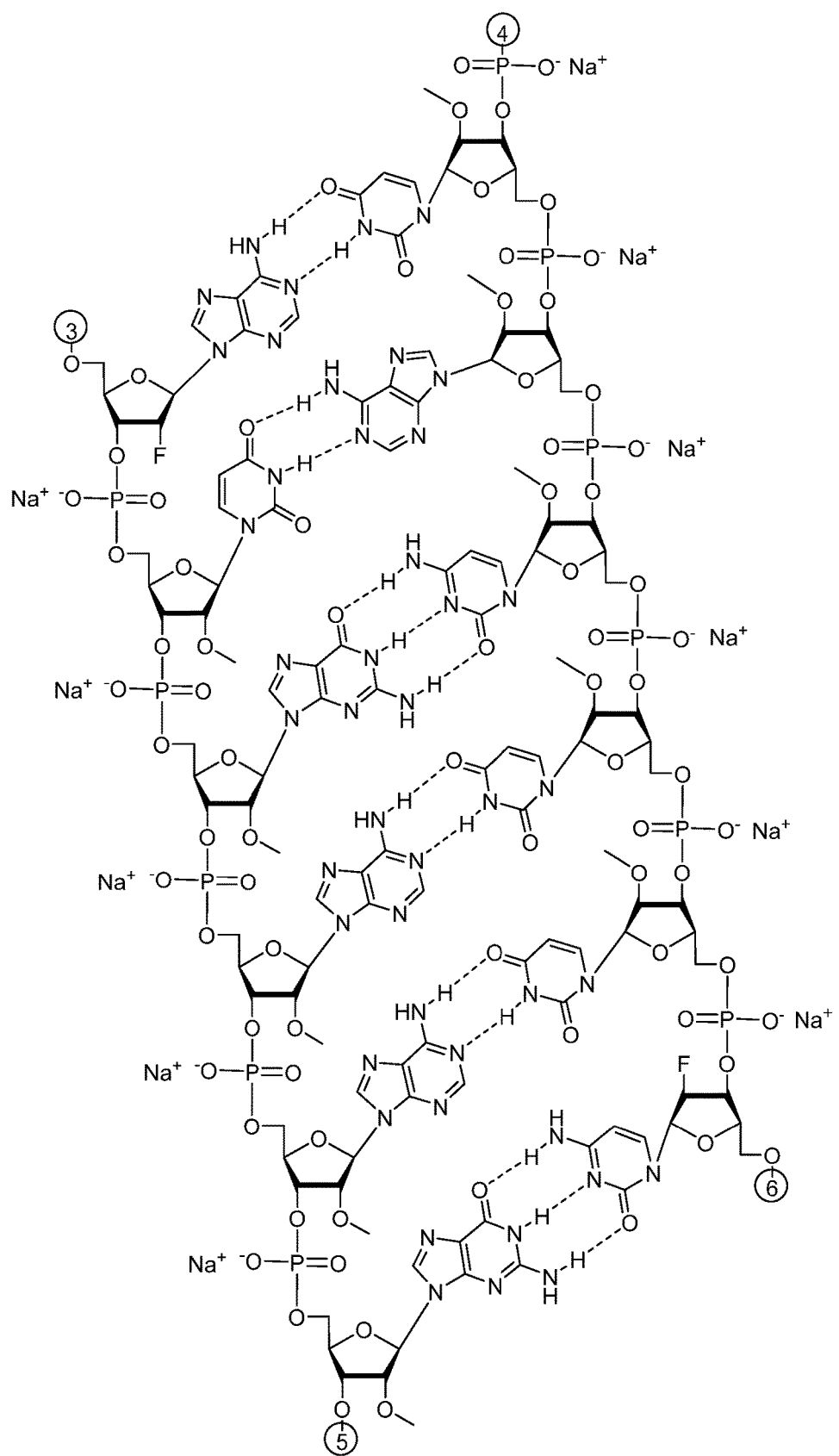
Figure 2D:
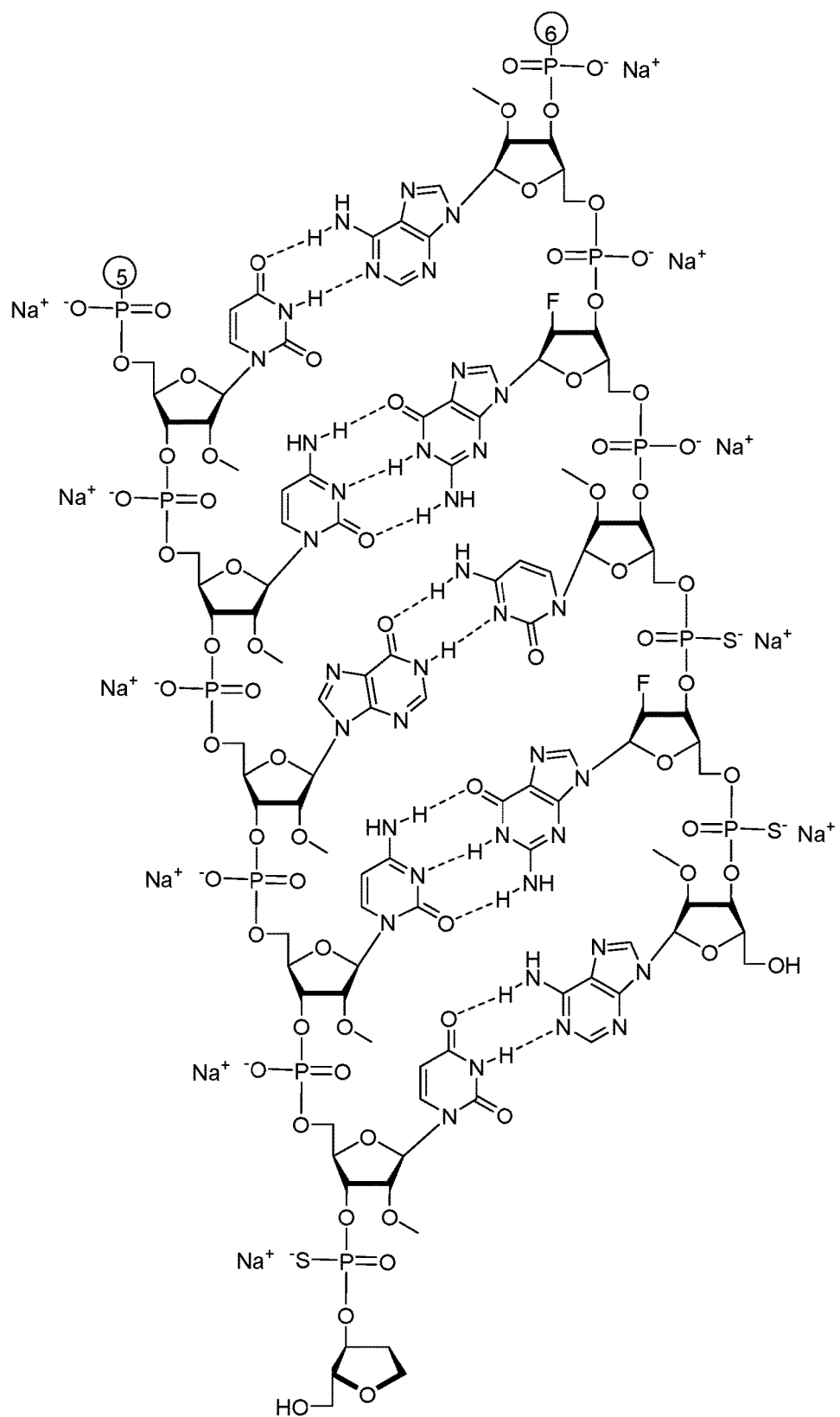
Figure 3A:
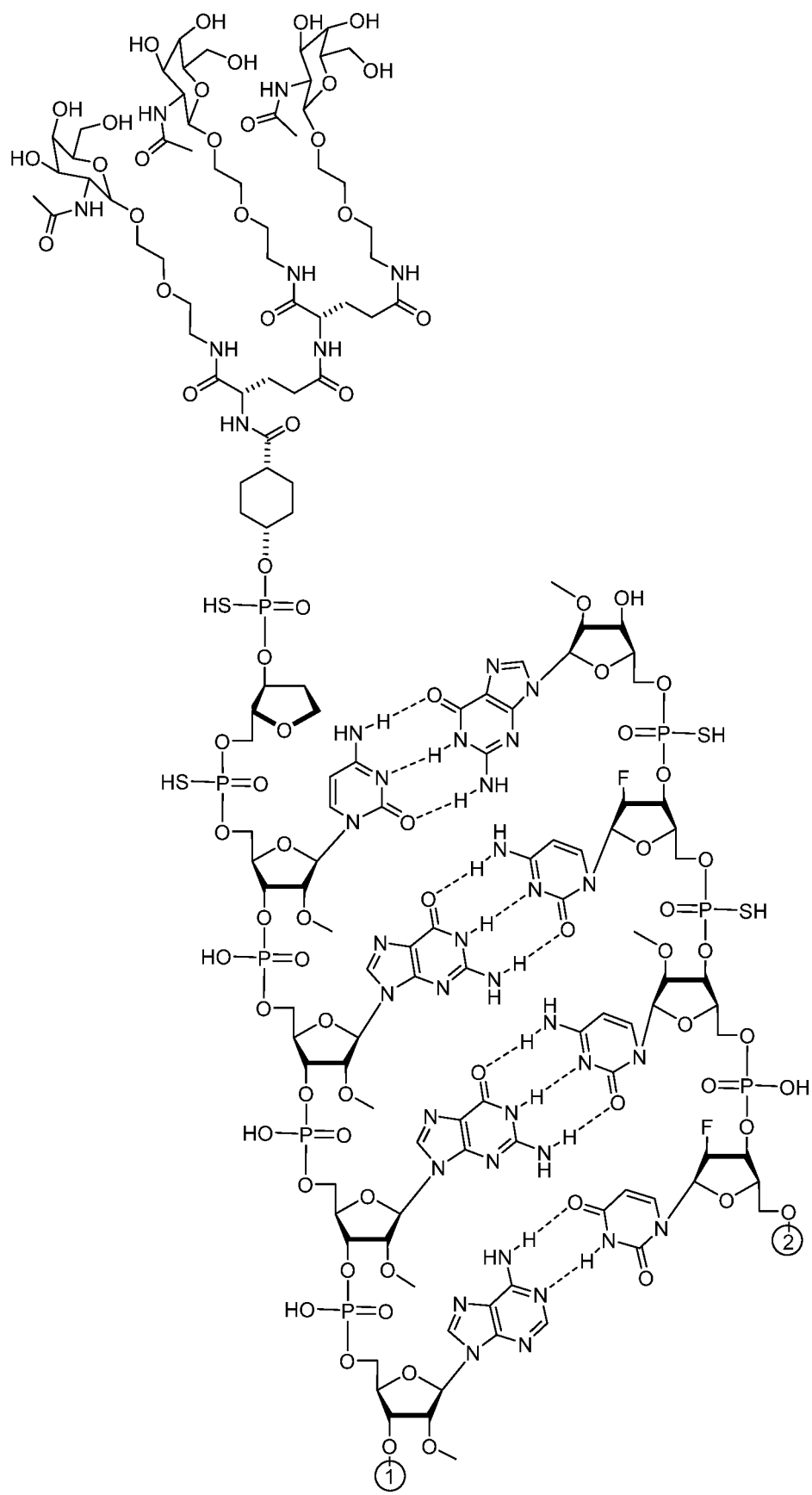
Figure 3B:
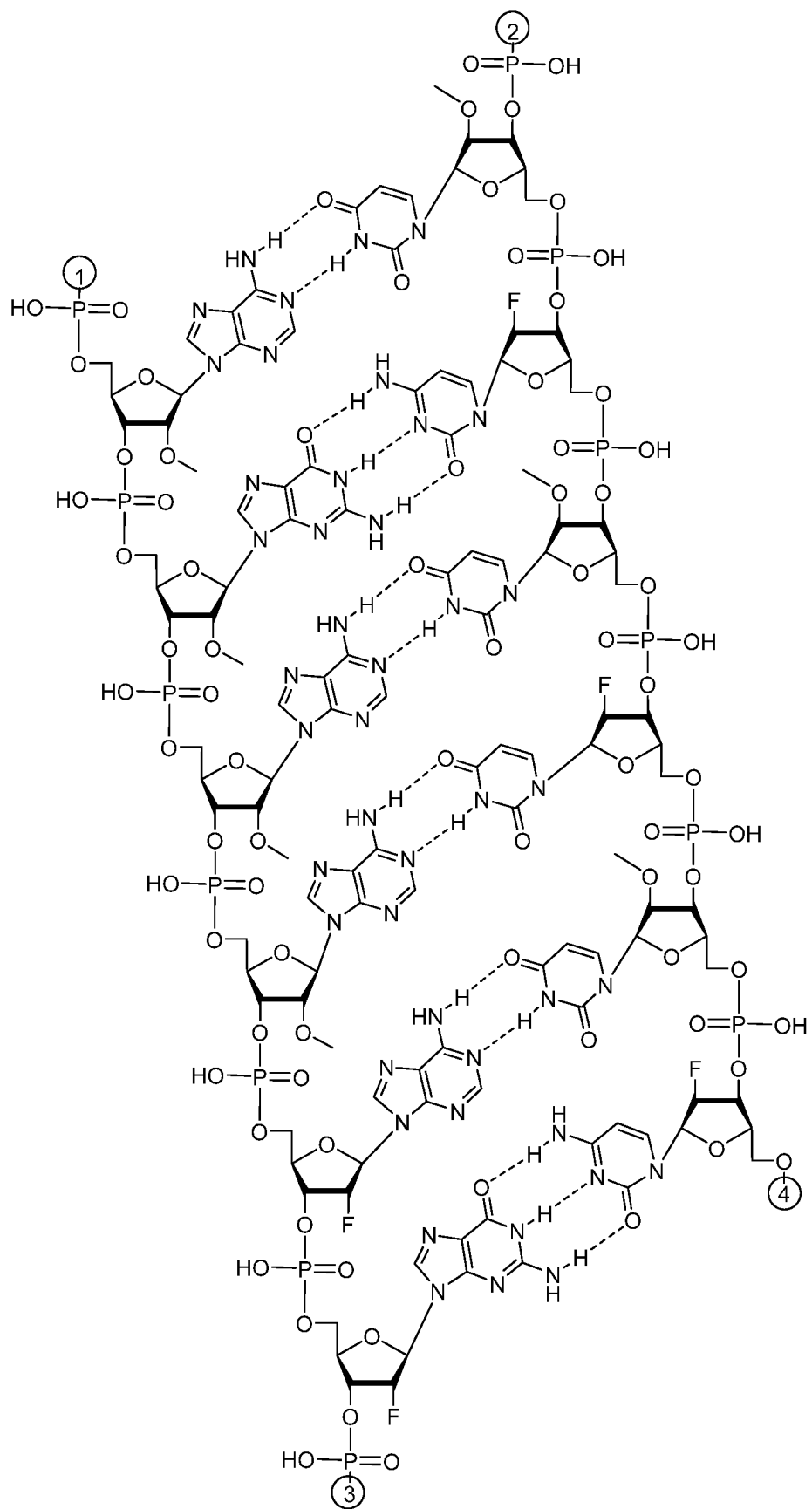
Figure 3C:
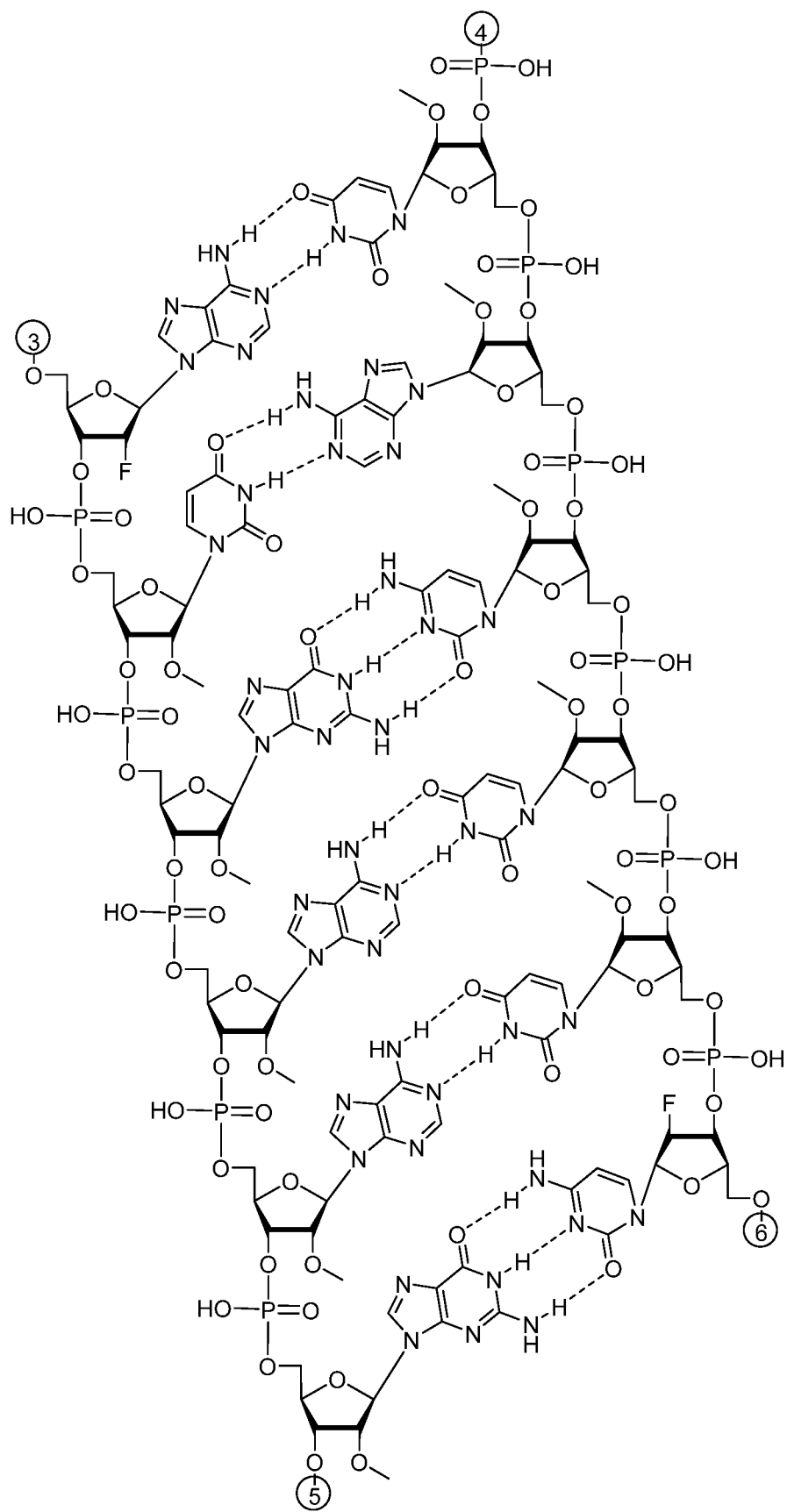
Figure 3D:
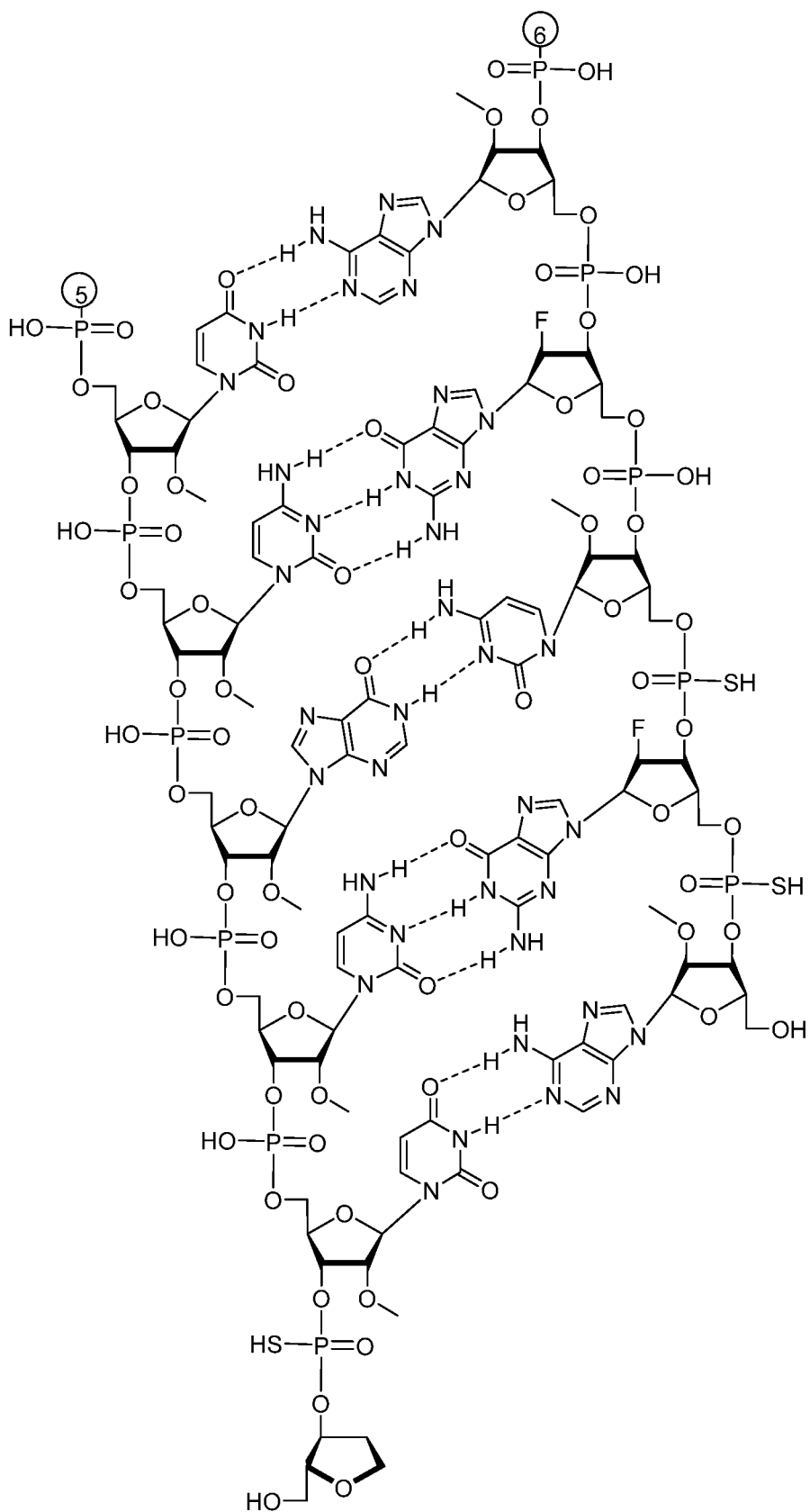
Figure 4A:
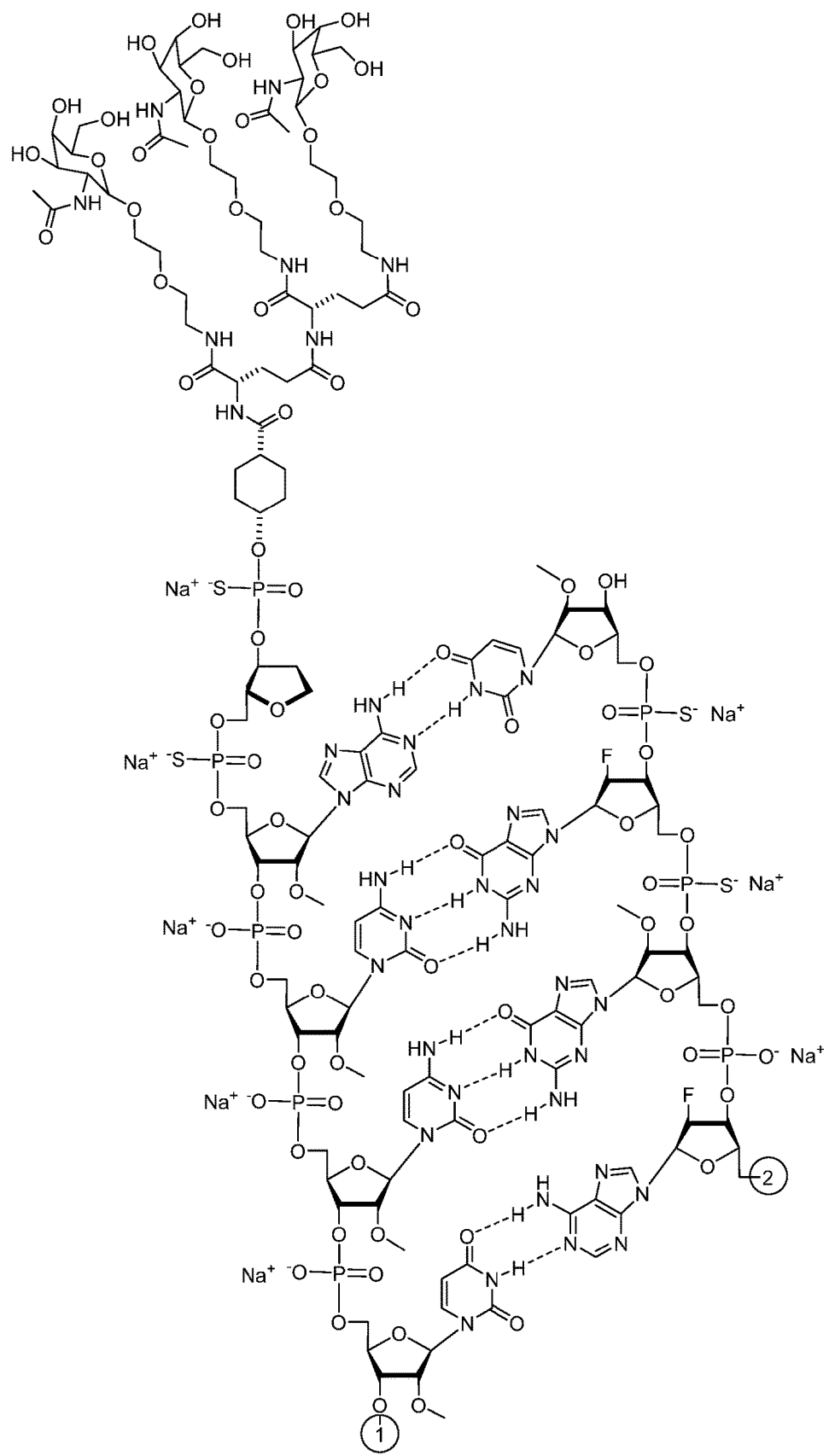
Figure 4B:
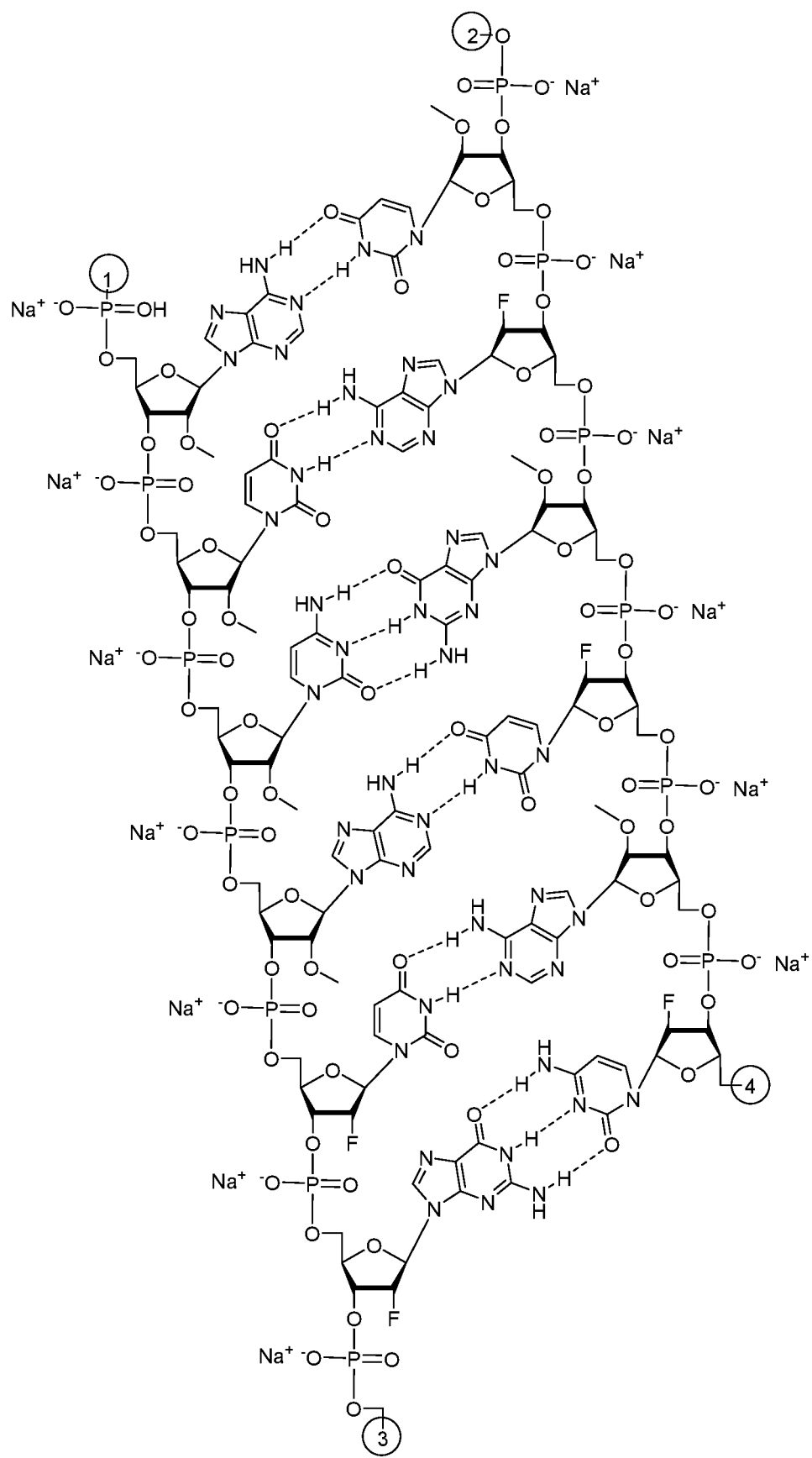
Figure 4C:
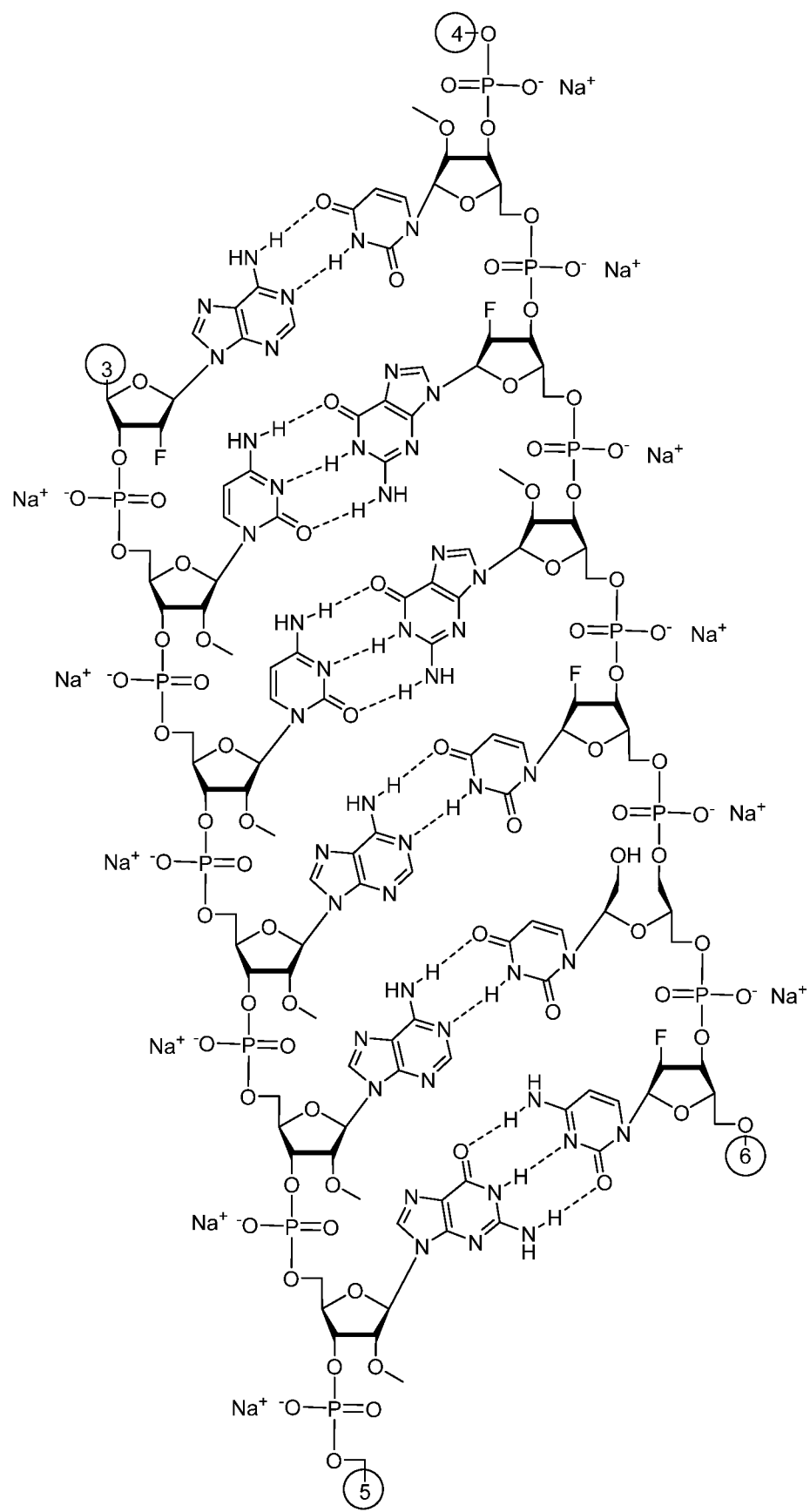
Figure 4D:
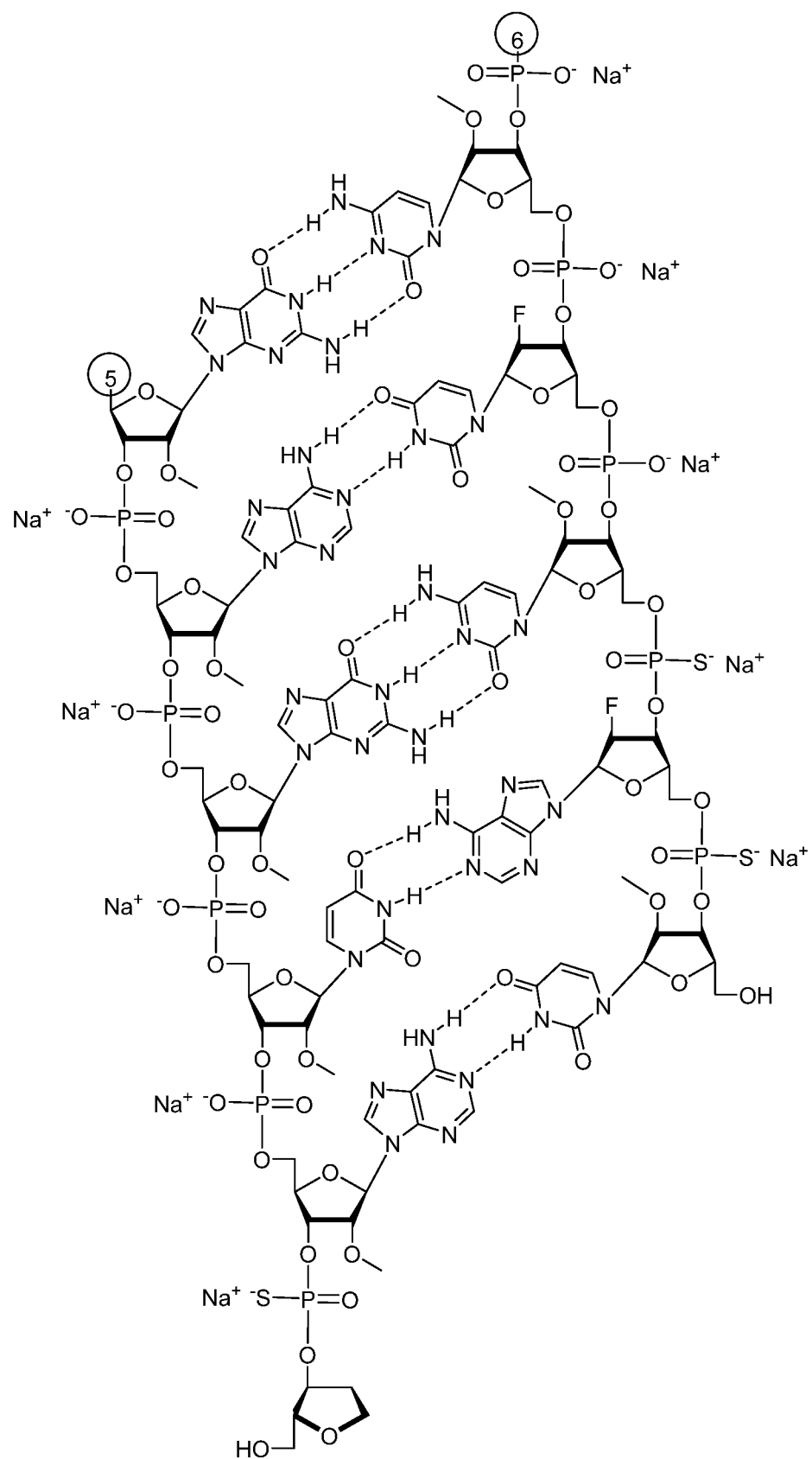
Figure 5A:
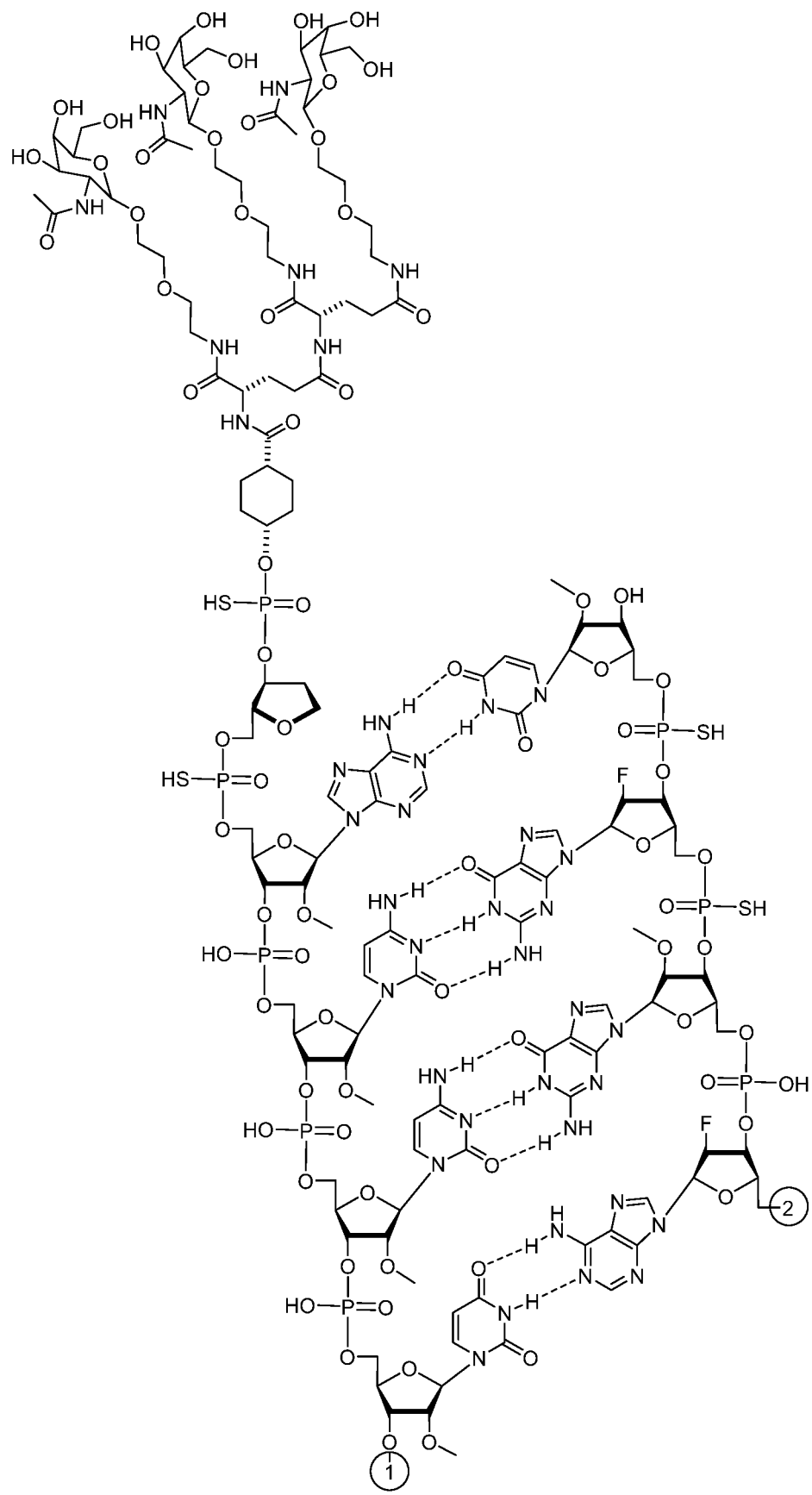
Figure 5B:
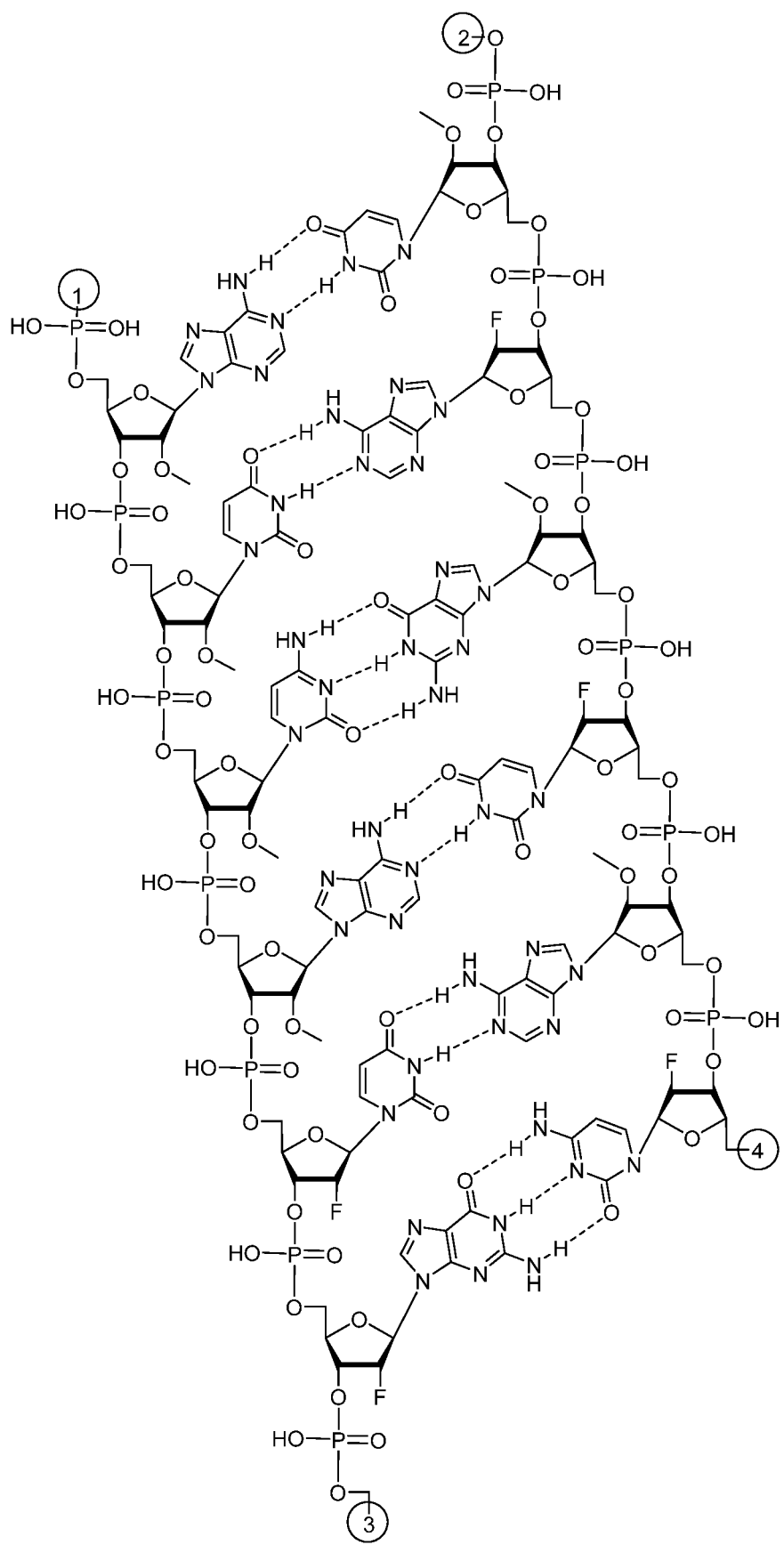
Figure 5C:
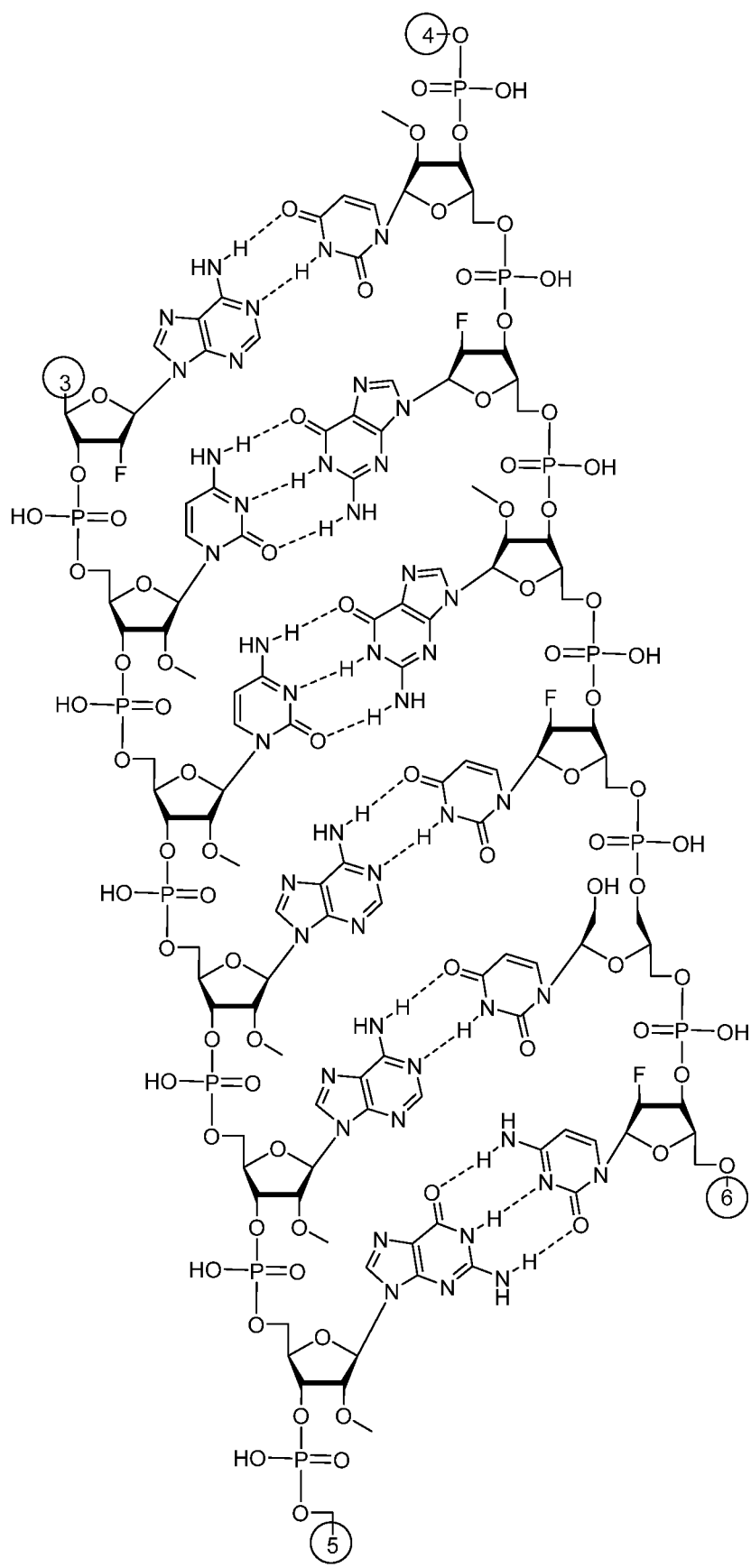
Figure 5D:
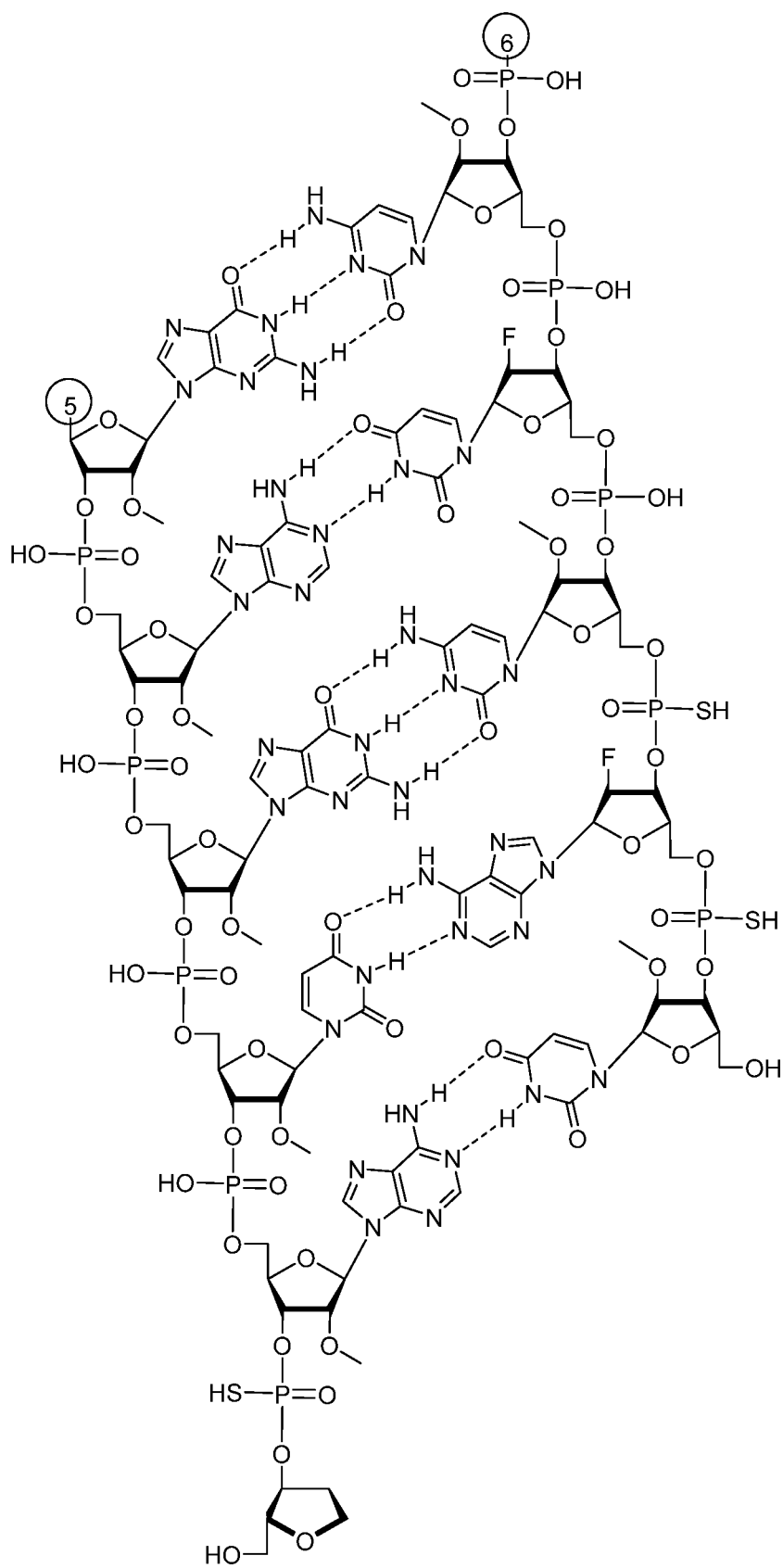

FIG. 1L. Schematic diagram of the modified sense and antisense strands of ASGR1 RNAi agent AD05609 (see Tables 3-5), conjugated to an N-acetyl-galactosamine tridentate ligand having the structure of (NAG37)s (see Table 6). FIG. 1L discloses SEQ ID NOs: 7 and 708.

Figure 1M:
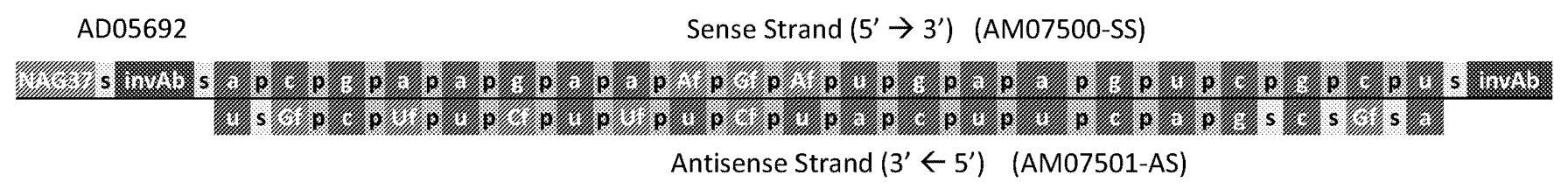

FIG. 1M. Schematic diagram of the modified sense and antisense strands of ASGR1 RNAi agent AD05692 (see Tables 3-5), conjugated to an N-acetyl-galactosamine tridentate ligand having the structure of (NAG37)s (see Table 6). FIG. 1M discloses SEQ ID NOs: 9 and 721.

FIG. 2A to 2D. Chemical structure representation of ASGR1 RNAi agent AD05193, conjugated to an N-acetyl-galactosamine tridentate ligand having the structure of (NAG37)s (see Table 6) at the 5' terminal end of the sense strand, shown in a sodium salt form.

FIG. 3A to 3D. Chemical structure representation of ASGR1 RNAi agent AD05193, conjugated to an N-acetyl-galactosamine tridentate ligand having the structure of (NAG37)s (see Table 6) at the 5' terminal end of the sense strand, shown in a free acid form.

FIG. 4A to 4D. Chemical structure representation of ASGR1 RNAi agent AD05209, conjugated to an N-acetyl-galactosamine tridentate ligand having the structure of (NAG37)s (see Table 6) at the 5' terminal end of the sense strand, shown in a sodium salt form.

FIG. 5A to 5D. Chemical structure representation of ASGR1 RNAi agent AD05209, conjugated to an N-acetyl-galactosamine tridentate ligand having the structure of (NAG37)s (see Table 6) at the 5' terminal end of the sense strand, shown in a free acid form.

DETAILED DESCRIPTION

Definitions

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. ASGR1 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an ASGR1 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the preventative treatment, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol $\lambda$ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

RNAi Agents

Described herein are RNAi agents for inhibiting expression of an ASGR1 gene (referred to herein as ASGR1 RNAi agents or ASGR1 RNAi triggers). Each ASGR1 RNAi agent comprises a sense strand and an antisense strand. The sense strand and the antisense strand each can be 16 to 30 nucleotides in length. In some embodiments, the sense and antisense strands each can be 17 to 26 nucleotides in length. The sense and antisense strands can be either the same length or they can be different lengths. In some embodiments, the sense and antisense strands are each independently 17-21 nucleotides in length. In some embodiments, the sense and antisense strands are each 21-26 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, both the sense and antisense strands are each 26 nucleotides in length. In some embodiments, a sense strand is 22 nucleotides in length and an antisense strand is 21 nucleotides in length. In some embodiments, a sense strand is 19 nucleotides in length and an antisense strand is 21 nucleotides in length. In some embodiments, the RNAi agent sense and antisense strands are each independently 17, 18, 19, 20, 21, 22, 23, 24, 25, or 26 nucleotides in length.

In some embodiments, a double-stranded RNAi agent has a duplex length of about 16, 17, 18, 19, 20, 21, 22, 23 or 24 nucleotides. This region of perfect or substantial complementarity between the sense strand and the antisense strand is typically 15-26 (e.g., 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly or substantially complementary).

The sense strand and antisense strand each contain a core stretch sequence that is 16 to 23 nucleobases in length. An antisense strand core stretch sequence is 100% (perfectly) complementary or at least about 85% (substantially) complementary to a nucleotide sequence (sometimes referred to, e.g., as a target sequence) present in the ASGR1 mRNA target. A sense strand core stretch sequence is 100% (perfectly) complementary or at least about 85% (substantially) complementary to a core stretch sequence in the antisense strand, and thus the sense strand core stretch sequence is perfectly identical or at least about 85% identical to a nucleotide sequence (target sequence) present in the ASGR1 mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of sense and antisense strand nucleotide sequences used in forming ASGR1 RNAi agents are provided in Tables 2, 3 and 4. Examples of RNAi agent duplexes, that include the sense strand and antisense strand sequences in Tables 3 and 4, are shown in Table 5.

The ASGR1 RNAi agent sense and antisense strands anneal to form a duplex. A sense strand and an antisense strand of an ASGR1 RNAi agent may be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an ASGR1 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an ASGR1 RNAi agent disclosed herein differs by 0, 1, 2, or 3 nucleotides from any of the antisense strand sequences in Table 2 or Table 3. In some embodiments, the sense strand of an ASGR1 RNAi agent disclosed herein differs by 0, 1, 2, or 3 nucleotides from any of the sense strand sequences in Table 2 or Table 4.

The sense strand and/or the antisense strand may optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in an ASGR1 mRNA. The sense strand additional nucleotides, if present, may or may not be identical to the corresponding sequence in an ASGR1 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an ASGR1 RNAi agent has an antisense strand having a 3' extension and a sense strand having a 5' extension.

In some embodiments, an ASGR1 RNAi agent comprises an antisense strand having a 3' extension of 1, 2, 3, 4, 5, or 6 nucleotides in length. In other embodiments, an ASGR1 RNAi agent comprises an antisense strand having a 3' extension of 1, 2, or 3 nucleotides in length. In some embodiments, one or more of the antisense strand extension nucleotides comprise uracil or thymidine nucleotides or nucleotides which are complementary to the correspondingASGR1 mRNA sequence. In some embodiments, a 3' antisense strand extension includes or consists of one of the following sequences, but is not limited to: AUA, UGCUU, CUG, UG, UGCC, CUGCC, CGU, CUU, UGCCUA, CUGCCU, UGCCU, UGAUU, GCCUAU, T, TT, U, UU (each listed 5' to 3').

In some embodiments, the 3' end of the antisense strand may include additional abasic residues or sites (Ab). An "abasic residue" or "abasic site" is a nucleotide or nucleoside that lacks a nucleobase at the 1' position of the sugar. In some embodiments, Ab or AbAb may be added to the 3' end of the antisense strand. In some embodiments, the abasic residue(s) may be added as inverted abasic residue(s) (see Table 6). (See, e.g., F. Czauderna, Nucleic Acids Res., 2003, 31(11), 2705-16).

In some embodiments, an ASGR1 RNAi agent comprises an antisense strand having a 5' extension of 1, 2, 3, 4, or 5 nucleotides in length. In other embodiments, an ASGR1 RNAi agent comprises an antisense strand having a 5' extension of 1 or 2 nucleotides in length. In some embodiments, one or more of the antisense strand extension nucleotides comprises uracil or thymidine nucleotides or nucleotides which are complementary to the corresponding ASGR1 mRNA sequence. In some embodiments, the 5' antisense strand extension includes or consists of one of the following sequences, but is not limited to: UA, TU, U, T, UU, TT, CUC (each listed 5' to 3'). An antisense strand may have any of the 3' extensions described above in combination with any of the 5' antisense strand extensions described, if present.

In some embodiments, an ASGR1 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides which correspond to nucleotides in the ASGR1 mRNA sequence. In some embodiments, the 3' sense strand extension includes or consists of one of the following sequences, but is not limited to: T, UT, TT, UU, UUT, TTT, or TTTT (each listed 5' to 3').

In some embodiments, the 3' end of the sense strand may include additional abasic residues. In some embodiments, UUAb, UAb, or Ab may be added to the 3' end of the sense strand. In some embodiments, the one or more abasic residues added to the 3' end of the sense strand may be inverted (invAb). In some embodiments, one or more inverted abasic residues may be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent.

In some embodiments, an ASGR1 RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides which correspond to nucleotides in the ASGR1 mRNA sequence. In some embodiments, the sense strand 5' extension can be one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand may have a 3' extension and/or a 5' extension.

In some embodiments, the 5' end of the sense strand may include one or more additional abasic residues (e.g., (Ab) or (AbAb)). In some embodiments, the one or more abasic residues added to the 5' end of the sense strand may be inverted (e.g., invAb). In some embodiments, one or more inverted abasic residues may be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent.

In some embodiments, the 3' end of the sense strand core stretch sequence, or the 3' end of the sense strand sequence, may include an inverted abasic residue (invAb (see Table 6)). In some embodiments, the 5' end of the sense core stretch, or the 5' end of the sense strand sequence, may include an inverted abasic site or residue. In some embodiments, both the 3' and 5' ends of the sense strand core stretch sequence may include an inverted abasic residue. In some embodiments, both the 3' and 5' ends of the sense strand sequence may include an inverted abasic residue.

In some embodiments, the 3' end of the antisense strand core stretch sequence, or the 3' end of the antisense strand sequence, may include an inverted abasic residue (invAb (see Table 6)). In some embodiments, the 5' end of the antisense core stretch, or the 5' end of the antisense strand sequence, may include an inverted abasic site or residue. In some embodiments, both the 3' and 5' ends of the antisense strand core stretch sequence may include an inverted abasic residue. In some embodiments, both the 3' and 5' ends of the antisense strand sequence may include an inverted abasic residue.

Examples of sequences used in forming ASGR1 RNAi agents are provided in Tables 2, 3, and 4. In some embodiments, an ASGR1 RNAi agent antisense strand includes a sequence of any of the sequences in Tables 2 or 3. In some embodiments, an ASGR1 RNAi agent antisense strand includes the sequence of nucleotides 1-17, 2-15, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Tables 2 or 3. In certain embodiments, an ASGR1 RNAi agent antisense strand comprises or consists of a modified sequence of any one of the modified sequences in Table 3. In some embodiments, an ASGR1 RNAi agent sense strand includes the sequence of any of the sequences in Tables 2 or 4. In some embodiments, an ASGR1 RN Ai agent sense strand includes the sequence of nucleotides 1-18, 1-19, 1-20, 1-21, 1-22, 1-23, 1-24, 1-25, 1-26, 2-19, 2-20, 2-21, 2-22, 2-23, 2-24, 2-25, 2-26, 3-20, 3-21, 3-22, 3-23, 3-24, 3-25, 3-26, 4-21, 4-22, 4-23, 4-24, 4-25, 4-26, 5-22, 5-23, 5-24, 5-25, 5-26, 6-23, 6-24, 6-25, 6-26, 7-24, 7-25, 7-25, 8-25, 8-26 of any of the sequences in Tables 2 or 4. In certain embodiments, an ASGR1 RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a blunt end refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands form a pair (i.e. do not form an overhang) but are not complementary (i.e. form a non-complementary pair). As used herein, an overhang is a stretch of one or more unpaired nucleotides at the end of one strand of a double stranded RNAi agent. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends.

A nucleotide base (or nucleobase) is a heterocyclic pyrimidine or purine compound which is a constituent of all nucleic acids and includes adenine (A), guanine (G), cytosine (C), thymine (T), and uracil (U). As used herein, the term "nucleotide" can include a modified nucleotide (such as, for example, a nucleotide mimic, abasic site or residue (Ab), or a surrogate replacement moiety). Modified nucleotides, when used in various polynucleotide or oligonucleotide constructs, may preserve activity of the compound in cells while at the same time increasing the serum stability of these compounds, and can also minimize the possibility of activating interferon activity in humans upon administering of the polynucleotide or oligonucleotide construct.

In some embodiments, an ASGR1 RNAi agent is prepared or provided as a salt, mixed salt, or a free-acid. In some embodiments, an ASGR1 RNAi agent is prepared as a sodium salt. Such forms are within the scope of the inventions disclosed herein.

Modified Nucleotides

In some embodiments, an ASGR1 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn, invAb), modified nucleobase-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification may be incorporated in a single ASGR1 RNAi agent or even in a single nucleotide thereof. The ASGR1 RNAi agent sense strands and antisense strands may be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides. As used herein, a sense strand wherein substantially all of the nucleotides present are modified nucleotides is a sense strand having two or fewer (i.e., 0, 1, or 2) nucleotides in the sense strand being ribonucleotides. As used herein, an antisense sense strand wherein substantially all of the nucleotides present are modified nucleotides is an antisense strand having two or fewer (i.e., 0, 1, or 2) nucleotides in the sense strand being ribonucleotides. In some embodiments, one or more nucleotides of an RNAi agent is a ribonucleotide.

Modified Internucleoside Linkages

In some embodiments, one or more nucleotides of an ASGR1 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, amino alkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an ASGR1 RNAi agent can contain 1, 2, 3, 4, 5, or 6 phosphorothioate linkages, an antisense strand of an ASGR1 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an ASGR1 RNAi agent can contain 1, 2, 3, or 4 phosphorothioate linkages, an antisense strand of an ASGR1 RNAi agent can contain 1, 2, 3, or 4 phosphorothioate linkages, or both the sense strand and the antisense strand independently can contain 1, 2, 3, or 4 phosphorothioate linkages.

In some embodiments, an ASGR1 RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, one phosphorothioate internucleoside linkage is at the 5' end of the sense strand, and another phosphorothioate linkage is at the 3' end of the sense strand. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage. In some embodiments, an ASGR1 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, an ASGR1 RNAi agent contains at least two phosphorothioate internucleoside linkages in the sense strand and three or four phosphorothioate internucleoside linkages in the antisense strand.

In some embodiments, an ASGR1 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, an ASGR1 RNAi agent contains at least three or four phosphorothioate internucleoside linkages in the antisense strand.

In some embodiments, an ASGR1 RNAi agent contains one or more modified nucleotides and one or more modified internucleoside linkages. In some embodiments, a 2'-modified nucleoside is combined with modified internucleoside linkage.

ASGR1 RNAi Agents

In some embodiments, the ASGR1 RNAi agents disclosed herein target an ASGR1 gene at or near the positions of the ASGR1 gene shown in Table 1. In some embodiments, the antisense strand of an ASGR1 RNAi agent disclosed herein includes a core stretch sequence that is fully, substantially, or at least partially complementary to a target ASGR1 19-mer sequence disclosed in Table 1.

TABLE 1

ASGR1 19-mer mRNA Target Sequences (taken from human ASGR1 (transcript variant 1) cDNA, GenBank NM_001671.4 (SEQ ID NO: 1)).

| SEQ ID No. | ASGR1 19-mer Target Sequences (5' → 3') | Corresponding Gene Positions (taken from SEQ ID NO: 1) |
|---|---|---|
| 37 | AGCCCUAUCAUGACCAAGG | 392-410 |
| 38 | CCUAUCAUGACCAAGGAGU | 395-413 |
| 39 | CUAUCAUGACCAAGGAGUA | 396-414 |
| 40 | UAUCAUGACCAAGGAGUAU | 397-415 |
| 41 | AUCAUGACCAAGGAGUAUC | 398-416 |
| 42 | CAUGACCAAGGAGUAUCAA | 400-418 |
| 43 | GGAGAGUGACCACCAUCAG | 442-460 |
| 44 | GAGUGACCACCAUCAGCUC | 445-463 |
| 45 | CAACUUCACAGCGAGCACG | 634-652 |
| 46 | AGGGAGGCAAUGUGGGAAG | 681-699 |
| 47 | GGAGGCAAUGUGGGAAGAA | 683-701 |

TABLE 1-continued

ASGR1 19-mer mRNA Target Sequences (taken from human ASGR1 (transcript variant 1) cDNA, GenBank NM_001671.4 (SEQ ID NO: 1)).

| SEQ ID No. | ASGR1 19-mer Target Sequences (5' → 3') | Corresponding Gene Positions (taken from SEQ ID NO: 1) |
|---|---|---|
| 48 | GGCAAUGUGGGAAGAAAGA | 686-704 |
| 49 | CAAUGUGGGAAGAAAGAUG | 688-706 |
| 50 | AAUGUGGGAAGAAAGAUGA | 689-707 |
| 51 | GUGGGAAGAAAGAUGAAGU | 692-710 |
| 52 | GGAAGAAAGAUGAAGUCGC | 695-713 |
| 53 | GAAGAAAGAUGAAGUCGCU | 696-714 |
| 54 | UGCUGCUCCACGUGAAGCA | 768-786 |
| 55 | CUGCUCCACGUGAAGCAGU | 770-788 |
| 56 | UGCUCCACGUGAAGCAGUU | 771-789 |
| 57 | GCUCCACGUGAAGCAGUUC | 772-790 |
| 58 | UCCACGUGAAGCAGUUCGU | 774-792 |
| 59 | GCUCCAGGGCAAUGGCUCA | 829-847 |
| 60 | CACGAGCGCAGCUGCUACU | 881-899 |
| 61 | AGCGCAGCUGCUACUGGUU | 885-903 |
| 62 | GCGCAGCUGCUACUGGUUC | 886-904 |
| 63 | GACGCCGACAACUACUGCC | 929-947 |
| 64 | ACCUGGUGGUGGUCACGUC | 963-981 |
| 65 | UGGUGGUGGUCACGUCCUG | 966-984 |
| 66 | AGGAGCAGAAAUUUGUCCA | 987-1005 |
| 67 | GCAGAAAUUUGUCCAGCAC | 991-1009 |
| 68 | GCCUCCACGACCAAAACGG | 1038-1056 |
| 69 | GGACGGGACGGACUACGAG | 1072-1090 |
| 70 | GACGGGACGGACUACGAGA | 1073-1091 |
| 71 | ACGGGACGGACUACGAGAC | 1074-1092 |
| 72 | CAGCCGGACGACUGGUACG | 1118-1136 |
| 73 | CGCUGGAACGACGACGUCU | 1187-1205 |
| 74 | GGUCUGCGAGACAGAGCUG | 1225-1243 |
| 75 | GGAGCCACCUCUCCUUUAA | 1258-1276 |
| 76 | GAGCCACCUCUCCUUUAAU | 1259-1277 |
| 77 | AGCCACCUCUCCUUUAAUU | 1260-1278 |
| 78 | UCUCCUUUAAUUUAUUUCU | 1267-1285 |

In some embodiments, an ASGR1 RNAi agent includes an antisense strand wherein position 19 of the antisense strand (5'→3') is capable of forming a base pair with position 1 of a 19-mer target sequence disclosed in Table 1. In some embodiments, an ASGR1 RNAi agent includes an antisense strand wherein position 1 of the antisense strand (5'→3') is capable of forming a base pair with position 19 of the 19-mer target sequence disclosed in Table 1.

In some embodiments, an ASGR1 RNAi agent includes an antisense strand wherein position 2 of the antisense strand (5'→3') is capable of forming a base pair with position 18 of the 19-mer target sequence disclosed in Table 1. In some embodiments, an ASGR1 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the ASGR1 gene, or can be non-complementary to the ASGR1 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

In some embodiments, an ASGR1 RNAi agent antisense strand comprises the sequence of nucleotides (from 5' end→3' end) 2-18 or 2-19 of any of the antisense strand sequences in Table 2 or Table 3. In some embodiments, an ASGR1 RNAi sense strand comprises the sequence of nucleotides (from 5' end→3' end) 1-17, 1-18, or 2-18 of any of the sense strand sequences in Table 2 or Table 4.

In some embodiments, an ASGR1 RNAi agent is comprised of (i) an antisense strand comprising the sequence of nucleotides (from 5' end 3' end) 2-18 or 2-19 of any of the antisense strand sequences in Table 2 or Table 3, and (ii) a sense strand comprising the sequence of nucleotides (from 5' end 3' end) 1-17, 1-18, or 2-18 of any of the sense strand sequences in Table 2 or Table 4.

In some embodiments, the ASGR1 RNAi agents include core 19-mer nucleotide sequences in the sense strand, antisense strand, or both the sense and antisense strands, shown in the following Table 2.

TABLE 2

Example ASGR1 RNAi Agent Antisense Strand and Sense Strand Core Stretch Base Sequences

| Antisense SEQ ID No. | Antisense Sequence (5' → 3') (19-mer) | Sense SEQ ID No. | Sense Sequence (5' → 3') (19-mer) | Gene Position (taken from SEQ ID NO: 1) |
|---|---|---|---|---|
| 79 | CCUUGGUCAU GAUAGGGCU | 242 | AGCCCUAUCAU GACCAAGG | 392-410 |
| 80 | UCUUGGUCAU GAUAGGGCU | 243 | AGCCCUAUCAU GACCAAGA | 392-410 |
| 81 | NCUUGGUCAU GAUAGGGCU | 244 | AGCCCUAUCAU GACCAAGN | 392-410 |
| 82 | NCUUGGUCAU GAUAGGGCN | 245 | NGCCCUAUCAU GACCAAGN | 392-410 |
| 83 | ACUCCUUGGU CAUGAUAGG | 246 | CCUAUCAUGA CCAAGGAGU | 395-413 |
| 84 | UCUCCUUGGU CAUGAUAGG | 247 | CCUAUCAUGA CCAAGGAGA | 395-413 |
| 85 | NCUCCUUGGU CAUGAUAGG | 248 | CCUAUCAUGA CCAAGGAGN | 395-413 |

TABLE 2-continued

Example ASGR1 RNAi Agent Antisense Strand and Sense Strand Core Stretch Base Sequences

| SEQ ID No. | Antisense Sequence (5' → 3') (19-mer) | SEQ ID No. | Sense Sequence (5' → 3') (19-mer) | Gene Position (taken from SEQ ID NO: 1) |
|---|---|---|---|---|
| 86 | NCUCCUUGGUCAUGAUAGN | 249 | NCUAUCAUGACCAAGGAGN | 395-413 |
| 87 | UACUCCUUGGUCAUGAUAG | 250 | CUAUCAUGACCAAGGAGUA | 396-414 |
| 88 | NACUCCUUGGUCAUGAUAG | 251 | CUAUCAUGACCAAGGAGUN | 396-414 |
| 89 | NACUCCUUGGUCAUGAUAN | 252 | NUAUCAUGACCAAGGAGUN | 396-414 |
| 87 | UACUCCUUGGUCAUGAUAG | 253 | CUAUCAUGACCAAGGAIUA | 396-414 |
| 88 | NACUCCUUGGUCAUGAUAG | 254 | CUAUCAUGACCAAGGAIUN | 396-414 |
| 89 | NACUCCUUGGUCAUGAUAN | 255 | NUAUCAUGACCAAGGAIUN | 396-414 |
| 89 | NACUCCUUGGUCAUGAUAN | 256 | NUAUCAUGACCAAGGANUN | 396-414 |
| 87 | UACUCCUUGGUCAUGAUAG | 257 | CUAUCAUGACCAAIGAIUA | 396-414 |
| 88 | NACUCCUUGGUCAUGAUAG | 258 | CUAUCAUGACCAAIGAIUN | 396-414 |
| 89 | NACUCCUUGGUCAUGAUAN | 259 | NUAUCAUGACCAAIGAIUN | 396-414 |
| 89 | NACUCCUUGGUCAUGAUAN | 260 | NUAUCAUGACCAANGANUN | 396-414 |
| 90 | AUACUCCUUGGUCAUGAUA | 261 | UAUCAUGACCAAGGAGUAU | 397-415 |
| 91 | UUACUCCUUGGUCAUGAUA | 262 | UAUCAUGACCAAGGAGUAA | 397-415 |
| 92 | NUACUCCUUGGUCAUGAUA | 263 | UAUCAUGACCAAGGAGUAN | 397-415 |
| 93 | NUACUCCUUGGUCAUGAUN | 264 | NAUCAUGACCAAGGAGUAN | 397-415 |
| 94 | GAUACUCCUUGGUCAUGAU | 265 | AUCAUGACCAAGGAGUAUC | 398-416 |
| 95 | UAUACUCCUUGGUCAUGAU | 266 | AUCAUGACCAAGGAGUAUA | 398-416 |
| 96 | NAUACUCCUUGGUCAUGAU | 267 | AUCAUGACCAAGGAGUAUN | 398-416 |
| 97 | NAUACUCCUUGGUCAUGAN | 268 | NUCAUGACCAAGGAGUAUN | 398-416 |
| 98 | UUGAUACUCCUUGGUCAUG | 269 | CAUGACCAAGGAGUAUCAA | 400-418 |
| 99 | NUGAUACUCCUUGGUCAUG | 270 | CAUGACCAAGGAGUAUCAN | 400-418 |
| 100 | NUGAUACUCCUUGGUCAUN | 271 | NAUGACCAAGGAGUAUCAN | 400-418 |
| 101 | CUGAUGGUGGUCACUCUCC | 272 | GGAGAGUGACCACCAUCAG | 442-460 |
| 102 | UUGAUGGUGGUCACUCUCC | 273 | GGAGAGUGACCACCAUCAA | 442-460 |
| 103 | NUGAUGGUGGUCACUCUCC | 274 | GGAGAGUGACCACCAUCAN | 442-460 |
| 104 | NUGAUGGUGGUCACUCUCN | 275 | NGAGAGUGACCACCAUCAN | 442-460 |
| 105 | GAGCUGAUGGUGGUCACUC | 276 | GAGUGACCACCAUCAGCUC | 445-463 |
| 106 | UAGCUGAUGGUGGUCACUC | 277 | GAGUGACCACCAUCAGCUA | 445-463 |
| 107 | NAGCUGAUGGUGGUCACUC | 278 | GAGUGACCACCAUCAGCUN | 445-463 |
| 108 | NAGCUGAUGGUGGUCACUN | 279 | NAGUGACCACCAUCAGCUN | 445-463 |
| 109 | CGUGCUCGCUGUGAAGUUG | 280 | CAACUUCACAGCGAGCACG | 634-652 |
| 110 | UGUGCUCGCUGUGAAGUUG | 281 | CAACUUCACAGCGAGCACA | 634-652 |
| 111 | NGUGCUCGCUGUGAAGUUG | 282 | CAACUUCACAGCGAGCACN | 634-652 |
| 112 | NGUGCUCGCUGUGAAGUUN | 283 | NAACUUCACAGCGAGCACN | 634-652 |
| 113 | CUUCCCACAUUGCCUCCCA | 284 | AGGGAGGCAAUGUGGGAAG | 681-699 |
| 114 | UUUCCCACAUUGCCUCCCA | 285 | AGGGAGGCAAUGUGGGAAA | 681-699 |
| 115 | NUUCCCACAUUGCCUCCCA | 286 | AGGGAGGCAAUGUGGGAAN | 681-699 |
| 116 | NUUCCCACAUUGCCUCCCN | 287 | NGGGAGGCAAUGUGGGAAN | 681-699 |
| 117 | UUCUUCCCACAUUGCCUCC | 288 | GGAGGCAAUGUGGGAAGAA | 683-701 |
| 118 | NUCUUCCCACAUUGCCUCC | 289 | GGAGGCAAUGUGGGAAGAN | 683-701 |
| 119 | NUCUUCCCACAUUGCCUCN | 290 | NGAGGCAAUGUGGGAAGAN | 683-701 |
| 120 | UCUUUCUUCCCACAUUGCC | 291 | GGCAAUGUGGGAAGAAAGA | 686-704 |
| 121 | NCUUUCUUCCCACAUUGCC | 292 | GGCAAUGUGGGAAGAAAGN | 686-704 |
| 122 | NCUUUCUUCCCACAUUGCN | 293 | NGCAAUGUGGGAAGAAAGN | 686-704 |
| 123 | CAUCUUUCUUCCCACAUUG | 294 | CAAUGUGGGAAGAAAGAUG | 688-706 |
| 124 | UAUCUUUCUUCCCACAUUG | 295 | CAAUGUGGGAAGAAAGAUA | 688-706 |
| 125 | NAUCUUUCUUCCCACAUUG | 296 | CAAUGUGGGAAGAAAGAUN | 688-706 |

TABLE 2-continued

Example ASGR1 RNAi Agent Antisense Strand and Sense Strand Core Stretch Base Sequences

| SEQ ID No. | Antisense Sequence (5'→3') (19-mer) | SEQ ID No. | Sense Sequence (5'→3') (19-mer) | Gene Position (taken from SEQ ID NO: 1) |
|---|---|---|---|---|
| 126 | NAUCUUUCUU CCCACAUUN | 297 | NAAUGUGGGA AGAAAGAUN | 688-706 |
| 127 | NAUCUUUCUU CCCACAUUN | 298 | NAAUGUNGGA AGAAAGAUN | 688-706 |
| 128 | NAUCUUUCUU CCCACAUUN | 299 | NAAUGUGNGA AGAAAGAUN | 688-706 |
| 129 | UCAUCUUUCU UCCCACAUU | 300 | AAUGUGGGAA GAAAGAUGA | 689-707 |
| 130 | NCAUCUUUCU UCCCACAUU | 301 | AAUGUGGGAA GAAAGAUGN | 689-707 |
| 131 | NCAUCUUUCU UCCCACAUN | 302 | NAUGUGGGAA GAAAGAUGN | 689-707 |
| 132 | NCAUCUUUCU UCCCACAUN | 303 | NAUGUNGGAA GAAAGAUGN | 689-707 |
| 133 | ACUUCAUCUU UCUUCCCAC | 304 | GUGGGAAGAA AGAUGAAGU | 692-710 |
| 134 | UCUUCAUCUU UCUUCCCAC | 305 | GUGGGAAGAA AGAUGAAGA | 692-710 |
| 135 | NCUUCAUCUU UCUUCCCAC | 306 | GUGGGAAGAA AGAUGAAGN | 692-710 |
| 136 | NCUUCAUCUU UCUUCCCAN | 307 | NUGGGAAGAA AGAUGAAGN | 692-710 |
| 137 | GCGACUUCAU CUUUCUUCC | 308 | GGAAGAAAGA UGAAGUCGC | 695-713 |
| 138 | UCGACUUCAU CUUUCUUCC | 309 | GGAAGAAAGA UGAAGUCGA | 695-713 |
| 139 | NCGACUUCAU CUUUCUUCC | 310 | GGAAGAAAGA UGAAGUCGN | 695-713 |
| 140 | NCGACUUCAU CUUUCUUCN | 311 | NGAAGAAAGA UGAAGUCGN | 695-713 |
| 141 | AGCGACUUCA UCUUUCUUC | 312 | GAAGAAAGAU GAAGUCGCU | 696-714 |
| 142 | UGCGACUUCA UCUUUCUUC | 313 | GAAGAAAGAU GAAGUCGCA | 696-714 |
| 143 | NGCGACUUCA UCUUUCUUC | 314 | GAAGAAAGAU GAAGUCGCN | 696-714 |
| 144 | NGCGACUUCA UCUUUCUUN | 315 | NAAGAAAGAU GAAGUCGCN | 696-714 |
| 141 | AGCGACUUCA UCUUUCUUC | 316 | GAAGAAAGAU GAAGUCICU | 696-714 |
| 142 | UGCGACUUCA UCUUUCUUC | 317 | GAAGAAAGAU GAAGUCICA | 696-714 |
| 143 | NGCGACUUCA UCUUUCUUC | 318 | GAAGAAAGAU GAAGUCICN | 696-714 |
| 144 | NGCGACUUCA UCUUUCUUN | 319 | NAAGAAAGAU GAAGUCICN | 696-714 |
| 145 | NGCGACUUCA UCUUUCUUN | 320 | NAAGAAAGAU GAAGUCNCN | 696-714 |
| 141 | AGCGACUUCA UCUUUCUUC | 852 | GAAGAAAGAU GAAIUCICU | 696-714 |
| 142 | UGCGACUUCA UCUUUCUUC | 879 | GAAGAAAGAU GAAIUCICA | 696-714 |
| 143 | NGCGACUUCA UCUUUCUUC | 883 | GAAGAAAGAU GAAIUCICN | 696-714 |
| 144 | NGCGACUUCA UCUUUCUUN | 886 | NAAGAAAGAU GAAIUCICN | 696-714 |
| 145 | NGCGACUUCA UCUUUCUUN | 892 | NAAGAAAGAU GAANUCNCN | 696-714 |
| 146 | UGCUUCACGU GGAGCAGCA | 321 | UGCUGCUCCA CGUGAAGCA | 768-786 |
| 147 | NGCUUCACGU GGAGCAGCA | 322 | UGCUGCUCCA CGUGAAGCN | 768-786 |
| 148 | NGCUUCACGU GGAGCAGCN | 323 | NGCUGCUCCA CGUGAAGCN | 768-786 |
| 149 | ACUGCUUCAC GUGGAGCAG | 324 | CUGCUCCACG UGAAGCAGU | 770-788 |
| 150 | UCUGCUUCAC GUGGAGCAG | 325 | CUGCUCCACG UGAAGCAGA | 770-788 |
| 151 | NCUGCUUCAC GUGGAGCAG | 326 | CUGCUCCACG UGAAGCAGN | 770-788 |
| 152 | NCUGCUUCAC GUGGAGCAN | 327 | NUGCUCCACG UGAAGCAGN | 770-788 |
| 153 | AACUGCUUCA CGUGGAGCA | 328 | UGCUCCACGU GAAGCAGUU | 771-789 |
| 154 | UACUGCUUCA CGUGGAGCA | 329 | UGCUCCACGU GAAGCAGUA | 771-789 |
| 155 | NACUGCUUCA CGUGGAGCA | 330 | UGCUCCACGU GAAGCAGUN | 771-789 |
| 156 | NACUGCUUCA CGUGGAGCN | 331 | NGCUCCACGU GAAGCAGUN | 771-789 |
| 157 | GAACUGCUUC ACGUGGAGC | 332 | GCUCCACGUG AAGCAGUUC | 772-790 |
| 158 | UAACUGCUUC ACGUGGAGC | 333 | GCUCCACGUG AAGCAGUUA | 772-790 |
| 159 | NAACUGCUUC ACGUGGAGC | 334 | GCUCCACGUG AAGCAGUUN | 772-790 |
| 160 | NAACUGCUUC ACGUGGAGN | 335 | NCUCCACGUG AAGCAGUUN | 772-790 |
| 161 | ACGAACUGCU UCACGUGGA | 336 | UCCACGUGAA GCAGUUCGU | 774-792 |
| 162 | UCGAACUGCU UCACGUGGA | 337 | UCCACGUGAA GCAGUUCGA | 774-792 |
| 163 | NCGAACUGCU UCACGUGGA | 338 | UCCACGUGAA GCAGUUCGN | 774-792 |
| 164 | NCGAACUGCU UCACGUGGN | 339 | NCCACGUGAA GCAGUUCGN | 774-792 |

TABLE 2-continued

Example ASGR1 RNAi Agent Antisense Strand and Sense Strand Core Stretch Base Sequences

| SEQ ID No. | Antisense Sequence (5' → 3') (19-mer) | SEQ ID No. | Sense Sequence (5' → 3') (19-mer) | Gene Position (taken from SEQ ID NO: 1) |
|---|---|---|---|---|
| 165 | UGAGCCAUUGCCCUGGAGC | 340 | GCUCCAGGGCAAUGGCUCA | 829-847 |
| 166 | NGAGCCAUUGCCCUGGAGC | 341 | GCUCCAGGGCAAUGGCUCN | 829-847 |
| 167 | NGAGCCAUUGCCCUGGAGN | 342 | NCUCCAGGGCAAUGGCUCN | 829-847 |
| 168 | AGUAGCAGCUGCGCUCGUG | 343 | CACGAGCGCAGCUGCUACU | 881-899 |
| 169 | UGUAGCAGCUGCGCUCGUG | 344 | CACGAGCGCAGCUGCUACA | 881-899 |
| 170 | NGUAGCAGCUGCGCUCGUG | 345 | CACGAGCGCAGCUGCUACN | 881-899 |
| 171 | NGUAGCAGCUGCGCUCGUN | 346 | NACGAGCGCAGCUGCUACN | 881-899 |
| 172 | AACCAGUAGCAGCUGCGCU | 347 | AGCGCAGCUGCUACUGGUU | 885-903 |
| 173 | UACCAGUAGCAGCUGCGCU | 348 | AGCGCAGCUGCUACUGGUA | 885-903 |
| 174 | NACCAGUAGCAGCUGCGCU | 349 | AGCGCAGCUGCUACUGGUN | 885-903 |
| 175 | NACCAGUAGCAGCUGCGCN | 350 | NGCGCAGCUGCUACUGGUN | 885-903 |
| 176 | GAACCAGUAGCAGCUGCGC | 351 | GCGCAGCUGCUACUGGUUC | 886-904 |
| 177 | UAACCAGUAGCAGCUGCGC | 352 | GCGCAGCUGCUACUGGUUA | 886-904 |
| 178 | NAACCAGUAGCAGCUGCGC | 353 | GCGCAGCUGCUACUGGUUN | 886-904 |
| 179 | NAACCAGUAGCAGCUGCGN | 354 | NCGCAGCUGCUACUGGUUN | 886-904 |
| 180 | GGCAGUAGUUGUCGGCGUC | 355 | GACGCCGACAACUACUGCC | 929-947 |
| 181 | UGCAGUAGUUGUCGGCGUC | 356 | GACGCCGACAACUACUGCA | 929-947 |
| 182 | NGCAGUAGUUGUCGGCGUC | 357 | GACGCCGACAACUACUGCN | 929-947 |
| 183 | NGCAGUAGUUGUCGGCGUN | 358 | NACGCCGACAACUACUGCN | 929-947 |
| 184 | GACGUGACCACCACCAGGU | 359 | ACCUGGUGGUGGUCACGUC | 963-981 |
| 185 | UACGUGACCACCACCAGGU | 360 | ACCUGGUGGUGGUCACGUA | 963-981 |
| 186 | NACGUGACCACCACCAGGU | 361 | ACCUGGUGGUGGUCACGUN | 963-981 |
| 187 | NACGUGACCACCACCAGGN | 362 | NCCUGGUGGUGGUCACGUN | 963-981 |
| 188 | CAGGACGUGACCACCACCA | 363 | UGGUGGUGGUCACGUCCUG | 966-984 |
| 189 | UAGGACGUGACCACCACCA | 364 | UGGUGGUGGUCACGUCCUA | 966-984 |
| 190 | NAGGACGUGACCACCACCA | 365 | UGGUGGUGGUCACGUCCUN | 966-984 |
| 191 | NAGGACGUGACCACCACCN | 366 | NGGUGGUGGUCACGUCCUN | 966-984 |
| 192 | UGGACAAAUUUCUGCUCCU | 367 | AGGAGCAGAAAUUUGUCCA | 987-1005 |
| 193 | NGGACAAAUUUCUGCUCCU | 368 | AGGAGCAGAAAUUUGUCCN | 987-1005 |
| 194 | NGGACAAAUUUCUGCUCCN | 369 | NGGAGCAGAAAUUUGUCCN | 987-1005 |
| 195 | GUGCUGGACAAAUUUCUGC | 370 | GCAGAAAUUUGUCCAGCAC | 991-1009 |
| 196 | UUGCUGGACAAAUUUCUGC | 371 | GCAGAAAUUUGUCCAGCAA | 991-1009 |
| 197 | NUGCUGGACAAAUUUCUGC | 372 | GCAGAAAUUUGUCCAGCAN | 991-1009 |
| 198 | NUGCUGGACAAAUUUCUGN | 373 | NCAGAAAUUUGUCCAGCAN | 991-1009 |
| 199 | CCGUUUUGGUCGUGGAGGC | 374 | GCCUCCACGACCAAAACGG | 1038-1056 |
| 200 | UCGUUUUGGUCGUGGAGGC | 375 | GCCUCCACGACCAAAACGA | 1038-1056 |
| 201 | NCGUUUUGGUCGUGGAGGC | 376 | GCCUCCACGACCAAAACGN | 1038-1056 |
| 202 | NCGUUUUGGUCGUGGAGGN | 377 | NCCUCCACGACCAAAACGN | 1038-1056 |
| 203 | CUCGUAGUCCGUCCCGUCC | 378 | GGACGGGACGGACUACGAG | 1072-1090 |
| 204 | UUCGUAGUCCGUCCCGUCC | 379 | GGACGGGACGGACUACGAA | 1072-1090 |
| 205 | NUCGUAGUCCGUCCCGUCC | 380 | GGACGGGACGGACUACGAN | 1072-1090 |
| 206 | NUCGUAGUCCGUCCCGUCN | 381 | NGACGGGACGGACUACGAN | 1072-1090 |
| 207 | UCUCGUAGUCCGUCCCGUC | 382 | GACGGGACGGACUACGAGA | 1073-1091 |
| 208 | NCUCGUAGUCCGUCCCGUC | 383 | GACGGGACGGACUACGAGN | 1073-1091 |
| 209 | NCUCGUAGUCCGUCCCGUN | 384 | NACGGGACGGACUACGAGN | 1073-1091 |
| 210 | GUCUCGUAGUCCGUCCCGU | 385 | ACGGGACGGACUACGAGAC | 1074-1092 |
| 211 | UUCUCGUAGUCCGUCCCGU | 386 | ACGGGACGGACUACGAGAA | 1074-1092 |
| 212 | NUCUCGUAGUCCGUCCCGU | 387 | ACGGGACGGACUACGAGAN | 1074-1092 |

TABLE 2-continued

Example ASGR1 RNAi Agent Antisense Strand and Sense Strand Core Stretch Base Sequences

| Antisense SEQ ID No. | Sequence (5' → 3') (19-mer) | Sense SEQ ID No. | Sequence (5' → 3') (19-mer) | Gene Position (taken from SEQ ID NO: 1) |
|---|---|---|---|---|
| 213 | NUCUCGUAGU CCGUCCCGN | 388 | NCGGGACGGA CUACGAGAN | 1074-1092 |
| 214 | CGUACCAGUC GUCCGGCUG | 389 | CAGCCGGACG ACUGGUACG | 1118-1136 |
| 215 | UGUACCAGUC GUCCGGCUG | 390 | CAGCCGGACG ACUGGUACA | 1118-1136 |
| 216 | NGUACCAGUC GUCCGGCUG | 391 | CAGCCGGACG ACUGGUACN | 1118-1136 |
| 217 | NGUACCAGUC GUCCGGCUN | 392 | NAGCCGGACG ACUGGUACN | 1118-1136 |
| 218 | AGACGUCGUC GUUCCAGCG | 393 | CGCUGGAACG ACGACGUCU | 1187-1205 |
| 219 | UGACGUCGUC GUUCCAGCG | 394 | CGCUGGAACG ACGACGUCA | 1187-1205 |
| 220 | NGACGUCGUC GUUCCAGCG | 395 | CGCUGGAACG ACGACGUCN | 1187-1205 |
| 221 | NGACGUCGUC GUUCCAGCN | 396 | NGCUGGAACG ACGACGUCN | 1187-1205 |
| 222 | NGACGUCGUC GUUCCAGCN | 397 | NGCUGGAACG ACGANGUCN | 1187-1205 |
| 223 | CAGCUCUGUC UCGCAGACC | 398 | GGUCUGCGAG ACAGAGCUG | 1225-1243 |
| 224 | UAGCUCUGUC UCGCAGACC | 399 | GGUCUGCGAG ACAGAGCUA | 1225-1243 |
| 225 | NAGCUCUGUC UCGCAGACC | 400 | GGUCUGCGAG ACAGAGCUN | 1225-1243 |
| 226 | NAGCUCUGUC UCGCAGACN | 401 | NGUCUGCGAG ACAGAGCUN | 1225-1243 |
| 227 | UUAAAGGAGA GGUGGCUCC | 402 | GGAGCCACCU CUCCUUUAA | 1258-1276 |
| 228 | NUAAAGGAGA GGUGGCUCC | 403 | GGAGCCACCU CUCCUUUAN | 1258-1276 |
| 229 | NUAAAGGAGA GGUGGCUCN | 404 | NGAGCCACCU CUCCUUUAN | 1258-1276 |
| 230 | AUUAAAGGAG AGGUGGCUC | 405 | GAGCCACCUC UCCUUUAAU | 1259-1277 |
| 231 | UUUAAAGGAG AGGUGGCUC | 406 | GAGCCACCUC UCCUUUAAA | 1259-1277 |
| 232 | NUUAAAGGAG AGGUGGCUC | 407 | GAGCCACCUC UCCUUUAAN | 1259-1277 |
| 233 | NUUAAAGGAG AGGUGGCUN | 408 | NAGCCACCUC UCCUUUAAN | 1259-1277 |
| 234 | AAUUAAAGGA GAGGUGGCU | 409 | AGCCACCUCU CCUUUAAUU | 1260-1278 |
| 235 | UAUUAAAGGA GAGGUGGCU | 410 | AGCCACCUCU CCUUUAAUA | 1260-1278 |
| 236 | NAUUAAAGGA GAGGUGGCU | 411 | AGCCACCUCU CCUUUAAUN | 1260-1278 |
| 237 | NAUUAAAGGA GAGGUGGCN | 412 | NGCCACCUCU CCUUUAAUN | 1260-1278 |
| 238 | AGAAAUAAAU UAAAGGAGA | 413 | UCUCCUUUAA UUUAUUUCU | 1267-1285 |
| 239 | UGAAAUAAAU UAAAGGAGA | 414 | UCUCCUUUAA UUUAUUUCA | 1267-1285 |
| 240 | NGAAAUAAAU UAAAGGAGA | 415 | UCUCCUUUAA UUUAUUUCN | 1267-1285 |
| 241 | NGAAAUAAAU UAAAGGAGN | 416 | NCUCCUUUAA UUUAUUUCN | 1267-1285 |

(N = any nucleobase; I = inosine(hypoxanthine)nucleotide).

The ASGR1 RNAi agent sense strands and antisense strands that comprise or consist of the nucleotide sequences in Table 2 can be modified nucleotides or unmodified nucleotides. In some embodiments, the ASGR1 RNAi agents having the sense and antisense strand sequences that comprise or consist of the nucleotide sequences in Table 2 are all or substantially all modified nucleotides.

In some embodiments, the antisense strand of an ASGR1 RNAi agent disclosed herein differs by 0, 1, 2, or 3 nucleotides from any of the antisense strand sequences in Table 2. In some embodiments, the sense strand of an ASGR1 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified ASGR1 RNAi agent sense and antisense strands are provided in Table 3 and Table 4. Certain modified ASGR1 RNAi agent antisense strands, as well as their underlying unmodified nucleobase sequences, are provided in Table 3. Certain modified ASGR1 RNAi agent sense strands, as well as their underlying unmodified sequences, are provided in Table 4. In forming ASGR1 RNAi agents, each of the nucleotides in each of the unmodified sequences listed in Tables 3 and 4, as well as in Table 2, above, can be a modified nucleotide.

The ASGR1 RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, an ASGR1 RNAi agent antisense strand comprises a nucleotide sequence of any of the sequences in Table 2 or Table 3.

In some embodiments, an ASGR1 RNAi agent comprises or consists of a duplex having the nucleobase sequences of the sense strand and the antisense strand of any of the sequences in Table 2, Table 3, or Table 4.

Examples of antisense strands containing modified nucleotides are provided in Table 3. Examples of sense strands containing modified nucleotides are provided in Table 4.

As used in Tables 3 and 4, the following notations are used to indicate modified nucleotides, targeting groups, and linking groups. As the person of ordinary skill in the art would readily understand, unless otherwise indicated by the sequence, that when present in an oligonucleotide, the monomers are mutually linked by 5'-3'-phosphodiester bonds:

A=adenosine-3'-phosphate;
    C=cytidine-3'-phosphate;
    G=guanosine-3'-phosphate;
    U=uridine-3'-phosphate
    I=inosine-3'-phosphate
    n=any 2'-O-methyl modified nucleotide
    a=2'-O-methyladenosine-3'-phosphate
    as =2'-O-methyladenosine-3'-phosphorothioate
    c=2'-O-methylcytidine-3'-phosphate
    cs=2'-O-methylcytidine-3'-phosphorothioate
    g=2'-O-methylguanosine-3'-phosphate
    gs=2'-O-methylguanosine-3'-phosphorothioate
    t=2'-O-methyl-5-methyluridine-3'-phosphate
    ts=2'-O-methyl-5-methyluridine-3'-phosphorothioate
    u=2'-O-methyluridine-3'-phosphate
    us=2'-O-methyluridine-3'-phosphorothioate
    i=2'-O-methylinosine-3'-phosphate
    is=2'-O-methylinosine-3'-phosphorothioate
    Nf=any 2'-fluoro modified nucleotide
    Af=2'-fluoroadenosine-3'-phosphate
    Afs=2'-fluoroadenosine-3'-phosporothioate
    Cf=2'-fluorocytidine-3'-phosphate
    Cfs=2'-fluorocytidine-3'-phosphorothioate
    Gf=2'-fluoroguanosine-3'-phosphate
    Gfs=2'-fluoroguanosine-3'-phosphorothioate
    Tf=2'-fluoro-5'-methyluridine-3'-phosphate
    Tfs=2'-fluoro-5'-methyluridine-3'-phosphorothioate
    Uf=2'-fluorouridine-3'-phosphate
    Ufs=2'-fluorouridine-3'-phosphorothioate
    dN=any 2'-deoxyribonucleotide
    dA=2'-deoxyadenosine-3'-phosphate
    dAs=2'-deoxyadenosine-3'-phosphorothioate
    dC=2'-deoxycytidine-3'-phosphate
    dCs=2'-deoxycytidine-3'-phosphorothioate
    dG=2'-deoxyguanosine-3'-phosphate
    dGs=2'-deoxyguanosine-3'-phosphorothioate
    dT=2'-deoxythymidine-3'-phosphate
    dTs=2'-deoxythymidine-3'-phosphorothioate
    dU=2'-deoxyuridine-3'-phosphate
    dUs=2'-deoxyuridine-3'-phosphorothioate
    $N_{UNA}$=2',3'-seco nucleotide mimics (unlocked nucleobase analogs)-3'-Phosphate
    $N_{UNAS}$=2',3'-seco nucleotide mimics (unlocked nucleobase analogs)-3'-phosphorothioate
    $A_{UNA}$=2',3'-seco-adenosine-3'-phosphate
    $A_{UNAS}$=2',3'-seco-adenosine-3'-phosphorothioate
    $C_{UNA}$=2',3'-seco-cytidine-3'-phosphate
    $C_{UNAS}$=2',3'-seco-cytidine-3'-phosphorothioate
    $G_{UNA}$=2',3'-seco-guanosine-3'-phosphate
    $G_{UNAS}$=2',3'-seco-guanosine-3'-phosphorothioate
    $U_{UNA}$=2',3'-seco-uridine-3'-phosphate
    $U_{UNAS}$=2',3'-seco-uridine-3'-phosphorothioate
    a_2N=see Table 6
    a_2Ns=see Table 6
    pu_2N=see Table 6
    pu_2Ns=see Table 6
    $N_{LNA}$=locked nucleotide
    $Nf_{ANA}$ 2'-F-Arabino nucleotide
    NM=2'-O-methoxyethyl nucleotide
    AM=2'-O-methoxyethyladenosine-3'-phosphate
    AMs=2'-O-methoxyethyladenosine-3'-phosphorothioate
    TM=2'-O-methoxyethylthymidine-3'-phosphate
    TMs=2'-O-methoxyethylthymidine-3'-phosphorothioate
    R=ribitol
    (invdN)=any inverted deoxyribonucleotide (3'-3' linked nucleotide)
    (invAb)=inverted (3'-3' linked) abasic deoxyribonucleotide, see Table 6
    (invAb)s=inverted (3'-3' linked) abasic deoxyribonucleotide-5'-phosphorothioate, see Table 6
    (invn)=any inverted 2'-OMe nucleotide (3'-3' linked nucleotide)
    s=phosphorothioate linkage
    sp=see Table 6
    vpdN=vinyl phosphonate deoxyribonucleotide
    (5Me-Nf)=5'-Me, 2'-fluoro nucleotide
    cPrp=cyclopropyl phosphonate, see Table 6
    epTcPr=see Table 6
    epTM=see Table 6

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A through 1M showing all internucleoside linkages). Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Moreover, as the person of ordinary skill would readily understand and appreciate, while the phosphorothioate chemical structures depicted herein typically show the anion on the sulfur atom, the inventions disclosed herein encompass all phosphorothioate tautomers and/or diastereomers (e.g., where the sulfur atom has a double-bond and the anion is on an oxygen atom). Unless expressly indicated otherwise herein, such understandings of the person of ordinary skill in the art are used when describing the ASGR1 RNAi agents and compositions of ASGR1 RNAi agents disclosed herein.

Certain examples of targeting groups and linking groups used with the ASGR1 RNAi agents disclosed herein are provided below in Table 6. More specifically, targeting groups and linking groups include the following, for which their chemical structures are provided below in Table 6: (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed herein, as well as other targeting or linking groups, conjugated to the 5' and/or 3' end of the sequence.

TABLE 3

ASGR1 RNAi Agent Antisense Strand Sequences.

| Antisense Strand ID: | SEQ ID NO. | Antisense Sequence (Modified) (5' → 3') | SEQ ID NO. | Underlying Base Sequence (5' → 3') |
|---|---|---|---|---|
| AM05757-AS | 417 | asCfsusUfcAfuCfuUfuCfuUfcCfcAfcusu | 722 | ACUUCAUCUUUCUUCCCACUU |
| AM05761-AS | 418 | usAfsgsAfaCfcAfgUfaGfcAfgCfuGfcusu | 723 | UAGAACCAGUAGCAGCUGCUU |
| AM05919-AS | 419 | asCfsusUfcAfuCfUfUfuCfuUfcCfcAfcAfsu | 724 | ACUUCAUCUUUCUUCCCACAU |
| AM05920-AS | 420 | asCfsusUfcAfucuuuCfuUfcCfcAfcAfsu | 724 | ACUUCAUCUUUCUUCCCACAU |
| AM05921-AS | 421 | asCfsusUfcAfuCfuUfuCfuUfcCfcAfcAfsu | 724 | ACUUCAUCUUUCUUCCCACAU |
| AM05922-AS | 422 | asCfsusUfcAfuCfuUfuCfuUfcCfcAfcAfuUfsg | 725 | ACUUCAUCUUUCUUCCCACAUUG |
| AM05927-AS | 423 | usCfsusUfcAfuCfuUfuCfuUfcCfcAfcAfsu | 726 | UCUUCAUCUUUCUUCCCACAU |
| AM06016-AS | 424 | usAfscUfcCfuUfgGfuCfaUfgAfuAfgsgsg | 727 | UACUCCUUGGUCAUGAUAGGG |
| AM06017-AS | 425 | usAfscUfcCfuUfgGfuCfaUfgAfuAfgsgsu | 3 | UACUCCUUGGUCAUGAUAGGU |
| AM06020-AS | 426 | usCfsuCfgUfaGfuCfcGfuCfcCfgUfcscsa | 729 | UCUCGUAGUCCGUCCCGUCCA |
| AM06021-AS | 427 | usCfsuCfgUfaGfuCfcGfuCfcCfgUfcsusu | 730 | UCUCGUAGUCCGUCCCGUCUU |
| AM06023-AS | 428 | usUfsaAfaGfgAfgAfgGfuGfgCfuCfcsusg | 731 | UUAAAGGAGAGGUGGCUCCUG |
| AM06026-AS | 429 | usGfsuAfgCfaGfcUfgCfgCfuCfgUfgscsu | 732 | UGUAGCAGCUGCGCUCGUGCU |
| AM06027-AS | 430 | usGfsuAfgCfaGfcUfgCfgCfuCfgUfgsusu | 733 | UGUAGCAGCUGCGCUCGUGUU |
| AM06029-AS | 431 | usGfsuGfcUfcGfcUfgUfgAfaGfuUfgscsu | 734 | UGUGCUCGCUGUGAAGUUGCU |
| AM06030-AS | 432 | usGfsuGfcUfcGfcUfgUfgAfaGfuUfgcsusg | 735 | UGUGCUCGCUGUGAAGUUGCUG |
| AM06033-AS | 433 | usUfsgAfuGfgUfgGfuCfaCfuCfuCfcsusc | 736 | UUGAUGGUGGUCACUCUCCUC |
| AM06172-AS | 434 | usUfsgAfuGfgUfgGfuCfaCfuCfuCfcsusu | 737 | UUGAUGGUGGUCACUCUCCUU |
| AM06175-AS | 435 | usGfsaCfgUfcGfuCfgUfuCfcAfgCfgusu | 738 | UGACGUCGUCGUUCCAGCGUU |
| AM06176-AS | 436 | asGfsaCfgUfcGfuCfgUfuCfcAfgCfgusu | 739 | AGACGUCGUCGUUCCAGCGUU |
| AM06179-AS | 437 | usAfsgCfuGfaUfgGfuGfgUfcAfcUfcsusc | 740 | UAGCUGAUGGUGGUCACUCUC |
| AM06180-AS | 438 | usAfsgCfuGfaUfgGfuGfgUfcAfcUfcusu | 741 | UAGCUGAUGGUGGUCACUCUU |
| AM06183-AS | 439 | usGfsasGfcCfaUfuGfccCfcUfgGfaGfcusu | 742 | UGAGCCAUUGCCCUGGAGCUU |
| AM06185-AS | 440 | usAfscGfuGfaCfcAfcCfaCfcAfgGfuusu | 743 | UACGUGACCACCACCAGGUUU |
| AM06186-AS | 441 | usAfscGfuGfaCfcAfcCfaCfcAfgGfusgsc | 744 | UACGUGACCACCACCAGGUGC |
| AM06189-AS | 442 | usCfsuGfcUfuCfaCfgUfgGfaGfcAfgsusu | 745 | UCUGCUUCACGUGGAGCAGUU |
| AM06192-AS | 443 | spasCfsusUfcAfuCfuUfuCfuUfcCfcAfcusu | 722 | ACUUCAUCUUUCUUCCCACUU |
| AM06193-AS | 444 | cPrpusCfsusUfcAfuCfuUfuCfuUfcCfcAfcusu | 746 | UCUUCAUCUUUCUUCCCACUU |
| AM06200-AS | 445 | cPrpdUsCfsusUfcAfuCfuUfuCfuUfcCfcAfcusu | 746 | UCUUCAUCUUUCUUCCCACUU |
| AM06201-AS | 446 | usCfsusUfcAfuCfuUfuCfuUfcCfcAfcusu | 746 | UCUUCAUCUUUCUUCCCACUU |
| AM06248-AS | 447 | usAfscUfcCfuUfgGfuCfaUfgAfuAfggsusu | 747 | UACUCCUUGGUCAUGAUAGGUU |
| AM06249-AS | 448 | usAfscUfcCfuUfgGfuCfaUfgAfuAfsgsg | 748 | UACUCCUUGGUCAUGAUAGG |
| AM06250-AS | 449 | usAfscUfcCfuUfgGfuCfaUfgAfusasg | 749 | UACUCCUUGGUCAUGAUAG |
| AM06251-AS | 450 | usAfscUfcCfuUfgGfuCfaUfgAfuAfgsusu | 750 | UACUCCUUGGUCAUGAUAGUU |

TABLE 3-continued

ASGR1 RNAi Agent Antisense Strand Sequences.

| Antisense Strand ID: | SEQ ID NO. | Antisense Sequence (Modified) (5' → 3') | SEQ ID NO. | Underlying Base Sequence (5' → 3') |
|---|---|---|---|---|
| AM06252-AS | 451 | usAfscUfcCfuUfgGfuCfaUfgAfuAfggsgsc | 751 | UACUCCUUGGUCAUGAUAGGGC |
| AM06253-AS | 452 | cPrpdUAfcUfcCfuUfgGfuCfaUfgAfuAfgg(invAb) | 748 | UACUCCUUGGUCAUGAUAGG |
| AM06254-AS | 453 | cPrpdUsAfscUfcCfuUfgGfuCfaUfgAfuAfgsgsu | 3 | UACUCCUUGGUCAUGAUAGGU |
| AM06442-AS | 454 | usUfsaAfaGfaGfaGfgUfGfgCfuCfcsusu | 752 | UUAAAGGAGAGGUGGCUCCUU |
| AM06443-AS | 455 | cPrpdUsUfsaAfaGfaGfaGfgUfGfgCfuCfcsusu | 752 | UUAAAGGAGAGGUGGCUCCUU |
| AM06444-AS | 456 | cPrpusUfsaAfaGfaGfaGfgUfGfgCfuCfcsusu | 752 | UUAAAGGAGAGGUGGCUCCUU |
| AM06445-AS | 457 | usUfsaAfaGfagagGfuGfgCfuCfcsusu | 752 | UUAAAGGAGAGGUGGCUCCUU |
| AM06446-AS | 458 | usUfsaaaggAfgAfgGfuGfgcuccsusu | 752 | UUAAAGGAGAGGUGGCUCCUU |
| AM06447-AS | 459 | usUfsaAfaGfaGfaGfgUfGfgCfuscsc | 753 | UUAAAGGAGAGGUGGCUCC |
| AM06448-AS | 460 | usUfsaAfaGfaGfaGfgUfGfgCfuCfcusgsg | 754 | UUAAAGGAGAGGUGGCUCCUGG |
| AM06575-AS | 461 | asGfsaCfgUfcGfuCfgUfuCfcAfgCfgsusu | 739 | AGACGUCGUCGUUCCAGCGUU |
| AM06578-AS | 462 | usGfsaCfgUfcGfuCfgUfuCfcAfgCfgsusu | 738 | UGACGUCGUCGUUCCAGCGUU |
| AM06579-AS | 463 | cPrpusGfsaCfgUfcGfuCfgUfuCfcAfgCfgsusu | 738 | UGACGUCGUCGUUCCAGCGUU |
| AM06581-AS | 464 | usCfsuCfgUfaguccGfuCfcCfgUfcsusu | 730 | UCUCGUAGUCCGUCCCGUCUU |
| AM06582-AS | 465 | cPrpusCfsuCfgUfaguccGfuCfcCfgUfcsusu | 730 | UCUCGUAGUCCGUCCCGUCUU |
| AM06584-AS | 466 | asCfsuCfgUfaguccGfuCfcCfgUfcsusu | 755 | ACUCGUAGUCCGUCCCGUCUU |
| AM06586-AS | 467 | asCfsuCfgUfaguccGfuCfcCfgsUfsc | 756 | ACUCGUAGUCCGUCCCGUC |
| AM06598-AS | 468 | usAfscUfcCfuUfgGfuCfaUfgAfuAfgsGfsg | 727 | UACUCCUUGGUCAUGAUAGGG |
| AM06599-AS | 469 | usAfscUfcCfuugguCfaUfgAfuAfgsGfsg | 727 | UACUCCUUGGUCAUGAUAGGG |
| AM06601-AS | 2 | usAfscUfcCfuUfgGfuCfaUfgAfuAfgsGfsu | 3 | UACUCCUUGGUCAUGAUAGGU |
| AM06639-AS | 470 | usAfscsUfcCfuugguCfaUfgAfuAfgsGfsg | 727 | UACUCCUUGGUCAUGAUAGGG |
| AM06641-AS | 471 | usAfscsUfcCfuUfgGfuCfaUfgAfuAfgsusu | 750 | UACUCCUUGGUCAUGAUAGUU |
| AM06643-AS | 472 | usAfscsUfcCfuugguCfaUfgAfuAfgGfsgs(invAb) | 727 | UACUCCUUGGUCAUGAUAGGG |
| AM06645-AS | 473 | usGfscsUfuCfacgugGfaGfcAfgCfaGfsg | 757 | UGCUUCACGUGGAGCAGCAGG |
| AM06647-AS | 474 | usCfsgsUfuUfugguCfGfuGfaGfgCfCfsu | 758 | UCGUUUGGUCGUGGAGGCCU |
| AM06649-AS | 475 | usUfsusCfcCfacauuGfcCfuCfcCfuGfsg | 759 | UUUCCCACAUUGCCUCCCUGG |
| AM06651-AS | 476 | asAfscsCfaGfuagcaGfcUfgCfgCfuCfsg | 760 | AACCAGUAGCAGCUGCGCUCG |
| AM06653-AS | 477 | asAfscsCfaGfuagcaGfcUfgCfgCfuusu | 761 | AACCAGUAGCAGCUGCGCUUU |
| AM06655-AS | 478 | usGfscAfgUfaguugUfcGfgCfgUfcsAfsg | 762 | UGCAGUAGUUGUCGGCGUCAG |
| AM06657-AS | 479 | usAfsgsGfaCfgugacCfaCfcAfcCfaGfsg | 763 | UAGGACGUGACCACCACCAGG |
| AM06659-AS | 480 | usUfsgsCfuGfgAfcAfaAfuUfuCfuGfcUfsc | 764 | UUGCUGGACAAAUUUCUGCUC |
| AM06661-AS | 481 | usUfscsGfuAfguccgUfcCfcCfgUfcCfaAfsc | 765 | UUCGUAGUCCGUCCCGUCCAC |
| AM06663-AS | 482 | usUfscsUfcGfuagucCfgUfcCfcCfgUfcCfsu | 766 | UUCUCGUAGUCCGUCCCGUCU |
| AM06665-AS | 483 | usGfsusAfcCfagucgUfcCfgGfcUfgusu | 767 | UGUACCAGUCGUCCGGCUGUU |
| AM06667-AS | 484 | asGfsasCfgUfcgucgUfuCfcAfgCfgusu | 739 | AGACGUCGUCGUUCCAGCGUU |
| AM06669-AS | 485 | usAfsasCfuGfcuucaCfgUfgGfaGfcAfsg | 768 | UAACUGCUUCACGUGGAGCAG |
| AM06671-AS | 486 | usUfscsUfuCfccacaUfuGfcCfuCfcCfsu | 769 | UUCUUCCCACAUUGCCUCCCU |

TABLE 3-continued

ASGR1 RNAi Agent Antisense Strand Sequences.

| Antisense Strand ID: | SEQ ID NO. | Antisense Sequence (Modified) (5' → 3') | SEQ ID NO. | Underlying Base Sequence (5' → 3') |
|---|---|---|---|---|
| AM06673-AS | 487 | usUfscsUfuCfccacaUfuGfcCfuCfcusu | 770 | UUCUUCCCACAUUGCCUCCUU |
| AM06675-AS | 488 | usGfscGfaCfuucauCfuUfuCfuUfcsCfsc | 771 | UGCGACUUCAUCUUUCUUCCC |
| AM06677-AS | 489 | asGfscGfaCfuucauCfuUfuCfutUfsCfsc | 772 | AGCGACUUCAUCUUUCUUCCC |
| AM06679-AS | 490 | usUfsuAfaAfgGfaGfaGfgUfgGfcUfcsCfsu | 773 | UUUAAAGGAGAGGUGGCUCCU |
| AM06681-AS | 491 | asUfsuAfaAfgGfaGfaGfgUfgGfcUfcsCfsu | 774 | AUUAAAGGAGAGGUGGCUCCU |
| AM06683-AS | 492 | asAfsusUfaAfaGfaGfgAfgGfuGfgCfuCfsc | 775 | AAUUAAAGGAGAGGUGGCUCC |
| AM06685-AS | 493 | asAfsusUfaAfaGfGfAfgAfgGfuGfgCfuCfsc | 775 | AAUUAAAGGAGAGGUGGCUCC |
| AM06687-AS | 494 | usAfsaCfcAfguagcAfgCfuGfcGfcsUfsc | 776 | UAACCAGUAGCAGCUGCGCUC |
| AM06689-AS | 495 | usAfsgCfuCfugucuCfgCfaGfaCfcsCfsa | 777 | UAGCUCUGUCUCGCAGACCCA |
| AM06703-AS | 496 | cPrpusCfsusUfcAfuCfaAfaCfuUfcCfcAfcusu | 778 | UCUUCAUCAAACUUCCCACUU |
| AM06705-AS | 497 | usAfscUfcCfuUfcCfaCfaUfgAfuAfgsgsu | 779 | UACUCCUUCCACAUGAUAGGU |
| AM06708-AS | 498 | asCfsusUfcAfuCfuUfuCfuUfcCfcAfcAfsc | 780 | ACUUCAUCUUUCUUCCCACAC |
| AM06710-AS | 10 | asCfsusUfcAfuCfuUfuCfuUfcCfcAfcGfsc | 11 | ACUUCAUCUUUCUUCCCACGC |
| AM06756-AS | 499 | asCfsusUfcAfuCfuUfuCfuUfcCfcAfgGfsc | 781 | ACUUCAUCUUUCUUCCCAGGC |
| AM06796-AS | 500 | usAfscsUfcCfuugguCfaUfgAfuAfgGfsc | 782 | UACUCCUUGGUCAUGAUAGGC |
| AM06798-AS | 501 | usAfscsUfcCfuugguCfaUfgAfuAfgCfsc | 783 | UACUCCUUGGUCAUGAUAGCC |
| AM06799-AS | 502 | usAfscsUfcCfuugguCfaUfgAfuAfgGfsu | 3 | UACUCCUUGGUCAUGAUAGGU |
| AM06806-AS | 503 | usAfscUfcCfuugguCfaUfgAfuAfgsGfsu | 3 | UACUCCUUGGUCAUGAUAGGU |
| AM06808-AS | 504 | asAfscUfcCfuUfgGfuCfaUfgAfuAfgsGfsu | 784 | AACUCCUUGGUCAUGAUAGGU |
| AM06810-AS | 505 | usGfscsUfcCfacgugGfaGfcAfgCfausu | 785 | UGCUUCACGUGGAGCAGCAUU |
| AM06815-AS | 5 | asGfscGfaCfuucauCfuUfuCfuUfcsCfsg | 6 | AGCGACUUCAUCUUUCUUCCG |
| AM06820-AS | 506 | asCfsusCfcUfuGfgUfcAfuGfaUfaGfgGfsc | 786 | ACUCCUUGGUCAUGAUAGGGC |
| AM06822-AS | 507 | usAfsusCfuUfuCfuUfcCfcAfcAfuUfgCfsc | 787 | UAUCUUUCUUCCCACAUUGCC |
| AM06824-AS | 508 | usCfsgsAfcUfuCfaUfcUfuUfcUfuCfcCfsa | 788 | UCGACUUCAUCUUUCUUCCCA |
| AM06826-AS | 509 | asAfscsUfgCfuUfcAfcGfuGfgAfgCfausu | 789 | AACUGCUUCACGUGGAGCAUU |
| AM06828-AS | 510 | asCfsgsAfaCfuGfcUfuCfaCfgUfgGfausu | 790 | ACGAACUGCUUCACGUGGAUU |
| AM06830-AS | 511 | usGfsgsAfcAfaAfuUfcUfgCfuCfcUfcCfsc | 791 | UGGACAAAUUCUGCUCCUCC |
| AM06832-AS | 512 | usUfsgAfuAfcUfcCfuUfgGfuCfaUfgsAfsu | 792 | UUGAUACUCCUUGGUCAUGAU |
| AM06834-AS | 513 | usCfsuUfuCfuUfcCfcAfcAfuUfgCfcsUfsc | 793 | UCUUUCUUCCCACAUUGCCUC |
| AM06836-AS | 514 | usCfsaUfcUfuUfcUfuCfcCfaCfaUfusGfsc | 794 | UCAUCUUUCUUCCCACAUUGC |
| AM06838-AS | 28 | usGfsaAfaUfaAfaUfuAfaAfgGfaGfasGfsg | 27 | UGAAAUAAAUUAAAGGAGAGG |
| AM06840-AS | 515 | usGfsaAfaUfaAfaUfuAfaAfgGfaGfcsGfsg | 795 | UGAAAUAAAUUAAAGGAGCGG |
| AM06842-AS | 516 | asGfsaAfaUfaAfaUfuAfaAfgGfaGfcsGfsg | 796 | AGAAAUAAAUUAAAGGAGCGG |
| AM06851-AS | 4 | usAfscUfcCfuU$_{UNA}$UfgGfuCfaUfgAfuAfgsGfsu | 3 | UACUCCUUGGUCAUGAUAGGU |
| AM06853-AS | 517 | usCfsusUfgGfucaugAfuAfgGfgCfuGfsu | 797 | UCUUGGUCAUGAUAGGGCUGU |
| AM06855-AS | 518 | asCfsusCfcUfugguCfaUfgAfaUfaGfgGfsu | 798 | ACUCCUUGGUCAUGAUAGGGU |
| AM06857-AS | 519 | asUfsasCfuCfcuuggUfcAfuGfaUfaGfsc | 799 | AUACUCCUUGGUCAUGAUAGC |

TABLE 3-continued

ASGR1 RNAi Agent Antisense Strand Sequences.

| Antisense Strand ID: | SEQ ID NO. | Antisense Sequence (Modified) (5' → 3') | SEQ ID NO. | Underlying Base Sequence (5' → 3') |
|---|---|---|---|---|
| AM06859-AS | 520 | usAfsusAfcUfccuugGfuCfaUfgAfuCfsc | 800 | UAUACUCCUUGGUCAUGAUCC |
| AM06861-AS | 521 | usAfsusAfcUfccuugGfuCfaUfgAfuAfsc | 801 | UAUACUCCUUGGUCAUGAUAC |
| AM06911-AS | 522 | usAfscsUfcCfuuggUfCfaUfgAfuAfgGfsg | 727 | UACUCCUUGGUCAUGAUAGGG |
| AM06796-AS | 523 | usAfscsUfcCfuuggUfCfaUfgAfuAfgGfsc | 782 | UACUCCUUGGUCAUGAUAGGC |
| AM06914-AS | 524 | asGfscsGfaCfuucauCfuUfuCfuUfcCfsc | 772 | AGCGACUUCAUCUUUCUUCCC |
| AM06916-AS | 525 | asGfscsGfaCfuucauCfuUfuCfuUfcCfsg | 6 | AGCGACUUCAUCUUUCUUCCG |
| AM06918-AS | 526 | usUfsusAfaAfGfGfaGfaGfgUfgGfcUfcusu | 803 | UUUAAAGGAGAGGUGGCUCUU |
| AM06920-AS | 527 | usUfsusAfaAfGfGfaGfaGfgUfgGfcUfgusu | 804 | UUUAAAGGAGAGGUGGCUGUU |
| AM07073-AS | 528 | usUfsgAfuAfcUfcCfuUfgGfuCfaUfgsGfsu | 805 | UUGAUACUCCUUGGUCAUGGU |
| AM07075-AS | 529 | usUfsgAfuAfcUfcCfuUfgGfuCfaUfgsAfsg | 806 | UUGAUACUCCUUGGUCAUGAG |
| AM07077-AS | 530 | usUfsgAfuAfcuccuUfgGfuCfaUfgsGfsc | 807 | UUGAUACUCCUUGGUCAUGGC |
| AM07079-AS | 531 | usAfsusCfuUfucuucCfcAfcAfuUfgCfsg | 808 | UAUCUUUCUUCCCACAUUGCG |
| AM07083-AS | 532 | usAfsusCfuUfucuucCfcAfcAfuUfgGfsg | 809 | UAUCUUUCUUCCCACAUUGGG |
| AM07085-AS | 533 | usCfsaUfcUfuUfcUfcCfcAfcAfuUfsGfsg | 810 | UCAUCUUUCUUCCCACAUUGG |
| AM07088-AS | 534 | usCfsaUfcUfuUfcUfcCfcAfcAfuUfsCfsg | 811 | UCAUCUUUCUUCCCACAUUCG |
| AM07090-AS | 535 | usCfsaUfcUfuUfcUfcCfcAfcAfuCfsGfsg | 812 | UCAUCUUUCUUCCCACAUCGG |
| AM07092-AS | 536 | usGfsaAfaUfaAfaUfuAfaAfgGfaGfasGfsc | 813 | UGAAAUAAAUUAAAGGAGAGC |
| AM07096-AS | 537 | usGfsaAfaUfaAfaUfuAfaAfgGfaGfgsGfsg | 814 | UGAAAUAAAUUAAAGGAGGGG |
| AM07098-AS | 538 | usGfsaAfaUfaAfaUfuAfaAfgGfaGfgsGfsc | 815 | UGAAAUAAAUUAAAGGAGGGC |
| AM07209-AS | 539 | asGfscGfaCfU$_{UNA}$ucauCfuUfuCfuUfcsCfsc | 772 | AGCGACUUCAUCUUUCUUCCC |
| AM07210-AS | 540 | asGfscGfaCfU$_{UNA}$ucauCfuUfuCfuUfcsCfsg | 6 | AGCGACUUCAUCUUUCUUCCG |
| AM07213-AS | 541 | asGfscC$_{UNA}$GfaCfuucauCfuUfuCfuUfcsCfsg | 6 | AGCGACUUCAUCUUUCUUCCG |
| AM07214-AS | 542 | asGfscG$_{UNA}$aCfuucauCfuUfuCfuUfcsCfsg | 6 | AGCGACUUCAUCUUUCUUCCG |
| AM07216-AS | 543 | asGfscGfaCfuucauCfuUfuCfuUfcsCfsu | 816 | AGCGACUUCAUCUUUCUUCCU |
| AM07390-AS | 544 | asGfscGfaCfuucauCfuUfuCfuUfcsusu | 817 | AGCGACUUCAUCUUUCUUCUU |
| AM07392-AS | 545 | asGfscGfaCfuucauCfuUfuCfUfcsCfsa | 818 | AGCGACUUCAUCUUUCUUCCA |
| AM07394-AS | 546 | asGfscGfaCfuucauCfuUfuCfuUfcsGfsg | 819 | AGCGACUUCAUCUUUCUUCGG |
| AM07396-AS | 7 | asGfscGfaCfuucauCfuUfuCfuUfcsGfsu | 8 | AGCGACUUCAUCUUUCUUCGU |
| AM07398-AS | 547 | asGfscGfaCfuucauCfuUfuCfuUfcsGfsc | 820 | AGCGACUUCAUCUUUCUUCGC |
| AM07449-AS | 548 | asGfscGfA$_{UNA}$CfuucauCfuUfuCfuUfcsCfsg | 6 | AGCGACUUCAUCUUUCUUCCG |
| AM07487-AS | 549 | usAfscsuccuugGfuCfaUfgAfuAfgGfsu | 3 | UACUCCUUGGUCAUGAUAGGU |
| AM07488-AS | 550 | usAfscscuccU$_{UNA}$ugguCfaUfgAfuAfgGfsu | 3 | UACUCCUUGGUCAUGAUAGGU |
| AM07489-AS | 551 | asGfscsgacuucauCfuUfuCfuUfcCfsg | 6 | AGCGACUUCAUCUUUCUUCCG |
| AM07490-AS | 552 | asGfscsgacU$_{UNA}$ucauCfuUfuCfuUfcCfsg | 6 | AGCGACUUCAUCUUUCUUCCG |
| AM07492-AS | 553 | asGfscGfaCfU$_{UNA}$uguaCfuUfuCfuUfcsCfsg | 821 | AGCGACUUGUACUUUCUUCCG |

TABLE 3-continued

ASGR1 RNAi Agent Antisense Strand Sequences.

| Antisense Strand ID: | SEQ ID NO. | Antisense Sequence (Modified) (5' → 3') | SEQ ID NO. | Underlying Base Sequence (5' → 3') |
|---|---|---|---|---|
| AM07501-AS | 9 | asGfscsgacuucauCfuUfuCfuUfcGfsu | 8 | AGCGACUUCAUCUUUCUUCGU |
| AM07576-AS | 554 | usAfscuccuugguCfaUfgAfuAfgsGfsu | 3 | UACUCCUUGGUCAUGAUAGGU |
| AM07577-AS | 555 | usAfscuccU$_{UNA}$ugguCfaUfgAfuAfgsGfsu | 3 | UACUCCUUGGUCAUGAUAGGU |

TABLE 4

ASGR1 RNAi Agent Sense Strand Sequences.

| Sense Strand ID: | SEQ ID NO. | Sense Sequence (Modified) (5' → 3') | SEQ ID NO. | Underlying Base Sequence (5' → 3') |
|---|---|---|---|---|
| AM05756-SS | 556 | (NAG31)(invAb)GfuGfgGfaAfGfAfaAfgaugaaguuus(invAb) | 822 | GUGGGAAGAAAGAUGAAGUUU |
| AM05760-SS | 557 | (NAG31)(invAb)gcagcuGfCfUfacugguucuauus(invAb) | 823 | GCAGCUGCUACUGGUUCUAUU |
| AM05923-SS | 558 | (NAG25)s(invAb)sauGfuGfgGfaAfGfAfaAfGfaUfGfaAfgus(invAb) | 824 | AUGUGGGAAGAAAGAUGAAGU |
| AM05924-SS | 559 | (NAG25)s(invAb)saugugggaAfGfAfaagaugaagus(invAb) | 824 | AUGUGGGAAGAAAGAUGAAGU |
| AM05925-SS | 560 | (NAG25)s(invAb)sgugggaAfGfAfaagaugaagus(invAb) | 825 | GUGGGAAGAAAGAUGAAGU |
| AM05926-SS | 561 | (NAG25)s(invAb)sgugggaAfGfAfaagaugaaguuus(invAb) | 822 | GUGGGAAGAAAGAUGAAGUUU |
| AM05928-SS | 562 | (NAG25)s(invAb)saugugggaAfGfAfaagaugaagas(invAb) | 826 | AUGUGGGAAGAAAGAUGAAGA |
| AM06018-SS | 563 | (NAG25)s(invAb)scccuaucaUfGfAfccaaggagus(invdA) | 827 | CCCUAUCAUGACCAAGGAGUA |
| AM06019-SS | 564 | (NAG25)s(invAb)sccuaucaUfGfAfccaaggagus(invdA) | 828 | CCUAUCAUGACCAAGGAGUA |
| AM06022-SS | 565 | (NAG25)s(invAb)sgacgggAfCfGfgacuacgags(invdA) | 829 | GACGGGACGGACUACGAGA |
| AM06024-SS | 566 | (NAG25)s(invAb)sggagccAfCfCfucuccuuuas(invdA) | 830 | GGAGCCACCUCUCCUUUAA |
| AM06025-SS | 567 | (NAG25)s(invAb)scaggagccAfCfCfucuccuuuas(invdA) | 831 | CAGGAGCCACCUCUCCUUUAA |
| AM06028-SS | 568 | (NAG25)s(invAb)scacgagCfGfCfagcugcuacs(invdA) | 832 | CACGAGCGCAGCUGCUACA |
| AM06031-SS | 569 | (NAG25)s(invAb)sagcaacuuCfAfCfagcgagcacs(invdA) | 833 | AGCAACUUCACAGCGAGCACA |
| AM06032-SS | 570 | (NAG25)s(invAb)scagcaacuuCfAfCfagcgagcacs(invdA) | 834 | CAGCAACUUCACAGCGAGCACA |
| AM06034-SS | 571 | (NAG25)s(invAb)sgaggagagUfGfAfccaccaucas(invdA) | 835 | GAGGAGAGUGACCACCAUCAA |
| AM06173-SS | 572 | (NAG25)s(invAb)sggagagUfGfAfccaccaucas(invdA) | 836 | GGAGAGUGACCACCAUCAA |
| AM06174-SS | 573 | (NAG25)sgsaggagagUfGfAfccaccaucas(invdA) | 835 | GAGGAGAGUGACCACCAUCAA |
| AM06177-SS | 574 | (NAG25)s(invAb)scgcuggAfAfCfgacgacgucs(invdA) | 837 | CGCUGGAACGACGACGUCA |
| AM06178-SS | 575 | (NAG25)s(invAb)scgcuggAfAfCfgacgacgucus(invAb) | 838 | CGCUGGAACGACGACGUCU |
| AM06181-SS | 576 | (NAG25)sgsagagugaCfCfAfccaucagcus(invAb) | 839 | GAGAGUGACCACCAUCAGCUA |
| AM06182-SS | 577 | (NAG25)s(invAb)sgagugaCfCfAfccaucagcus(invAb) | 840 | GAGUGACCACCAUCAGCUA |
| AM06184-SS | 578 | (NAG25)s(invAb)sgcuccaGfGfGfcaauggcucs(invAb) | 841 | GCUCCAGGGCAAUGGCUCA |
| AM06187-SS | 579 | (NAG25)s(invAb)saccuggUfGfGfuggucacgus(invAb) | 842 | ACCUGGUGGUGGUCACGUA |
| AM06188-SS | 580 | (NAG25)sgscaccuggUfGfGfugguggucacgus(invAb) | 843 | GCACCUGGUGGUGGUCACGUA |
| AM06190-SS | 581 | (NAG25)s(invAb)scugcucCfAfCfgugaagcags(invAb) | 844 | CUGCUCCACGUGAAGCAGA |
| AM06194-SS | 582 | (NAG25)s(invAb)sgugggaAfGfAfaagaugaagas(invAb) | 845 | GUGGGAAGAAAGAUGAAGA |
| AM06255-SS | 583 | (NAG37)s(invAb)sccuaucaUfGfAfccaaggagus(invdA) | 828 | CCUAUCAUGACCAAGGAGUA |
| AM06256-SS | 584 | (NAG37)s(invAb)scuaucaUfGfAfccaaggagus(invdA) | 846 | CUAUCAUGACCAAGGAGUA |

TABLE 4-continued

ASGR1 RNAi Agent Sense Strand Sequences.

| Sense Strand ID: | SEQ ID NO. | Sense Sequence (Modified) (5' → 3') | SEQ ID NO. | Underlying Base Sequence (5' → 3') |
|---|---|---|---|---|
| AM06257-SS | 585 | (NAG37)s(invAb)sccuaucaUfGfAfccaaggagus(invdA) | 827 | CCCUAUCAUGACCAAGGAGUA |
| AM06258-SS | 586 | (NAG37)sgscccuaucaUfGfAfccaaggagus(invdA) | 847 | GCCCUAUCAUGACCAAGGAGUA |
| AM06259-SS | 587 | (NAG37)s(invAb)sgcccuaucaUfGfAfccaaggagus(invdA) | 847 | GCCCUAUCAUGACCAAGGAGUA |
| AM06260-SS | 588 | (NAG37)(invAb)ccuaucaUfGfAfccaaggagu(invdA) | 828 | CCUAUCAUGACCAAGGAGUA |
| AM06440-SS | 589 | (NAG37)s(invAb)sgugggaAfGfAfaagaugaagus(invAb) | 825 | GUGGGAAGAAAGAUGAAGU |
| AM06441-SS | 590 | (NAG37)s(invAb)sggagccAfCfCfucuccuuuas(invdA) | 830 | GGAGCCACCUCUCCUUUAA |
| AM06449-SS | 591 | (NAG37)sgsgagccAfCfCfucuccuuuas(invdA) | 830 | GGAGCCACCUCUCCUUUAA |
| AM06450-SS | 592 | (NAG37)scsaggagccAfCfCfucuccuuuas(invdA) | 831 | CAGGAGCCACCUCUCCUUUAA |
| AM06451-SS | 593 | (NAG37)scscaggagccAfCfCfucuccuuuas(invdA) | 848 | CCAGGAGCCACCUCUCCUUUAA |
| AM06458-SS | 594 | (NAG37)s(invAb)sgugggaAfGfAfaagaugaagas(invAb) | 845 | GUGGGAAGAAAGAUGAAGA |
| AM06574-SS | 595 | (NAG37)s(invAb)scgcuggAfAfCfgacgacgucus(invAb) | 838 | CGCUGGAACGACGACGUCU |
| AM06576-SS | 596 | (NAG37)s(invAb)scgcuggAfAfCfgacgaugucus(invAb) | 849 | CGCUGGAACGACGAUGUCU |
| AM06577-SS | 597 | (NAG37)s(invAb)scgcuggAfAfCfgacgacgucas(invAb) | 837 | CGCUGGAACGACGACGUCA |
| AM06580-SS | 598 | (NAG37)s(invAb)sgacgggAfCfGfgacuacgagas(invAb) | 829 | GACGGGACGGACUACGAGA |
| AM06583-SS | 599 | (NAG37)s(invAb)sgacgggAfCfGfgacuacgagus(invAb) | 850 | GACGGGACGGACUACGAGU |
| AM06585-SS | 600 | (NAG37)s(invAb)sgacgggAfCfGfgacuacgagauus(invAb) | 851 | GACGGGACGGACUACGAGAUU |
| AM06597-SS | 601 | (NAG37)s(invAb)scccuaucaUfGfAfccaaggaguas(invAb) | 827 | CCCUAUCAUGACCAAGGAGUA |
| AM06600-SS | 602 | (NAG37)s(invAb)saccaucaUfGfAfccaaggaguas(invAb) | 13 | ACCAUCAUGACCAAGGAGUA |
| AM06640-SS | 603 | (NAG37)s(invAb)scuaucaUfGfAfccaaggaguauus(invAb) | 853 | CUAUCAUGACCAAGGAGUAUU |
| AM06644-SS | 604 | (NAG37)s(invAb)sccugcugcUfCfCfacgugaagcas(invAb) | 854 | CCUGCUGCUCCACGUGAAGCA |
| AM06646-SS | 605 | (NAG37)s(invAb)saggccuccAfCfGfaccaaaacgas(invAb) | 855 | AGGCCUCCACGACCAAAACGA |
| AM06648-SS | 606 | (NAG37)s(invAb)sccagggagGfCfAfauguggggaaas(invAb) | 856 | CCAGGGAGGCAAUGUGGGAAA |
| AM06650-SS | 607 | (NAG37)s(invAb)scgagcgcaGfCfUfgcuacugguus(invAb) | 857 | CGAGCGCAGCUGCUACUGGUU |
| AM06652-SS | 608 | (NAG37)s(invAb)sagcgcaGfCfUfgcuacugguuuus(invAb) | 858 | AGCGCAGCUGCUACUGGUUUU |
| AM06654-SS | 609 | (NAG37)s(invAb)scugacgccGfAfCfaacuacugcas(invAb) | 859 | CUGACGCCGACAACUACUGCA |
| AM06656-SS | 610 | (NAG37)s(invAb)sccugguggUfGfGfucacguccuas(invAb) | 860 | CCUGGUGGUGGUCACGUCCUA |
| AM06658-SS | 611 | (NAG37)s(invAb)sgagcagaaAfUfUfuguccagcaas(invAb) | 861 | GAGCAGAAAUUUGUCCAGCAA |
| AM06660-SS | 612 | (NAG37)s(invAb)sguggacggGfAfCfggacuacgaas(invAb) | 862 | GUGGACGGGACGGACUACGAA |
| AM06662-SS | 613 | (NAG37)s(invAb)sagacgggaCfGfGfacuacgagaas(invAb) | 863 | AGACGGGACGGACUACGAGAA |
| AM06664-SS | 614 | (NAG37)s(invAb)saacagccgGfAfCfgacugguacas(invAb) | 864 | AACAGCCGGACGACUGGUACA |
| AM06666-SS | 615 | (NAG37)s(invAb)scgcuggAfAfCfgacgacgucuuus(invAb) | 865 | CGCUGGAACGACGACGUCUUU |
| AM06668-SS | 616 | (NAG37)s(invAb)scugcuccaCfGfUfgaagcaguuas(invAb) | 866 | CUGCUCCACGUGAAGCAGUUA |
| AM06670-SS | 617 | (NAG37)s(invAb)sagggaggcAfAfUfgugggaagaas(invAb) | 867 | AGGGAGGCAAUGUGGGAAGAA |
| AM06672-SS | 618 | (NAG37)s(invAb)sggaggcAfAfUfgugggaagaauus(invAb) | 868 | GGAGGCAAUGUGGGAAGAAUU |
| AM06674-SS | 619 | (NAG37)s(invAb)sgggaagaaAfGfAfugaagucgcas(invAb) | 869 | GGGAAGAAAGAUGAAGUCGCA |
| AM06676-SS | 620 | (NAG37)s(invAb)sgggaagaaAfGfAfugaagucgcus(invAb) | 870 | GGGAAGAAAGAUGAAGUCGCU |
| AM06678-SS | 621 | (NAG37)s(invAb)saggagccaCfCfUfcuccuuuaaas(invAb) | 871 | AGGAGCCACCUCUCCUUUAAA |

TABLE 4-continued

ASGR1 RNAi Agent Sense Strand Sequences.

| Sense Strand ID: | SEQ ID NO. | Sense Sequence (Modified) (5' → 3') | SEQ ID NO. | Underlying Base Sequence (5' → 3') |
|---|---|---|---|---|
| AM06680-SS | 622 | (NAG37)s(invAb)saggagccaCfCfUfcuccuuuaaus(invAb) | 872 | AGGAGCCACCUCUCCUUUAAU |
| AM06682-SS | 623 | (NAG37)s(invAb)sggagccacCfUfCfuccuuuaauus(invAb) | 873 | GGAGCCACCUCUCCUUUAAUU |
| AM06684-SS | 624 | (NAG37)s(invAb)sGfgAfgCfcAfcCfUfCfuCfcUfuUfaAfuus(invAb) | 873 | GGAGCCACCUCUCCUUUAAUU |
| AM06686-SS | 625 | (NAG37)s(invAb)sgagcgcagCfUfGfcuacugguuas(invAb) | 874 | GAGCGCAGCUGCUACUGGUUA |
| AM06688-SS | 626 | (NAG37)s(invAb)sugggucugCfGfAfgacagagcuas(invAb) | 875 | UGGGUCUGCGAGACAGAGCUA |
| AM06702-SS | 627 | (NAG37)s(invAb)sgugggaAfGfUfuugaugaagas(invAb) | 876 | GUGGGAAGUUUGAUGAAGA |
| AM06704-SS | 628 | (NAG37)s(invAb)sccuaucaUfGfUfggaaggagus(invdA) | 877 | CCUAUCAUGUGGAAGGAGUA |
| AM06706-SS | 629 | (NAG37)s(invAb)saugugggaAfGfAfaagaugaagus(invAb) | 824 | AUGUGGGAAGAAAGAUGAAGU |
| AM06707-SS | 630 | (NAG37)s(invAb)sgugugggaAfGfAfaagaugaagus(invAb) | 878 | GUGUGGGAAGAAAGAUGAAGU |
| AM06709-SS | 631 | (NAG37)s(invAb)sgcgugggaAfGfAfaagaugaagus(invAb) | 18 | GCGUGGGAAGAAAGAUGAAGU |
| AM06754-SS | 632 | (NAG37)gscgugggaAfGfAfaagaugaagus(invAb) | 18 | GCGUGGGAAGAAAGAUGAAGU |
| AM06755-SS | 633 | (NAG37)gsccugggaAfGfAfaagaugaagus(invAb) | 880 | GCCUGGGAAGAAAGAUGAAGU |
| AM06795-SS | 634 | (NAG37)s(invAb)sgccuaucaUfGfAfccaaggaguas(invAb) | 881 | GCCUAUCAUGACCAAGGAGUA |
| AM06797-SS | 635 | (NAG37)s(invAb)sggcuaucaUfGfAfccaaggaguas(invAb) | 882 | GGCUAUCAUGACCAAGGAGUA |
| AM06802-SS | 636 | (NAG37)s(invAb)saccuaucaUfGfAfccaaggaivas(invAb) | 12 | ACCUAUCAUGACCAAGGAIUA |
| AM06803-SS | 637 | (NAG37)s(invAb)saccuaucaUfGfAfccaagiaguas(invAb) | 884 | ACCUAUCAUGACCAAGIAGUA |
| AM06804-SS | 638 | (NAG37)s(invAb)saccuaucaUfGfAfccaaigaguas(invAb) | 885 | ACCUAUCAUGACCAAIGAGUA |
| AM06805-SS | 639 | (NAG37)s(invAb)saccuaucaUfGfAfccaaigaiuas(invAb) | 14 | ACCUAUCAUGACCAAIGAIUA |
| AM06807-SS | 640 | (NAG37)s(invAb)saccuaucaUfGfAfccaaggaguus(invAb) | 887 | ACCUAUCAUGACCAAGGAGUU |
| AM06809-SS | 641 | (NAG37)s(invAb)sugcugcUfCfCfacgugaagcauus(invAb) | 888 | UGCUGCUCCACGUGAAGCAUU |
| AM06811-SS | 642 | (NAG37)s(invAb)sugcugcUfCfCfacgugaaicauus(invAb) | 889 | UGCUGCUCCACGUGAAICAUU |
| AM06812-SS | 643 | (NAG37)s(invAb)sugcugcUfCfCfacguiaagcauus(invAb) | 890 | UGCUGCUCCACGUIAAGCAUU |
| AM06813-SS | 644 | (NAG37)s(invAb)sugcugcUfCfCfacguiaaicauus(invAb) | 891 | UGCUGCUCCACGUIAAICAUU |
| AM06814-SS | 645 | (NAG37)s(invAb)scggaagaaAfGfAfugaagucicus(invAb) | 15 | CGGAAGAAAGAUGAAGUCICU |
| AM06816-SS | 646 | (NAG37)s(invAb)scggaagaaAfGfAfugaaiucgcus(invAb) | 893 | CGGAAGAAAGAUGAAIUCGCU |
| AM06817-SS | 647 | (NAG37)s(invAb)scggaagaaAfGfAfugaaiucicus(invAb) | 31 | CGGAAGAAAGAUGAAIUCICU |
| AM06818-SS | 648 | (NAG37)s(invAb)scggaagaaAfGfAfugaagucgcus(invAb) | 33 | CGGAAGAAAGAUGAAGUCGCU |
| AM06819-SS | 649 | (NAG37)s(invAb)sgcccuaucAfUfGfaccaaggagus(invAb) | 896 | GCCCUAUCAUGACCAAGGAGU |
| AM06821-SS | 650 | (NAG37)s(invAb)sggcaauguGfGfGfaagaaagauas(invAb) | 897 | GGCAAUGUGGGAAGAAAGAUA |
| AM06823-SS | 651 | (NAG37)s(invAb)sugggaagaAfAfGfaugaagucgas(invAb) | 898 | UGGGAAGAAAGAUGAAGUCGA |
| AM06825-SS | 652 | (NAG37)s(invAb)sugcuccAfCfGfugaagcaguuus(invAb) | 899 | UGCUCCACGUGAAGCAGUUUU |
| AM06827-SS | 653 | (NAG37)s(invAb)succacgUfGfAfagcaguucguuus(invAb) | 900 | UCCACGUGAAGCAGUUCGUUU |
| AM06829-SS | 654 | (NAG37)s(invAb)sggaggagcAfGfAfaauuuguccas(invAb) | 901 | GGAGGAGCAGAAAUUUGUCCA |
| AM06831-SS | 655 | (NAG37)s(invAb)saucaugacCfAfAfggaguaucaas(invAb) | 902 | AUCAUGACCAAGGAGUAUCAA |
| AM06833-SS | 656 | (NAG37)s(invAb)sgaggcaauGfUfGfggaagaaagas(invAb) | 903 | GAGGCAAUGUGGGAAGAAAGA |
| AM06835-SS | 657 | (NAG37)s(invAb)sgcaaugugGfGfAfagaaagaugas(invAb) | 904 | GCAAUGUGGGAAGAAAGAUGA |

TABLE 4-continued

ASGR1 RNAi Agent Sense Strand Sequences.

| Sense Strand ID: | SEQ ID NO. | Sense Sequence (Modified) (5' → 3') | SEQ ID NO. | Underlying Base Sequence (5' → 3') |
|---|---|---|---|---|
| AM06837-SS | 658 | (NAG37)s(invAb)sccucuccuUfUfAfauuuauuucas(invAb) | 35 | CCUCUCCUUUAAUUUAUUUCA |
| AM06839-SS | 659 | (NAG37)s(invAb)sccgcuccuUfUfAfauuuauuucas(invAb) | 906 | CCGCUCCUUUAAUUUAUUUCA |
| AM06841-SS | 660 | (NAG37)s(invAb)sccgcuccuUfUfAfauuuauuucus(invAb) | 907 | CCGCUCCUUUAAUUUAUUUCU |
| AM06852-SS | 661 | (NAG37)s(invAb)sacagcccuAfUfCfaugaccaagas(invAb) | 908 | ACAGCCCUAUCAUGACCAAGA |
| AM06854-SS | 662 | (NAG37)s(invAb)sacccuaucAfUfGfaccaaggagus(invAb) | 909 | ACCCUAUCAUGACCAAGGAGU |
| AM06856-SS | 663 | (NAG37)s(invAb)sgcuaucauGfAfCfcaaggaguaus(invAb) | 910 | GCUAUCAUGACCAAGGAGUAU |
| AM06858-SS | 664 | (NAG37)s(invAb)sggaucaugAfCfCfaaggaguauas(invAb) | 911 | GGAUCAUGACCAAGGAGUAUA |
| AM06860-SS | 665 | (NAG37)s(invAb)sguaucaugAfCfCfaaggaguauas(invAb) | 912 | GUAUCAUGACCAAGGAGUAUA |
| AM06909-SS | 666 | (NAG37)asccuaucaUfGfAfccaaggaguas(invAb) | 13 | ACCUAUCAUGACCAAGGAGUA |
| AM06910-SS | 667 | (NAG37)csccuaucaUfGfAfccaaggaguas(invAb) | 827 | CCCUAUCAUGACCAAGGAGUA |
| AM06912-SS | 668 | (NAG37)gsccuaucaUfGfAfccaaggaguas(invAb) | 881 | GCCUAUCAUGACCAAGGAGUA |
| AM06913-SS | 669 | (NAG37)gsggaagaaAfGfAfugaagucgcus(invAb) | 870 | GGGAAGAAAGAUGAAGUCGCU |
| AM06915-SS | 670 | (NAG37)csggaagaaAfGfAfugaagucgcus(invAb) | 33 | CGGAAGAAAGAUGAAGUCGCU |
| AM06917-SS | 671 | (NAG37)s(invAb)sgagccaCfCfUfcuccuuuaaauus(invAb) | 913 | GAGCCACCUCUCCUUUAAAUU |
| AM06919-SS | 672 | (NAG37)s(invAb)scagccaCfCfUfcuccuuuaaauus(invAb) | 914 | CAGCCACCUCUCCUUUAAAUU |
| AM06921-SS | 673 | (NAG37)gsagccaCfCfUfcuccuuuaaauus(invAb) | 913 | GAGCCACCUCUCCUUUAAAUU |
| AM06930-SS | 674 | (NAG37)s(invAb)saccuaucaUfGfAfcCaaggaguas(invAb) | 13 | ACCUAUCAUGACCAAGGAGUA |
| AM06931-SS | 675 | (NAG37)asccuaucaUfGfAfcCaaggaguas(invAb) | 13 | ACCUAUCAUGACCAAGGAGUA |
| AM06935-SS | 676 | (NAG37)s(invAb)scggaagaaAfGfAfugaagucpu_2Ncus(invAb) | 915 | CGGAAGAAAGAUGAAGUC(pu$^{2N}$)CU |
| AM06936-SS | 677 | (NAG37)s(invAb)scggaagaaAfGfAfugaagucacus(invAb) | 916 | CGGAAGAAAGAUGAAGUCACU |
| AM06937-SS | 678 | (NAG37)s(invAb)scggaagaaAfGfAfugaagucucus(invAb) | 917 | CGGAAGAAAGAUGAAGUCUCU |
| AM06938-SS | 679 | (NAG37)s(invAb)scggaagaaAfGfAfugaaguccus(invAb) | 918 | CGGAAGAAAGAUGAAGUCCCU |
| AM06939-SS | 680 | (NAG37)s(invAb)scggaagaaAfGfAfuGaagucicus(invAb) | 15 | CGGAAGAAAGAUGAAGUCICU |
| AM06940-SS | 681 | (NAG37)s(invAb)scggaagaaAfGfAfUgaagucicus(invAb) | 15 | CGGAAGAAAGAUGAAGUCICU |
| AM06941-SS | 682 | (NAG37)s(invAb)scggaagaaAfGfAfudGaagucicus(invAb) | 15 | CGGAAGAAAGAUGAAGUCICU |
| AM07072-SS | 683 | (NAG37)s(invAb)saccaugacCfAfAfggaguaucaas(invAb) | 919 | ACCAUGACCAAGGAGUAUCAA |
| AM07074-SS | 684 | (NAG37)s(invAb)scucaugacCfAfAfggaguaucaas(invAb) | 920 | CUCAUGACCAAGGAGUAUCAA |
| AM07076-SS | 685 | (NAG37)s(invAb)sgccaugacCfAfAfggaguaucaas(invAb) | 921 | GCCAUGACCAAGGAGUAUCAA |
| AM07078-SS | 686 | (NAG37)s(invAb)scgcaauguGfGfGfaagaaagauas(invAb) | 922 | CGCAAUGUGGGAAGAAAGAUA |
| AM07080-SS | 687 | (NAG37)s(invAb)scgcaauguGfiGfaagaaagauas(invAb) | 923 | CGCAAUGUGIAAGAAAGAUA |
| AM07081-SS | 688 | (NAG37)s(invAb)scgcaauguiGfGfaagaaagauas(invAb) | 924 | CGCAAUGUIGGAAGAAAGAUA |
| AM07082-SS | 689 | (NAG37)s(invAb)scccaauguGfGfGfaagaaagauas(invAb) | 925 | CCCAAUGUGGGAAGAAAGAUA |
| AM07084-SS | 690 | (NAG37)s(invAb)sccaaugugGfGfAfagaaagaugas(invAb) | 926 | CCAAUGUGGGAAGAAAGAUGA |
| AM07086-SS | 691 | (NAG37)s(invAb)sccaauguiGfGfAfagaaagaugas(invAb) | 927 | CCAAUGUIGGAAGAAAGAUGA |
| AM07087-SS | 692 | (NAG37)s(invAb)scgaaugugGfGfAfagaaagaugas(invAb) | 928 | CGAAUGUGGGAAGAAAGAUGA |
| AM07089-SS | 693 | (NAG37)s(invAb)sccgaugugGfGfAfagaaagaugas(invAb) | 929 | CCGAUGUGGGAAGAAAGAUGA |
| AM07091-SS | 694 | (NAG37)s(invAb)sgcucuccuUfUfAfauuuauuucas(invAb) | 930 | GCUCUCCUUUAAUUUAUUUCA |

TABLE 4-continued

ASGR1 RNAi Agent Sense Strand Sequences.

| Sense Strand ID: | SEQ ID NO. | Sense Sequence (Modified) (5' → 3') | SEQ ID NO. | Underlying Base Sequence (5' → 3') |
|---|---|---|---|---|
| AM07093-SS | 695 | (NAG37)s(invAb)sgcucuccuUfUfAfauuua_2Nuuucas(invAb) | 931 | GCUCUCCUUUAAUUU(A$^{2N}$)UUUCA |
| AM07094-SS | 696 | (NAG37)s(invAb)sgcucuccuUfUfAfa_2Nuuuauuucas(invAb) | 932 | GCUCUCCUUUA(A$^{2N}$)UUUAUUUCA |
| AM07095-SS | 697 | (NAG37)s(invAb)sccccuccuUfUfAfauuuauuucas(invAb) | 933 | CCCCUCCUUUAAUUUAUUUCA |
| AM07097-SS | 698 | (NAG37)s(invAb)sgcccuccuUfUfAfauuuauuucas(invAb) | 934 | GCCCUCCUUUAAUUUAUUUCA |
| AM07109-SS | 699 | (NAG37)s(invAb)saccuaucaUfGfAfcCaaggaiuas(invAb) | 12 | ACCUAUCAUGACCAAGGAIUA |
| AM07110-SS | 700 | (NAG37)s(invAb)saccuaucaUfGfAfcCaaigaiuas(invAb) | 14 | ACCUAUCAUGACCAAIGAIUA |
| AM07211-SS | 701 | (NAG37)s(invAb)scggaagaaAfGfAfudGaagucgcus(invAb) | 33 | CGGAAGAAAGAUGAAGUCGCU |
| AM07212-SS | 702 | (NAG37)s(invAb)scggaagaaAfGfAfuGaagucgcus(invAb) | 33 | CGGAAGAAAGAUGAAGUCGCU |
| AM07215-SS | 703 | (NAG37)s(invAb)saggaagaaAfGfAfugaagucicus(invAb) | 935 | AGGAAGAAAGAUGAAGUCICU |
| AM07388-SS | 704 | (NAG37)csggaagaaAfGfAfudGaagucgcus(invAb) | 33 | CGGAAGAAAGAUGAAGUCGCU |
| AM07389-SS | 705 | (NAG37)s(invAb)sgaagaaAfGfAfugaagucicuuus(invAb) | 936 | GAAGAAAGAUGAAGUCICUUU |
| AM07391-SS | 706 | (NAG37)s(invAb)suggaagaaAfGfAfugaagucicus(invAb) | 937 | UGGAAGAAAGAUGAAGUCICU |
| AM07393-SS | 707 | (NAG37)s(invAb)sccgaagaaAfGfAfugaagucicus(invAb) | 938 | CCGAAGAAAGAUGAAGUCICU |
| AM07395-SS | 708 | (NAG37)s(invAb)sacgaagaaAfGfAfugaagucicus(invAb) | 16 | ACGAAGAAAGAUGAAGUCICU |
| AM07397-SS | 709 | (NAG37)s(invAb)sgcgaagaaAfGfAfugaagucicus(invAb) | 940 | GCGAAGAAAGAUGAAGUCICU |
| AM07414-SS | 710 | (NAG37)s(invAb)scggaagaaAfGfAfudGaA$_{UNA}$gucgcus(invAb) | 33 | CGGAAGAAAGAUGAAGUCGCU |
| AM07444-SS | 711 | (NAG37)s(invAb)scggaagaaAfGfAfugaA$_{UNA}$gucgcus(invAb) | 33 | CGGAAGAAAGAUGAAGUCGCU |
| AM07445-SS | 712 | (NAG37)s(invAb)scggaagaaAfGfAfugaA$_{UNA}$gucicus(invAb) | 15 | CGGAAGAAAGAUGAAGUCICU |
| AM07446-SS | 713 | (NAG37)s(invAb)scggaagaaAfGfAfuGaA$_{UNA}$gucgcus(invAb) | 33 | CGGAAGAAAGAUGAAGUCGCU |
| AM07447-SS | 714 | (NAG37)s(invAb)scggaagaaAfGfAfudGaA$_{UNA}$gucicus(invAb) | 15 | CGGAAGAAAGAUGAAGUCICU |
| AM07448-SS | 715 | (NAG37)s(invAb)scggaagaaAfGfAfugaagU$_{UNA}$cgcus(invAb) | 33 | CGGAAGAAAGAUGAAGUCGCU |
| AM07450-SS | 716 | (NAG37)s(invAb)scggaagaaAfGfAfdTgaagucgcus(invAb) | 941 | CGGAAGAAAGATGAAGUCGCU |
| AM07451-SS | 717 | (NAG37)s(invAb)saccuaucaUfGfAfcdCaaggaguas(invAb) | 13 | ACCUAUCAUGACCAAGGAGUA |
| AM07452-SS | 718 | (NAG37)s(invAb)saccuaucaUfGfAfcdCaaggaiuas(invAb) | 12 | ACCUAUCAUGACCAAGGAIUA |
| AM07491-SS | 719 | (NAG33)s(invAb)scggaagaaAfGfUfadCaagucgcus(invAb) | 943 | CGGAAGAAAGUACAAGUCGCU |
| AM07494-SS | 720 | (NAG33)s(invAb)scggaagaaAfGfAfudGaagucgcus(invAb) | 33 | CGGAAGAAAGAUGAAGUCGCU |
| AM07500-SS | 721 | (NAG37)s(invAb)sacgaagaaAfGfAfugaagucgcus(invAb) | 17 | ACGAAGAAAGAUGAAGUCGCU |

(A$^{2N}$) = 2-aminoadenine nucleotide
(pu$^{2N}$) = 2-aminopurine nucleotide

The ASGR1 RNAi agents described herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of an ASGR1 RNAi agent disclosed herein differs by 0, 1, 2, or 3 nucleotides from any of the antisense strand sequences in Table 3. In some embodiments, the sense strand of an ASGR1 RNAi agent disclosed herein differs by 0, 1, 2, or 3 nucleotides from any of the sense strand sequences in Table 4.

In some embodiments, an ASGR1 RNAi agent antisense strand comprises a nucleotide sequence of any of the sequences in Table 2 or Table 3. In some embodiments, an ASGR1 RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Table 2 or Table 3. In certain embodiments, an ASGR1 RNAi agent antisense strand comprises or consists of a modified sequence of any one of the modified sequences in Table 3.

In some embodiments, an ASGR1 RNAi agent sense strand comprises the nucleotide sequence of any of the sequences in Table 2 or Table 4. In some embodiments, an ASGR1 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, 4-24, 1-25, 2-25, 3-25, 4-25, 1-26, 2-26, 3-26, or 4-26 of any of the sequences in Table 2 or Table 4. In certain embodiments, an ASGR1 RNAi agent sense strand comprises or consists of a modified sequence of any one of the modified sequences in Table 4.

For the ASGR1 RNAi agents disclosed herein, the nucleotide at position 1 of the antisense strand (from 5' end→3' end) can be perfectly complementary to an ASGR1 gene, or can be non-complementary to an ASGR1 gene. In some embodiments, the nucleotide at position 1 of the antisense strand (from 5' end→3' end) is a U, A, or dT (or a modified version thereof).

In some embodiments, the nucleotide at position 1 of the antisense strand (from 5' end→3' end) forms an A:U or U:A base pair with the sense strand.

In some embodiments, an ASGR1 RNAi agent antisense strand comprises the sequence of nucleotides (from 5' end→3' end) 2-18 or 2-19 of any of the antisense strand sequences in Table 2 or Table 3. In some embodiments, an ASGR1 RNAi sense strand comprises the sequence of nucleotides (from 5' end→3' end) 1-17 or 1-18 of any of the sense strand sequences in Table 2 or Table 4.

In some embodiments, an ASGR1 RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the ASGR1 RNAi agent has a sense strand consisting of the modified sequence of any of the modified sequences in Table 4, and an antisense strand consisting of the modified sequence of any of the modified sequences in Table 3. Representative sequence pairings are exemplified by the Duplex ID Nos. shown in Table 5.

In some embodiments, an ASGR1 RNAi agent comprises any of the duplexes represented by any of the Duplex ID Nos. presented herein. In some embodiments, an ASGR1 RNAi agent consists of any of the duplexes represented by any of the Duplex ID Nos. presented herein. In some embodiments, an ASGR1 RNAi agent comprises the sense strand and antisense strand nucleotide sequences of any of the duplexes represented by any of the Duplex ID Nos. presented herein. In some embodiments, an ASGR1 RNAi agent comprises the sense strand and antisense strand nucleotide sequences of any of the duplexes represented by any of the Duplex ID Nos. presented herein and a targeting group and/or linking group, wherein the targeting group and/or linking group is covalently linked (i.e. conjugated) to the sense strand or the antisense strand. In some embodiments, an ASGR1 RNAi agent comprises a sense strand and an antisense strand having the modified nucleotide sequences of any of the duplexes represented by any of the Duplex ID Nos. presented herein. In some embodiments, an ASGR1 RNAi agent comprises a sense strand and an antisense strand having the modified nucleotide sequences of any of the duplexes represented by any of the Duplex ID Nos. presented herein and a targeting group and/or linking group, wherein the targeting group and/or linking group is covalently linked to the sense strand or the antisense strand.

In some embodiments, an ASGR1 RNAi agent comprises an antisense strand and a sense strand having the nucleotide sequences of any of the antisense strand/sense strand duplexes of Table 2 or Table 5, and further comprises a targeting group. In some embodiments, an ASGR1 RNAi agent comprises an antisense strand and a sense strand having the nucleotide sequences of any of the antisense strand/sense strand duplexes of Table 2 or Table 5, and further comprises an asialoglycoprotein receptor ligand targeting group.

In some embodiments, an ASGR1 RNAi agent comprises an antisense strand and a sense strand having the nucleotide sequences of any of the antisense strand/sense strand duplexes of Table 2 or Table 5, and further comprises a targeting group selected from the group consisting of (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined in Table 6. In some embodiments, the targeting group is (NAG25) or (NAG25)s as defined in Table 6. In other embodiments, the targeting group is (NAG37) or (NAG37)s as defined in Table 6.

In some embodiments, an ASGR1 RNAi agent comprises an antisense strand and a sense strand having the modified nucleotide sequence of any of the antisense strand and/or sense strand nucleotide sequences of any of the duplexes of Table 5.

In some embodiments, an ASGR1 RNAi agent comprises an antisense strand and a sense strand having a modified nucleotide sequence of any of the antisense strand and/or sense strand nucleotide sequences of any of the duplexes of Table 5, and comprises an asialoglycoprotein receptor ligand targeting group.

In some embodiments, an ASGR1 RNAi agent comprises any of the duplexes of Table 2 or Table 5. In certain embodiments, an ASGR1 RNAi agent comprises a duplex selected from the group consisting of AD05126, AD05150, AD05183, AD05186, AD05193, AD05195, AD05196, AD05206, AD05209, AD05256, AD05374, AD05609, and AD05692 or a salt thereof.

In some embodiments, an ASGR1 RNAi agent consists of any of the duplexes of Table 2 or Table 5. In certain embodiments, an ASGR1 RNAi agent consists of a duplex selected from the group consisting of AD05126, AD05150, AD05183, AD05186, AD05193, AD05195, AD05196, AD05206, AD05209, AD05256, AD05374, AD05609, and AD05692 or a salt thereof.

TABLE 5

ASGR1 RNAi Agent Duplexes Identified by Duplex ID No. with Corresponding Sense and Antisense Strands.

| Duplex ID | Antisense Strand ID | Sense Strand ID |
| --- | --- | --- |
| AD04518 | AM05757-AS | AM05756-SS |
| AD04519 | AM05761-AS | AM05760-SS |
| AD04629 | AM05919-AS | AM05923-SS |
| AD04630 | AM05920-AS | AM05924-SS |
| AD04631 | AM05921-AS | AM05924-SS |
| AD04632 | AM05921-AS | AM05925-SS |
| AD04633 | AM05921-AS | AM05926-SS |

TABLE 5-continued

ASGR1 RNAi Agent Duplexes Identified by Duplex ID No. with Corresponding Sense and Antisense Strands.

| Duplex ID | Antisense Strand ID | Sense Strand ID |
|---|---|---|
| AD04634 | AM05757-AS | AM05925-SS |
| AD04635 | AM05922-AS | AM05924-SS |
| AD04636 | AM05927-AS | AM05928-SS |
| AD04697 | AM06016-AS | AM06018-SS |
| AD04698 | AM06017-AS | AM06019-SS |
| AD04699 | AM06020-AS | AM06022-SS |
| AD04700 | AM06021-AS | AM06022-SS |
| AD04701 | AM06023-AS | AM06024-SS |
| AD04702 | AM06023-AS | AM06025-SS |
| AD04703 | AM06026-AS | AM06028-SS |
| AD04704 | AM06027-AS | AM06028-SS |
| AD04705 | AM06029-AS | AM06031-SS |
| AD04706 | AM06030-AS | AM06032-SS |
| AD04707 | AM06033-AS | AM06034-SS |
| AD04791 | AM06172-AS | AM06173-SS |
| AD04792 | AM06033-AS | AM06174-SS |
| AD04793 | AM06175-AS | AM06177-SS |
| AD04794 | AM06176-AS | AM06178-SS |
| AD04795 | AM06179-AS | AM06181-SS |
| AD04796 | AM06180-AS | AM06182-SS |
| AD04797 | AM06183-AS | AM06184-SS |
| AD04798 | AM06185-AS | AM06187-SS |
| AD04799 | AM06186-AS | AM06188-SS |
| AD04800 | AM06189-AS | AM06190-SS |
| AD04801 | AM06192-AS | AM05925-SS |
| AD04802 | AM06193-AS | AM06194-SS |
| AD04810 | AM06200-AS | AM06194-SS |
| AD04811 | AM06201-AS | AM06194-SS |
| AD04847 | AM06017-AS | AM06255-SS |
| AD04848 | AM06248-AS | AM06255-SS |
| AD04849 | AM06249-AS | AM06255-SS |
| AD04850 | AM06250-AS | AM06256-SS |
| AD04851 | AM06251-AS | AM06256-SS |
| AD04852 | AM06016-AS | AM06257-SS |
| AD04853 | AM06252-AS | AM06258-SS |
| AD04854 | AM06252-AS | AM06259-SS |
| AD04855 | AM06253-AS | AM06260-SS |
| AD04856 | AM06254-AS | AM06255-SS |
| AD04964 | AM05757-AS | AM06440-SS |
| AD04965 | AM06023-AS | AM06441-SS |
| AD04966 | AM06442-AS | AM06441-SS |
| AD04967 | AM06443-AS | AM06441-SS |
| AD04968 | AM06444-AS | AM06441-SS |
| AD04969 | AM06445-AS | AM06441-SS |
| AD04970 | AM06446-AS | AM06441-SS |
| AD04971 | AM06447-AS | AM06441-SS |
| AD04972 | AM06447-AS | AM06449-SS |
| AD04973 | AM06023-AS | AM06450-SS |
| AD04974 | AM06448-AS | AM06451-SS |
| AD04975 | AM06193-AS | AM06458-SS |
| AD05046 | AM06575-AS | AM06574-SS |
| AD05047 | AM06575-AS | AM06576-SS |
| AD05048 | AM06578-AS | AM06577-SS |
| AD05049 | AM06579-AS | AM06577-SS |
| AD05050 | AM06581-AS | AM06580-SS |
| AD05051 | AM06582-AS | AM06580-SS |
| AD05052 | AM06584-AS | AM06583-SS |
| AD05053 | AM06581-AS | AM06585-SS |
| AD05054 | AM06586-AS | AM06583-SS |
| AD05065 | AM06598-AS | AM06597-SS |
| AD05066 | AM06599-AS | AM06597-SS |
| AD05067 | AM06601-AS | AM06600-SS |
| AD05089 | AM06639-AS | AM06597-SS |
| AD05090 | AM06641-AS | AM06640-SS |
| AD05092 | AM06643-AS | AM06597-SS |
| AD05093 | AM06645-AS | AM06644-SS |
| AD05094 | AM06647-AS | AM06646-SS |
| AD05095 | AM06649-AS | AM06648-SS |
| AD05096 | AM06651-AS | AM06650-SS |
| AD05097 | AM06653-AS | AM06652-SS |
| AD05098 | AM06655-AS | AM06654-SS |
| AD05099 | AM06657-AS | AM06656-SS |
| AD05100 | AM06659-AS | AM06658-SS |
| AD05101 | AM06661-AS | AM06660-SS |
| AD05102 | AM06663-AS | AM06662-SS |
| AD05103 | AM06665-AS | AM06664-SS |
| AD05104 | AM06667-AS | AM06666-SS |
| AD05105 | AM06669-AS | AM06668-SS |
| AD05106 | AM06671-AS | AM06670-SS |
| AD05107 | AM06673-AS | AM06672-SS |
| AD05108 | AM06675-AS | AM06674-SS |
| AD05109 | AM06677-AS | AM06676-SS |
| AD05110 | AM06679-AS | AM06678-SS |
| AD05111 | AM06681-AS | AM06680-SS |
| AD05112 | AM06683-AS | AM06682-SS |
| AD05113 | AM06685-AS | AM06684-SS |
| AD05114 | AM06687-AS | AM06686-SS |
| AD05115 | AM06689-AS | AM06688-SS |
| AD05122 | AM06703-AS | AM06702-SS |
| AD05123 | AM06705-AS | AM06704-SS |
| AD05124 | AM05921-AS | AM06706-SS |
| AD05125 | AM06708-AS | AM06707-SS |
| AD05126 | AM06710-AS | AM06709-SS |
| AD05150 | AM06710-AS | AM06754-SS |
| AD05151 | AM06756-AS | AM06755-SS |
| AD05180 | AM06796-AS | AM06795-SS |
| AD05181 | AM06798-AS | AM06797-SS |
| AD05182 | AM06799-AS | AM06600-SS |
| AD05183 | AM06601-AS | AM06802-SS |
| AD05184 | AM06601-AS | AM06803-SS |
| AD05185 | AM06601-AS | AM06804-SS |
| AD05186 | AM06601-AS | AM06805-SS |
| AD05187 | AM06806-AS | AM06804-SS |
| AD05188 | AM06808-AS | AM06807-SS |
| AD05189 | AM06810-AS | AM06809-SS |
| AD05190 | AM06810-AS | AM06811-SS |
| AD05191 | AM06810-AS | AM06812-SS |
| AD05192 | AM06810-AS | AM06813-SS |
| AD05193 | AM06815-AS | AM06814-SS |
| AD05194 | AM06815-AS | AM06816-SS |
| AD05195 | AM06815-AS | AM06817-SS |
| AD05196 | AM06815-AS | AM06818-SS |
| AD05197 | AM06820-AS | AM06819-SS |
| AD05198 | AM06822-AS | AM06821-SS |
| AD05199 | AM06824-AS | AM06823-SS |
| AD05200 | AM06826-AS | AM06825-SS |
| AD05201 | AM06828-AS | AM06827-SS |
| AD05202 | AM06830-AS | AM06829-SS |
| AD05203 | AM06832-AS | AM06831-SS |
| AD05204 | AM06834-AS | AM06833-SS |
| AD05205 | AM06836-AS | AM06835-SS |
| AD05206 | AM06838-AS | AM06837-SS |
| AD05207 | AM06840-AS | AM06839-SS |
| AD05208 | AM06842-AS | AM06841-SS |
| AD05209 | AM06851-AS | AM06600-SS |
| AD05210 | AM06853-AS | AM06852-SS |
| AD05211 | AM06855-AS | AM06854-SS |
| AD05212 | AM06857-AS | AM06856-SS |
| AD05213 | AM06859-AS | AM06858-SS |
| AD05214 | AM06861-AS | AM06860-SS |
| AD05240 | AM06601-AS | AM06909-SS |
| AD05241 | AM06799-AS | AM06909-SS |
| AD05242 | AM06911-AS | AM06910-SS |
| AD05243 | AM06796-AS | AM06912-SS |
| AD05244 | AM06914-AS | AM06913-SS |
| AD05245 | AM06916-AS | AM06915-SS |
| AD05246 | AM06918-AS | AM06917-SS |
| AD05247 | AM06920-AS | AM06919-SS |
| AD05248 | AM06918-AS | AM06921-SS |
| AD05256 | AM06601-AS | AM06930-SS |
| AD05257 | AM06601-AS | AM06931-SS |
| AD05261 | AM06916-AS | AM06818-SS |
| AD05262 | AM06916-AS | AM06935-SS |
| AD05263 | AM06916-AS | AM06936-SS |
| AD05264 | AM06916-AS | AM06937-SS |
| AD05265 | AM06916-AS | AM06938-SS |
| AD05266 | AM06916-AS | AM06939-SS |
| AD05267 | AM06916-AS | AM06940-SS |
| AD05268 | AM06916-AS | AM06941-SS |
| AD05352 | AM07073-AS | AM07072-SS |

TABLE 5-continued

ASGR1 RNAi Agent Duplexes Identified by Duplex ID
No. with Corresponding Sense and Antisense Strands.

| Duplex ID | Antisense Strand ID | Sense Strand ID |
|---|---|---|
| AD05353 | AM07075-AS | AM07074-SS |
| AD05354 | AM07077-AS | AM07076-SS |
| AD05355 | AM07079-AS | AM07078-SS |
| AD05356 | AM07079-AS | AM07080-SS |
| AD05357 | AM07079-AS | AM07081-SS |
| AD05358 | AM07083-AS | AM07082-SS |
| AD05359 | AM07085-AS | AM07084-SS |
| AD05360 | AM07085-AS | AM07086-SS |
| AD05361 | AM07088-AS | AM07087-SS |
| AD05362 | AM07090-AS | AM07089-SS |
| AD05363 | AM07092-AS | AM07091-SS |
| AD05364 | AM07092-AS | AM07093-SS |
| AD05365 | AM07092-AS | AM07094-SS |
| AD05366 | AM07096-AS | AM07095-SS |
| AD05367 | AM07098-AS | AM07097-SS |
| AD05373 | AM06601-AS | AM07109-SS |
| AD05374 | AM06601-AS | AM07110-SS |
| AD05375 | AM06851-AS | AM06930-SS |
| AD05376 | AM06851-AS | AM06802-SS |
| AD05377 | AM06851-AS | AM07109-SS |
| AD05378 | AM06851-AS | AM06805-SS |
| AD05379 | AM06851-AS | AM07110-SS |
| AD05380 | AM06806-AS | AM06802-SS |
| AD05460 | AM07209-AS | AM06676-SS |
| AD05461 | AM07210-AS | AM06818-SS |
| AD05462 | AM07210-AS | AM07211-SS |
| AD05463 | AM07210-AS | AM07212-SS |
| AD05464 | AM07213-AS | AM06818-SS |
| AD05465 | AM07214-AS | AM06818-SS |
| AD05466 | AM07210-AS | AM06814-SS |
| AD05467 | AM07210-AS | AM06941-SS |
| AD05468 | AM07213-AS | AM06814-SS |
| AD05469 | AM07214-AS | AM06814-SS |
| AD05470 | AM07216-AS | AM07215-SS |
| AD05603 | AM06815-AS | AM07212-SS |
| AD05604 | AM06815-AS | AM07211-SS |
| AD05605 | AM07210-AS | AM07388-SS |
| AD05606 | AM07390-AS | AM07389-SS |
| AD05607 | AM07392-AS | AM07391-SS |
| AD05608 | AM07394-AS | AM07393-SS |
| AD05609 | AM07396-AS | AM07395-SS |
| AD05610 | AM07398-AS | AM07397-SS |
| AD05624 | AM06815-AS | AM07414-SS |
| AD05640 | AM06815-AS | AM07444-SS |
| AD05641 | AM06815-AS | AM07445-SS |
| AD05642 | AM06815-AS | AM07446-SS |
| AD05643 | AM06815-AS | AM07447-SS |
| AD05644 | AM06815-AS | AM07448-SS |
| AD05645 | AM07449-AS | AM07211-SS |
| AD05646 | AM06815-AS | AM07450-SS |
| AD05647 | AM07210-AS | AM07450-SS |
| AD05648 | AM06601-AS | AM07451-SS |
| AD05649 | AM06851-AS | AM07451-SS |
| AD05650 | AM06601-AS | AM07452-SS |
| AD05651 | AM06851-AS | AM07452-SS |
| AD05674 | AM07487-AS | AM06802-SS |
| AD05675 | AM07488-AS | AM06600-SS |
| AD05676 | AM07487-AS | AM07110-SS |
| AD05677 | AM07489-AS | AM06818-SS |
| AD05678 | AM07489-AS | AM06814-SS |
| AD05679 | AM07490-AS | AM07211-SS |
| AD05680 | AM07492-AS | AM07491-SS |
| AD05682 | AM07210-AS | AM07494-SS |
| AD05692 | AM07501-AS | AM07500-SS |
| AD05740 | AM07576-AS | AM06600-SS |
| AD05741 | AM07577-AS | AM06600-SS |
| AD05742 | AM07576-AS | AM06802-SS |

In some embodiments, an ASGR1 RNAi agent is prepared or provided as a salt, mixed salt, or a free-acid. The RNAi agents described herein, upon delivery to a cell expressing an ASGR1 gene, inhibit or knockdown expression of one or more ASGR1 genes in vivo.

Targeting Groups, Linking Groups, and Delivery Vehicles

In some embodiments, an ASGR1 RNAi agent is conjugated to one or more non-nucleotide groups including, but not limited to, a targeting group, linking group, delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, an ASGR1 RNAi agent contains a non-nucleotide group linked to the 3' and/or 5' end of the sense strand. In some embodiments, anon-nucleotide group is linked to the 5' end of an ASGR1 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which can in some instances serve as linkers. In some embodiments, a targeting group comprises a galactose-derivative cluster.

The ASGR1 RNAi agents described herein may be synthesized having a reactive group, such as an amino group (also referred to herein as an amine), at the 5'-terminus and/or the 3'-terminus. The reactive group may be used to subsequently attach a targeting group using methods typical in the art.

In some embodiments, a targeting group comprises an asialoglycoprotein receptor ligand. As used herein, an asialoglycoprotein receptor ligand is a ligand that contains a compound having affinity for the asialoglycoprotein receptor. As noted herein, the asialoglycoprotein receptor is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative) or multimeric (e.g., having multiple galactose derivatives). The galactose derivative or galactose derivative cluster may be attached to the 3' or 5' end of the sense or antisense strand of the RNAi agent using methods known in the art. The preparation of targeting groups, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem. 1995 Vol. 39 p. 1538-1546). In some embodiments, the PEG spacer is a PEGS spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering an ASGR1 RNAi agent to a liver cell in vivo. Such pharmaceutical compositions can include, for example, an ASGR1 RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

Targeting groups include, but are not limited to, (PAZ), (NAG13), (NAG13)s, (NAG18), (NAG18)s, (NAG24), (NAG24)s, (NAG25), (NAG25)s, (NAG26), (NAG26)s, (NAG27) (NAG27)s, (NAG28) (NAG28)s, (NAG29) (NAG29)s, (NAG30) (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s, as defined in Table 6. Other targeting groups, including galactose cluster targeting ligands, are known in the art.

In some embodiments, a linking group is conjugated to the RNAi agent. The linking group facilitates covalent linkage of the agent to a targeting group or delivery polymer or delivery vehicle. The linking group can be linked to the 3' or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include, but are not limited to: reactive groups such a primary amines and alkynes, alkyl groups, abasic nucleotides, ribitol (abasic ribose), and/or PEG groups.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

Any of the ASGR1 RNAi agent nucleotide sequences listed in Tables 2, 3 or 4, whether modified or unmodified, may contain 3' or 5' targeting groups or linking groups. Any of the ASGR1 RNAi agent sequences listed in Tables 3 or 4 which contain a 3' or 5' targeting group or linking group, may alternatively contain no 3' or 5' targeting group or linking group, or may contain a different 3' or 5' targeting group or linking group including, but not limited to, those depicted in Table 6. Any of the ASGR1 RNAi agent duplexes listed in Table 2 or Table 5, whether modified or unmodified, may further comprise a targeting group or linking group, including, but not limited to, those depicted in Table 6, and the targeting group or linking group may be attached to the 3' or 5' terminus of either the sense strand or the antisense strand of the ASGR1 RNAi agent duplex.

Examples of targeting groups and linking groups are provided in Table 6. Table 4 provides several embodiments of ASGR1 RNAi agent sense strands having a targeting group or linking group linked to the 5' or 3' end.

TABLE 6
Structures Representing Various Modified Nucleotides, Targeting Groups, and Linking Groups.
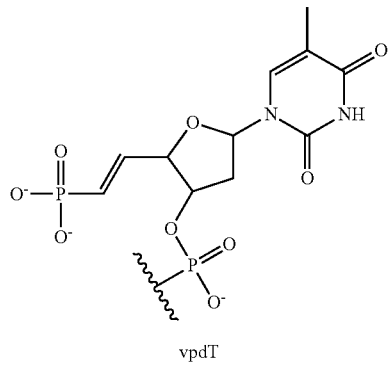 [SMILES: *P(=O)([O-])OC1CC(n2cc(C)c(=O)[nH]c2=O)OC1/C=C/P(=O)([O-])[O-]]
vpdT
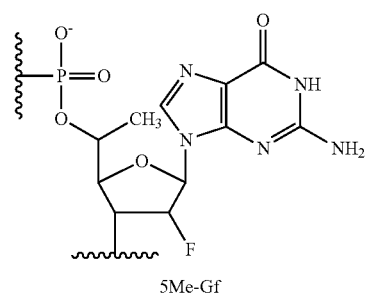 [SMILES: *C1C(F)C(n2cnc3c(=O)[nH]c(N)nc32)OC1C(C)OP(*)(=O)[O-]]
5Me-Gf
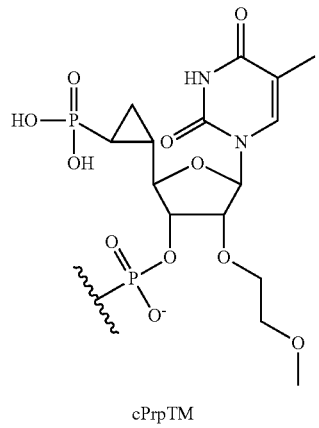 [SMILES: *P(=O)([O-])OC1C(C2CC2P(=O)(O)O)OC(n2cc(C)c(=O)[nH]c2=O)C1OCCOC]
cPrpTM
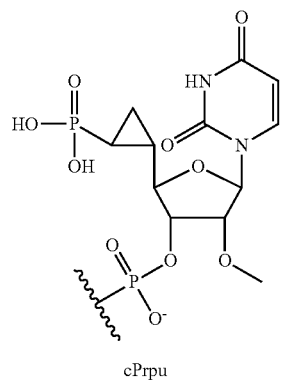 [SMILES: *P(=O)([O-])OC1C(C2CC2P(=O)(O)O)OC(n2ccc(=O)[nH]c2=O)C1OC]
cPrpu TABLE 6-continued
Structures Representing Various Modified Nucleotides, Targeting Groups, and Linking Groups.
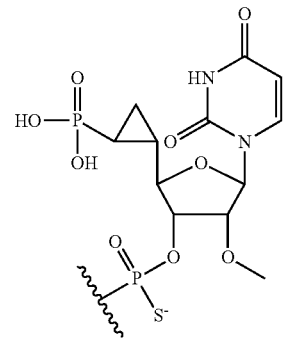
cPrpus
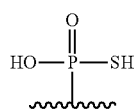
sp
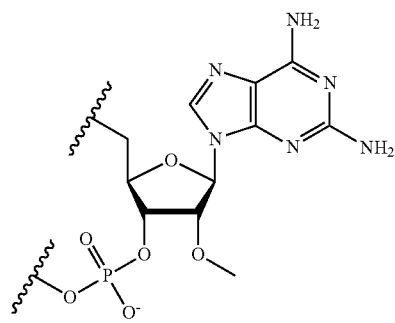
a_2N
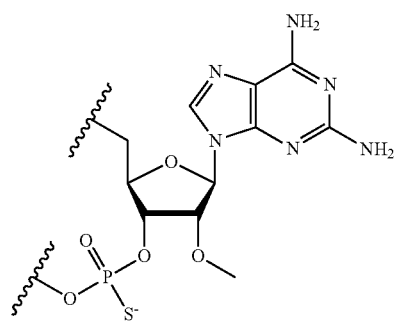
a_2Ns
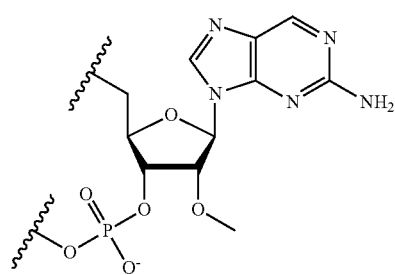
pu_2N

TABLE 6-continued
Structures Representing Various Modified Nucleotides, Targeting Groups, and Linking Groups.
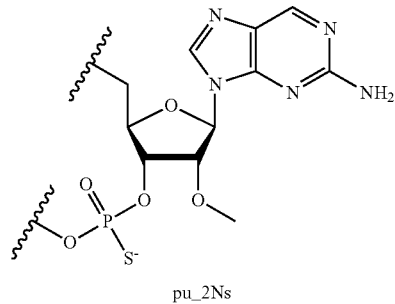
pu_2Ns
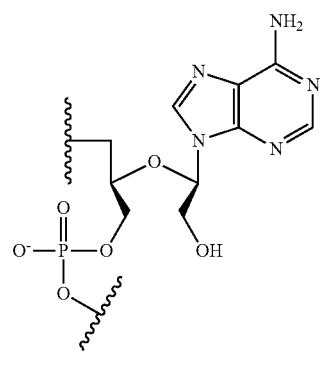
A$_{UNA}$
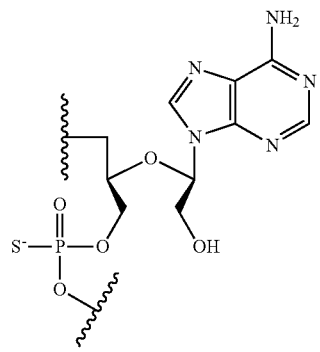
A$_{UNAS}$
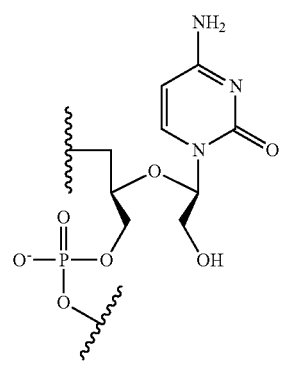
C$_{UNA}$ TABLE 6-continued
Structures Representing Various Modified Nucleotides, Targeting Groups, and Linking Groups.
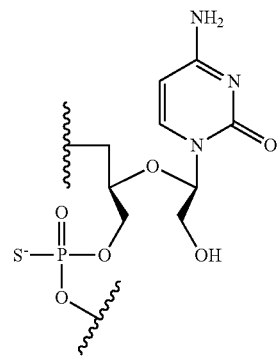
C<sub>UNAS</sub>
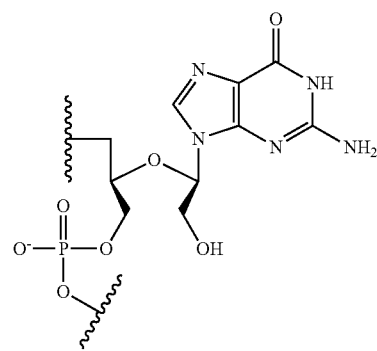
G<sub>UNA</sub>
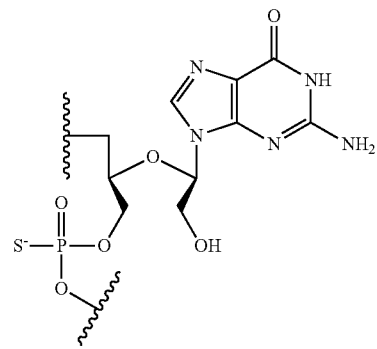
G<sub>UNAS</sub>
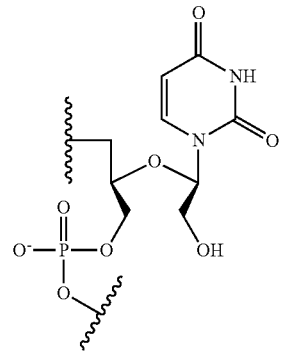
U<sub>UNA</sub>

TABLE 6-continued
Structures Representing Various Modified Nucleotides, Targeting Groups, and Linking Groups.
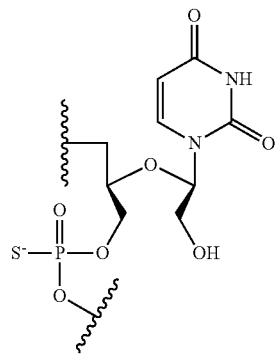
U$_{UNAS}$
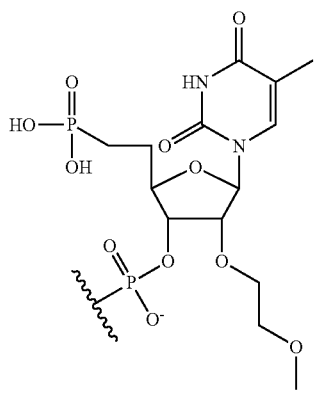
epTM
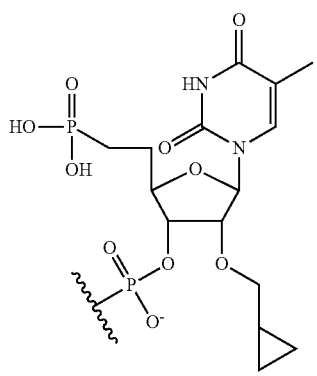
epTcPr
When positioned internally in oligonucleotide:
linkage towards 5' end of oligonucleotide
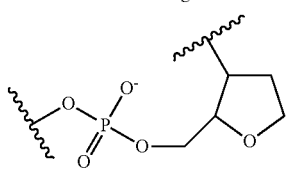
linkage towards 3' end of oligonucleotide
(invAb)

TABLE 6-continued

Structures Representing Various Modified Nucleotides, Targeting Groups, and Linking Groups.

When positioned internally in oligonucleotide:

linkage towards 5' end of oligonucleotide

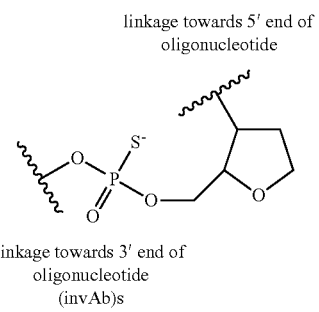

linkage towards 3' end of oligonucleotide
(invAb)s

When positioned at the 3' terminal end of oligonucleotide:

linkage towards 5' end of oligonucleotide

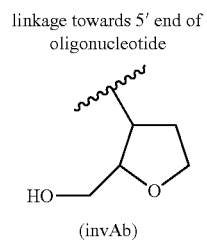

(invAb)

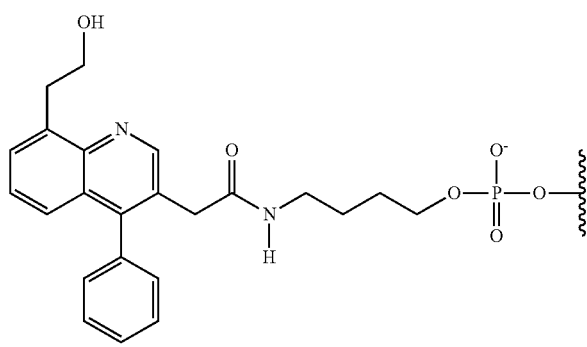

(PAZ)

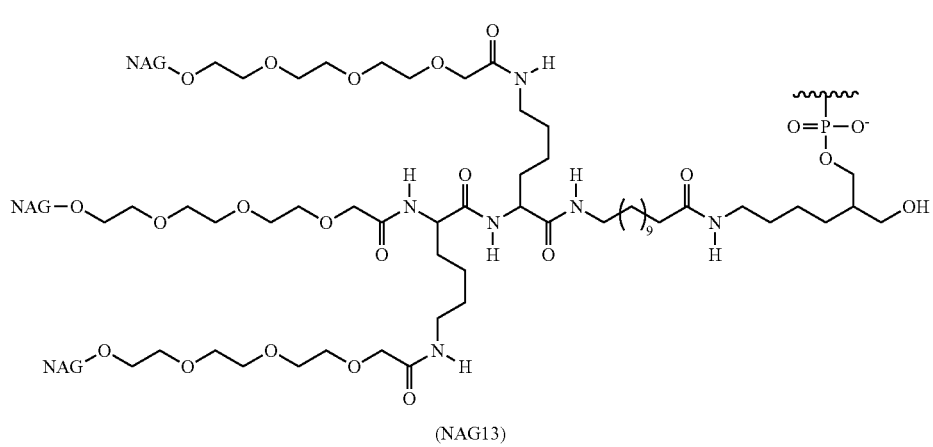

(NAG13)

TABLE 6-continued
Structures Representing Various Modified Nucleotides, Targeting Groups, and Linking Groups.
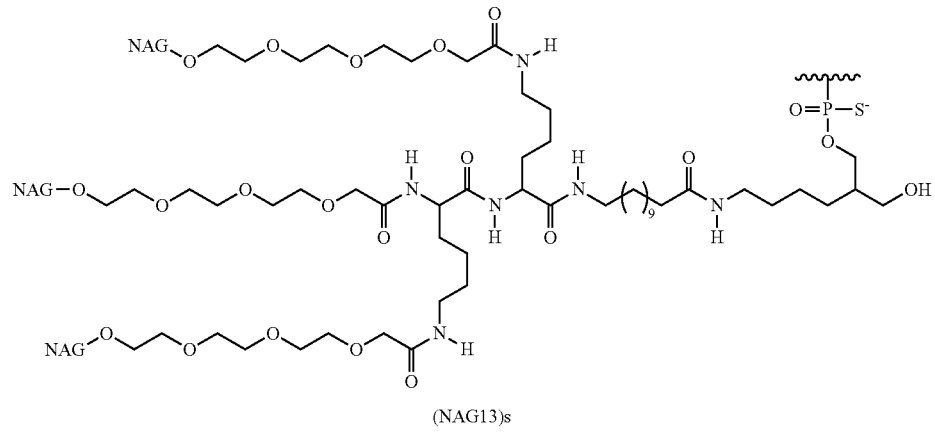
(NAG13)s
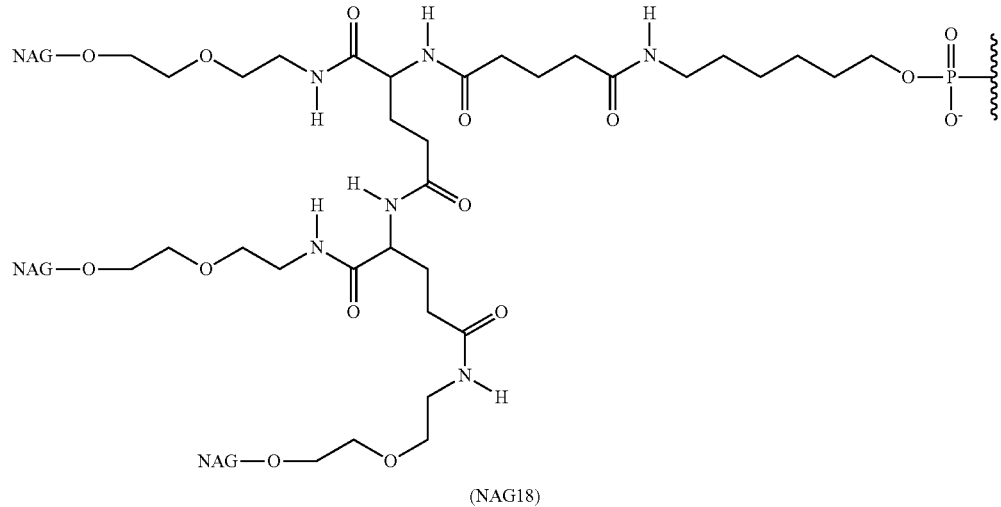
(NAG18)
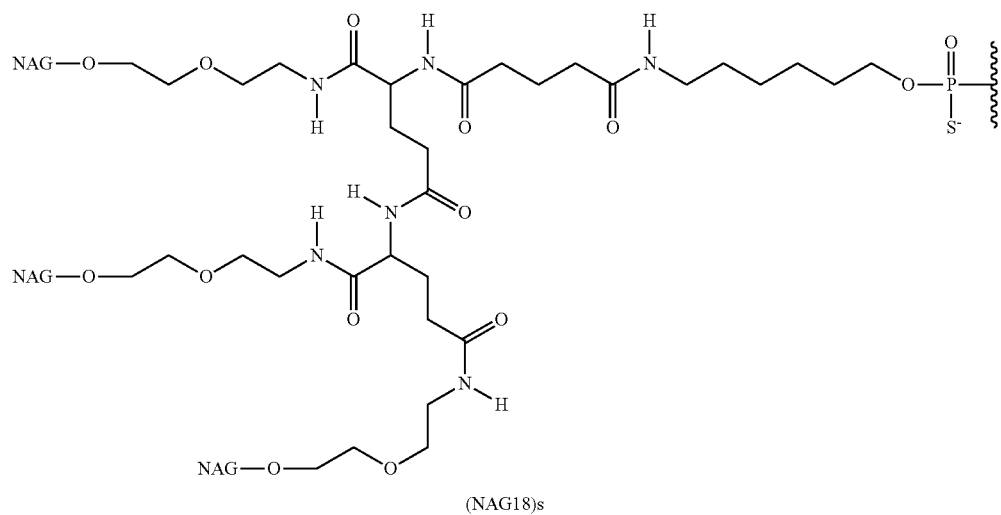
(NAG18)s TABLE 6-continued
Structures Representing Various Modified Nucleotides, Targeting Groups, and Linking Groups.
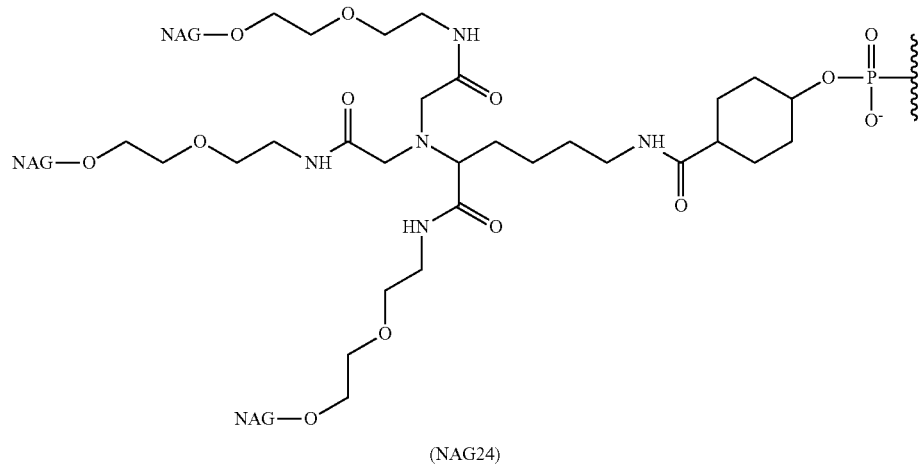
(NAG24)
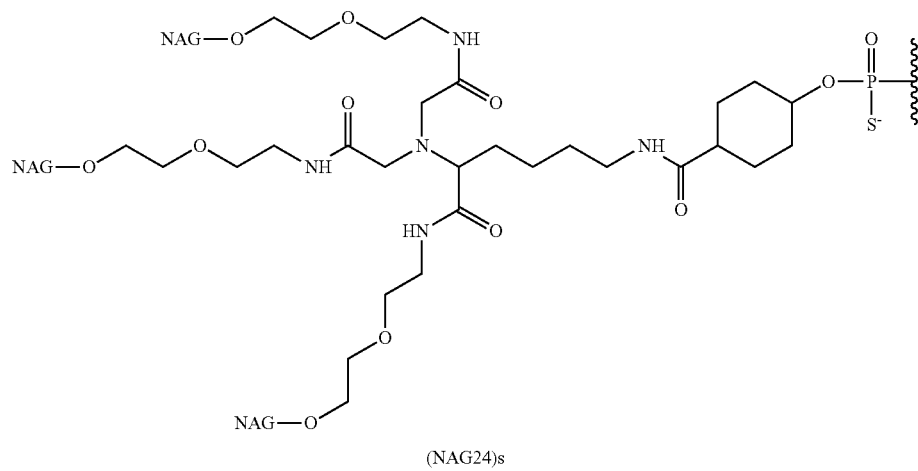
(NAG24)s
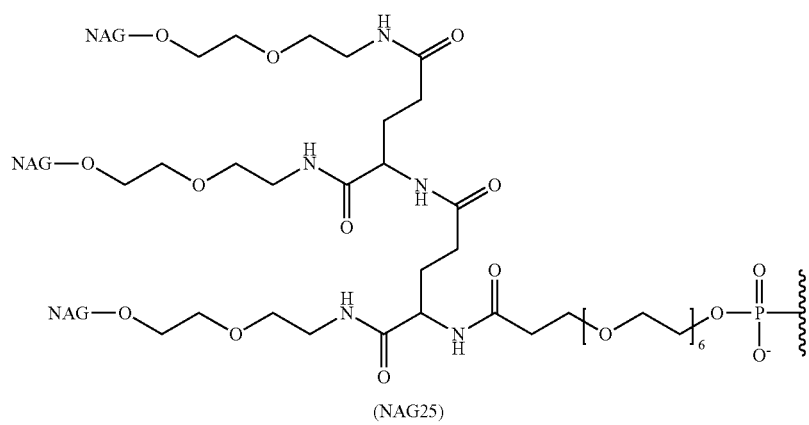
(NAG25)

TABLE 6-continued
Structures Representing Various Modified Nucleotides, Targeting Groups, and Linking Groups.
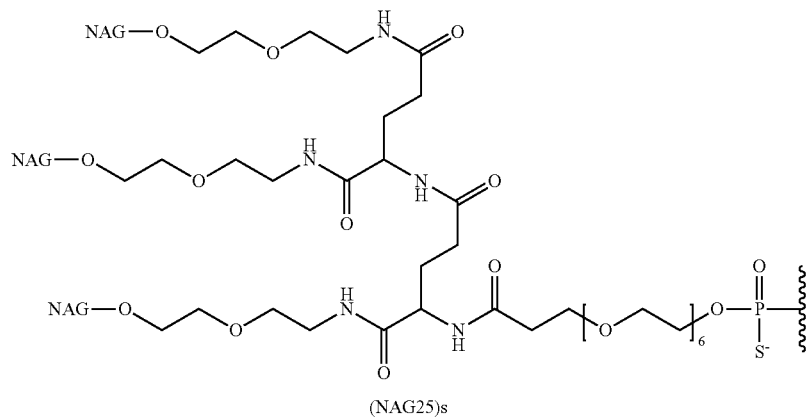
(NAG25)s
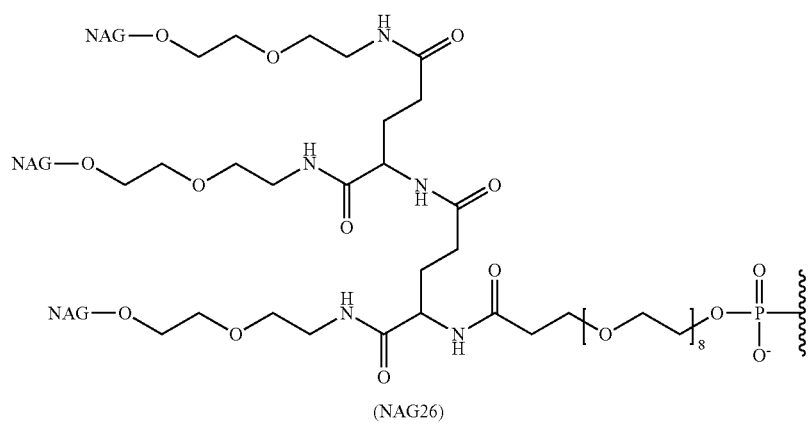
(NAG26)
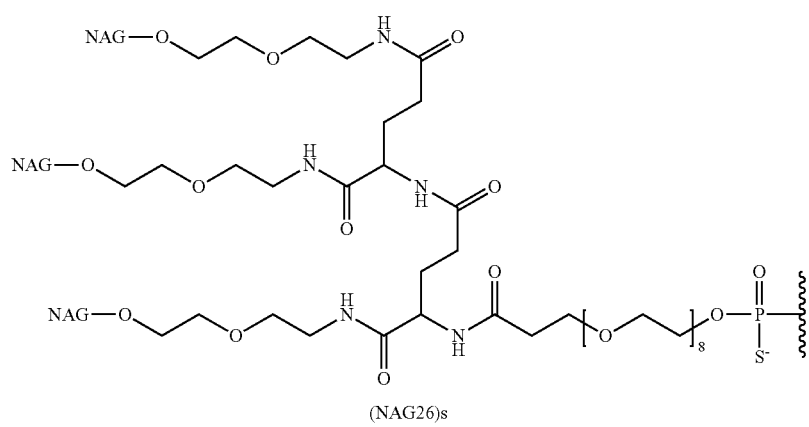
(NAG26)s TABLE 6-continued
Structures Representing Various Modified Nucleotides, Targeting Groups, and Linking Groups.
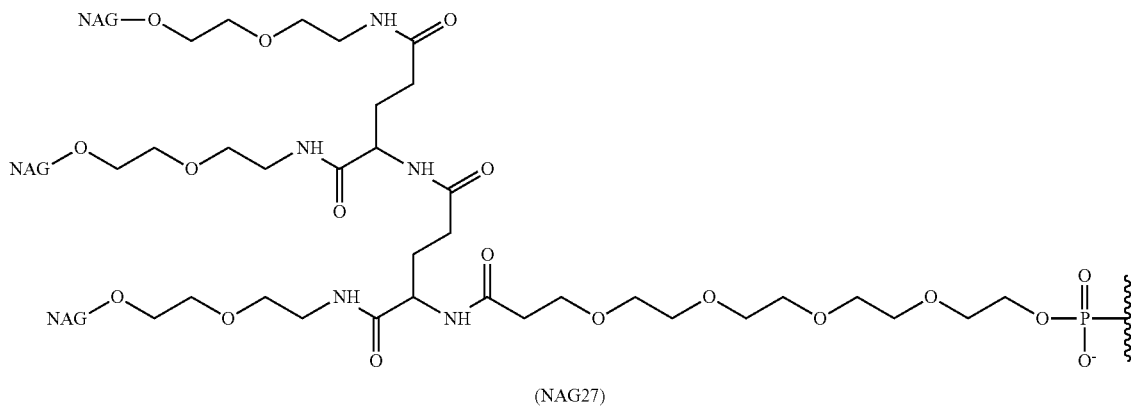
(NAG27)
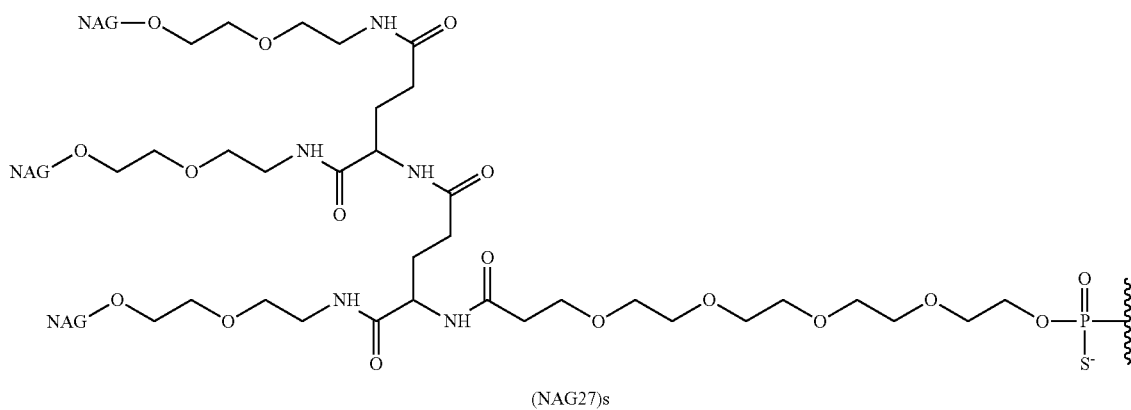
(NAG27)s
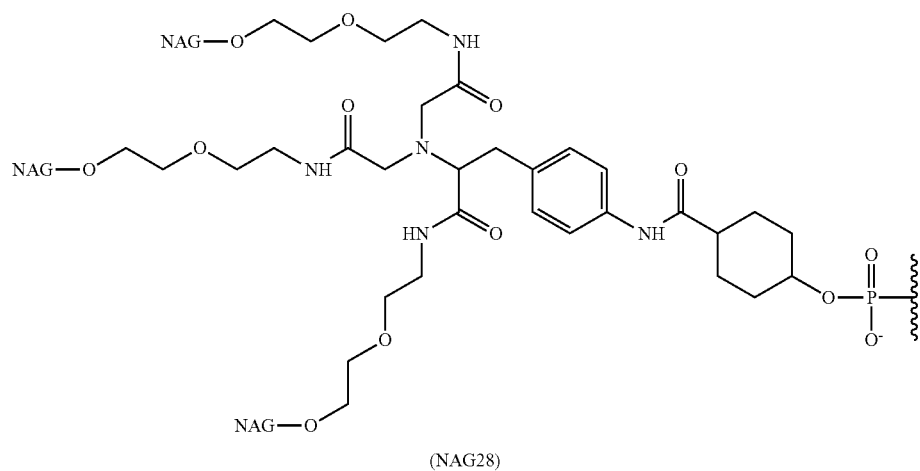
(NAG28)

TABLE 6-continued
Structures Representing Various Modified Nucleotides, Targeting Groups, and Linking Groups.
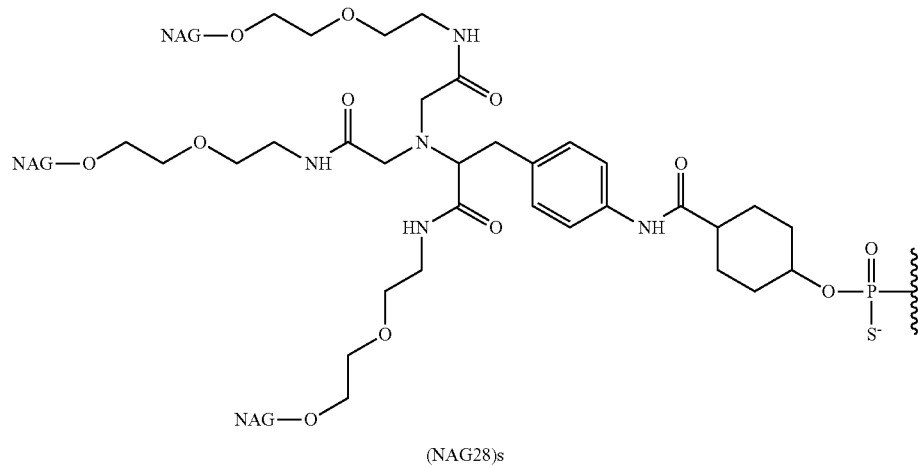
(NAG28)s
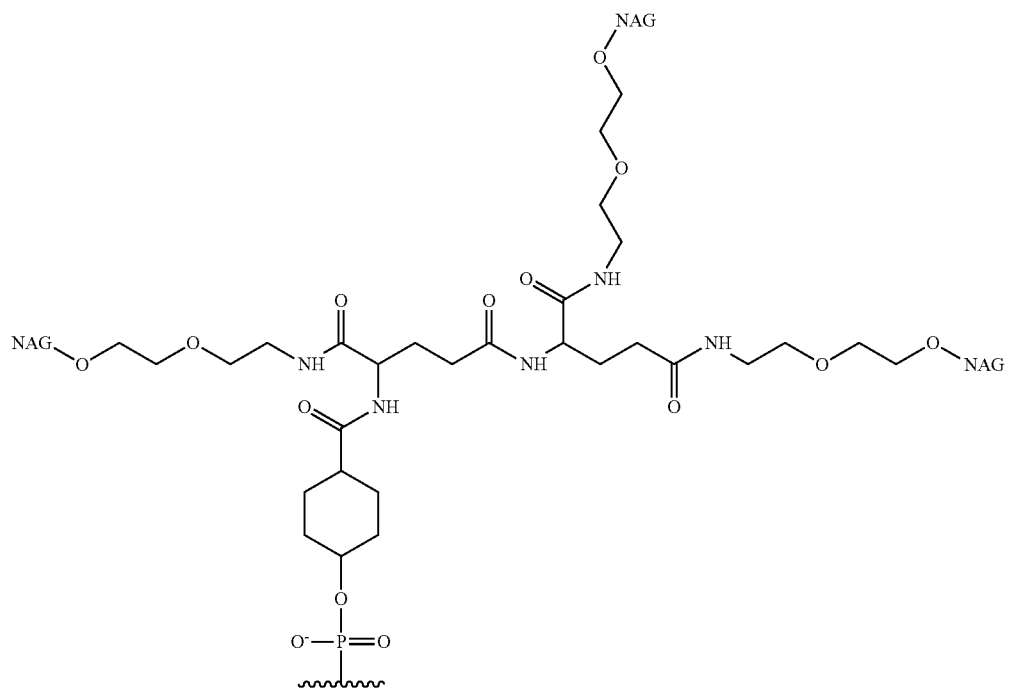
(NAG29)

TABLE 6-continued
Structures Representing Various Modified Nucleotides, Targeting Groups, and Linking Groups.
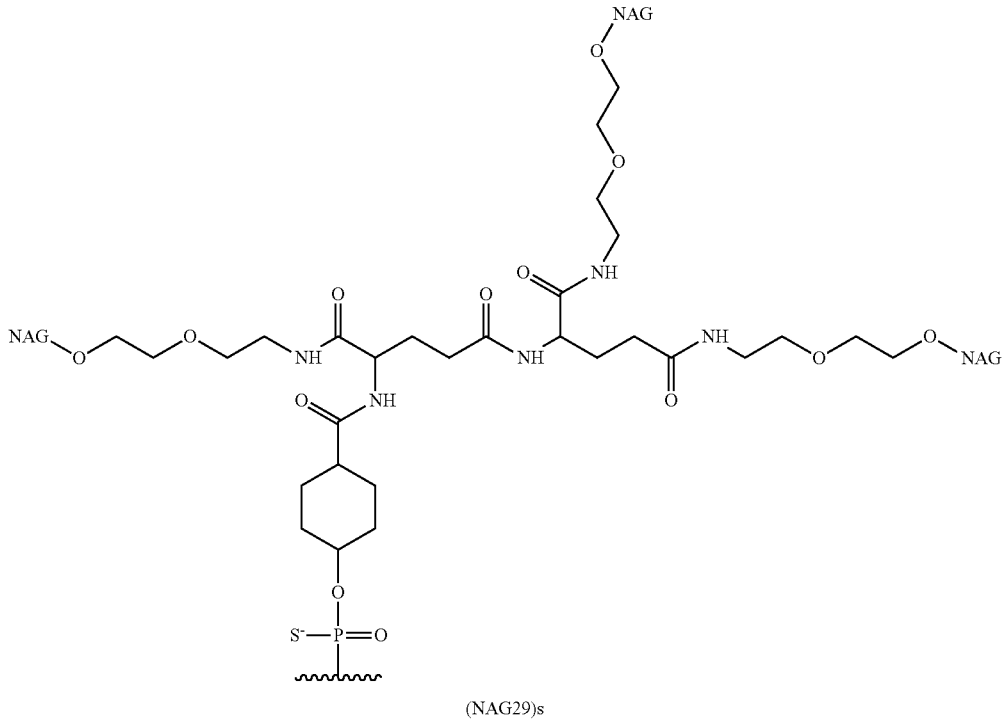
(NAG29)s
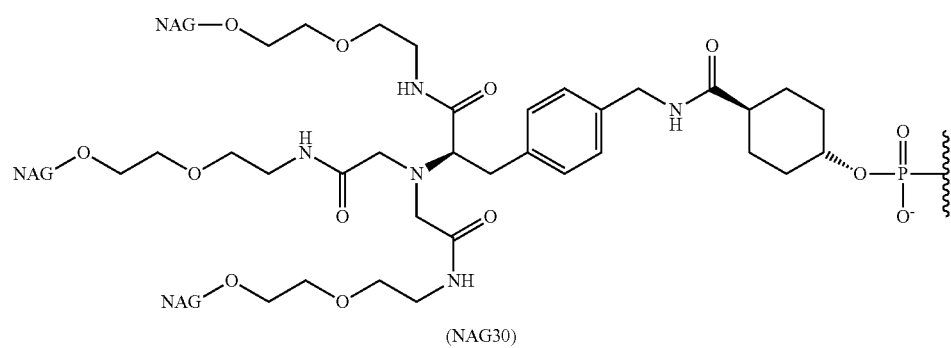
(NAG30)
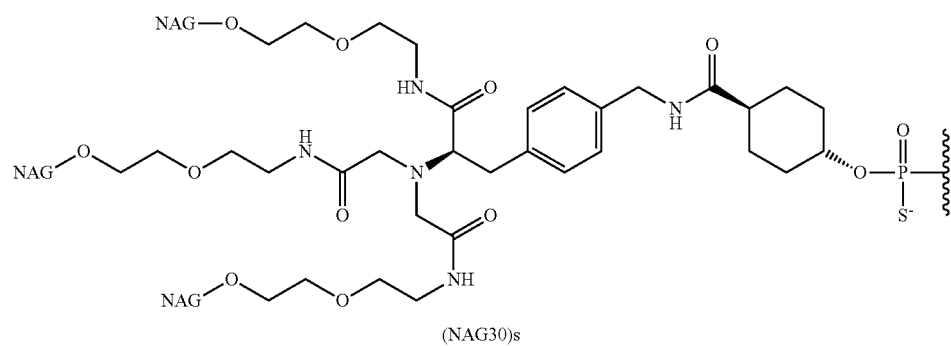
(NAG30)s TABLE 6-continued
Structures Representing Various Modified Nucleotides, Targeting Groups, and Linking Groups.
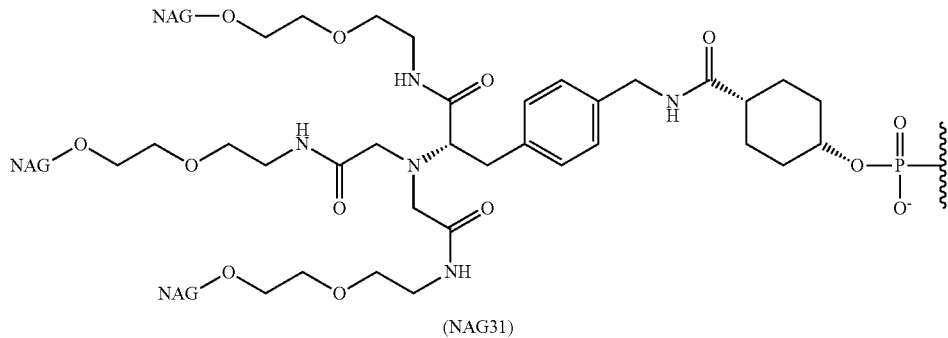
(NAG31)
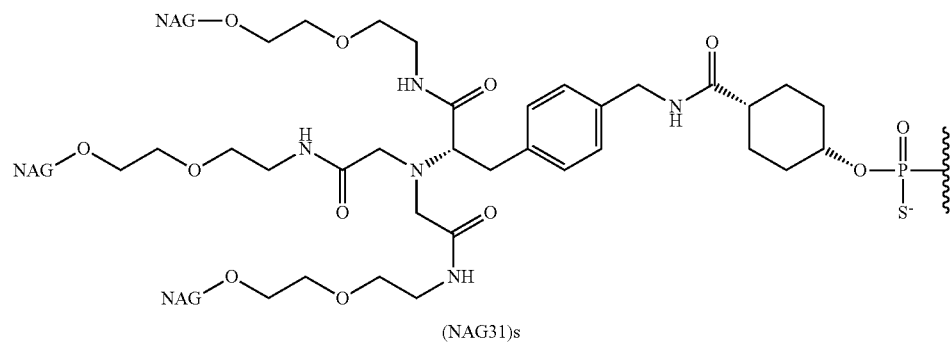
(NAG31)s
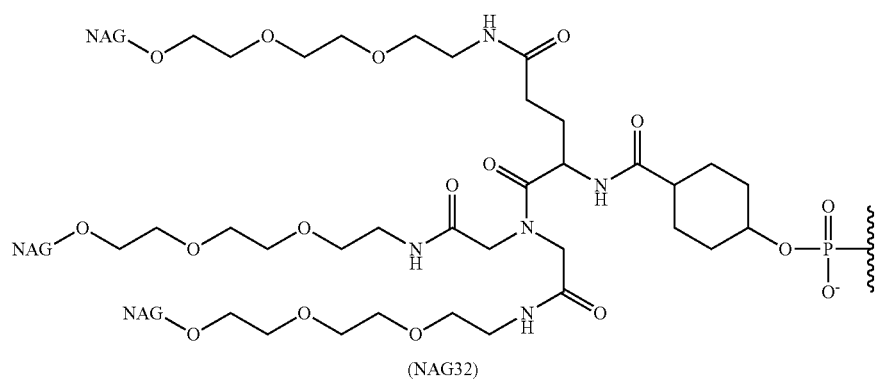
(NAG32)
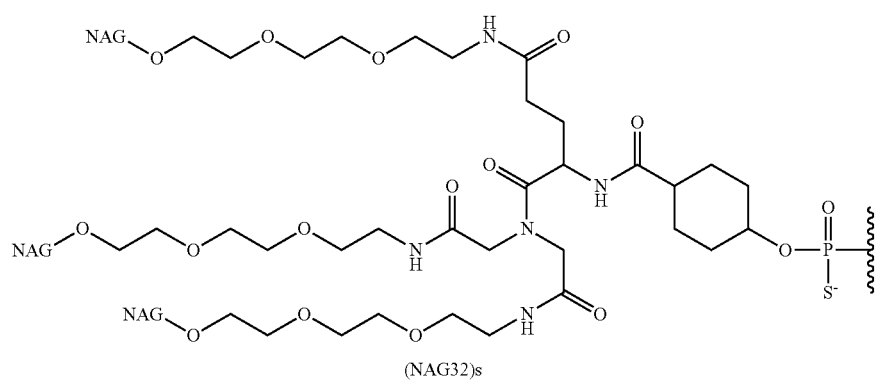
(NAG32)s TABLE 6-continued
Structures Representing Various Modified Nucleotides, Targeting Groups, and Linking Groups.
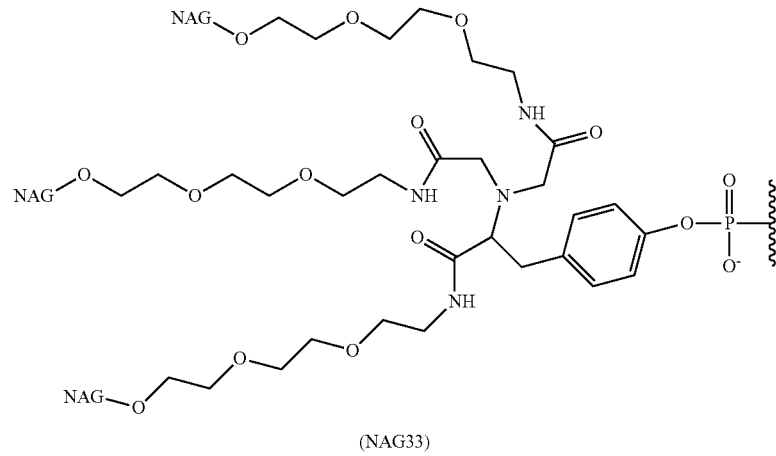
(NAG33)
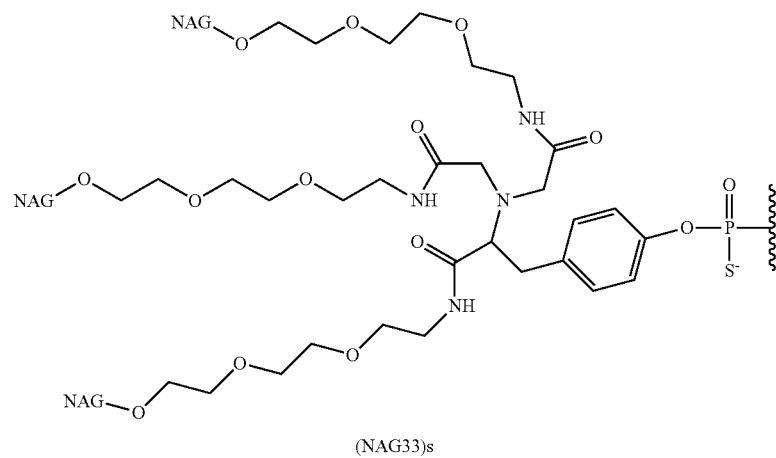
(NAG33)s
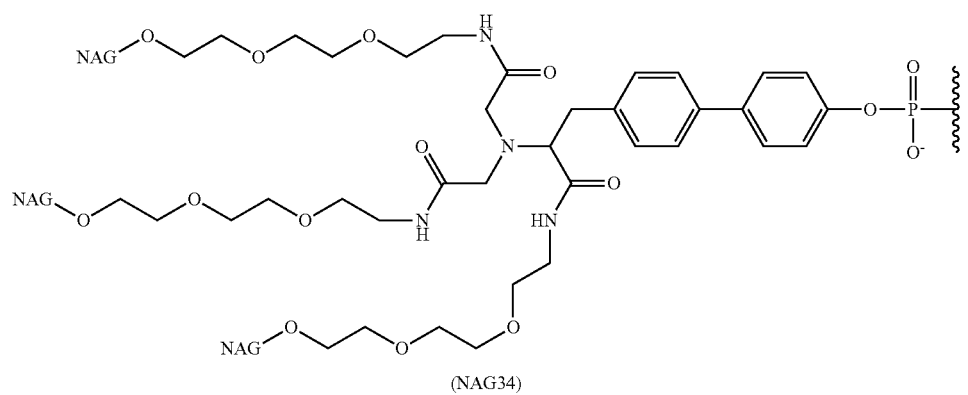
(NAG34)

TABLE 6-continued
Structures Representing Various Modified Nucleotides, Targeting Groups, and Linking Groups.
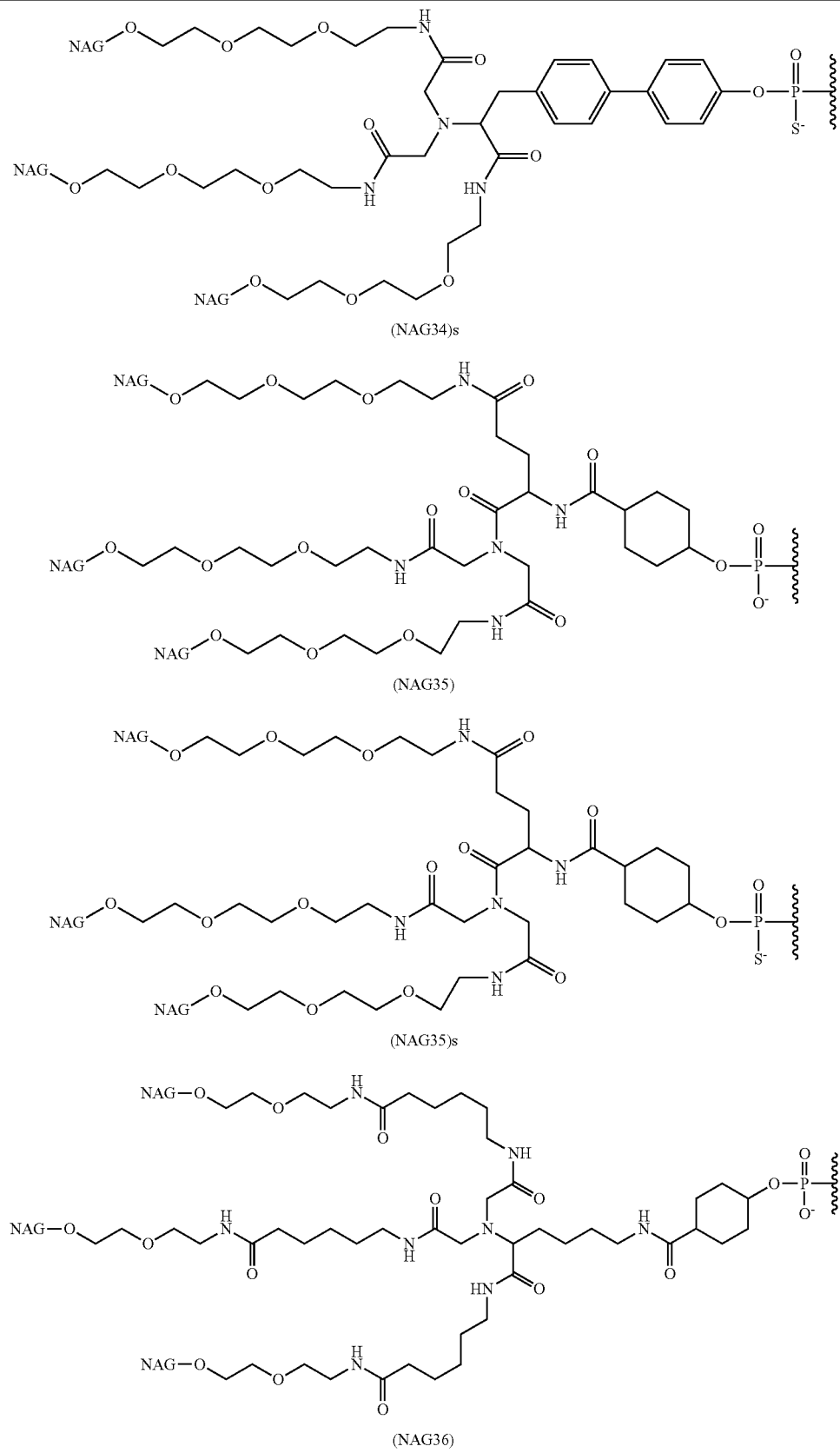

TABLE 6-continued
Structures Representing Various Modified Nucleotides, Targeting Groups, and Linking Groups.
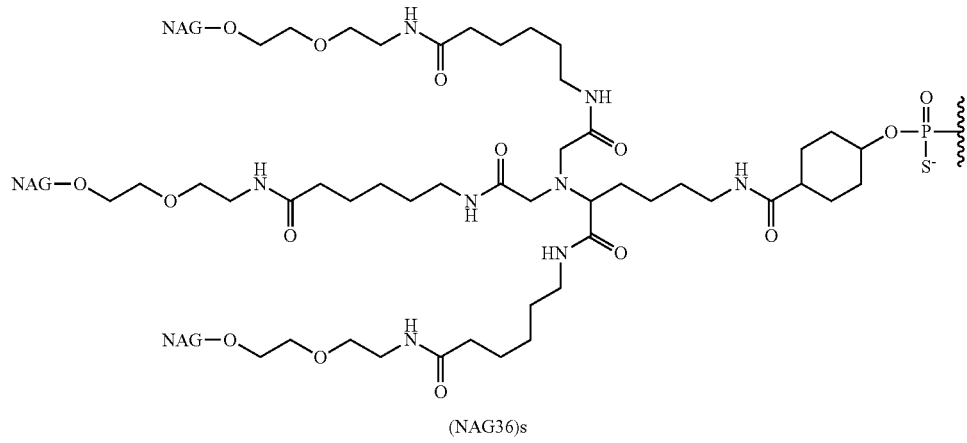
(NAG36)s
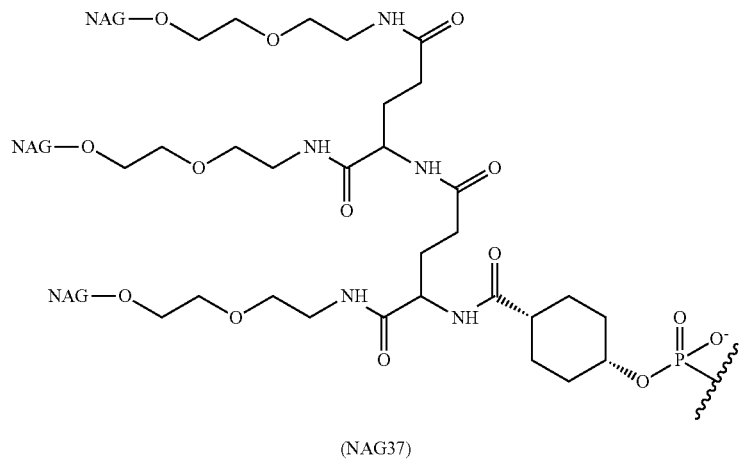
(NAG37)
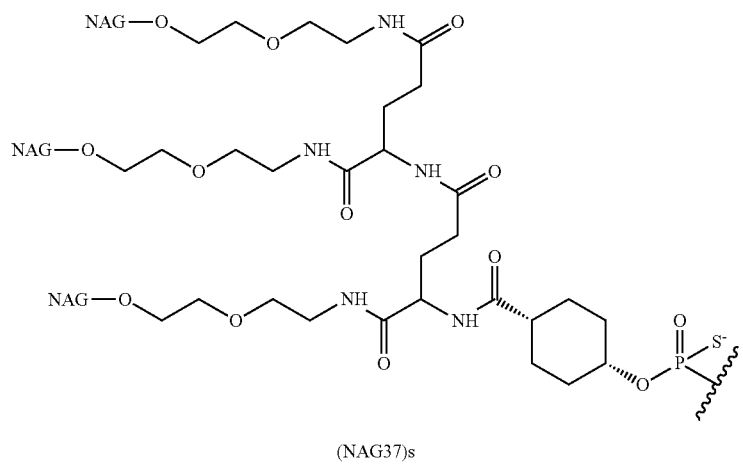
(NAG37)s TABLE 6-continued
Structures Representing Various Modified Nucleotides, Targeting Groups, and Linking Groups.
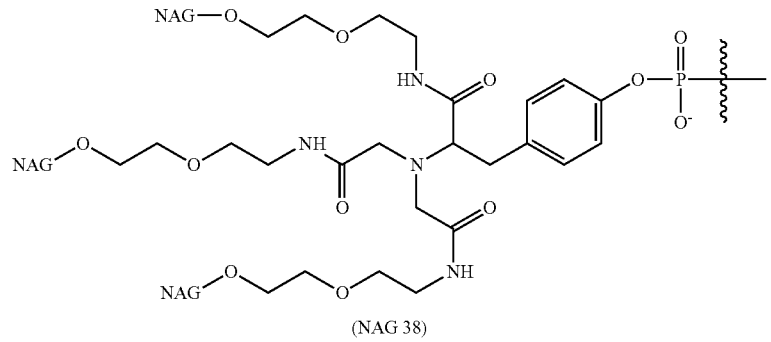
(NAG 38)
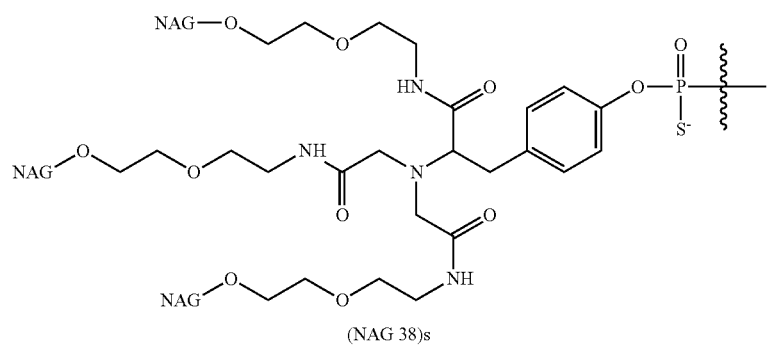
(NAG 38)s
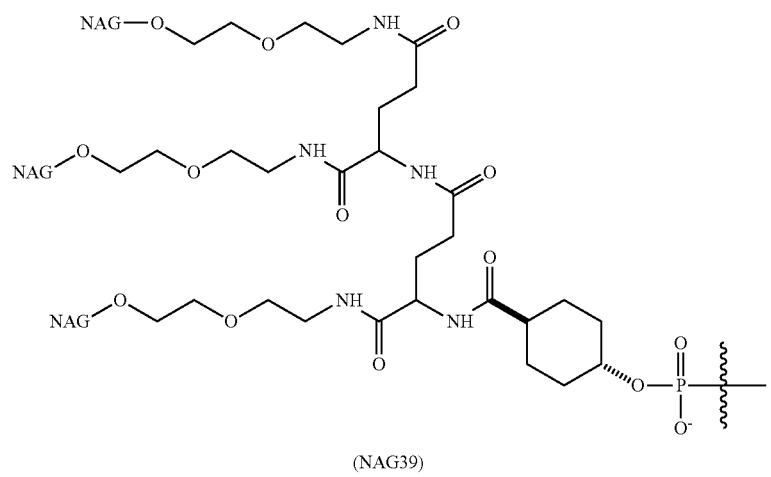
(NAG39)

TABLE 6-continued

Structures Representing Various Modified Nucleotides, Targeting Groups, and Linking Groups.

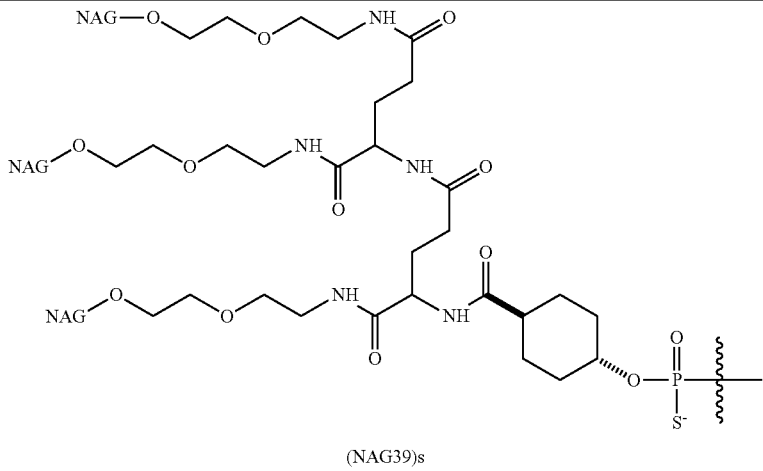

(NAG39)s

In each of the above structures in Table 6, NAG comprises an N-acetyl-galactosamine or another asialoglycoprotein receptor ligand, as would be understood by a person of ordinary skill in the art to be attached in view of the structures above and description provided herein. For example, in some embodiments, NAG in the structures provided in Table 6 is represented by the following structure:

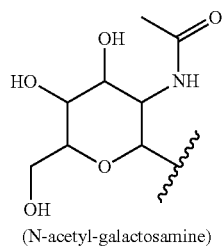 [SMILES: *C1OC(CO)C(O)C(O)C1NC(C)=O]

(N-acetyl-galactosamine)

Each (NAGx) may be attached to an ASGR1 RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

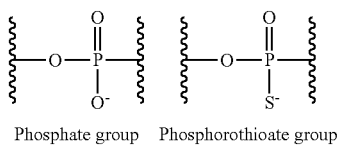 [SMILES: *OP(*)(=O)[O-] ; *OP(*)(=O)[S-]]

Phosphate group   Phosphorothioate group

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

Pharmaceutical Compositions and Formulations

The ASGR1 RNAi agents disclosed herein can be prepared as pharmaceutical compositions or formulations (also referred to herein as "medicaments"). In some embodiments, pharmaceutical compositions include at least one ASGR1 RNAi agent. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering an ASGR1 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions including an ASGR1 RNAi agent, thereby forming a pharmaceutical formulation suitable for in vivo delivery to a subject, including a human.

The pharmaceutical compositions that include an ASGR1 RNAi agent and methods disclosed herein decrease the level of the target mRNA in a cell, group of cells, group of cells, tissue, or subject, including by administering to the subject a therapeutically effective amount of a herein described ASGR1 RNAi agent, thereby inhibiting the expression of ASGR1 mRNA in the subject. In some embodiments, the subject has been previously identified as having a pathogenic upregulation of the target gene in the targeted cell or tissue.

In some embodiments, the described pharmaceutical compositions including an ASGR1 RNAi agent are used for treating or managing clinical presentations associated with elevated non-HDL-C levels, and/or elevated LDL-C levels, and/or elevated total cholesterol levels, and/or elevated TG levels, and/or over-expression of ASGR1 mRNA. In some embodiments, a therapeutically or prophylactically effective amount of one or more of pharmaceutical compositions is administered to a subject in need of such treatment, prevention or management. In some embodiments, administration of any of the disclosed ASGR1 RNAi agents can be used to decrease the number, severity, and/or frequency of symptoms of a disease in a subject. In some embodiments, the subject has been previously identified or diagnosed as having elevated cholesterol levels, elevated triglyceride levels, and/or some other dyslipidemia.

The described pharmaceutical compositions including an ASGR1 RNAi agent can be used to treat at least one symptom in a subject having a disease or disorder that would benefit from reduction or inhibition in expression of ASGR1 mRNA. In some embodiments, the subject is administered a therapeutically effective amount of one or more pharmaceutical compositions including an ASGR1 RNAi agent thereby treating the symptom. In other embodiments, the subject is administered a prophylactically effective amount of one or more ASGR1 RNAi agents, thereby preventing the at least one symptom.

The route of administration is the path by which an ASGR1 RNAi agent is brought into contact with the body. In general, methods of administering drugs, oligonucleotides, and nucleic acids, for treatment of a mammal, are well known in the art and can be applied to administration of the compositions described herein. The ASGR1 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including an ASGR1 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the herein described compositions. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable excipients. In some embodiments, the pharmaceutical compositions described herein can be formulated for administration to a subject.

As used herein, a pharmaceutical composition or medicament includes a pharmacologically effective amount of at least one of the described ASGR1 RNAi agents and one or more pharmaceutically acceptable excipients. Pharmaceutically acceptable excipients (excipients) are substances other than the Active Pharmaceutical Ingredient (API, therapeutic product, e.g., ASGR1 RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The ASGR1 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including an ASGR1 RNAi agent can be combined with an excipient or with a second therapeutic agent or treatment including, but not limited to: a second or other RNAi agent, a small molecule drug, an antibody, an antibody fragment, peptide and/or aptamer.

The described ASGR1 RNAi agents, when added to pharmaceutically acceptable excipients or adjuvants, can be packaged into kits, containers, packs, or dispensers. The pharmaceutical compositions described herein may be packaged in pre-filled syringes or vials.

Methods of Treatment and Inhibition of Expression

The ASGR1 RNAi agents disclosed herein can be used to treat a subject (e.g., a human or other mammal) having a disease or disorder that would benefit from administration of the compound. In some embodiments, the RNAi agents disclosed herein can be used to treat a subject (e.g., a human) having a disease or disorder that would benefit from reduction or inhibition in expression of ASGR1 mRNA. The subject is administered a therapeutically effective amount of any one or more of the ASGR1 RNAi agents described herein. The subject can be a human, patient, or human patient. The subject may be an adult, adolescent, child, or infant. The described pharmaceutical compositions including an ASGR1 RNAi agent can be used to provide methods for the therapeutic treatment of diseases. Such methods include administration of a pharmaceutical composition described herein to a human being or animal.

In some embodiments, the ASGR1 RNAi agents described herein are used to treat a subject with an ASGR1-related disease or disorder. An "ASGR1-related disease or disorder" refers to conditions, diseases, or disorders in which ASGR1 expression levels are altered or where elevated expression levels of ASGR1 are associated with an increased risk of developing the condition, disease or disorder. ASGR1-related diseases or disorders include, but are not limited to, obesity, metabolic syndrome, hyperlipidemia, hypertriglyceridemia, hypercholesterolemia, abnormal lipid and/or cholesterol metabolism, atherosclerosis, diabetes, cardiovascular disease, coronary artery disease, myocardial infarction, peripheral vascular disease, cerebrovascular disease and other metabolic-related disorders and diseases. In some embodiments, the described ASGR1 RNAi agents are used to treat at least one symptom in a subject having an ASGR1-related disease or disorder. The subject is administered a therapeutically effective amount of any one or more of the described RNAi agents. In some embodiments, the present invention provides for the use of an ASGR1 RNAi agent described herein for the preparation of a medicament for treating an ASGR1-related disease or disorder in a patient in need thereof. In other embodiments, the present invention provides an ASGR1 RNAi agent described herein for use in a method for treating ASGR1-related diseases in a patient in need thereof.

In certain embodiments, the present invention provides a method for reducing the risk of myocardial infarction in a patient in need thereof comprising administering to the patient any of the ASGR1 RNAi agents described herein. A patient who is at risk of having a myocardial infarction may be a patient who has a history of myocardial infarction (e.g. has had a previous myocardial infarction). A patient at risk of having a myocardial infarction may also be a patient who has a familial history of myocardial infarction or who has one or more risk factors of myocardial infarction. Such risk factors include, but are not limited to, hypertension, elevated levels of non-HDL cholesterol, elevated levels of triglycerides, diabetes, obesity, or history of autoimmune diseases (e.g. rheumatoid arthritis, lupus). In one embodiment, a patient who is at risk of having a myocardial infarction is a patient who has or is diagnosed with coronary artery disease. The risk of myocardial infarction in these and other patients can be reduced by administering to the patients any of the ASGR1 RNAi agents described herein. In some embodiments, the present invention provides for the use of an ASGR1 RNAi agent described herein for the preparation of a medicament for reducing the risk of myocardial infarction in a patient in need thereof. In other embodiments, the present invention provides an ASGR1 RNAi agent described herein for use in a method for reducing the risk of myocardial infarction in a patient in need thereof.

In some embodiments, the present invention provides a method for reducing non-HDL cholesterol in a patient in need thereof by administering to the patient any of the ASGR1 RNAi agents described herein. Non-HDL cholesterol is a measure of all cholesterol-containing proatherogenic lipoproteins, including LDL cholesterol, very low-density lipoprotein, intermediate-density lipoprotein, lipoprotein(a), chylomicron, and chylomicron remnants. Non-HDL cholesterol has been reported to be a good predictor of cardiovascular risk (Rana et al., Curr. Atheroscler. Rep., Vol. 14:130-134, 2012). Non-HDL cholesterol levels can be calculated by subtracting HDL cholesterol levels from total cholesterol levels. In one embodiment, a patient's LDL cholesterol levels are reduced following administration of the ASGR1 RNAi agent. In another embodiment, a patient's lipoprotein (a) levels are reduced following administration of the ASGR1 RNAi agent. In some embodiments, the present invention provides for the use of an ASGR1 RNAi agent described herein for the preparation of a medicament for reducing non-HDL cholesterol in a patient in need thereof. In other embodiments, the present invention provides an ASGR1 RNAi agent described herein for use in a method for reducing non-HDL cholesterol in a patient in need thereof.

In some embodiments, a patient to be treated according to the methods of the invention is a patient who has elevated levels of non-HDL cholesterol (e.g. elevated serum levels of non-HDL cholesterol). Ideally, levels of non-HDL cholesterol should be about 30 mg/dL above the target for LDL cholesterol levels for any given patient. In particular embodiments, a patient is administered an ASGR1 RNAi agent of the invention if the patient has a non-HDL cholesterol level of about 130 mg/dL or greater. In one embodiment, a patient is administered an ASGR1 RNAi agent of the invention if the patient has a non-HDL cholesterol level of about 160 mg/dL or greater. In another embodiment, a patient is administered an ASGR1 RNAi agent of the invention if the patient has a non-HDL cholesterol level of about 190 mg/dL or greater. In still another embodiment, a patient is administered an ASGR1 RNAi agent of the invention if the patient has a non-HDL cholesterol level of about 220 mg/dL or greater. In certain embodiments, a patient is administered an ASGR1 RNAi agent of the invention if the patient is at a high or very high risk of cardiovascular disease according to the 2013 ACC/AHA Guideline on the Assessment of Cardiovascular Risk (Goff et al., ACC/AHA guideline on the assessment of cardiovascular risk: a report of the American College of Cardiology/American Heart Association Task Force on Practice Guidelines. Circulation. 2013; 00:000-000) and has a non-HDL cholesterol level of about 100 mg/dL or greater.

In some embodiments of the methods of the invention, a patient is administered an ASGR1 RNAi agent described herein if they are at a moderate risk or higher for cardiovascular disease according to the 2013 ACC/AHA Guideline on the Assessment of Cardiovascular Risk (referred to herein as the "2013 Guidelines"). In certain embodiments, an ASGR1 RNAi agent of the invention is administered to a patient if the patient's LDL cholesterol level is greater than about 160 mg/dL. In other embodiments, an ASGR1 RNAi agent of the invention is administered to a patient if the patient's LDL cholesterol level is greater than about 130 mg/dL and the patient has a moderate risk of cardiovascular disease according to the 2013 Guidelines. In still other embodiments, an ASGR1 RNAi agent of the invention is administered to a patient if the patient's LDL cholesterol level is greater than 100 mg/dL and the patient has a high or very high risk of cardiovascular disease according to the 2013 Guidelines.

In some embodiments, the ASGR1 RNAi agents are used to treat or manage a clinical presentation of a subject with an ASGR1-related disease or disorder. The subject is administered a therapeutically effective amount of one or more of the ASGR1 RNAi agents or ASGR1 RNAi agent-containing compositions described herein. In some embodiments, the method comprises administering a composition comprising an ASGR1 RNAi agent described herein to a subject to be treated.

In some embodiments, the gene expression level and/or mRNA level of an ASGR1 gene in a subject to whom a described ASGR1 RNAi agent is administered is reduced by at least about 5%, 10%, 15%, 20%, 25%, 30%, 35%, 40%, 45%, 50%, 55%, 60%, 65%, 70%, 75%, 80%, 85%, 95%, 96%, 97%, 98%, 99%, or greater than 99% relative to the subject prior to being administered the ASGR1 RNAi agent or to a subject not receiving the ASGR1 RNAi agent. The gene expression level and/or mRNA level in the subject may be reduced in a cell, group of cells, and/or tissue of the subject. In some embodiments, the protein level of ASGR1 in a subject to whom a described ASGR1 RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the ASGR1 RNAi agent or to a subject not receiving the ASGR1 RNAi agent. The protein level in the subject may be reduced in a cell, group of cells, tissue, blood, and/or other fluid of the subject. A reduction in gene expression, mRNA, or protein levels can be assessed by any methods known in the art. Reduction or decrease in ASGR1 mRNA level and/or protein level are collectively referred to herein as a reduction or decrease in ASGR1 or inhibiting or reducing the expression of ASGR1.

Cells, Tissues, Organs, and Non-Human Organisms

Cells, tissues, organs, and non-human organisms that include at least one of the ASGR1 RNAi agents described herein is contemplated. The cell, tissue, organ, or non-human organism is made by delivering the RNAi agent to the cell, tissue, organ or non-human organism.

The above provided embodiments and items are now illustrated with the following, non-limiting examples.

EXAMPLES

Example 1. Synthesis of ASGR1 RNAi Agents

ASGR1 RNAi agent duplexes shown in Table 5 (with corresponding sense and antisense strand sequences identified in Tables 3 and 4) above, were synthesized in accordance with the following:

A. Synthesis.

The sense and antisense strands of the ASGR1 RNAi agents were synthesized according to phosphoramidite technology on solid phase used in oligonucleotide synthesis. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). The 2'-O-methyl phosphoramidites included the following: (5'-O-dimethoxytrityl-N$^6$-(benzoyl)-2'-O-methyl-adenosine-3'-O-(2-cyanoethyl-N,N-diisopropylamino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-(4,4'-Dimethoxytrityl)-2',3'-seco-uridine-2'-benzoyl-3'-[(2-cyanoethyl)-(N,N-diisopropyl)]-phosphoramidite was also purchased from Thermo Fisher Scientific. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, Mass., USA).

Targeting ligand containing phosphoramidites were dissolved in anhydrous dichloromethane or anhydrous acetonitrile (50 mM), while all other amidites were dissolved in anhydrous acetonitrile (50 mM or 100 mM, depending on scale) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous acetonitrile was employed. Unless specifically identified as a "naked" RNAi agent having no targeting ligand present, each of the ASGR1 RNAi agent duplexes synthesized and tested in the following Examples utilized N-acetyl-galactosamine as "NAG" in the targeting ligand chemical structures represented in Table 6.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 µm column and Shimadzu LC-20AP system. Buffer A was 20 mM Tris, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1× Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1× Phosphate-Buffered Saline. The solution absorbance at 260 nm was then multiplied by a conversion factor and the dilution factor to determine the duplex concentration. The conversion factor used was either 0.037 mg/(mL·cm) or was calculated from an experimentally determined extinction coefficient.

Example 2. ASGR1-SEAP Mouse Model

To assess the potency of the RNAi agents, an ASGR1-SEAP mouse model was used. Six to eight week old female C57BL/6 albino mice were transiently transfected in vivo with plasmid by hydrodynamic tail vein injection, administered at least 15 days prior to administration of an ASGR1 RNAi agent or control. The plasmid contains the ASGR1 cDNA sequence (GenBank NM_001671.4 (SEQ ID NO:1)) inserted into the 3' UTR of the SEAP (secreted human placental alkaline phosphatase) reporter gene. 50 µg of the plasmid containing the ASGR1 cDNA sequence in Ringer's Solution in a total volume of 10% of the animal's body weight was injected into mice via the tail vein to create ASGR1-SEAP model mice. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737). Inhibition of expression of ASGR1 by an ASGR1 RNAi agent results in concomitant inhibition of SEAP expression, which is measured by the Phospha-Light™ SEAP Reporter Gene Assay System (Invitrogen). Prior to treatment, SEAP expression levels in serum were measured and the mice were grouped according to average SEAP levels.

Analyses:

SEAP levels may be measured at various times, both before and after administration of ASGR1 RNAi agents.

i) Serum Collection:

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

ii) Serum SEAP Levels:

Serum was collected and measured by the Phospha-Light™ SEAP Reporter Gene Assay System (Invitrogen) according to the manufacturer's instructions. Serum SEAP levels for each animal was normalized to the control group of mice injected with saline in order to account for the non-treatment related decline in ASGR1 expression with this model. First, the SEAP level for each animal at a time point was divided by the pre-treatment level of expression in that animal ("pre-treatment") in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal saline control group. Alternatively, in some Examples set forth herein, the serum SEAP levels for each animal were assessed by normalizing to pre-treatment levels only.

Example 3. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 3.0 mg/kg (mpk) of an ASGR1 RNAi agent or 200 µl of saline without an ASGR1 RNAi agent to be used as a control, according to the following Table 7.

TABLE 7

Dosing groups of ASGR1-SEAP mice of Example 3.

| Group | RNAi Agent and Dose | Dosing Regimen |
|---|---|---|
| 1 | Saline (no RNAi agent) | Single injection on day 1 |
| 2 | 3.0 mg/kg AD04634 | Single injection on day 1 |
| 3 | 3.0 mg/kg AD04698 | Single injection on day 1 |
| 4 | 3.0 mg/kg AD04699 | Single injection on day 1 |
| 5 | 3.0 mg/kg AD04700 | Single injection on day 1 |
| 6 | 3.0 mg/kg AD04701 | Single injection on day 1 |
| 7 | 3.0 mg/kg AD04702 | Single injection on day 1 |
| 8 | 3.0 mg/kg AD04703 | Single injection on day 1 |
| 9 | 3.0 mg/kg AD04704 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 3, day 8, day 15, day 22, day 29, and day 36, and SEAP expression levels were determined pursuant to the procedure set forth in Example 2, above. Data from the experiment are shown in the following Table 8, with Average SEAP reflecting the normalized average value of SEAP:

TABLE 8

Average SEAP normalized to pre-treatment and saline control in ASGR1-SEAP mice from Example 3.

| Group ID | Day 3 Avg SEAP | Day 3 Std Dev (+/−) | Day 8 Avg SEAP | Day 8 Std Dev (+/−) | Day 15 Avg SEAP | Day 15 Std Dev (+/−) | Day 22 Avg SEAP | Day 22 Std Dev (+/−) |
|---|---|---|---|---|---|---|---|---|
| Group 1 (Saline) | 1.000 | 0.192 | 1.000 | 0.176 | 1.000 | 0.614 | 1.000 | 0.287 |
| Group 2 (3.0 mg/kg AD04634) | 0.757 | 0.404 | 0.282 | 0.164 | 0.235 | 0.202 | 0.316 | 0.243 |
| Group 3 (3.0 mg/kg AD04698) | 0.442 | 0.395 | 0.068 | 0.067 | 0.010 | 0.011 | 0.049 | 0.047 |
| Group 4 (3.0 mg/kg AD04699) | 0.904 | 0.324 | 0.380 | 0.130 | 0.253 | 0.115 | 0.427 | 0.236 |
| Group 5 (3.0 mg/kg AD04700) | 0.924 | 0.487 | 0.382 | 0.117 | 0.246 | 0.089 | 0.392 | 0.164 |
| Group 6 (3.0 mg/kg AD04701) | 0.480 | 0.263 | 0.234 | 0.135 | 0.133 | 0.085 | 0.362 | 0.244 |
| Group 7 (3.0 mg/kg AD04702) | 0.480 | 0.283 | 0.379 | 0.349 | 0.351 | 0.170 | 0.331 | 0.157 |
| Group 8 (3.0 mg/kg AD04703) | 0.669 | 0.283 | 0.429 | 0.226 | 0.313 | 0.267 | 0.285 | 0.202 |
| Group 9 (3.0 mg/kg AD04704) | 0.674 | 0.367 | 0.343 | 0.178 | 0.296 | 0.228 | 0.303 | 0.184 |

| Group ID | Day 29 Avg SEAP | Day 29 Std Dev (+/−) | Day 36 Avg SEAP | Day 36 Std Dev (+/−) |
|---|---|---|---|---|
| Group 1 (Saline) | 1.000 | 0.258 | 1.000 | 0.241 |
| Group 2 (3.0 mg/kg AD04634) | 0.284 | 0.196 | 0.262 | 0.187 |
| Group 3 (3.0 mg/kg AD04698) | 0.071 | 0.078 | 0.094 | 0.101 |
| Group 4 (3.0 mg/kg AD04699) | 0.395 | 0.216 | 0.424 | 0.191 |
| Group 5 (3.0 mg/kg AD04700) | 0.383 | 0.218 | 0.376 | 0.165 |
| Group 6 (3.0 mg/kg AD04701) | 0.484 | 0.307 | 0.552 | 0.306 |
| Group 7 (3.0 mg/kg AD04702) | 0.360 | 0.121 | 0.264 | 0.257 |
| Group 8 (3.0 mg/kg AD04703) | 0.472 | 0.411 | 0.380 | 0.288 |
| Group 9 (3.0 mg/kg AD04704) | 0.545 | 0.537 | 0.610 | 0.503 |

Each of the ASGR1 RNAi agents in each of the dosing groups (i.e., Groups 2 through 9) showed reduction in SEAP as compared to the saline control (Group 1) across all measured time points, which as described herein, indicates inhibition of ASGR1 in the ASGR1-SEAP mouse model. For example, Group 3 showed normalized SEAP levels of 0.010 (±0.011) on day 15, which indicates a 99% inhibition of expression at that time point after a single administration of 3.0 mg/kg of duplex AD04698.

Example 4. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 μl containing either 3.0 mg/kg of an ASGR1 RNAi agent or 200 μl of saline without an ASGR1 RNAi agent to be used as a control, according to the following Table 9.

TABLE 9

Dosing groups of ASGR1-SEAP mice of Example 4.

| Group | RNAi Agent and Dose | Dosing Regimen |
|---|---|---|
| 1 | Saline (no RNAi agent) | Single injection on day 1 |
| 2 | 3.0 mg/kg AD04634 | Single injection on day 1 |
| 3 | 3.0 mg/kg AD04705 | Single injection on day 1 |
| 4 | 3.0 mg/kg AD04706 | Single injection on day 1 |
| 5 | 3.0 mg/kg AD04707 | Single injection on day 1 |
| 6 | 3.0 mg/kg AD04791 | Single injection on day 1 |
| 7 | 3.0 mg/kg AD04792 | Single injection on day 1 |
| 8 | 3.0 mg/kg AD04793 | Single injection on day 1 |
| 9 | 3.0 mg/kg AD04794 | Single injection on day 1 |
| 10 | 3.0 mg/kg AD04797 | Single injection on day 1 |
| 11 | 3.0 mg/kg AD04800 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 4, day 8, day 15, day 22, and day 29, and SEAP expression levels were determined pursuant to the procedure set forth in Example 2, above. Data from the experiment are shown in the following Table 10, with Average SEAP reflecting the normalized average value of SEAP:

TABLE 10

Average SEAP normalized to pre-treatment and saline control in ASGR1-SEAP mice from Example 4.

| Group ID | Day 4 Avg SEAP | Day 4 Std Dev (+/−) | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|---|---|
| Group 1 (Saline) | 1.000 | 0.271 | 1.000 | 0.036 | 1.000 | 0.546 | 1.000 | 0.428 | 1.000 | 0.517 |
| Group 2 (3.0 mg/kg AD04634) | 0.505 | 0.105 | 0.357 | 0.066 | 0.333 | 0.079 | 0.276 | 0.076 | 0.308 | 0.200 |
| Group 3 (3.0 mg/kg AD04705) | 0.747 | 0.305 | 0.734 | 0.293 | 0.509 | 0.111 | 0.387 | 0.149 | 0.430 | 0.186 |
| Group 4 (3.0 mg/kg AD04706) | 0.830 | 0.239 | 0.885 | 0.133 | 0.555 | 0.160 | 0.519 | 0.165 | 0.568 | 0.087 |
| Group 5 (3.0 mg/kg AD04707) | 0.625 | 0.035 | 0.763 | 0.187 | 0.596 | 0.134 | 0.595 | 0.059 | 0.393 | 0.073 |
| Group 6 (3.0 mg/kg AD04791) | 1.236 | 0.622 | 0.834 | 0.197 | 0.650 | 0.148 | 0.713 | 0.030 | 0.654 | 0.131 |
| Group 7 (3.0 mg/kg AD04792) | 1.345 | 1.033 | 0.988 | 0.400 | 0.886 | 0.175 | 0.796 | 0.602 | 1.120 | 0.647 |
| Group 8 (3.0 mg/kg AD04793) | 1.431 | 1.439 | 0.496 | 0.044 | 0.368 | 0.110 | 0.346 | 0.168 | 0.343 | 0.091 |
| Group 9 (3.0 mg/kg AD04794) | 1.066 | 1.144 | 0.491 | 0.092 | 0.453 | 0.209 | 0.795 | 0.334 | 0.880 | 0.303 |
| Group 10 (3.0 mg/kg AD04797) | 0.764 | 0.617 | 1.156 | 0.366 | 0.939 | 0.412 | 1.113 | 0.490 | 1.344 | 0.375 |
| Group 11 (3.0 mg/kg AD04800) | 0.412 | 0.235 | 1.641 | 1.240 | 0.869 | 0.234 | 0.829 | 0.144 | 0.615 | 0.199 |

Example 5. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 μl containing either 0.5 mg/kg, 1.0 mg/kg, or 3.0 mg/kg of an ASGR1 RNAi agent, or 200 μl of saline without an ASGR1 RNAi agent to be used as a control, according to the following Table 11.

TABLE 11

Dosing groups of ASGR1-SEAP mice of Example 5.

| Group | RNAi Agent and Dose | Dosing Regimen |
|---|---|---|
| 1 | Saline (no RNAi agent) | Single injection on day 1 |
| 2 | 3.0 mg/kg AD04634 | Single injection on day 1 |
| 3 | 1.0 mg/kg AD04697 | Single injection on day 1 |
| 4 | 3.0 mg/kg AD04697 | Single injection on day 1 |
| 5 | 0.5 mg/kg AD04698 | Single injection on day 1 |
| 6 | 1.0 mg/kg AD04698 | Single injection on day 1 |
| 7 | 3.0 mg/kg AD04698 | Single injection on day 1 |
| 8 | 3.0 mg/kg AD04795 | Single injection on day 1 |
| 9 | 3.0 mg/kg AD04796 | Single injection on day 1 |
| 10 | 3.0 mg/kg AD04798 | Single injection on day 1 |
| 11 | 3.0 mg/kg AD04799 | Single injection on day 1 |

Each of the ASGR1 RNAi agents included N-acetyl-galactosamine targeting ligands conjugated to the 5′-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, and day 29, and SEAP expression levels were determined pursuant to the procedure set forth in Example 2, above. Data from the experiment are shown in the following Table 12, with Average SEAP reflecting the normalized average value of SEAP:

TABLE 12

Average SEAP normalized to pre-treatment and saline control in ASGR1-SEAP mice from Example 5.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline) | 1.000 | 0.253 | 1.000 | 0.145 | 1.000 | 0.372 | 1.000 | 0.593 |
| Group 2 (3.0 mg/kg AD04634) | 0.323 | 0.032 | 0.351 | 0.050 | 0.343 | 0.055 | 0.451 | 0.252 |
| Group 3 (1.0 mg/kg AD04697) | 0.384 | 0.145 | 0.364 | 0.066 | 0.363 | 0.184 | 0.563 | 0.353 |
| Group 4 (3.0 mg/kg AD04697) | 0.236 | 0.073 | 0.144 | 0.007 | 0.119 | 0.044 | 0.207 | 0.047 |
| Group 5 (0.5 mg/kg AD04698) | 0.557 | 0.112 | 0.633 | 0.137 | 0.688 | 0.245 | 1.134 | 0.293 |
| Group 6 (1.0 mg/kg AD04698) | 0.331 | 0.030 | 0.301 | 0.041 | 0.242 | 0.010 | 0.560 | 0.109 |
| Group 7 (3.0 mg/kg AD04698) | 0.186 | 0.024 | 0.094 | 0.013 | 0.079 | 0.012 | 0.203 | 0.033 |
| Group 8 (3.0 mg/kg AD04795) | 0.601 | 0.258 | 0.754 | 0.292 | 0.862 | 0.565 | 1.863 | 1.301 |
| Group 9 (3.0 mg/kg AD04796) | 0.532 | 0.093 | 0.949 | 0.199 | 0.729 | 0.076 | 1.068 | 0.257 |
| Group 10 (3.0 mg/kg AD04798) | 0.643 | 0.154 | 1.310 | 0.700 | 1.063 | 0.323 | 1.252 | 0.251 |
| Group 11 (3.0 mg/kg AD04799) | 0.489 | 0.220 | 0.373 | 0.161 | 0.400 | 0.135 | 0.519 | 0.315 |

Example 6. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 1.0 mg/kg or 3.0 mg/kg of an ASGR1 RNAi agent, or 200 µl of saline without an ASGR1 RNAi agent to be used as a control, according to the following Table 13.

TABLE 13

Dosing groups of ASGR1-SEAP mice of Example 6.

| Group | RNAi Agent and Dose | Dosing Regimen |
|---|---|---|
| 1 | Saline (no RNAi agent) | Single injection on day 1 |
| 2 | 1.0 mg/kg AD04634 | Single injection on day 1 |
| 3 | 3.0 mg/kg AD04634 | Single injection on day 1 |
| 4 | 1.0 mg/kg AD04964 | Single injection on day 1 |
| 5 | 3.0 mg/kg AD04964 | Single injection on day 1 |
| 6 | 1.0 mg/kg AD04698 | Single injection on day 1 |
| 7 | 3.0 mg/kg AD04698 | Single injection on day 1 |
| 8 | 1.0 mg/kg AD04847 | Single injection on day 1 |
| 9 | 3.0 mg/kg AD04847 | Single injection on day 1 |
| 10 | 1.0 mg/kg AD04701 | Single injection on day 1 |
| 11 | 3.0 mg/kg AD04701 | Single injection on day 1 |
| 12 | 1.0 mg/kg AD04965 | Single injection on day 1 |
| 13 | 3.0 mg/kg AD04965 | Single injection on day 1 |
| 14 | 3.0 mg/kg AD04700 | Single injection on day 1 |
| 15 | 3.0 mg/kg AD04793 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Four (4) mice in each group were tested (n=4). Serum was collected on day 8, day 13, day 22, and day 29, and SEAP expression levels were determined pursuant to the procedure set forth in Example 2, above. Data from the experiment are shown in the following Table 14, with Average SEAP reflecting the normalized average value of SEAP:

Example 7. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 1.0 mg/kg or 3.0 mg/kg of an ASGR1 RNAi agent, or 200 µl of saline without an ASGR1 RNAi agent to be used as a control, according to the following Table 15.

TABLE 15

Dosing groups of ASGR1-SEAP mice of Example 7.

| Group | RNAi Agent and Dose | Dosing Regimen |
|---|---|---|
| 1 | Saline (no RNAi agent) | Single injection on day 1 |
| 2 | 1.0 mg/kg AD04698 | Single injection on day 1 |
| 3 | 3.0 mg/kg AD04698 | Single injection on day 1 |
| 4 | 1.0 mg/kg AD04847 | Single injection on day 1 |
| 5 | 3.0 mg/kg AD04847 | Single injection on day 1 |
| 6 | 1.0 mg/kg AD04802 | Single injection on day 1 |
| 7 | 3.0 mg/kg AD04802 | Single injection on day 1 |
| 8 | 1.0 mg/kg AD04975 | Single injection on day 1 |
| 9 | 3.0 mg/kg AD04975 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Four (4) mice in each group were tested (n=4). Serum was collected on day 8, day 15, day 22, and day 29, and SEAP expression levels were determined pursuant to the procedure set forth in Example 2, above. Data from the experiment are shown in the following Table 16, with Average SEAP reflecting the normalized average value of SEAP:

TABLE 14

Average SEAP normalized to pre-treatment and saline control in ASGR1-SEAP mice from Example 6.

| Group ID | Day 8 Avg SEAP | Day 8 Std Dev (+/−) | Day 13 Avg SEAP | Day 13 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline) | 1.000 | 0.639 | 1.000 | 0.384 | 1.000 | 0.364 | 1.000 | 0.477 |
| Group 2 (1.0 mg/kg AD04634) | 0.851 | 0.116 | 0.825 | 0.222 | 0.576 | 0.086 | 0.491 | 0.208 |
| Group 3 (3.0 mg/kg AD04634) | 0.538 | 0.128 | 0.355 | 0.150 | 0.194 | 0.057 | 0.249 | 0.098 |
| Group 4 (1.0 mg/kg AD04964) | 0.608 | 0.217 | 0.564 | 0.138 | 0.358 | 0.090 | 0.402 | 0.244 |
| Group 5 (3.0 mg/kg AD04964) | 0.476 | 0.255 | 0.374 | 0.194 | 0.325 | 0.204 | 0.327 | 0.247 |
| Group 6 (1.0 mg/kg AD04698) | 0.404 | 0.163 | 0.198 | 0.069 | 0.191 | 0.067 | 0.186 | 0.079 |
| Group 7 (3.0 mg/kg AD04698) | 0.256 | 0.073 | 0.078 | 0.026 | 0.083 | 0.048 | 0.138 | 0.103 |
| Group 8 (1.0 mg/kg AD04787) | 0.307 | 0.129 | 0.138 | 0.056 | 0.145 | 0.068 | 0.210 | 0.119 |
| Group 9 (3.0 mg/kg AD04787) | 0.383 | 0.161 | 0.193 | 0.154 | 0.147 | 0.191 | 0.230 | 0.231 |
| Group 10 (1.0 mg/kg AD04701) | 0.788 | 0.122 | 0.925 | 0.142 | 0.759 | 0.141 | 0.726 | 0.078 |
| Group 11 (3.0 mg/kg AD04701) | 0.491 | 0.138 | 0.640 | 0.206 | 0.436 | 0.067 | 0.651 | 0.130 |
| Group 12 (1.0 mg/kg AD04965) | 0.813 | 0.248 | 0.900 | 0.209 | 0.643 | 0.124 | 0.904 | 0.504 |
| Group 13 (3.0 mg/kg AD04965) | 0.672 | 0.338 | 0.845 | 0.129 | 0.523 | 0.155 | 0.394 | 0.090 |
| Group 14 (3.0 mg/kg AD04700) | 0.743 | 0.063 | 0.793 | 0.378 | 0.438 | 0.287 | 0.424 | 0.215 |
| Group 15 (3.0 mg/kg AD04793) | 0.504 | 0.072 | 0.525 | 0.142 | 0.417 | 0.140 | 0.458 | 0.108 |

TABLE 16

Average SEAP normalized to pre-treatment and saline control in ASGR1-SEAP mice from Example 7.

| Group ID | Day 8 | | Day 15 | | Day 22 | | Day 29 | |
| --- | --- | --- | --- | --- | --- | --- | --- | --- |
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline) | 1.000 | 0.412 | 1.000 | 0.421 | 1.000 | 0.497 | 1.000 | 0.582 |
| Group 2 (1.0 mg/kg AD04698) | 0.494 | 0.104 | 0.295 | 0.149 | 0.239 | 0.080 | 0.377 | 0.108 |
| Group 3 (3.0 mg/kg AD04698) | 0.188 | 0.032 | 0.077 | 0.028 | 0.076 | 0.048 | 0.143 | 0.131 |
| Group 4 (1.0 mg/kg AD04847) | 0.517 | 0.196 | 0.304 | 0.129 | 0.297 | 0.109 | 0.533 | 0.184 |
| Group 5 (3.0 mg/kg AD04847) | 0.160 | 0.069 | 0.071 | 0.030 | 0.085 | 0.031 | 0.153 | 0.025 |
| Group 6 (1.0 mg/kg AD04802) | 0.579 | 0.170 | 0.372 | 0.127 | 0.336 | 0.152 | 0.403 | 0.229 |
| Group 7 (3.0 mg/kg AD04802) | 0.304 | 0.075 | 0.185 | 0.083 | 0.220 | 0.131 | 0.297 | 0.172 |
| Group 8 (1.0 mg/kg AD04975) | 0.487 | 0.069 | 0.338 | 0.069 | 0.453 | 0.295 | 0.689 | 0.537 |
| Group 9 (3.0 mg/kg AD04975) | 0.193 | 0.046 | 0.097 | 0.031 | 0.247 | 0.060 | 0.125 | 0.042 |

Example 8. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 1.0 mg/kg or 3.0 mg/kg of an ASGR1 RNAi agent, or 200 µl of saline without an ASGR1 RNAi agent to be used as a control, according to the following Table 17.

TABLE 17

Dosing groups of ASGR1-SEAP mice of Example 8.

| Group | RNAi Agent and Dose | Dosing Regimen |
| --- | --- | --- |
| 1 | Saline (no RNAi agent) | Single injection on day 1 |
| 2 | 1.0 mg/kg AD04847 | Single injection on day 1 |
| 3 | 1.0 mg/kg AD04634 | Single injection on day 1 |
| 4 | 1.0 mg/kg AD05067 | Single injection on day 1 |
| 5 | 1.0 mg/kg AD05090 | Single injection on day 1 |
| 6 | 1.0 mg/kg AD05065 | Single injection on day 1 |
| 7 | 1.0 mg/kg AD05066 | Single injection on day 1 |
| 8 | 1.0 mg/kg AD05089 | Single injection on day 1 |
| 9 | 1.0 mg/kg AD05092 | Single injection on day 1 |
| 10 | 1.0 mg/kg AD05093 | Single injection on day 1 |
| 11 | 3.0 mg/kg AD05093 | Single injection on day 1 |
| 12 | 1.0 mg/kg AD05094 | Single injection on day 1 |
| 13 | 3.0 mg/kg AD05094 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, and day 29, and SEAP expression levels were determined pursuant to the procedure set forth in Example 2, above. Data from the experiment are shown in the following Table 18, with Average SEAP reflecting the normalized average value of SEAP:

TABLE 18

Average SEAP normalized to pre-treatment and saline control in ASGR1-SEAP mice from Example 8.

| Group ID | Day 8 | | Day 15 | | Day 22 | | Day 29 | |
| --- | --- | --- | --- | --- | --- | --- | --- | --- |
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline) | 1.000 | 0.160 | 1.000 | 0.202 | 1.000 | 0.132 | 1.000 | 0.346 |
| Group 2 (1.0 mg/kg AD04847) | 0.444 | 0.181 | 0.404 | 0.186 | 0.372 | 0.226 | 0.369 | 0.184 |
| Group 3 (1.0 mg/kg AD04634) | 0.619 | 0.033 | 0.673 | 0.209 | 0.716 | 0.480 | 0.671 | 0.048 |
| Group 4 (1.0 mg/kg AD05067) | 0.679 | 0.059 | 0.454 | 0.129 | 0.200 | 0.174 | 0.416 | 0.557 |
| Group 5 (1.0 mg/kg AD05090) | 0.540 | 0.054 | 0.489 | 0.265 | 0.499 | 0.176 | 0.598 | 0.240 |
| Group 6 (1.0 mg/kg AD05065) | 0.605 | 0.056 | 0.537 | 0.118 | 0.416 | 0.192 | 0.483 | 0.221 |
| Group 7 (1.0 mg/kg AD05066) | 0.967 | 0.193 | 0.837 | 0.649 | 0.426 | 0.345 | 0.746 | 0.488 |
| Group 8 (1.0 mg/kg AD05089) | 1.017 | 0.434 | 0.547 | 0.041 | 0.446 | 0.134 | 0.406 | 0.071 |
| Group 9 (1.0 mg/kg AD05092) | 1.191 | 0.462 | 1.315 | 0.217 | 1.269 | 0.442 | 1.143 | 0.337 |
| Group 10 (1.0 mg/kg AD05093) | 1.698 | 0.150 | 1.075 | 0.577 | 1.056 | 0.243 | 0.900 | 0.365 |
| Group 11 (3.0 mg/kg AD05093) | 1.437 | 0.307 | 1.368 | 0.637 | 1.254 | 0.589 | 1.000 | 0.496 |
| Group 12 (1.0 mg/kg AD05094) | 1.838 | 0.167 | 1.367 | 0.548 | 1.455 | 0.552 | 2.236 | 1.451 |
| Group 13 (3.0 mg/kg AD05094) | 1.197 | 0.622 | 1.567 | 0.658 | 1.451 | 0.371 | 1.719 | 0.279 |

Example 9. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 1.0 mg/kg or 3.0 mg/kg of an ASGR1 RNAi agent, or 200 µl of saline without an ASGR1 RNAi agent to be used as a control, according to the following Table 19.

TABLE 19

Dosing groups of ASGR1-SEAP mice of Example 9.

| Group | RNAi Agent and Dose | Dosing Regimen |
|---|---|---|
| 1 | Saline (no RNAi agent) | Single injection on day 1 |
| 2 | 1.0 mg/kg AD04847 | Single injection on day 1 |
| 3 | 3.0 mg/kg AD04634 | Single injection on day 1 |
| 4 | 3.0 mg/kg AD04700 | Single injection on day 1 |
| 5 | 3.0 mg/kg AD05053 | Single injection on day 1 |
| 6 | 3.0 mg/kg AD05096 | Single injection on day 1 |
| 7 | 3.0 mg/kg AD05097 | Single injection on day 1 |
| 8 | 3.0 mg/kg AD05108 | Single injection on day 1 |
| 9 | 3.0 mg/kg AD05109 | Single injection on day 1 |
| 10 | 3.0 mg/kg AD05110 | Single injection on day 1 |
| 11 | 3.0 mg/kg AD05111 | Single injection on day 1 |
| 12 | 3.0 mg/kg AD05112 | Single injection on day 1 |
| 13 | 3.0 mg/kg AD05113 | Single injection on day 1 |
| 14 | 3.0 mg/kg AD05114 | Single injection on day 1 |
| 15 | 3.0 mg/kg AD05115 | Single injection on day 1 |
| 16 | 1.0 mg/kg AD05180 | Single injection on day 1 |
| 17 | 1.0 mg/kg AD05181 | Single injection on day 1 |
| 18 | 1.0 mg/kg AD05182 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 13, day 22, day 29, and day 36, and SEAP expression levels were determined pursuant to the procedure set forth in Example 2, above. Data from the experiment are shown in the following Table 20, with Average SEAP reflecting the normalized average value of SEAP:

Example 10. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 1.0 mg/kg or 3.0 mg/kg of an ASGR1 RNAi agent, or 200 µl of saline without an ASGR1 RNAi agent to be used as a control, according to the following Table 21.

TABLE 21

Dosing groups of ASGR1-SEAP mice of Example 10.

| Group | RNAi Agent and Dose | Dosing Regimen |
|---|---|---|
| 1 | Saline (no RNAi agent) | Single injection on day 1 |
| 2 | 1.0 mg/kg AD04847 | Single injection on day 1 |
| 3 | 3.0 mg/kg AD05183 | Single injection on day 1 |
| 4 | 3.0 mg/kg AD05184 | Single injection on day 1 |
| 5 | 3.0 mg/kg AD05185 | Single injection on day 1 |
| 6 | 3.0 mg/kg AD05186 | Single injection on day 1 |
| 7 | 3.0 mg/kg AD05187 | Single injection on day 1 |
| 8 | 3.0 mg/kg AD05188 | Single injection on day 1 |
| 9 | 3.0 mg/kg AD05189 | Single injection on day 1 |
| 10 | 3.0 mg/kg AD05190 | Single injection on day 1 |
| 11 | 3.0 mg/kg AD05191 | Single injection on day 1 |
| 12 | 3.0 mg/kg AD05192 | Single injection on day 1 |
| 13 | 3.0 mg/kg AD05193 | Single injection on day 1 |
| 14 | 3.0 mg/kg AD05194 | Single injection on day 1 |
| 15 | 3.0 mg/kg AD05195 | Single injection on day 1 |
| 16 | 3.0 mg/kg AD05196 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, day 29, and day 36, and SEAP expression levels were determined pursuant to the procedure set forth in Example 2, above. Data from the experiment are shown in the following Table 22, with Average SEAP reflecting the normalized average value of SEAP:

TABLE 20

Average SEAP normalized to pre-treatment and saline control in ASGR1-SEAP mice from Example 9.

| | Day 8 | | Day 13 | | Day 22 | | Day 29 | | Day 36 | |
|---|---|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) | Avg SEAP | Std Dev (+/−) |
| Group 1 (Saline) | 1.000 | 0.323 | 1.000 | 0.356 | 1.000 | 0.183 | 1.000 | 0.045 | 1.000 | 0.188 |
| Group 2 (1.0 mg/kg AD04847) | 0.411 | 0.129 | 0.289 | 0.121 | 0.491 | 0.259 | 0.631 | 0.428 | 1.115 | 0.941 |
| Group 3 (3.0 mg/kg AD04634) | 0.430 | 0.127 | 0.466 | 0.232 | 0.356 | 0.142 | 0.583 | 0.341 | 0.600 | 0.421 |
| Group 4 (3.0 mg/kg AD04700) | 0.550 | 0.021 | 0.597 | 0.139 | 0.826 | 0.228 | 0.770 | 0.131 | 0.847 | 0.340 |
| Group 5 (3.0 mg/kg AD05053) | 0.591 | 0.116 | 0.396 | 0.068 | 0.658 | 0.214 | 0.745 | 0.191 | 0.649 | 0.226 |
| Group 6 (3.0 mg/kg AD05096) | 0.511 | 0.089 | 0.445 | 0.030 | 0.421 | 0.085 | 0.503 | 0.129 | 0.532 | 0.098 |
| Group 7 (3.0 mg/kg AD05097) | 0.588 | 0.095 | 0.987 | 0.221 | 0.996 | 0.217 | 1.083 | 0.206 | 1.425 | 0.289 |
| Group 8 (3.0 mg/kg AD05108) | 0.253 | 0.126 | 0.155 | 0.093 | 0.132 | 0.074 | 0.134 | 0.091 | 0.191 | 0.093 |
| Group 9 (3.0 mg/kg AD05109) | 0.219 | 0.022 | 0.141 | 0.021 | 0.109 | 0.041 | 0.105 | 0.027 | 0.181 | 0.089 |
| Group 10 (3.0 mg/kg AD05110) | 0.217 | 0.061 | 0.285 | 0.097 | 0.335 | 0.110 | 0.491 | 0.073 | 0.575 | 0.244 |
| Group 11 (3.0 mg/kg AD05111) | 0.470 | 0.255 | 0.592 | 0.160 | 0.596 | 0.167 | 0.821 | 0.138 | 0.803 | 0.477 |
| Group 12 (3.0 mg/kg AD05112) | 0.600 | 0.173 | 0.862 | 0.252 | 0.905 | 0.517 | 0.992 | 0.343 | 0.905 | 0.252 |
| Group 13 (3.0 mg/kg AD05113) | 0.897 | 0.105 | 1.156 | 0.170 | 1.124 | 0.122 | 0.920 | 0.319 | 0.789 | 0.207 |
| Group 14 (3.0 mg/kg AD05114) | 0.567 | 0.053 | 0.640 | 0.087 | 0.602 | 0.015 | 0.763 | 0.321 | 0.532 | 0.185 |
| Group 15 (3.0 mg/kg AD05115) | 0.619 | 0.283 | 0.608 | 0.264 | 0.627 | 0.198 | 0.570 | 0.246 | 0.514 | 0.178 |
| Group 16 (1.0 mg/kg AD05180) | 0.491 | 0.111 | 0.337 | 0.152 | 0.466 | 0.084 | 0.573 | 0.152 | 0.429 | 0.041 |
| Group 17 (1.0 mg/kg AD05181) | 0.493 | 0.155 | 0.448 | 0.338 | 0.490 | 0.298 | 0.617 | 0.475 | 0.428 | 0.322 |
| Group 18 (1.0 mg/kg AD05182) | 0.453 | 0.057 | 0.405 | 0.071 | 0.379 | 0.065 | 0.592 | 0.134 | 0.718 | 0.149 |

TABLE 22

Average SEAP normalized to pre-treatment and saline control in ASGR1-SEAP mice from Example 10.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) | Day 36 Avg SEAP | Day 36 Std Dev (+/−) |
|---|---|---|---|---|---|---|---|---|---|---|
| Group 1 (Saline) | 1.000 | 0.018 | 1.000 | 0.190 | 1.000 | 0.205 | 1.000 | 0.178 | 1.000 | 0.191 |
| Group 2 (1.0 mg/kg AD04847) | 0.318 | 0.103 | 0.339 | 0.056 | 0.247 | 0.074 | 0.412 | 0.095 | 0.456 | 0.114 |
| Group 3 (3.0 mg/kg AD05183) | 0.106 | 0.015 | 0.043 | 0.025 | 0.062 | 0.017 | 0.062 | 0.009 | 0.119 | 0.055 |
| Group 4 (3.0 mg/kg AD05184) | 0.134 | 0.030 | 0.143 | 0.109 | 0.170 | 0.150 | 0.146 | 0.151 | 0.215 | 0.248 |
| Group 5 (3.0 mg/kg AD05185) | 0.186 | 0.060 | 0.141 | 0.052 | 0.095 | 0.039 | 0.147 | 0.018 | 0.150 | 0.044 |
| Group 6 (3.0 mg/kg AD05186) | 0.107 | 0.030 | 0.097 | 0.032 | 0.141 | 0.063 | 0.170 | 0.087 | 0.195 | 0.069 |
| Group 7 (3.0 mg/kg AD05187) | 0.255 | 0.132 | 0.264 | 0.138 | 0.420 | 0.204 | 0.520 | 0.341 | 0.678 | 0.388 |
| Group 8 (3.0 mg/kg AD05188) | 0.188 | 0.061 | 0.160 | 0.075 | 0.182 | 0.158 | 0.367 | 0.297 | 0.487 | 0.323 |
| Group 9 (3.0 mg/kg AD05189) | 0.538 | 0.300 | 0.755 | 0.256 | 0.924 | 0.312 | 0.752 | 0.578 | 0.720 | 0.486 |
| Group 10 (3.0 mg/kg AD05190) | 0.540 | 0.049 | 0.697 | 0.037 | 0.653 | 0.150 | 0.812 | 0.340 | 1.114 | 0.559 |
| Group 11 (3.0 mg/kg AD05191) | 0.489 | 0.293 | 0.769 | 0.706 | 0.686 | 0.636 | 0.550 | 0.566 | 0.685 | 0.693 |
| Group 12 (3.0 mg/kg AD05192) | 1.307 | 0.511 | 1.908 | 1.094 | 2.401 | 0.835 | 1.826 | 0.514 | 3.280 | 1.958 |
| Group 13 (3.0 mg/kg AD05193) | 0.279 | 0.403 | 0.204 | 0.275 | 0.137 | 0.171 | 0.226 | 0.280 | 0.475 | 0.622 |
| Group 14 (3.0 mg/kg AD05194) | 0.954 | 1.497 | 0.523 | 0.774 | 0.377 | 0.570 | 0.487 | 0.702 | 0.908 | 1.380 |
| Group 15 (3.0 mg/kg AD05195) | 0.153 | 0.228 | 0.137 | 0.187 | 0.130 | 0.151 | 0.094 | 0.098 | 0.046 | 0.039 |
| Group 16 (3.0 mg/kg AD05196) | 0.358 | 0.550 | 0.024 | 0.008 | 0.200 | 0.297 | 0.294 | 0.440 | 0.479 | 0.707 |

Example 11. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing 1.0 mg/kg of an ASGR1 RNAi agent, or 200 µl of saline without an ASGR1 RNAi agent to be used as a control, according to the following Table 23.

TABLE 23

Dosing groups of ASGR1-SEAP mice of Example 11.

| Group | RNAi Agent and Dose | Dosing Regimen |
|---|---|---|
| 1 | Saline (no RNAi agent) | Single injection on day 1 |
| 2 | 1.0 mg/kg AD05067 | Single injection on day 1 |
| 3 | 1.0 mg/kg AD05209 | Single injection on day 1 |
| 4 | 1.0 mg/kg AD05240 | Single injection on day 1 |
| 5 | 1.0 mg/kg AD05256 | Single injection on day 1 |
| 6 | 1.0 mg/kg AD05257 | Single injection on day 1 |
| 7 | 1.0 mg/kg AD05245 | Single injection on day 1 |
| 8 | 1.0 mg/kg AD05246 | Single injection on day 1 |
| 9 | 1.0 mg/kg AD05210 | Single injection on day 1 |
| 10 | 1.0 mg/kg AD05211 | Single injection on day 1 |
| 11 | 1.0 mg/kg AD05213 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, day 29, and day 36, and SEAP expression levels were determined pursuant to the procedure set forth in Example 2, above. Data from the experiment are shown in the following Table 24, with Average SEAP reflecting the normalized average value of SEAP:

TABLE 24

Average SEAP normalized to pre-treatment and saline control in ASGR1-SEAP mice from Example 11.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) | Day 36 Avg SEAP | Day 36 Std Dev (+/−) |
|---|---|---|---|---|---|---|---|---|---|---|
| Group 1 (Saline) | 1.000 | 0.378 | 1.000 | 0.326 | 1.000 | 0.308 | 1.000 | 0.264 | 1.000 | 0.513 |
| Group 2 (1.0 mg/kg AD05067) | 0.380 | 0.065 | 0.251 | 0.090 | 0.185 | 0.060 | 0.296 | 0.011 | 0.413 | 0.082 |
| Group 3 (1.0 mg/kg AD05209) | 0.190 | 0.023 | 0.103 | 0.025 | 0.106 | 0.079 | 0.164 | 0.154 | 0.210 | 0.175 |
| Group 4 (1.0 mg/kg AD05240) | 0.358 | 0.158 | 0.254 | 0.148 | 0.354 | 0.207 | 0.344 | 0.183 | 0.463 | 0.303 |
| Group 5 (1.0 mg/kg AD05256) | 0.237 | 0.155 | 0.135 | 0.081 | 0.147 | 0.092 | 0.108 | 0.052 | 0.106 | 0.062 |
| Group 6 (1.0 mg/kg AD05257) | 0.313 | 0.136 | 0.172 | 0.097 | 0.267 | 0.152 | 0.300 | 0.141 | 0.337 | 0.164 |
| Group 7 (1.0 mg/kg AD05245) | 0.278 | 0.029 | 0.227 | 0.061 | 0.324 | 0.080 | 0.414 | 0.130 | 0.469 | 0.214 |
| Group 8 (1.0 mg/kg AD05246) | 0.793 | 0.290 | 1.056 | 0.066 | 1.529 | 0.334 | 1.297 | 0.359 | 1.132 | 0.308 |
| Group 9 (1.0 mg/kg AD05210) | 0.451 | 0.018 | 0.394 | 0.082 | 0.585 | 0.075 | 0.509 | 0.100 | 0.715 | 0.194 |
| Group 10 (1.0 mg/kg AD05211) | 0.637 | 0.160 | 0.680 | 0.273 | 0.660 | 0.216 | 0.782 | 0.209 | 0.890 | 0.212 |
| Group 11 (1.0 mg/kg AD05213) | 0.280 | 0.123 | 0.206 | 0.070 | 0.334 | 0.165 | 0.469 | 0.240 | 0.658 | 0.459 |

Example 12. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing 1.0 mg/kg of an ASGR1 RNAi agent, or 200 µl of saline without an ASGR1 RNAi agent to be used as a control, according to the following Table 25.

TABLE 25

Dosing groups of ASGR1-SEAP mice of Example 12.

| Group | RNAi Agent and Dose | Dosing Regimen |
|---|---|---|
| 1 | Saline (no RNAi agent) | Single injection on day 1 |
| 2 | 1.0 mg/kg AD05109 | Single injection on day 1 |
| 3 | 1.0 mg/kg AD05193 | Single injection on day 1 |
| 4 | 1.0 mg/kg AD05196 | Single injection on day 1 |
| 5 | 1.0 mg/kg AD05262 | Single injection on day 1 |
| 6 | 1.0 mg/kg AD05263 | Single injection on day 1 |
| 7 | 1.0 mg/kg AD05264 | Single injection on day 1 |
| 8 | 1.0 mg/kg AD05265 | Single injection on day 1 |
| 9 | 1.0 mg/kg AD05266 | Single injection on day 1 |
| 10 | 1.0 mg/kg AD05267 | Single injection on day 1 |
| 11 | 1.0 mg/kg AD05268 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 23, day 29, and day 36, and SEAP expression levels were determined pursuant to the procedure set forth in Example 2, above. Data from the experiment are shown in the following Table 26, with Average SEAP reflecting the normalized average value of SEAP:

TABLE 26

Average SEAP normalized to pre-treatment and saline control in ASGR1-SEAP mice from Example 12.

| Group ID | Day 8 Avg SEAP | Day 8 Std Dev (+/−) | Day 15 Avg SEAP | Day 15 Std Dev (+/−) | Day 23 Avg SEAP | Day 23 Std Dev (+/−) | Day 29 Avg SEAP | Day 29 Std Dev (+/−) | Day 36 Avg SEAP | Day 36 Std Dev (+/−) |
|---|---|---|---|---|---|---|---|---|---|---|
| Group 1 (Saline) | 1.000 | 0.418 | 1.000 | 0.481 | 1.000 | 0.215 | 1.000 | 0.643 | 1.000 | 0.655 |
| Group 2 (1.0 mg/kg AD05109) | 0.372 | 0.050 | 0.255 | 0.047 | 0.358 | 0.190 | 0.205 | 0.005 | 0.184 | 0.125 |
| Group 3 (1.0 mg/kg AD05193) | 0.166 | 0.074 | 0.093 | 0.061 | 0.122 | 0.092 | 0.087 | 0.063 | 0.085 | 0.081 |
| Group 4 (1.0 mg/kg AD05196) | 0.177 | 0.034 | 0.142 | 0.049 | 0.219 | 0.088 | 0.191 | 0.098 | 0.132 | 0.055 |
| Group 5 (1.0 mg/kg AD05262) | 0.768 | 0.215 | 0.606 | 0.192 | 1.108 | 0.429 | 0.642 | 0.344 | 0.717 | 0.422 |
| Group 6 (1.0 mg/kg AD05263) | 0.267 | 0.084 | 0.162 | 0.042 | 0.215 | 0.023 | 0.263 | 0.042 | 0.206 | 0.084 |
| Group 7 (1.0 mg/kg AD05264) | 0.420 | 0.016 | 0.425 | 0.049 | 0.715 | 0.239 | 0.744 | 0.103 | 0.498 | 0.163 |
| Group 8 (1.0 mg/kg AD05265) | 0.561 | 0.280 | 0.703 | 0.391 | 1.105 | 0.732 | 0.793 | 0.532 | 0.652 | 0.412 |
| Group 9 (1.0 mg/kg AD05266) | 0.329 | 0.071 | 0.338 | 0.050 | 1.021 | 0.541 | 0.456 | 0.195 | 0.397 | 0.229 |
| Group 10 (1.0 mg/kg AD05267) | 0.369 | 0.038 | 0.652 | 0.223 | 1.581 | 0.403 | 0.748 | 0.255 | 0.653 | 0.079 |
| Group 11 (1.0 mg/kg AD05268) | 0.216 | 0.093 | 0.201 | 0.067 | 0.299 | 0.134 | 0.151 | 0.050 | 0.213 | 0.034 |

Example 13. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing 1.0 mg/kg of an ASGR1 RNAi agent, or 200 µl of saline without an ASGR1 RNAi agent to be used as a control, according to the following Table 27.

TABLE 27

Dosing groups of ASG7R1-SEAP mice of Example 13.

| Group | RNAi Agent and Dose | Dosing Regimen |
|---|---|---|
| 1 | Saline (no RNAi agent) | Single injection on day 1 |
| 2 | 1.0 mg/kg AD05067 | Single injection on day 1 |
| 3 | 1.0 mg/kg AD05241 | Single injection on day 1 |
| 4 | 1.0 mg/kg AD05242 | Single injection on day 1 |
| 5 | 1.0 mg/kg AD05243 | Single injection on day 1 |
| 6 | 1.0 mg/kg AD05109 | Single injection on day 1 |
| 7 | 1.0 mg/kg AD05244 | Single injection on day 1 |
| 8 | 1.0 mg/kg AD05247 | Single injection on day 1 |
| 9 | 1.0 mg/kg AD05248 | Single injection on day 1 |
| 10 | 1.0 mg/kg AD05212 | Single injection on day 1 |
| 11 | 1.0 mg/kg AD05214 | Single injection on day 1 |
| 12 | 1.0 mg/kg AD05206 | Single injection on day 1 |
| 13 | 1.0 mg/kg AD05207 | Single injection on day 1 |
| 14 | 1.0 mg/kg AD05208 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 16, day 22, day 29, and day 36, and SEAP expression levels were determined pursuant to the procedure set forth in Example 2, above. Data from the experiment are shown in the following Table 28, with Average SEAP reflecting the normalized average value of SEAP:

TABLE 28

Average SEAP normalized to pre-treatment and saline control in ASGR1-SEAP mice from Example 13.

| Group ID | Day 8 Avg SEAP | Day 8 Std Dev (+/−) | Day 16 Avg SEAP | Day 16 Std Dev (+/−) | Day 22 Avg SEAP | Day 22 Std Dev (+/−) | Day 29 Avg SEAP | Day 29 Std Dev (+/−) | Day 36 Avg SEAP | Day 36 Std Dev (+/−) |
|---|---|---|---|---|---|---|---|---|---|---|
| Group 1 (Saline) | 1.000 | 0.252 | 1.000 | 0.134 | 1.000 | 0.375 | 1.000 | 0.454 | 1.000 | 0.337 |
| Group 2 (1.0 mg/kg AD05067) | 0.353 | 0.107 | 0.203 | 0.074 | 0.239 | 0.044 | 0.270 | 0.039 | 0.307 | 0.064 |
| Group 3 (1.0 mg/kg AD05241) | 0.457 | 0.177 | 0.338 | 0.184 | 0.217 | 0.093 | 0.236 | 0.129 | 0.325 | 0.186 |
| Group 4 (1.0 mg/kg AD05242) | 0.302 | 0.181 | 0.209 | 0.147 | 0.209 | 0.148 | 0.214 | 0.099 | 0.164 | 0.019 |
| Group 5 (1.0 mg/kg AD05243) | 0.379 | 0.133 | 0.141 | 0.022 | 0.111 | 0.040 | 0.134 | 0.033 | 0.158 | 0.041 |
| Group 6 (1.0 mg/kg AD05109) | 0.454 | 0.087 | 0.171 | 0.054 | 0.114 | 0.036 | 0.136 | 0.063 | 0.176 | 0.066 |
| Group 7 (1.0 mg/kg AD05244) | 0.468 | 0.138 | 0.363 | 0.209 | 0.274 | 0.189 | 0.170 | 0.096 | 0.244 | 0.086 |
| Group 8 (1.0 mg/kg AD05247) | 0.662 | 0.249 | 0.670 | 0.299 | 0.569 | 0.232 | 0.594 | 0.288 | 0.804 | 0.531 |
| Group 9 (1.0 mg/kg AD05248) | 0.597 | 0.127 | 0.325 | 0.252 | 0.276 | 0.182 | 0.246 | 0.241 | 0.293 | 0.301 |
| Group 10 (1.0 mg/kg AD05212) | 0.413 | 0.045 | 0.244 | 0.122 | 0.123 | 0.072 | 0.119 | 0.047 | 0.171 | 0.077 |
| Group 11 (1.0 mg/kg AD05214) | 0.486 | 0.049 | 0.252 | 0.104 | 0.213 | 0.063 | 0.198 | 0.015 | 0.189 | 0.023 |
| Group 12 (1.0 mg/kg AD05206) | 0.359 | 0.166 | 0.196 | 0.066 | 0.214 | 0.089 | 0.284 | 0.104 | 0.416 | 0.127 |
| Group 13 (1.0 mg/kg AD05207) | 1.109 | 0.103 | 0.484 | 0.223 | 0.381 | 0.275 | 0.404 | 0.247 | 0.605 | 0.382 |
| Group 14 (1.0 mg/kg AD05208) | 0.529 | 0.063 | 0.252 | 0.022 | 0.221 | 0.026 | 0.160 | 0.042 | 0.303 | 0.112 |

Example 14. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 µl containing either 0.5 mg/kg, 1.0 mg/kg, or 3.0 mg/kg of an ASGR1 RNAi agent, or 200 µl of saline without an ASGR1 RNAi agent to be used as a control, according to the following Table 29.

TABLE 29

Dosing groups of ASGR1-SEAP mice of Example 14.

| Group | RNAi Agent and Dose | Dosing Regimen |
|---|---|---|
| 1 | Saline (no RNAi agent) | Single injection on day 1 |
| 2 | 0.5 mg/kg AD05067 | Single injection on day 1 |
| 3 | 1.0 mg/kg AD05067 | Single injection on day 1 |
| 4 | 3.0 mg/kg AD05067 | Single injection on day 1 |
| 5 | 0.5 mg/kg AD05183 | Single injection on day 1 |
| 6 | 1.0 mg/kg AD05183 | Single injection on day 1 |
| 7 | 3.0 mg/kg AD05183 | Single injection on day 1 |
| 8 | 0.5 mg/kg AD05209 | Single injection on day 1 |
| 9 | 1.0 mg/kg AD05209 | Single injection on day 1 |
| 10 | 4.0 mg/kg AD05209 | Single injection on day 1 |
| 11 | 0.5 mg/kg AD05256 | Single injection on day 1 |
| 12 | 1.0 mg/kg AD05256 | Single injection on day 1 |
| 13 | 3.0 mg/kg AD05256 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, day 29, and day 36, and SEAP expression levels were determined pursuant to the procedure set forth in Example 2, above. Data from the experiment are shown in the following Table 30, with Average SEAP reflecting the normalized average value of SEAP:

TABLE 30

Average SEAP normalized to pre-treatment and saline control in ASGR1-SEAP mice from Example 14.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) | Day 36 Avg SEAP | Day 36 Std Dev (+/−) |
|---|---|---|---|---|---|---|---|---|---|---|
| Group 1 (Saline) | 1.000 | 0.479 | 1.000 | 0.737 | 1.000 | 0.401 | 1.000 | 0.359 | 1.000 | 0.601 |
| Group 2 (0.5 mg/kg AD05067) | 0.315 | 0.178 | 0.215 | 0.087 | 0.175 | 0.072 | 0.143 | 0.047 | 0.218 | 0.042 |
| Group 3 (1.0 mg/kg AD05067) | 0.265 | 0.136 | 0.129 | 0.071 | 0.139 | 0.025 | 0.165 | 0.029 | 0.238 | 0.046 |
| Group 4 (3.0 mg/kg AD05067) | 0.250 | 0.092 | 0.069 | 0.036 | 0.083 | 0.029 | 0.083 | 0.060 | 0.138 | 0.130 |
| Group 5 (0.5 mg/kg AD05183) | 0.274 | 0.140 | 0.156 | 0.053 | 0.173 | 0.069 | 0.215 | 0.039 | 0.261 | 0.111 |
| Group 6 (1.0 mg/kg AD05183) | 0.305 | 0.047 | 0.123 | 0.020 | 0.158 | 0.093 | 0.221 | 0.069 | 0.157 | 0.051 |
| Group 7 (3.0 mg/kg AD05183) | 0.182 | 0.060 | 0.052 | 0.028 | 0.069 | 0.036 | 0.070 | 0.045 | 0.069 | 0.068 |
| Group 8 (0.5 mg/kg AD05209) | 0.295 | 0.110 | 0.193 | 0.062 | 0.268 | 0.131 | 0.399 | 0.232 | 0.404 | 0.160 |
| Group 9 (1.0 mg/kg AD05209) | 0.185 | 0.034 | 0.073 | 0.031 | 0.113 | 0.051 | 0.120 | 0.055 | 0.175 | 0.106 |
| Group 10 (3.0 mg/kg AD05209) | 0.100 | 0.021 | 0.020 | 0.007 | 0.024 | 0.004 | 0.025 | 0.013 | 0.036 | 0.024 |
| Group 11 (0.5 mg/kg AD05256) | 0.618 | 0.069 | 0.334 | 0.087 | 0.397 | 0.128 | 0.430 | 0.312 | 0.484 | 0.298 |
| Group 12 (1.0 mg/kg AD05256) | 0.392 | 0.126 | 0.129 | 0.015 | 0.195 | 0.067 | 0.238 | 0.075 | 0.255 | 0.111 |
| Group 13 (3.0 mg/kg AD05256) | 0.199 | 0.063 | 0.070 | 0.033 | 0.110 | 0.078 | 0.134 | 0.079 | 0.121 | 0.063 |

As shown in Table 30 above, a dose response is observed for each of the ASGR1 RNAi agents tested. For example, on day 22, ASGR1 RNAi agent AD05209 showed knockdown of approximately 73% (0.268) at 0.5 mg/kg; approximately 89% (0.113) at 1.0 mg/kg; and approximately 98% (0.024) at 3.0 mg/kg administered dose.

Example 15. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates ("cynomolgus monkeys") were given a single subcutaneous injection of 0.3 mL/kg (approximately 2-3 mL volume, depending on animal mass) containing 5.0 mg/kg of ASGR1 RNAi agent AD05126 or AD05150, formulated in saline. Each of the ASGR1 RNAi agents included N-acetyl-galactosamine targeting ligands conjugated to the 5'-terminal end of the sense strand, as shown in Tables 4 and 5.

Two (2) monkeys in each group were tested (n=2). Blood samples were drawn and serum samples were analyzed on days 1 (predose), 8, 15, 22, 29, 36, and 50, for alkaline phosphatase (referred to as "ALP", "ALKP", or "Alk-Phos") and standard clinical chemistry panel. As ALP is a substrate of ASGR1, reduction of ASGR1 is expected to increase ALP levels, as observed in the ASGR1 del12 carriers in the human population. Overall, reduction of ASGR1 levels by 50% in ASGR1 del12 carriers showed an increase in ALP levels of around 50.1%. Therefore, ALP has been shown to serve as a surrogate biomarker for monitoring reduction in ASGR1 and inhibition of an ASGR1 gene. (Nioi et al., 2016). ALP levels in serum were measured on a Cobas® Integra 400 (Roche Diagnostics), according to the manufacturer's recommendations.

Data from the experiment are shown in the following Tables 31 and 32, which report raw ALP values (units/L) as well as ALP normalized to averaged individual pre-treatment levels.

Each of cynomolgus monkeys dosed with either AD05126 or AD05150 showed in increase in ALP compared to pre-dose measurements across all measured time points, indicating a reduction in ASGR1 protein levels and inhibition of ASGR1.

Example 16. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates ("cynomolgus monkeys") were given a single subcutaneous injection of 0.3 mL/kg (approximately 2-3 mL volume, depending on animal mass) containing 5.0 mg/kg of ASGR1 RNAi agent AD05186 or AD05196, formulated in saline. Each of the ASGR1 RNAi agents included N-acetyl-galactosamine targeting ligands conjugated to the 5'-terminal end of the sense strand, as shown in Tables 4 and 5.

Two (2) monkeys in each group were tested (n=2). Blood samples were drawn and serum samples were analyzed on days 1 (predose), 8, 15, 22, 29, 36, and 43, for ALP and standard clinical chemistry panel. As noted in Example 15, ALP serves as a surrogate biomarker for monitoring reduction in ASGR1 and inhibition of an ASGR1 gene. ALP levels in serum were measured on a Cobas® Integra 400 (Roche Diagnostics), according to the manufacturer's recommendations.

Data from the experiment are shown in the following Tables 33 and 34, which report raw ALP values (units/L) as well as ALP normalized to averaged individual pre-treatment levels.

TABLE 31

ALP levels from cynomolgus monkeys from Example 15 (ALP levels reported in units/L) from Cobas ®.

| Group ID | Mean Predose ALP | Day 8 ALP | Day 15 ALP | Day 22 ALP | Day 29 ALP | Day 36 ALP | Day 50 ALP |
|---|---|---|---|---|---|---|---|
| AD05126 (Cyno A) (5.0 mg/kg) | 74 | 88 | 100 | 120 | 122 | 115 | 107 |
| AD05126 (Cyno B) (5.0 mg/kg) | 115 | 128 | 151 | 159 | 160 | 146 | 159 |
| AD05150 (Cyno A) (5.0 mg/kg) | 90 | 100 | 103 | 110 | 104 | 111 | 101 |
| AD05150 (Cyno B) (5.0 mg/kg) | 105 | 112 | 136 | 152 | 165 | 153 | 161 |

TABLE 32

Normalized ALP levels from cynomolgus monkeys from Example 15 from Cobas ®.

| Group ID | Mean Predose ALP | Day 8 ALP | Day 15 ALP | Day 22 ALP | Day 29 ALP | Day 36 ALP | Day 50 ALP |
|---|---|---|---|---|---|---|---|
| AD05126 (Cyno A) (5.0 mg/kg) | 1.00 | 1.19 | 1.36 | 1.63 | 1.66 | 1.56 | 1.45 |
| AD05126 (Cyno B) (5.0 mg/kg) | 1.00 | 1.12 | 1.32 | 1.39 | 1.40 | 1.27 | 1.39 |
| AD05150 (Cyno A) (5.0 mg/kg) | 1.00 | 1.11 | 1.14 | 1.22 | 1.15 | 1.23 | 1.12 |
| AD05150 (Cyno B) (5.0 mg/kg) | 1.00 | 1.06 | 1.29 | 1.44 | 1.57 | 1.45 | 1.53 |

TABLE 33

ALP levels from cynomolgus monkeys from Example 16
(ALP levels reported in units/L) from Cobas ®.

| Group ID | Mean Predose ALP | Day 8 ALP | Day 15 ALP | Day 22 ALP | Day 29 ALP | Day 36 ALP | Day 43 ALP |
|---|---|---|---|---|---|---|---|
| AD05186 (Cyno A) (5.0 mg/kg) | 89 | 96 | 118 | 135 | 134 | 127 | 134 |
| AD05186 (Cyno B) (5.0 mg/kg) | 177 | 213 | 284 | 324 | 354 | 380 | 364 |
| AD05196 (Cyno A) (5.0 mg/kg) | 97 | 107 | 143 | 178 | 206 | 219 | 199 |
| AD05196 (Cyno B) (5.0 mg/kg) | 170 | 177 | 237 | 255 | 292 | 285 | 304 |

TABLE 34

Normalized ALP levels from cynomolgus monkeys from Example 16 from Cobas ®.

| Group ID | Mean Predose ALP | Day 8 ALP | Day 15 ALP | Day 22 ALP | Day 29 ALP | Day 36 ALP | Day 43 ALP |
|---|---|---|---|---|---|---|---|
| AD05186 (Cyno A) (5.0 mg/kg) | 1.00 | 1.08 | 1.33 | 1.52 | 1.51 | 1.43 | 1.51 |
| AD05186 (Cyno B) (5.0 mg/kg) | 1.00 | 1.21 | 1.61 | 1.84 | 2.01 | 2.15 | 2.06 |
| AD05196 (Cyno A) (5.0 mg/kg) | 1.00 | 1.10 | 1.47 | 1.84 | 2.12 | 2.26 | 2.05 |
| AD05196 (Cyno B) (5.0 mg/kg) | 1.00 | 1.04 | 1.40 | 1.50 | 1.72 | 1.68 | 1.79 |

Example 17. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates were given a single subcutaneous injection of 0.3 mL/kg (approximately 2-3 mL volume, depending on animal mass) containing 3.0 mg/kg of ASGR1 RNAi agent AD05183 or AD05193, formulated in saline. Each of the ASGR1 RNAi agents included N-acetyl-galactosamine targeting ligands conjugated to the 5'-terminal end of the sense strand, as shown in Tables 4 and 5.

Two (2) monkeys in each group were tested (n=2). Blood samples were drawn and serum samples were analyzed on days 8, 15, 22, 29, 36, and 43, for ALP and standard clinical chemistry panel. As noted in Example 15, ALP serves as a surrogate biomarker for monitoring reduction in ASGR1 and inhibition of an ASGR1 gene. ALP levels in serum were measured on a Cobas® Integra 400 (Roche Diagnostics), according to the manufacturer's recommendations.

Data from the experiment are shown in the following Tables 35 and 36, which report raw ALP values (units/L) as well as ALP normalized to averaged individual pre-treatment levels.

TABLE 35

ALP levels from cynomolgus monkeys from Example 17
(ALP levels reported in units/L) from Cobas ®.

| Group ID | Mean Predose ALP | Day 8 ALP | Day 15 ALP | Day 22 ALP | Day 29 ALP | Day 36 ALP | Day 43 ALP |
|---|---|---|---|---|---|---|---|
| AD05183 (Cyno A) (3.0 mg/kg) | 236 | 245 | 347 | 472 | 575 | 630 | 578 |
| AD05183 (Cyno B) (3.0 mg/kg) | 193 | 186 | 250 | 318 | 411 | 452 | 458 |
| AD05193 (Cyno A) (3.0 mg/kg) | 295 | 272 | 374 | 490 | 620 | 693 | 593 |
| AD05193 (Cyno B) (3.0 mg/kg) | 242 | 238 | 284 | 369 | 427 | 481 | 440 |

TABLE 36

Normalized ALP levels from cynomolgus monkeys from Example 17 from Cobas ®.

| Group ID | Mean Predose ALP | Day 8 ALP | Day 15 ALP | Day 22 ALP | Day 29 ALP | Day 36 ALP | Day 43 ALP |
|---|---|---|---|---|---|---|---|
| AD05183 (Cyno A) (3.0 mg/kg) | 1.00 | 1.04 | 1.47 | 2.00 | 2.44 | 2.67 | 2.45 |
| AD05183 (Cyno B) (3.0 mg/kg) | 1.00 | 0.97 | 1.30 | 1.65 | 2.13 | 2.35 | 2.38 |
| AD05193 (Cyno A) (3.0 mg/kg) | 1.00 | 0.92 | 1.27 | 1.66 | 2.10 | 2.35 | 2.01 |
| AD05193 (Cyno B) (3.0 mg/kg) | 1.00 | 0.98 | 1.17 | 1.52 | 1.76 | 1.99 | 1.82 |

Example 18. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates were given a single subcutaneous injection of 0.3 mL/kg (approximately 2-3 mL volume, depending on animal mass) containing 16.7 mg/mL for a total dose of 5.0 mg/kg of ASGR1 RNAi agent AD05209, AD05195, or AD05256, formulated in saline. Each of the ASGR1 RNAi agents included N-acetyl-galactosamine targeting ligands conjugated to the 5'-terminal end of the sense strand, as shown in Tables 4 and 5.

Two (2) monkeys in each group were tested, except for AD05195 where only 1 monkey was dosed. Blood samples were drawn and serum samples were analyzed on days 8, 15, 22, and 29, for ALP and standard clinical chemistry panel. As noted in Example 15, ALP serves as a surrogate biomarker for monitoring reduction in ASGR1 and inhibition of an ASGR1 gene. ALP levels in serum were measured on a Cobas® Integra 400 (Roche Diagnostics), according to the manufacturer's recommendations.

Data from the experiment are shown in the following Tables 37 and 38, which report raw ALP values (units/L) as well as ALP normalized to averaged individual pre-treatment levels.

TABLE 37

ALP levels from cynomolgus monkeys from Example 18 (ALP levels reported in units/L) from Cobas ®.

| Group ID | Mean Predose ALP | Day 8 ALP | Day 15 ALP | Day 22 ALP | Day 29 ALP |
|---|---|---|---|---|---|
| AD05209 (Cyno A) (5.0 mg/kg) | 64 | 77 | 147 | 199 | 231 |
| AD05209 (Cyno B) (5.0 mg/kg) | 81 | 114 | 174 | 214 | 223 |
| AD05195 (Cyno A) (5.0 mg/kg) | 116 | 122 | 161 | 181 | 177 |
| AD05256 (Cyno A) (5.0 mg/kg) | 69 | 73 | 79 | 86 | 91 |
| AD05256 (Cyno B) (5.0 mg/kg) | 122 | 163 | 255 | 313 | 352 |

TABLE 38

Normalized ALP levels from cynomolgus monkeys from Example 18 from Cobas ®.

| Group ID | Mean Predose ALP | Day 8 ALP | Day 15 ALP | Day 22 ALP | Day 29 ALP |
|---|---|---|---|---|---|
| AD05209 (Cyno A) (5.0 mg/kg) | 1.00 | 1.20 | 2.30 | 3.11 | 3.61 |
| AD05209 (Cyno B) (5.0 mg/kg) | 1.00 | 1.41 | 2.15 | 2.64 | 2.75 |
| AD05195 (Cyno A) (5.0 mg/kg) | 1.00 | 1.06 | 1.39 | 1.57 | 1.53 |
| AD05256 (Cyno A) (5.0 mg/kg) | 1.00 | 1.06 | 1.14 | 1.25 | 1.32 |
| AD05256 (Cyno B) (5.0 mg/kg) | 1.00 | 1.34 | 2.10 | 2.58 | 2.90 |

Example 19. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates were given a single subcutaneous injection of 0.3 mL/kg (approximately 2-3 mL volume, depending on animal mass) containing 10.0 mg/mL, 16.7 mg/mL, or 26.7 mg/mL, for a total dose of 3.0 mg/kg, 5.0 mg/kg, or 8.0 mg/kg, respectively, of ASGR1 RNAi agent AD05183 formulated in saline. An additional group was dosed with 0.3 mL/kg (approximately 2-3 mL volume, depending on animal mass) with saline to be used as a control. Each of ASGR1 RNAi agents included N-acetyl-galactosamine targeting ligands conjugated to the 5'-terminal end of the sense strand, as shown in Tables 4 and 5.

Two (2) monkeys in each group were tested, except that one of the monkeys dosed with saline control died prior to day 15. Blood samples were drawn and serum samples were analyzed on days 8, 15, 22, 29, 36, 43, 50 and 57 for ALP and standard clinical chemistry panel. As noted in Example 15, ALP serves as a surrogate biomarker for monitoring reduction in ASGR1 and inhibition of an ASGR1 gene. ALP levels in serum were measured on a Cobas® Integra 400 (Roche Diagnostics), according to the manufacturer's recommendations.

Data from the experiment are shown in the following Tables 39 and 40, which report raw ALP values (units/L) as well as ALP normalized to averaged individual pre-treatment levels.

TABLE 39

ALP levels from cynomolgus monkeys from Example 19 (ALP levels reported in units/L) from Cobas ®.

| Group ID | Day 1 (pre-dose) ALP | Day 8 ALP | Day 15 ALP | Day 22 ALP | Day 29 ALP | Day 36 ALP | Day 43 ALP | Day 50 ALP | Day 57 ALP |
|---|---|---|---|---|---|---|---|---|---|
| Saline vehicle (Cyno A) | 644 | 544 | | | | | | | |
| Saline vehicle (Cyno B) | 337 | 341 | 317 | 297 | 313 | 331 | 342 | 329 | 347 |
| 3.0 mg/kg AD05183 (Cyno A) | 350 | 421 | 698 | 919 | 847 | 739 | 727 | 776 | 759 |
| 3.0 mg/kg AD05183 (Cyno B) | 633 | 735 | 1053 | 1116 | 1423 | 1161 | 1181 | 1187 | 1130 |
| 5.0 mg/kg AD05183 (Cyno A) | 554 | 681 | 1079 | 1146 | 1317 | 1184 | 1179 | 1386 | 1391 |
| 5.0 mg/kg AD05183 (Cyno B) | 415 | 491 | 790 | 799 | 815 | 848 | 794 | 818 | 788 |
| 8.0 mg/kg AD05183 (Cyno A) | 459 | 592 | 874 | 1006 | 1249 | 1065 | 1028 | 1251 | 1120 |
| 8.0 mg/kg AD05183 (Cyno B) | 630 | 689 | 816 | 957 | 959 | 888 | 913 | 1007 | 959 |

TABLE 40

Normalized ALP levels from cynomolgus monkeys from Example 19 from Cobas ®.

| Group ID | Day 1 (pre-dose) ALP | Day 8 ALP | Day 15 ALP | Day 22 ALP | Day 29 ALP | Day 36 ALP | Day 43 ALP | Day 50 ALP | Day 57 ALP |
|---|---|---|---|---|---|---|---|---|---|
| Saline vehicle (Cyno A) | 1.00 | 0.85 | | | | | | | |
| Saline vehicle (Cyno B) | 1.00 | 1.01 | 0.94 | 0.88 | 0.93 | 0.98 | 1.02 | 0.98 | 1.03 |
| 3.0 mg/kg AD05183 (Cyno A) | 1.00 | 1.20 | 1.99 | 2.62 | 2.42 | 2.11 | 2.08 | 2.22 | 2.17 |
| 3.0 mg/kg AD05183 (Cyno B) | 1.00 | 1.16 | 1.66 | 1.76 | 2.25 | 1.84 | 1.87 | 1.88 | 1.79 |
| 5.0 mg/kg AD05183 (Cyno A) | 1.00 | 1.23 | 1.95 | 2.07 | 2.38 | 2.14 | 2.13 | 2.50 | 2.51 |
| 5.0 mg/kg AD05183 (Cyno B) | 1.00 | 1.18 | 1.90 | 1.93 | 1.96 | 2.04 | 1.91 | 1.97 | 1.90 |
| 8.0 mg/kg AD05183 (Cyno A) | 1.00 | 1.29 | 1.90 | 2.19 | 2.72 | 2.32 | 2.24 | 2.72 | 2.44 |
| 8.0 mg/kg AD05183 (Cyno B) | 1.00 | 1.09 | 1.30 | 1.52 | 1.52 | 1.41 | 1.45 | 1.60 | 1.52 |

Example 20. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 μl containing 1.0 mg/kg of an ASGR1 RNAi agent, or 200 μl of saline without an ASGR1 RNAi agent to be used as a control, according to the following Table 41.

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, day 29, and day 36, and SEAP expression levels were determined pursuant to the procedure set forth in Example 2, above. Data from the experiment are shown in the following Table 42, with Average SEAP reflecting the normalized average value of SEAP:

TABLE 42

Average SEAP normalized to pre-treatment and saline control in ASGR1-SEAP mice from Example 20.

| | Day 8 | | Day 15 | | Day 22 | | Day 29 | | Day 36 | |
|---|---|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) | Avg SEAP | Std Dev (+/−) |
| Group 1 (Saline) | 1.000 | 0.214 | 1.000 | 0.205 | 1.000 | 0.253 | 1.000 | 0.469 | 1.000 | 0.207 |
| Group 2 (1.0 mg/kg AD05067) | 0.490 | 0.126 | 0.303 | 0.102 | 0.284 | 0.099 | 0.286 | 0.173 | 0.570 | 0.459 |
| Group 3 (1.0 mg/kg AD05183) | 0.404 | 0.138 | 0.205 | 0.109 | 0.216 | 0.093 | 0.311 | 0.089 | 0.574 | 0.343 |
| Group 4 (1.0 mg/kg AD05209) | 0.209 | 0.100 | 0.110 | 0.084 | 0.146 | 0.101 | 0.233 | 0.209 | 0.483 | 0.403 |
| Group 5 (1.0 mg/kg AD05256) | 0.413 | 0.159 | 0.238 | 0.124 | 0.252 | 0.148 | 0.338 | 0.172 | 0.276 | 0.113 |
| Group 6 (1.0 mg/kg AD05373) | 0.397 | 0.091 | 0.236 | 0.091 | 0.572 | 0.136 | 0.654 | 0.233 | 0.987 | 0.489 |
| Group 7 (1.0 mg/kg AD05374) | 0.266 | 0.051 | 0.248 | 0.148 | 0.281 | 0.069 | 0.443 | 0.204 | 0.634 | 0.357 |
| Group 8 (1.0 mg/kg AD05375) | 0.388 | 0.156 | 0.519 | 0.255 | 0.672 | 0.090 | 1.005 | 0.327 | 1.208 | 0.523 |
| Group 9 (1.0 mg/kg AD05376) | 0.270 | 0.071 | 0.321 | 0.239 | 0.295 | 0.078 | 0.349 | 0.166 | 0.455 | 0.233 |
| Group 10 (1.0 mg/kg AD05377) | 0.442 | 0.085 | 0.624 | 0.228 | 0.846 | 0.308 | 1.012 | 0.413 | 1.133 | 0.236 |
| Group 11 (1.0 mg/kg AD05378) | 0.304 | 0.080 | 0.203 | 0.097 | 0.280 | 0.117 | 0.315 | 0.079 | 0.635 | 0.184 |
| Group 12 (1.0 mg/kg AD05379) | 0.372 | 0.029 | 0.366 | 0.077 | 0.471 | 0.191 | 0.660 | 0.185 | 1.169 | 0.244 |
| Group 13 (1.0 mg/kg AD05380) | 0.298 | 0.084 | 0.320 | 0.251 | 0.289 | 0.098 | 0.409 | 0.233 | 0.846 | 0.702 |

TABLE 41

Dosing groups of ASGR1-SEAP mice of Example 20.

| Group | RNAi Agent and Dose | Dosing Regimen |
|---|---|---|
| 1 | Saline (no RNAi agent) | Single injection on day 1 |
| 2 | 1.0 mg/kg AD05067 | Single injection on day 1 |
| 3 | 1.0 mg/kg AD05183 | Single injection on day 1 |
| 4 | 1.0 mg/kg AD05209 | Single injection on day 1 |
| 5 | 1.0 mg/kg AD05256 | Single injection on day 1 |
| 6 | 1.0 mg/kg AD05373 | Single injection on day 1 |
| 7 | 1.0 mg/kg AD05374 | Single injection on day 1 |
| 8 | 1.0 mg/kg AD05375 | Single injection on day 1 |
| 9 | 1.0 mg/kg AD05376 | Single injection on day 1 |
| 10 | 1.0 mg/kg AD05377 | Single injection on day 1 |
| 11 | 1.0 mg/kg AD05378 | Single injection on day 1 |
| 12 | 1.0 mg/kg AD05379 | Single injection on day 1 |
| 13 | 1.0 mg/kg AD05380 | Single injection on day 1 |

Example 21. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 μl containing 1.0 mg/kg of an ASGR1 RNAi agent, or 200 μl of saline without an ASGR1 RNAi agent to be used as a control, according to the following Table 43.

TABLE 43

Dosing groups of ASGR1-SEAP mice of Example 21.

| Group | RNAi Agent and Dose | Dosing Regimen |
|---|---|---|
| 1 | Saline (no RNAi agent) | Single injection on day 1 |
| 2 | 1.0 mg/kg AD05193 | Single injection on day 1 |
| 3 | 1.0 mg/kg AD05196 | Single injection on day 1 |
| 4 | 1.0 mg/kg AD05462 | Single injection on day 1 |

TABLE 43-continued

Dosing groups of ASGR1-SEAP mice of Example 21.

| Group | RNAi Agent and Dose | Dosing Regimen |
|---|---|---|
| 5 | 1.0 mg/kg AD05603 | Single injection on day 1 |
| 6 | 1.0 mg/kg AD05604 | Single injection on day 1 |
| 7 | 1.0 mg/kg AD05605 | Single injection on day 1 |
| 8 | 1.0 mg/kg AD05606 | Single injection on day 1 |
| 9 | 1.0 mg/kg AD05607 | Single injection on day 1 |
| 10 | 1.0 mg/kg AD05608 | Single injection on day 1 |
| 11 | 1.0 mg/kg AD05609 | Single injection on day 1 |
| 12 | 1.0 mg/kg AD05610 | Single injection on day 1 |
| 13 | 1.0 mg/kg AD05624 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, day 29, and day 36, and SEAP expression levels were determined pursuant to the procedure set forth in Example 2, above. Data from the experiment are shown in the following Table 44, with Average SEAP reflecting the normalized average value of SEAP:

TABLE 44

Average SEAP normalized to pre-treatment and saline control in ASGR1-SEAP mice from Example 21.

| Group ID | Day 8 | | Day 15 | | Day 22 | | Day 29 | | Day 36 | |
|---|---|---|---|---|---|---|---|---|---|---|
| | Avg SEAP | Std Dev (+/-) | Avg SEAP | Std Dev (+/-) | Avg SEAP | Std Dev (+/-) | Avg SEAP | Std Dev (+/-) | Avg SEAP | Std Dev (+/-) |
| Group 1 (Saline) | 1.000 | 0.349 | 1.000 | 0.246 | 1.000 | 0.152 | 1.00 | 0.330 | 1.000 | 0.305 |
| Group 2 (1.0 mg/kg AD05193) | 0.307 | 0.177 | 0.275 | 0.273 | 0.480 | 0.451 | 0.465 | 0.442 | 0.539 | 0.557 |
| Group 3 (1.0 mg/kg AD05196) | 0.176 | 0.072 | 0.120 | 0.052 | 0.181 | 0.053 | 0.186 | 0.107 | 0.481 | 0.272 |
| Group 4 (1.0 mg/kg AD05462) | 0.230 | 0.015 | 0.176 | 0.121 | 0.374 | 0.054 | 0.739 | 0.097 | 0.775 | 0.320 |
| Group 5 (1.0 mg/kg AD05603) | 0.186 | 0.060 | 0.242 | 0.033 | 0.529 | 0.170 | 0.645 | 0.134 | 1.321 | 0.295 |
| Group 6 (1.0 mg/kg AD05604) | 0.170 | 0.029 | 0.171 | 0.128 | 0.204 | 0.159 | 0.318 | 0.343 | 0.452 | 0.448 |
| Group 7 (1.0 mg/kg AD05605) | 0.149 | 0.026 | 0.127 | 0.036 | 0.222 | 0.036 | 0.304 | 0.018 | 0.404 | 0.115 |
| Group 8 (1.0 mg/kg AD05606) | 0.144 | 0.024 | 0.130 | 0.035 | 0.380 | 0.038 | 0.406 | 0.081 | 0.672 | 0.054 |
| Group 9 (1.0 mg/kg AD05607) | 0.166 | 0.032 | 0.095 | 0.046 | 0.137 | 0.049 | 0.194 | 0.084 | 0.268 | 0.176 |
| Group 10 (1.0 mg/kg AD05608) | 0.181 | 0.051 | 0.149 | 0.085 | 0.247 | 0.186 | 0.342 | 0.184 | 0.587 | 0.393 |
| Group 11 (1.0 mg/kg AD05609) | 0.120 | 0.008 | 0.118 | 0.031 | 0.223 | 0.047 | 0.210 | 0.109 | 0.493 | 0.333 |
| Group 12 (1.0 mg/kg AD05610) | 0.151 | 0.028 | 0.098 | 0.053 | 0.255 | 0.138 | 0.274 | 0.117 | 0.342 | 0.161 |
| Group 13 (1.0 mg/kg AD05624) | 0.165 | 0.072 | 0.595 | 0.582 | 0.912 | 1.128 | 0.391 | 0.306 | 0.611 | 0.757 |

Example 22. In Vivo Testing of ASGR1 RNAi Agents in Cynomolgus Monkeys

ASGR1 RNAi agents were evaluated in cynomolgus monkeys. On day 1, cynomolgus macaque (*Macaca fascicularis*) primates were given a single subcutaneous injection of 0.3 mL/kg (approximately 2-3 mL volume, depending on animal mass) containing 10.0 mg/mL, for a total dose of 3.0 mg/kg, of either ASGR1 RNAi agent AD05209, AD05374, AD05609, or AD05692, each formulated in saline. Each of ASGR1 RNAi agents included N-acetyl-galactosamine targeting ligands conjugated to the 5'-terminal end of the sense strand, as shown in Tables 4 and 5.

Two (2) monkeys in each group were tested. Blood samples were drawn and serum samples were analyzed on days 8, 15, 22, 29, and 36 for ALP and standard clinical chemistry panel. As noted in Example 15, ALP serves as a surrogate biomarker for monitoring reduction in ASGR1 and inhibition of an ASGR1 gene. ALP levels in serum were measured on a Cobas® Integra 400 (Roche Diagnostics), according to the manufacturer's recommendations.

Data from the experiment are shown in the following Tables 45 and 46, which report raw ALP values (units/L) as well as ALP normalized to the mean of the individual pre-treatment levels.

TABLE 45

ALP levels from cynomolgus monkeys from Example 22
(ALP levels reported in units/L) from Cobas ®

| Group ID | Mean Predose ALP | Day 8 ALP | Day 15 ALP | Day 22 ALP | Day 29 ALP | Day 36 ALP |
|---|---|---|---|---|---|---|
| 3.0 mg/kg AD05209 (Cyno A) | 342 | 427 | 616 | 750 | 707 | 754 |
| 3.0 mg/kg AD05209 (Cyno B) | 253 | 323 | 410 | 521 | 573 | 520 |
| 3.0 mg/kg AD05374 (Cyno A) | 298 | 345 | 406 | 420 | 420 | 415 |
| 3.0 mg/kg AD05374 (Cyno B) | 225 | 292 | 397 | 402 | 367 | 338 |
| 3.0 mg/kg AD05609 (Cyno A) | 320 | 365 | 428 | 475 | 542 | 532 |
| 3.0 mg/kg AD05609 (Cyno B) | 214 | 299 | 380 | 481 | 427 | 371 |
| 3.0 mg/kg AD05692 (Cyno A) | 320 | 370 | 405 | 406 | 388 | 430 |
| 3.0 mg/kg AD05692 (Cyno B) | 110 | 144 | 186 | 182 | 175 | 148 |

TABLE 46

Normalized ALP levels from cynomolgus monkeys from Example 22 from Cobas ®.

| Group ID | Mean Predose ALP | Day 8 ALP | Day 15 ALP | Day 22 ALP | Day 29 ALP | Day 36 ALP |
|---|---|---|---|---|---|---|
| 3.0 mg/kg AD05209 (Cyno A) | 1.00 | 1.25 | 1.80 | 2.19 | 2.07 | 2.20 |
| 3.0 mg/kg AD05209 (Cyno B) | 1.00 | 1.28 | 1.62 | 2.06 | 2.26 | 2.05 |
| 3.0 mg/kg AD05374 (Cyno A) | 1.00 | 1.16 | 1.36 | 1.41 | 1.41 | 1.39 |
| 3.0 mg/kg AD05374 (Cyno B) | 1.00 | 1.30 | 1.76 | 1.79 | 1.63 | 1.50 |
| 3.0 mg/kg AD05609 (Cyno A) | 1.00 | 1.14 | 1.34 | 1.49 | 1.70 | 1.66 |
| 3.0 mg/kg AD05609 (Cyno B) | 1.00 | 1.40 | 1.77 | 2.24 | 1.99 | 1.73 |
| 3.0 mg/kg AD05692 (Cyno A) | 1.00 | 1.16 | 1.27 | 1.27 | 1.21 | 1.35 |
| 3.0 mg/kg AD05692 (Cyno B) | 1.00 | 1.31 | 1.69 | 1.65 | 1.59 | 1.35 |

As shown in the data presented in Tables 45 and 46 above, each of the RNAi agents showed an increase in reported ALP levels after administration in cynomolgus monkeys. For example, both of the cynomolgus monkeys dosed with 3.0 mg/kg of AD05209 had their respective ALP levels doubled compared to baseline at days 22, 29, and 36 (see, e.g., Table 46 showing the ratio compared to baseline).

Example 23. In Vivo Testing of ASGR1 RNAi Agents in ASGR1-SEAP Mice

The ASGR1-SEAP mouse model described in Example 2, above, was used. At day 1, each mouse was given a single subcutaneous injection of 200 μl containing 1.0 mg/kg of an ASGR1 RNAi agent, or 200 μl of saline without an ASGR1 RNAi agent to be used as a control, according to the following Table 47.

TABLE 47

Dosing groups of ASGR1-SEAP mice of Example 23.

| Group | RNAi Agent and Dose | Dosing Regimen |
|---|---|---|
| 1 | Saline (no RNAi agent) | Single injection on day 1 |
| 2 | 1.0 mg/kg AD05183 | Single injection on day 1 |
| 3 | 1.0 mg/kg AD05209 | Single injection on day 1 |
| 4 | 1.0 mg/kg AD05648 | Single injection on day 1 |
| 5 | 1.0 mg/kg AD05649 | Single injection on day 1 |
| 6 | 1.0 mg/kg AD05650 | Single injection on day 1 |
| 7 | 1.0 mg/kg AD05651 | Single injection on day 1 |
| 8 | 1.0 mg/kg AD05674 | Single injection on day 1 |
| 9 | 1.0 mg/kg AD05675 | Single injection on day 1 |
| 10 | 1.0 mg/kg AD05676 | Single injection on day 1 |
| 11 | 1.0 mg/kg AD05740 | Single injection on day 1 |
| 12 | 1.0 mg/kg AD05741 | Single injection on day 1 |
| 13 | 1.0 mg/kg AD05742 | Single injection on day 1 |
| 14 | 1.0 mg/kg AD05193 | Single injection on day 1 |
| 15 | 1.0 mg/kg AD05692 | Single injection on day 1 |
| 16 | 1.0 mg/kg AD05677 | Single injection on day 1 |
| 17 | 1.0 mg/kg AD05678 | Single injection on day 1 |
| 18 | 1.0 mg/kg AD05679 | Single injection on day 1 |

Each of the ASGR1 RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3). Serum was collected on day 8, day 15, day 22, and day 29, and SEAP expression levels were determined pursuant to the procedure set forth in Example 2, above. Data from the experiment are shown in the following Table 48, showing Average SEAP reflecting the normalized average value of SEAP normalized to pre-treatment and control, and in the following Table 49, showing Average SEAP reflecting the normalized average value of SEAP normalized to pre-treatment levels only:

TABLE 48

Average SEAP normalized to pre-treatment and saline control in ASGR1-SEAP mice from Example 23.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline) | 1.000 | 0.326 | 1.000 | 0.281 | 1.000 | 0.554 | 1.000 | 0.346 |
| Group 2 (1.0 mg/kg AD05183) | 0.658 | 0.363 | 0.276 | 0.142 | 0.379 | 0.177 | 0.534 | 0.180 |
| Group 3 (1.0 mg/kg AD05209) | 0.290 | 0.104 | 0.272 | 0.236 | 0.300 | 0.302 | 0.467 | 0.387 |
| Group 4 (1.0 mg/kg AD05648) | 0.476 | 0.242 | 0.317 | 0.186 | 0.270 | 0.199 | 0.332 | 0.183 |
| Group 5 (1.0 mg/kg AD05649) | 0.215 | 0.119 | 0.121 | 0.099 | 0.174 | 0.156 | 0.353 | 0.312 |
| Group 6 (1.0 mg/kg AD05650) | 0.390 | 0.119 | 0.210 | 0.060 | 0.274 | 0.104 | 0.408 | 0.147 |
| Group 7 (1.0 mg/kg AD05651) | 0.316 | 0.198 | 0.189 | 0.116 | 0.343 | 0.154 | 0.943 | 0.275 |
| Group 8 (1.0 mg/kg AD05674) | 0.506 | 0.228 | 0.341 | 0.308 | 0.500 | 0.166 | 0.917 | 0.389 |
| Group 9 (1.0 mg/kg AD05675) | 0.337 | 0.040 | 0.158 | 0.059 | 0.251 | 0.221 | 0.470 | 0.453 |
| Group 10 (1.0 mg/kg AD05676) | 0.451 | 0.195 | 0.273 | 0.122 | 0.317 | 0.100 | 0.795 | 0.549 |
| Group 11 (1.0 mg/kg AD05740) | 0.345 | 0.217 | 0.258 | 0.170 | 0.266 | 0.201 | 0.368 | 0.247 |
| Group 12 (1.0 mg/kg AD05741) | 0.241 | 0.014 | 0.136 | 0.073 | 0.175 | 0.100 | 0.288 | 0.180 |
| Group 13 (1.0 mg/kg AD05742) | 0.294 | 0.076 | 0.210 | 0.138 | 0.405 | 0.285 | 0.641 | 0.387 |
| Group 14 (1.0 mg/kg AD05193) | 0.237 | 0.094 | 0.096 | 0.060 | 0.137 | 0.115 | 0.242 | 0.157 |
| Group 15 (1.0 mg/kg AD05692) | 0.468 | 0.285 | 0.304 | 0.325 | 0.545 | 0.497 | 0.718 | 0.902 |
| Group 16 (1.0 mg/kg AD05677) | 0.353 | 0.097 | 0.205 | 0.208 | 0.387 | 0.380 | 0.588 | 0.580 |
| Group 17 (1.0 mg/kg AD05678) | 0.274 | 0.065 | 0.236 | 0.143 | 0.309 | 0.286 | 0.715 | 0.568 |
| Group 18 (1.0 mg/kg AD05679) | 0.348 | 0.049 | 0.195 | 0.122 | 0.260 | 0.138 | 0.271 | 0.085 |

TABLE 49

Average SEAP normalized to pre-treatment only in ASGR1-SEAP mice from Example 23.

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline) | 0.756 | 0.247 | 0.574 | 0.161 | 0.421 | 0.233 | 0.400 | 0.138 |
| Group 2 (1.0 mg/kg AD05183) | 0.497 | 0.275 | 0.159 | 0.081 | 0.160 | 0.075 | 0.214 | 0.072 |
| Group 3 (1.0 mg/kg AD05209) | 0.220 | 0.079 | 0.156 | 0.136 | 0.126 | 0.127 | 0.187 | 0.155 |
| Group 4 (1.0 mg/kg AD05648) | 0.360 | 0.183 | 0.182 | 0.107 | 0.114 | 0.084 | 0.133 | 0.073 |
| Group 5 (1.0 mg/kg AD05649) | 0.162 | 0.090 | 0.070 | 0.057 | 0.073 | 0.066 | 0.141 | 0.125 |
| Group 6 (1.0 mg/kg AD05650) | 0.295 | 0.090 | 0.120 | 0.034 | 0.115 | 0.044 | 0.163 | 0.059 |
| Group 7 (1.0 mg/kg AD05651) | 0.239 | 0.150 | 0.109 | 0.067 | 0.145 | 0.065 | 0.377 | 0.110 |
| Group 8 (1.0 mg/kg AD05674) | 0.382 | 0.172 | 0.196 | 0.177 | 0.211 | 0.070 | 0.367 | 0.156 |
| Group 9 (1.0 mg/kg AD05675) | 0.255 | 0.031 | 0.091 | 0.034 | 0.106 | 0.093 | 0.188 | 0.181 |
| Group 10 (1.0 mg/kg AD05676) | 0.341 | 0.147 | 0.157 | 0.070 | 0.133 | 0.042 | 0.318 | 0.220 |
| Group 11 (1.0 mg/kg AD05740) | 0.261 | 0.164 | 0.148 | 0.098 | 0.112 | 0.085 | 0.147 | 0.099 |
| Group 12 (1.0 mg/kg AD05741) | 0.182 | 0.010 | 0.078 | 0.042 | 0.074 | 0.042 | 0.115 | 0.072 |
| Group 13 (1.0 mg/kg AD05742) | 0.240 | 0.062 | 0.130 | 0.085 | 0.186 | 0.130 | 0.267 | 0.161 |
| Group 14 (1.0 mg/kg AD05193) | 0.194 | 0.077 | 0.059 | 0.037 | 0.063 | 0.052 | 0.101 | 0.065 |
| Group 15 (1.0 mg/kg AD05692) | 0.382 | 0.232 | 0.187 | 0.200 | 0.250 | 0.228 | 0.299 | 0.375 |
| Group 16 (1.0 mg/kg AD05677) | 0.288 | 0.079 | 0.126 | 0.128 | 0.177 | 0.174 | 0.245 | 0.241 |
| Group 17 (1.0 mg/kg AD05678) | 0.224 | 0.053 | 0.145 | 0.088 | 0.142 | 0.131 | 0.297 | 0.236 |
| Group 18 (1.0 mg/kg AD05679) | 0.263 | 0.037 | 0.112 | 0.070 | 0.109 | 0.058 | 0.113 | 0.035 |

Example 24. In Vivo Testing of ASGR1 RNAi Agents in Cynomolgus Monkeys

ASGR1 RNAi agents were evaluated for reduction in ASGR1 mRNA levels in cynomolgus monkeys. On day 1, female cynomolgus macaque (*Macaca fascicularis*) primates ("cynomolgus monkeys") were given a single subcutaneous injection of 0.3 mL/kg (approximately 2-3 mL volume, depending on animal mass) containing 10.0 mg/mL, for a total dose of 3.0 mg/kg, of either ASGR1 RNAi agent AD05193 or AD05209, each formulated in saline. Each of ASGR1 RNAi agents included N-acetylgalactosamine targeting ligands conjugated to the 5'-terminal end of the sense strand having the structure of (NAG37)s, as shown in Tables 4, 5, and 6.

Four (4) monkeys in each group were tested. On days −7 (pre-dose), 15, 29, 43, and 57, liver biopsies were taken. On the date of each biopsy collection, the cynomolgus monkeys were anesthetized and ultrasound-guided liver biopsies were performed to extract liver tissue samples. Approximately 100 mg liver samples from the median lobes were collected and snap-frozen in liquid nitrogen for RNA isolation. The biopsy samples were then homogenized, and levels of ASGR1 mRNA in the cyno livers were measured by RT-qPCR. Resulting values were then normalized to the pre-dose (in this case, at day −7) ASGR1 mRNA measurements using the ΔΔCT method, which are reflected in the following Table 50.

Additionally, serum samples were taken on −14, −1, day 1 (pre-dose), day 8, day 15, day 22, day 29, day 36, day 43, day 57, day 71, and day 85, and ALP levels in serum for each day were measured on a Cobas® Integra 400 (Roche Diagnostics), according to the manufacturer's recommendations, which are reported in Tables 51 and 52, below.

TABLE 50

ASGR1 mRNA Expression Levels Relative to Pre-Dose (Day −7) from Example 24.

| | Day 15 | | | Day 29 | | | Day 43 | | | Day 57 | | |
|---|---|---|---|---|---|---|---|---|---|---|---|---|
| Group | Mean Relative ASGR1 mRNA Expression | Low Error | High Error | Mean Relative ASGR1 mRNA Expression | Low Error | High Error | Mean Relative ASGR1 mRNA Expression | Low Error | High Error | Mean Relative ASGR1 mRNA Expression | Low Error | High Error |
| AD05193 | 0.292 | 0.057 | 0.071 | 0.284 | 0.128 | 0.233 | 0.248 | 0.383 | 0.151 | 0.598 | 0.295 | 0.197 |
| AD05209 | 0.237 | 0.055 | 0.071 | 0.286 | 0.041 | 0.048 | 0.237 | 0.068 | 0.095 | 0.421 | 0.233 | 0.150 |

TABLE 51

Normalized ALP Levels By Group in Cynomolgus Monkeys from Example 24 (Normalized to Pre-Dose) from Cobas ®.

| Group ID | Day 8 ALP | Day 15 ALP | Day 22 ALP | Day 29 ALP | Day 36 ALP | Day 43 ALP | Day 57 ALP | Day 71 ALP | Day 85 ALP |
|---|---|---|---|---|---|---|---|---|---|
| AD05193 (3.0 mg/kg) | 1.44 | 2.08 | 2.27 | 2.60 | 2.33 | 2.33 | 2.09 | 1.49 | 1.47 |
| AD05209 (3.0 mg/kg) | 1.56 | 1.99 | 2.07 | 2.08 | 2.01 | 1.94 | 1.59 | 1.34 | 1.26 |

TABLE 52

Normalized ALP Levels in Cynomolgus Monkeys from Example 24 (Normalized to Pre-Dose) from Cobas ®.

| Group ID | Day 8 ALP | Day 15 ALP | Day 22 ALP | Day 29 ALP | Day 36 ALP | Day 43 ALP | Day 57 ALP | Day 71 ALP | Day 85 ALP |
|---|---|---|---|---|---|---|---|---|---|
| 3.0 mg/kg AD05193 (Cyno A) | 1.48 | 2.09 | 2.54 | 2.74 | 2.25 | 1.89 | 1.81 | 1.16 | 1.21 |
| 3.0 mg/kg AD05193 (Cyno B) | 1.51 | 2.61 | 2.39 | 2.88 | 2.54 | 2.44 | 2.15 | 1.54 | 1.53 |
| 3.0 mg/kg AD05193 (Cyno C) | 1.42 | 1.62 | 1.91 | 1.99 | 1.95 | 2.04 | 2.04 | 1.46 | 1.40 |
| 3.0 mg/kg AD05193 (Cyno D) | 1.37 | 2.00 | 2.24 | 2.77 | 2.60 | 2.97 | 2.34 | 1.82 | 1.73 |
| 3.0 mg/kg AD05209 (Cyno A) | 1.68 | 1.89 | 2.39 | 2.13 | 2.41 | 1.83 | 1.50 | 1.27 | 1.16 |
| 3.0 mg/kg AD05209 (Cyno B) | 1.40 | 1.66 | 1.50 | 1.31 | 1.17 | 1.17 | 1.05 | 1.00 | 0.96 |
| 3.0 mg/kg AD05209 (Cyno C) | 1.79 | 2.45 | 2.48 | 2.55 | 2.44 | 2.51 | 1.84 | 1.50 | 1.51 |
| 3.0 mg/kg AD05209 (Cyno D) | 1.36 | 1.94 | 1.91 | 2.32 | 2.01 | 2.23 | 1.95 | 1.60 | 1.43 |

The cynomolgus monkeys in both groups showed a significant reduction in liver-specific ASGR1 mRNA compared to pre-treatment measurements at all measured time points. On day 43, for example, the cynomolgus monkeys of Group 1 (AD05193) had a reduction of ASGR1 mRNA of approximately 75.2% (0.248), while cynomolgus monkeys of Group 2 (AD05209) had a reduction of approximately 76.3% (0.237), compared to pre-dose levels.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of an ASGR1 gene, wherein the antisense strand consists of, consists essentially of, or comprises the nucleotide sequence (5'→3'):

AGCGACUUCAUCUUUCUUCCG; (SEQ ID NO: 6)
or

AGCGACUUCAUCUUUCUUCGU; (SEQ ID NO: 8)

and
   a sense strand comprising a nucleotide sequence that is at least partially complementary to the antisense strand, wherein at least one nucleotide of the sense strand or the antisense strand is a modified nucleotide or wherein the RNAi agent comprises at least one modified internucleoside linkage.

2. The RNAi agent of claim 1, wherein the sense strand consists of, consists essentially of, or comprises a nucleotide sequence that differs by 0 or 1 nucleotides from one of the following nucleotide sequences (5'→3'):

CGGAAGAAAGAUGAAGUCICU; (SEQ ID NO: 15)

ACGAAGAAAGAUGAAGUCICU; (SEQ ID NO: 16)

ACGAAGAAAGAUGAAGUCGCU; (SEQ ID NO: 17)

CGGAAGAAAGAUGAAIUCICU; (SEQ ID NO: 31)
or

CGGAAGAAAGAUGAAGUCGCU; (SEQ ID NO: 33)

wherein I represents an inosine nucleotide.

3. The RNAi agent of claim 1, wherein 0, 1, 2, 3, or 4 nucleotides of the RNAi agent are ribonucleotides (2'-hydroxyl nucleotides).

4. The RNAi agent of claim 3, wherein the sense strand further includes inverted abasic residues at the 3' terminal end of the nucleotide sequence, at the 5' end of the nucleotide sequence, or at both the 3' and 5' terminal ends.

5. The RNAi agent of claim 1, wherein the antisense strand comprises, consists of, or consists essentially of the modified nucleotide sequence (5'→3'):

asGfscGfaCfuucauCfuUfuCfuUfcsCfsg; (SEQ ID NO: 5)

asGfscGfaCfuucauCfuUfuCfuUfcsGfsu; (SEQ ID NO: 7)

asGfscsgacuucauCfuUfuCfuUfcGfsu; (SEQ ID NO: 9)
or wherein a represents 2'-O-methyl adenosine, c represents 2'-O-methyl cytidine, g represents 2'-O-methyl guanosine, and u represents 2'-O-methyl uridine; Af represents 2'-fluoro adenosine, Cf represents 2'-fluoro cytidine, Gf represents 2'-fluoro guanosine, and Uf represents 2'-fluoro uridine; s represents a phosphorothioate linkage; and wherein 0, 1, or 2 nucleotides of the sense strand are ribonucleotides (2'-hydroxyl nucleotides).

6. The RNAi agent of claim 5, wherein the sense strand comprises, consists of, or consists essentially of a modified nucleotide sequence that differs by 0 or 1 nucleotides from one of the following nucleotide sequences (5'→3'):

cggaagaaAfGfAfugaagucicu; (SEQ ID NO: 23)

acgaagaaAfGfAfugaagucicu; (SEQ ID NO: 24)

acgaagaaAfGfAfugaagucgcu; (SEQ ID NO: 25)

cggaagaaAfGfAfugaaiucicu; (SEQ ID NO: 32)
or cggaagaaAfGfAfugaagucgcu; (SEQ ID NO: 34)

wherein a represents 2'-O-methyl adenosine, c represents 2'-O-methyl cytidine, g represents 2'-O-methyl guanosine, i represents 2'-O-methyl inosine, and u represents 2'-O-methyl uridine; and Af represents 2'-fluoro adenosine, Cf represents 2'-fluoro cytidine, Gf represents 2'-fluoro guanosine, and Uf represents 2'-fluoro uridine.

7. The RNAi agent of claim 1, wherein the sense strand and antisense strand for a duplex pair that comprises, consists of, or consists essentially of a modified nucleotide sequence that differs by 0 or 1 nucleotides from one of the following nucleotide sequence pairs (5'→3'):

asGfscGfaCfuucauCfuUfuCfuUfcsCfsg (SEQ ID NO: 5)
and cggaagaaAfGfAfugaagucicu; (SEQ ID NO: 23)

asGfscGfaCfuucauCfuUfuCfuUfcsGfsu (SEQ ID NO: 7)
and acgaagaaAfGfAfugaagucicu; (SEQ ID NO: 24)

asGfscsgacuucauCfuUfuCfuUfcGfsu (SEQ ID NO: 9)
and acgaagaaAfGfAfugaagucgcu; (SEQ ID NO: 25)

asGfscGfaCfuucauCfuUfuCfuUfcsCfsg (SEQ ID NO: 5)
and cggaagaaAfGfAfugaaiucicu; (SEQ ID NO: 32)
or asGfscGfaCfuucauCfuUfuCfuUfcsCfsg (SEQ ID NO: 5)
and cggaagaaAfGfAfugaagucgcu, (SEQ ID NO: 34)

wherein a represents 2'-O-methyl adenosine, c represents 2'-O-methyl cytidine, g represents 2'-O-methyl guanosine, i represents 2'-O-methyl inosine, and u represents 2'-O-methyl uridine, and Af represents 2'-fluoro adenosine, Cf represents 2'-fluoro cytidine, Gf represents 2'-fluoro guanosine, and Uf represents 2'-fluoro uridine.

8. The RNAi agent of claim 5, wherein the RNAi agent is conjugated to a targeting ligand at the 5' end of the sense strand.

9. The RNAi agent of claim 8, wherein the targeting ligand is a tridentate ligand that includes N-acetyl-galactosamine and has the structure selected from the group consisting of:

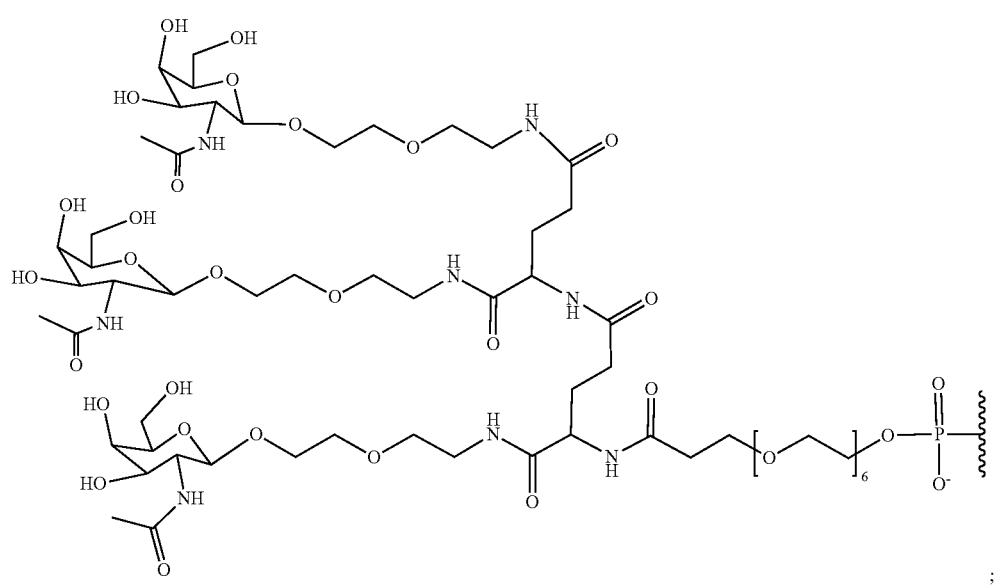

(NAG25)

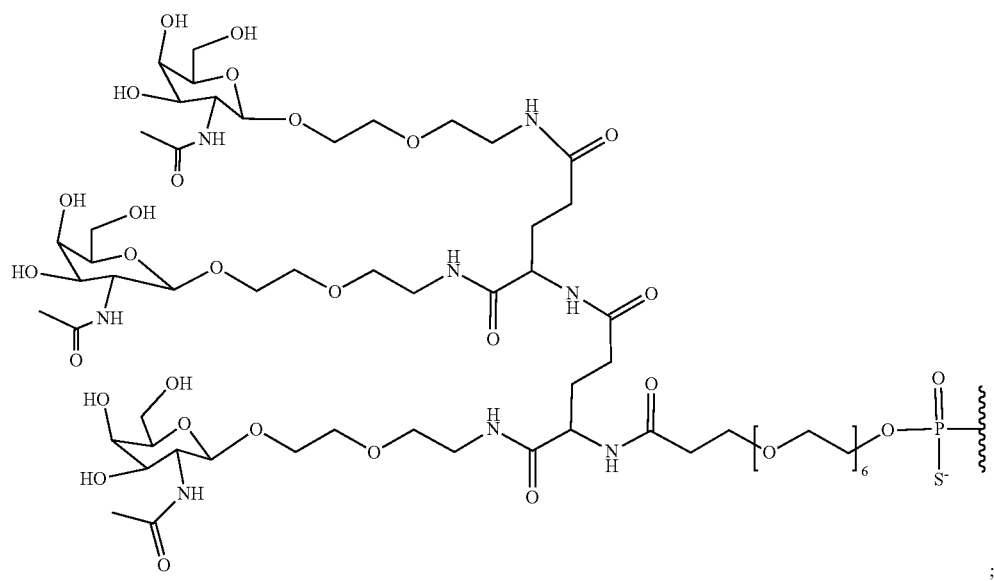

(NAG25)s

-continued (NAG37)

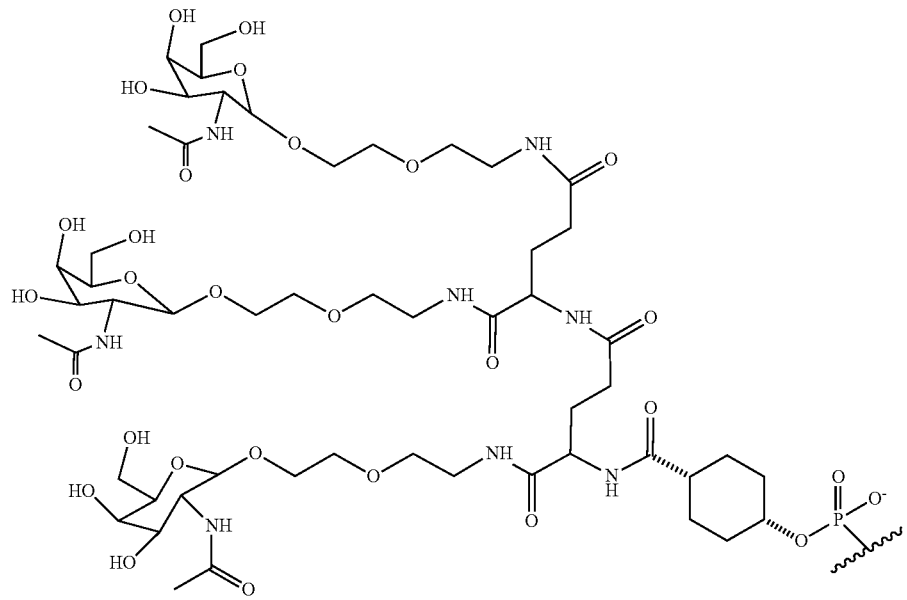

; and (NAG37)s

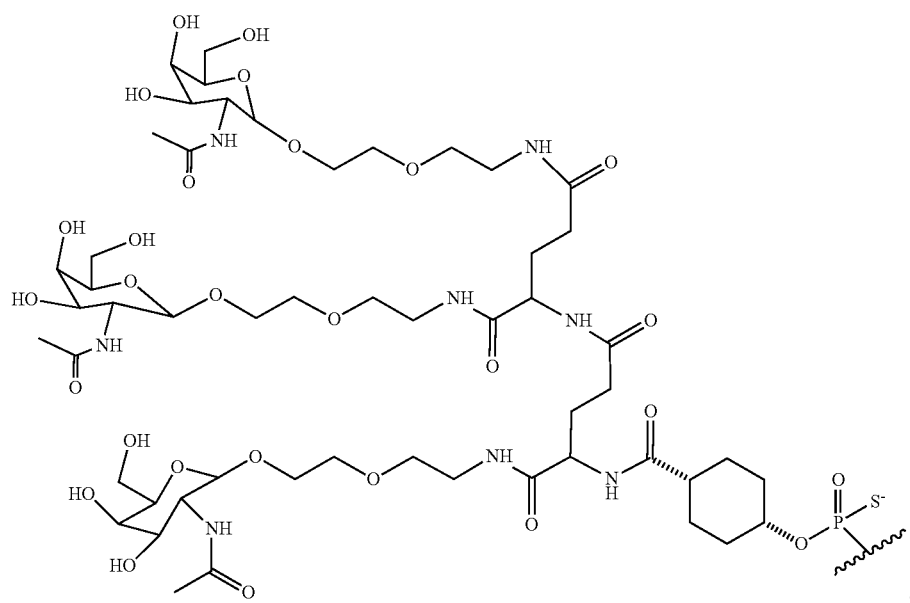

.

10. A composition comprising the RNAi agent of claim 1 and a pharmaceutically acceptable excipient.

11. A method for inhibiting expression of an ASGR1 gene in a cell, the method comprising administering to the cell the RNAi agent of claim 1.

12. The method of claim 11, wherein the cell is within a human subject.

13. A method for inhibiting expression of an ASGR1 gene in a subject, the method comprising administering to the subject the composition of claim 10.

14. A method of treating an ASGR1-related disease or disorder, the method comprising administering to a subject in need thereof an effective amount of the composition of claim 10.

15. The method of claim 14, wherein the ASGR1-related disease or disorder is obesity, metabolic syndrome, hyperlipidemia, hypertriglyceridemia, hypercholesterolemia, abnormal lipid and/or cholesterol metabolism, atherosclerosis, diabetes, cardiovascular disease, coronary artery disease, myocardial infarction, peripheral vascular disease, or cerebrovascular disease.

16. A method for reducing non-HDL cholesterol in a subject in need thereof, the method comprising administering to the subject an effective amount of the composition of claim 10.

17. The method of claim 16, wherein the non-HDL cholesterol is LDL cholesterol.

18. A method for reducing the risk of myocardial infarction in a subject in need thereof, the method comprising administering to the subject an effective amount of the composition of claim 10.

19. The method of claim 18, wherein the subject is diagnosed with coronary artery disease.

20. The method of claim 18, wherein the subject has elevated levels of non-HDL cholesterol.

21. The method of claim 11, wherein the RNAi agent is administered at a dose of about 0.05 mg/kg to about 5.0 mg/kg of body weight of the human subject.

* * * * *

SEQUENCE LISTING

```
<160> NUMBER OF SEQ ID NOS: 943

<210> SEQ ID NO 1
<211> LENGTH: 1519
<212> TYPE: DNA
<213> ORGANISM: Homo sapiens
<220> FEATURE:
<223> OTHER INFORMATION: Homo sapiens asialoglycoprotein receptor 1
      (ASGR1), transcript variant 1, NM_001671.4

<400> SEQUENCE: 1
```

```
cccaaacggt gcacggaaga gtgaggtgac tggcatgtgt gggggcaaca cgattctcct    60
ccctggggag cagagcagag gcaacccatc ccccactccc accccacac tcccctaagt    120 tccaatccat ttccacctct gtttactgtc caaagtcccg ggcactggag atgccacgtt   180
tggcgtgctt ggacacacag acacgcagac acagagacac cggggcccag ggccctccta   240
tggaccctgc ccgctcccct cccattgtcc acggctgtcc gcccaccccc attctccaag   300
cttcagcccc ctccttagtt cggcatctgc acagcactga agaacctggg aatcagaccc   360
tgagaccctg agcaatccca ggtccagcgc cagccctatc atgaccaagg agtatcaaga   420
ccttcagcat ctggacaatg aggagagtga ccaccatcag ctcagaaaag gccacctcc    480 tccccagccc ctcctgcagc gtctctgctc cggacctcgc ctcctcctgc tctccctggg   540
cctcagcctc ctgctgcttg tggttgtctg tgtgatcgga tcccaaaact cccagctgca   600
ggaggagctg cggggcctga gagagacgtt cagcaacttc acagcgagca cggaggccca   660
ggtcaagggc ttgagcaccc agggaggcaa tgtgggaaga agatgaagt cgctagagtc    720 ccagctggag aaacagcaga aggacctgag tgaagatcac tccagcctgc tgctccacgt   780
gaagcagttc gtgtctgacc tgcggagcct gagctgtcag atggcggcgc tccagggcaa   840
tggctcagaa aggacctgct gcccggtcaa ctgggtggag cacgagcgca gctgctactg   900
gttctctcgc tccgggaagg cctgggctga cgccgacaac tactgccggc tggaggacgc   960
gcacctggtg gtggtcacgt cctgggagga gcagaaattt gtccagcacc acataggccc   1020
tgtgaacacc tggatgggcc tccacgacca aaacgggccc tggaagtggg tggacgggac  1080
ggactacgag acgggcttca gaactggag gccggagcag ccggacgact ggtacggcca   1140
cgggctcgga ggaggcgagg actgtgccca cttcaccgac gacggccgct ggaacgacga  1200
cgtctgccag aggccctacc gctgggtctg cgagacagag ctggacaagg ccagccagga  1260
gccacctctc ctttaattta tttcttcaat gcctcgacct gccgcagggg tccgggattg  1320
ggaatccgcc catctggggg cctcttctgc tttctcggga attttcatct aggattttaa  1380
gggaagggga aggatagggt gatgttccga aggtgaggag cttgaaaccc gtggcgcttt  1440
ctgcagtttg caggttatca ttgtgaactt ttttttttta agagtaaaaa gaaatatacc   1500
taaaaaaaaa aaaaaaaa                                                 1519

<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2
uacuccuugg ucaugauagg u                                              21

<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 3
uacuccuugg ucaugauagg u                                              21

<210> SEQ ID NO 4
```

-continued

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 4
uacuccuugg ucaugauagg u                                             21

<210> SEQ ID NO 5
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 5
agcgacuuca ucuuucuucc g                                             21

<210> SEQ ID NO 6
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 6
agcgacuuca ucuuucuucc g                                             21

<210> SEQ ID NO 7
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 7
agcgacuuca ucuuucuucg u                                             21

<210> SEQ ID NO 8
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 8
agcgacuuca ucuuucuucg u                                             21

<210> SEQ ID NO 9
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 9
agcgacuuca ucuuucuucg u                                             21

<210> SEQ ID NO 10
<211> LENGTH: 21
<212> TYPE: RNA
<213> ORGANISM: Artificial sequence
<220> FEATURE:
<223> OTHER INFORMATION: RNAi agent antisense strand modified sequence

```
<400> SEQUENCE: 10
acuucaucuu ucucccacg c                                      21

<210> SEQ ID NO 11
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 11
acuucaucuu ucucccacg c                                      21

<210> SEQ ID NO 12
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 12 accaucaug accaagganu a                                      21

<210> SEQ ID NO 13
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 13 accaucaug accaaggagu a                                      21

<210> SEQ ID NO 14
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16, 19
<223> OTHER INFORMATION: n = hypoxanthine (inosine nucleotide)

<400> SEQUENCE: 14 accaucaug accaanganu a                                      21

<210> SEQ ID NO 15
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 15
```
cggaagaaag augaagucnc u                                              21

<210> SEQ ID NO 16
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 16
acgaagaaag augaagucnc u                                              21

<210> SEQ ID NO 17
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 17
acgaagaaag augaagucgc u                                              21

<210> SEQ ID NO 18
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 18
gcgugggaag aaagaugaag u                                              21

<210> SEQ ID NO 19
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 19
accuaucaug accaagganu a                                              21

<210> SEQ ID NO 20
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 20
accuaucaug accaaggagu a                                              21

<210> SEQ ID NO 21
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 21
accuaucaug accaaggagu a                                              21

<210> SEQ ID NO 22
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 22
accuaucaug accaanganu a                                              21

<210> SEQ ID NO 23
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 23
cggaagaaag augaagucnc u                                              21

<210> SEQ ID NO 24
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 24
acgaagaaag augaagucnc u                                              21

<210> SEQ ID NO 25
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 25
acgaagaaag augaagucgc u                                              21

<210> SEQ ID NO 26
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 26
gcgugggaag aaagaugaag u                                              21
```

```
<210> SEQ ID NO 27
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 27
ugaaauaaau uaaaggagag g                                                 21

<210> SEQ ID NO 28
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 28
ugaaauaaau uaaaggagag g                                                 21

<210> SEQ ID NO 29
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 29
gcgugggaag aaagaugaag u                                                 21

<210> SEQ ID NO 30
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 30
accuaucaug accaanganu a                                                 21

<210> SEQ ID NO 31
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16, 19
<223> OTHER INFORMATION: n = hypoxanthine (inosine nucleotide)

<400> SEQUENCE: 31
cggaagaaag augaanucnc u                                                 21

<210> SEQ ID NO 32
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
```

```
<222> LOCATION: 16, 19
<223> OTHER INFORMATION: n = 2'-O-methylinosine-3'-phosphate

<400> SEQUENCE: 32
cggaagaaag augaanucnc u                                              21

<210> SEQ ID NO 33
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 33
cggaagaaag augaagucgc u                                              21

<210> SEQ ID NO 34
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 34
cggaagaaag augaagucgc u                                              21

<210> SEQ ID NO 35
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 35
ccucuccuuu aauuuauuuc a                                              21

<210> SEQ ID NO 36
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 36
ccucuccuuu aauuuauuuc a                                              21

<210> SEQ ID NO 37
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 37
agcccuauca ugaccaagg                                                 19

<210> SEQ ID NO 38
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 38
```

```
ccuaucauga ccaaggagu                                                    19

<210> SEQ ID NO 39
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 39
cuaucaugac caaggagua                                                    19

<210> SEQ ID NO 40
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 40
uaucaugacc aaggaguau                                                    19

<210> SEQ ID NO 41
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 41
aucaugacca aggaguauc                                                    19

<210> SEQ ID NO 42
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 42
caugaccaag gaguaucaa                                                    19

<210> SEQ ID NO 43
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 43
ggagagugac caccaucag                                                    19

<210> SEQ ID NO 44
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 44
gagugaccac caucagcuc                                                    19

<210> SEQ ID NO 45
<211> LENGTH: 19
<212> TYPE: RNA
<213> ORGANISM: Artificial sequence
```

```
<220> FEATURE:
<223> OTHER INFORMATION: ASGR1 gene transcript (mRNA) target sequence

<400> SEQUENCE: 45
caacuucaca gcgagcacg                                                19

<210> SEQ ID NO 46
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 46
agggaggcaa ugugggaag                                                19

<210> SEQ ID NO 47
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 47
ggaggcaaug ugggaagaa                                                19

<210> SEQ ID NO 48
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 48 ggcaugugg gaagaaaga                                                 19

<210> SEQ ID NO 49
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 49
caauguggga agaaagaug                                                19

<210> SEQ ID NO 50
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 50
aaugugggaa gaaagauga                                                19

<210> SEQ ID NO 51
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 51
gugggaagaa agaugaagu                                                19
```

<210> SEQ ID NO 52
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 52
ggaagaaaga ugaagucgc                                                    19

<210> SEQ ID NO 53
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 53
gaagaaagau gaagucgcu                                                    19

<210> SEQ ID NO 54
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 54
ugcugcucca cgugaagca                                                    19

<210> SEQ ID NO 55
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 55
cugcuccacg ugaagcagu                                                    19

<210> SEQ ID NO 56
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 56
ugcuccacgu gaagcaguu                                                    19

<210> SEQ ID NO 57
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 57
gcuccacgug aagcaguuc                                                    19

<210> SEQ ID NO 58
<211> LENGTH: 19
<212> TYPE: RNA
<213> ORGANISM: Artificial sequence
<220> FEATURE:
<223> OTHER INFORMATION: ASGR1 gene transcript (mRNA) target sequence

```
<400> SEQUENCE: 58
uccacgugaa gcaguucgu                                                19

<210> SEQ ID NO 59
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 59
gcuccagggc aauggcuca                                                19

<210> SEQ ID NO 60
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 60
cacgagcgca gcugcuacu                                                19

<210> SEQ ID NO 61
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 61
agcgcagcug cuacugguu                                                19

<210> SEQ ID NO 62
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 62
gcgcagcugc uacugguuc                                                19

<210> SEQ ID NO 63
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 63
gacgccgaca acuacugcc                                                19

<210> SEQ ID NO 64
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 64
accugguggu ggucacguc                                                19

<210> SEQ ID NO 65
```

```
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 65 ugguggugguu cacguccug                                                    19

<210> SEQ ID NO 66
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 66
aggagcagaa auugucca                                                      19

<210> SEQ ID NO 67
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 67
gcagaaauuu guccagcac                                                     19

<210> SEQ ID NO 68
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 68
gccuccacga ccaaaacgg                                                     19

<210> SEQ ID NO 69
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 69
ggacgggacg gacuacgag                                                     19

<210> SEQ ID NO 70
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 70
gacgggacgg acuacgaga                                                     19

<210> SEQ ID NO 71
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 71
```
acgggacgga cuacgagac                                                19

<210> SEQ ID NO 72
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 72
cagccggacg acugguacg                                                19

<210> SEQ ID NO 73
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 73
cgcuggaacg acgacgucu                                                19

<210> SEQ ID NO 74
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 74
ggucugcgag acagagcug                                                19

<210> SEQ ID NO 75
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 75
ggagccaccu cuccuuuaa                                                19

<210> SEQ ID NO 76
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 76
gagccaccuc uccuuuaau                                                19

<210> SEQ ID NO 77
<211> LENGTH: 19
<212> TYPE: RNA
<213> ORGANISM: Artificial sequence
<220> FEATURE:
<223> OTHER INFORMATION: ASGR1 gene transcript (mRNA) target sequence

<400> SEQUENCE: 77
agccaccucu ccuuuaauu                                                19

<210> SEQ ID NO 78
<211> LENGTH: 19
<212> TYPE: RNA

```
<213> ORGANISM: Artificial sequence
<220> FEATURE:
<223> OTHER INFORMATION: ASGR1 gene transcript (mRNA) target sequence

<400> SEQUENCE: 78
ucuccuuuaa uuuauuucu                                                        19

<210> SEQ ID NO 79
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 79
ccuuggucau gauagggcu                                                        19

<210> SEQ ID NO 80
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 80
ucuuggucau gauagggcu                                                        19

<210> SEQ ID NO 81
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 81
ncuuggucau gauagggcu                                                        19

<210> SEQ ID NO 82
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 82
ncuuggucau gauagggcn                                                        19

<210> SEQ ID NO 83
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 83
```
acuccuuggu caugauagg                                                19

<210> SEQ ID NO 84
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 84
ucuccuuggu caugauagg                                                19

<210> SEQ ID NO 85
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 85
ncuccuuggu caugauagg                                                19

<210> SEQ ID NO 86
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 86
ncuccuuggu caugauagn                                                19

<210> SEQ ID NO 87
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 87
uacuccuugg ucaugauag                                                19

<210> SEQ ID NO 88
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 88
nacuccuugg ucaugauag                                                19

-continued

```
<210> SEQ ID NO 89
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 89
nacuccuugg ucaugauan                                                19

<210> SEQ ID NO 90
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 90
auacuccuug gucaugaua                                                19

<210> SEQ ID NO 91
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 91
uuacuccuug gucaugaua                                                19

<210> SEQ ID NO 92
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 92
nuacuccuug gucaugaua                                                19

<210> SEQ ID NO 93
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 93
nuacuccuug gucaugaun                                                19

<210> SEQ ID NO 94
```

```
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 94
gauacuccuu ggucaugau                                                      19

<210> SEQ ID NO 95
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 95
uauacuccuu ggucaugau                                                      19

<210> SEQ ID NO 96
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 96
nauacuccuu ggucaugau                                                      19

<210> SEQ ID NO 97
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 97
nauacuccuu ggucaugan                                                      19

<210> SEQ ID NO 98
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 98
uugauacucc uuggucaug                                                      19

<210> SEQ ID NO 99
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
```

```
<220> FEATURE:
<221> NAME/KEY: modified_base
<222> LOCATION: 1
<223> OTHER INFORMATION: n = any nucleobase

<400> SEQUENCE: 99
nugauacucc uuggucaug                                                    19

<210> SEQ ID NO 100
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 100
nugauacucc uuggucaun                                                    19

<210> SEQ ID NO 101
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 101
cugauggugg ucacucucc                                                    19

<210> SEQ ID NO 102
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 102
uugauggugg ucacucucc                                                    19

<210> SEQ ID NO 103
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 103
nugauggugg ucacucucc                                                    19

<210> SEQ ID NO 104
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
```

```
<222> LOCATION: 1, 19
<223> OTHER INFORMATION: n = any nucleobase

<400> SEQUENCE: 104
nugauggugg ucacucucn                                                  19

<210> SEQ ID NO 105
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 105
gagcugaugg uggucacuc                                                  19

<210> SEQ ID NO 106
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 106
uagcugaugg uggucacuc                                                  19

<210> SEQ ID NO 107
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 107
nagcugaugg uggucacuc                                                  19

<210> SEQ ID NO 108
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 108
nagcugaugg uggucacun                                                  19

<210> SEQ ID NO 109
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 109
cgugcucgcu gugaaguug                                                  19
```

<210> SEQ ID NO 110
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 110
ugugcucgcu gugaaguug                                              19

<210> SEQ ID NO 111
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 111
ngugcucgcu gugaaguug                                              19

<210> SEQ ID NO 112
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 112
ngugcucgcu gugaaguun                                              19

<210> SEQ ID NO 113
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 113
cuucccacau ugccuccca                                              19

<210> SEQ ID NO 114
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 114
uuucccacau ugccuccca                                              19

<210> SEQ ID NO 115
<211> LENGTH: 19
<212> TYPE: RNA
<213> ORGANISM: Artificial sequence

```
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 115
nuucccacau ugccuccca                                                       19

<210> SEQ ID NO 116
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 116
nuucccacau ugccuccn                                                        19

<210> SEQ ID NO 117
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 117
uucuucccac auugccucc                                                       19

<210> SEQ ID NO 118
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 118
nucuucccac auugccucc                                                       19

<210> SEQ ID NO 119
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 119
nucuucccac auugccucn                                                       19

<210> SEQ ID NO 120
<211> LENGTH: 19
```

```
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 120 ucuucuucc cacauugcc                                                   19

<210> SEQ ID NO 121
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 121 ncuucuucc cacauugcc                                                   19

<210> SEQ ID NO 122
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 122 ncuucuucc cacauugcn                                                   19

<210> SEQ ID NO 123
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 123
caucuuucuu cccacauug                                                  19

<210> SEQ ID NO 124
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 124
uaucuuucuu cccacauug                                                  19

<210> SEQ ID NO 125
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
```

```
<221> NAME/KEY: modified_base
<222> LOCATION: 1
<223> OTHER INFORMATION: n = any nucleobase

<400> SEQUENCE: 125
naucuuucuu cccacauug                                                    19

<210> SEQ ID NO 126
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 126
naucuuucuu cccacauun                                                    19

<210> SEQ ID NO 127
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 127
naucuuucuu cccacauun                                                    19

<210> SEQ ID NO 128
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 128
naucuuucuu cccacauun                                                    19

<210> SEQ ID NO 129
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 129
ucaucuuucu ucccacauu                                                    19

<210> SEQ ID NO 130
<211> LENGTH: 19
<212> TYPE: RNA
<213> ORGANISM: Artificial sequence
<220> FEATURE:
<223> OTHER INFORMATION: RNAi agent antisense strand core 19-mer base
``` sequence
<220> FEATURE:
<221> NAME/KEY: modified_base
<222> LOCATION: 1
<223> OTHER INFORMATION: n = any nucleobase

<400> SEQUENCE: 130
ncaucuuucu ucccacauu                                              19

<210> SEQ ID NO 131
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 131
ncaucuuucu ucccacaun                                              19

<210> SEQ ID NO 132
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 132
ncaucuuucu ucccacaun                                              19

<210> SEQ ID NO 133
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 133
acuucaucuu ucuucccac                                              19

<210> SEQ ID NO 134
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 134
ucuucaucuu ucuucccac                                              19

<210> SEQ ID NO 135
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:

<221> NAME/KEY: modified_base
<222> LOCATION: 1
<223> OTHER INFORMATION: n = any nucleobase

<400> SEQUENCE: 135
ncuucaucuu ucuucccac                                                    19

<210> SEQ ID NO 136
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 136
ncuucaucuu ucuucccan                                                    19

<210> SEQ ID NO 137
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 137
gcgacuucau cuuucuucc                                                    19

<210> SEQ ID NO 138
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 138
ucgacuucau cuuucuucc                                                    19

<210> SEQ ID NO 139
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 139
ncgacuucau cuuucuucc                                                    19

<210> SEQ ID NO 140
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19

<223> OTHER INFORMATION: n = any nucleobase

<400> SEQUENCE: 140
ncgacuucau cuuucuucn					19

<210> SEQ ID NO 141
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 141
agcgacuuca ucuuucuuc					19

<210> SEQ ID NO 142
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 142
ugcgacuuca ucuuucuuc					19

<210> SEQ ID NO 143
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 143
ngcgacuuca ucuuucuuc					19

<210> SEQ ID NO 144
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 144
ngcgacuuca ucuuucuun					19

<210> SEQ ID NO 145
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

```
<400> SEQUENCE: 145
ngcgacuuca ucuuucuun                                                    19

<210> SEQ ID NO 146
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 146
ugcuucacgu ggagcagca                                                    19

<210> SEQ ID NO 147
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 147
ngcuucacgu ggagcagca                                                    19

<210> SEQ ID NO 148
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 148
ngcuucacgu ggagcagcn                                                    19

<210> SEQ ID NO 149
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 149
acugcuucac guggagcag                                                    19

<210> SEQ ID NO 150
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 150
ucugcuucac guggagcag                                                    19

<210> SEQ ID NO 151
```

```
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 151
ncugcuucac guggagcag                                                   19

<210> SEQ ID NO 152
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 152
ncugcuucac guggagcan                                                   19

<210> SEQ ID NO 153
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 153
aacugcuuca cguggagca                                                   19

<210> SEQ ID NO 154
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 154
uacugcuuca cguggagca                                                   19

<210> SEQ ID NO 155
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 155
nacugcuuca cguggagca                                                   19

<210> SEQ ID NO 156
<211> LENGTH: 19
<212> TYPE: RNA
```

```
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 156
nacugcuuca cguggagcn                                                    19

<210> SEQ ID NO 157
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 157
gaacugcuuc acguggagc                                                    19

<210> SEQ ID NO 158
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 158
uaacugcuuc acguggagc                                                    19

<210> SEQ ID NO 159
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 159
naacugcuuc acguggagc                                                    19

<210> SEQ ID NO 160
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 160
naacugcuuc acguggagn                                                    19

<210> SEQ ID NO 161
<211> LENGTH: 19
<212> TYPE: RNA
<213> ORGANISM: Artificial sequence
<220> FEATURE:
```

```
<223> OTHER INFORMATION: RNAi agent antisense strand core 19-mer base
      sequence

<400> SEQUENCE: 161
acgaacugcu ucacgugga                                                    19

<210> SEQ ID NO 162
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 162
ucgaacugcu ucacgugga                                                    19

<210> SEQ ID NO 163
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 163
ncgaacugcu ucacgugga                                                    19

<210> SEQ ID NO 164
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 164
ncgaacugcu ucacguggn                                                    19

<210> SEQ ID NO 165
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 165
ugagccauug cccuggagc                                                    19

<210> SEQ ID NO 166
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase
```

-continued

```
<400> SEQUENCE: 166
ngagccauug cccuggagc                                                  19

<210> SEQ ID NO 167
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 167
ngagccauug cccuggagn                                                  19

<210> SEQ ID NO 168
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 168
aguagcagcu gcgcucgug                                                  19

<210> SEQ ID NO 169
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 169
uguagcagcu gcgcucgug                                                  19

<210> SEQ ID NO 170
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 170
nguagcagcu gcgcucgug                                                  19

<210> SEQ ID NO 171
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 171
```
nguagcagcu gcgcucgun					19

<210> SEQ ID NO 172
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 172
aaccaguagc agcugcgcu					19

<210> SEQ ID NO 173
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 173
uaccaguagc agcugcgcu					19

<210> SEQ ID NO 174
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 174
naccaguagc agcugcgcu					19

<210> SEQ ID NO 175
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 175
naccaguagc agcugcgcn					19

<210> SEQ ID NO 176
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 176
gaaccaguag cagcugcgc					19

<210> SEQ ID NO 177
<211> LENGTH: 19

```
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 177
uaaccaguag cagcugcgc                                                      19

<210> SEQ ID NO 178
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 178
naaccaguag cagcugcgc                                                      19

<210> SEQ ID NO 179
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 179
naaccaguag cagcugcgn                                                      19

<210> SEQ ID NO 180
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 180
ggcaguaguu gucggcguc                                                      19

<210> SEQ ID NO 181
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 181
ugcaguaguu gucggcguc                                                      19

<210> SEQ ID NO 182
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
```

```
<221> NAME/KEY: modified_base
<222> LOCATION: 1
<223> OTHER INFORMATION: n = any nucleobase

<400> SEQUENCE: 182
ngcaguaguu gucggcguc                                               19

<210> SEQ ID NO 183
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 183
ngcaguaguu gucggcgun                                               19

<210> SEQ ID NO 184
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 184
gacgugacca ccaccaggu                                               19

<210> SEQ ID NO 185
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 185
uacgugacca ccaccaggu                                               19

<210> SEQ ID NO 186
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 186
nacgugacca ccaccaggu                                               19

<210> SEQ ID NO 187
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
```

-continued

<223> OTHER INFORMATION: n = any nucleobase

<400> SEQUENCE: 187
nacgugacca ccaccaggn                                                19

<210> SEQ ID NO 188
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 188
caggacguga ccaccacca                                                19

<210> SEQ ID NO 189
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 189
uaggacguga ccaccacca                                                19

<210> SEQ ID NO 190
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 190
naggacguga ccaccacca                                                19

<210> SEQ ID NO 191
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 191
naggacguga ccaccaccn                                                19

<210> SEQ ID NO 192
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 192
uggacaaauu ucugcuccu                                                19

```
<210> SEQ ID NO 193
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 193
nggacaaauu ucugcuccu                                                  19

<210> SEQ ID NO 194
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 194
nggacaaauu ucugcuccn                                                  19

<210> SEQ ID NO 195
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 195
gugcuggaca aauuucugc                                                  19

<210> SEQ ID NO 196
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 196
uugcuggaca aauuucugc                                                  19

<210> SEQ ID NO 197
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 197
nugcuggaca aauuucugc                                                  19

<210> SEQ ID NO 198
```

<211> LENGTH: 19
    <212> TYPE: RNA
    <213> ORGANISM: Artificial sequence
    <220> FEATURE:
    <223> OTHER INFORMATION: RNAi agent antisense strand core 19-mer base
          sequence
    <220> FEATURE:
    <221> NAME/KEY: modified_base
    <222> LOCATION: 1, 19
    <223> OTHER INFORMATION: n = any nucleobase

<400> SEQUENCE: 198
nugcuggaca aauuucugn                                                    19

<210> SEQ ID NO 199
    <211> LENGTH: 19
    <212> TYPE: RNA
    <213> ORGANISM: Artificial sequence
    <220> FEATURE:
    <223> OTHER INFORMATION: RNAi agent antisense strand core 19-mer base
          sequence

<400> SEQUENCE: 199
ccguuuuggu cguggaggc                                                    19

<210> SEQ ID NO 200
    <211> LENGTH: 19
    <212> TYPE: RNA
    <213> ORGANISM: Artificial sequence
    <220> FEATURE:
    <223> OTHER INFORMATION: RNAi agent antisense strand core 19-mer base
          sequence

<400> SEQUENCE: 200
ucguuuuggu cguggaggc                                                    19

<210> SEQ ID NO 201
    <211> LENGTH: 19
    <212> TYPE: RNA
    <213> ORGANISM: Artificial sequence
    <220> FEATURE:
    <223> OTHER INFORMATION: RNAi agent antisense strand core 19-mer base
          sequence
    <220> FEATURE:
    <221> NAME/KEY: modified_base
    <222> LOCATION: 1
    <223> OTHER INFORMATION: n = any nucleobase

<400> SEQUENCE: 201
ncguuuuggu cguggaggc                                                    19

<210> SEQ ID NO 202
    <211> LENGTH: 19
    <212> TYPE: RNA
    <213> ORGANISM: Artificial sequence
    <220> FEATURE:
    <223> OTHER INFORMATION: RNAi agent antisense strand core 19-mer base
          sequence
    <220> FEATURE:
    <221> NAME/KEY: modified_base
    <222> LOCATION: 1, 19
    <223> OTHER INFORMATION: n = any nucleobase

<400> SEQUENCE: 202
ncguuuuggu cguggaggn                                                    19

<210> SEQ ID NO 203
    <211> LENGTH: 19
    <212> TYPE: RNA

```
<213> ORGANISM: Artificial sequence
<220> FEATURE:
<223> OTHER INFORMATION: RNAi agent antisense strand core 19-mer base
      sequence

<400> SEQUENCE: 203
cucguagucc gucccgucc                                              19

<210> SEQ ID NO 204
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 204
uucguagucc gucccgucc                                              19

<210> SEQ ID NO 205
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 205
nucguagucc gucccgucc                                              19

<210> SEQ ID NO 206
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 206
nucguagucc gucccgucn                                              19

<210> SEQ ID NO 207
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 207
ucucguaguc cgucccguc                                              19

<210> SEQ ID NO 208
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
```

<222> LOCATION: 1
<223> OTHER INFORMATION: n = any nucleobase

<400> SEQUENCE: 208
ncucguaguc cgucccguc                                            19

<210> SEQ ID NO 209
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 209
ncucguaguc cgucccgun                                            19

<210> SEQ ID NO 210
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 210
gucucguagu ccgucccgu                                            19

<210> SEQ ID NO 211
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 211
uucucguagu ccgucccgu                                            19

<210> SEQ ID NO 212
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 212
nucucguagu ccgucccgu                                            19

<210> SEQ ID NO 213
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

```
<400> SEQUENCE: 213
nucucguagu ccgucccgn                                                19

<210> SEQ ID NO 214
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 214
cguaccaguc guccggcug                                                19

<210> SEQ ID NO 215
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 215
uguaccaguc guccggcug                                                19

<210> SEQ ID NO 216
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 216
nguaccaguc guccggcug                                                19

<210> SEQ ID NO 217
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 217
nguaccaguc guccggcun                                                19

<210> SEQ ID NO 218
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 218
agacgucguc guuccagcg                                                19
```

```
<210> SEQ ID NO 219
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 219
ugacgucguc guuccagcg                                                   19

<210> SEQ ID NO 220
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 220
ngacgucguc guuccagcg                                                   19

<210> SEQ ID NO 221
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 221
ngacgucguc guuccagcn                                                   19

<210> SEQ ID NO 222
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 222
ngacgucguc guuccagcn                                                   19

<210> SEQ ID NO 223
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 223
cagcucuguc ucgcagacc                                                   19

<210> SEQ ID NO 224
<211> LENGTH: 19
```

```
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 224
uagcucuguc ucgcagacc                                                      19

<210> SEQ ID NO 225
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 225
nagcucuguc ucgcagacc                                                      19

<210> SEQ ID NO 226
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 226
nagcucuguc ucgcagacn                                                      19

<210> SEQ ID NO 227
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 227
uuaaaggaga ggugggcucc                                                     19

<210> SEQ ID NO 228
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 228
nuaaaggaga gguggcucc                                                      19

<210> SEQ ID NO 229
<211> LENGTH: 19
<212> TYPE: RNA
<213> ORGANISM: Artificial sequence
```

```
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 229
nuaaaggaga gguggcucn                                                      19

<210> SEQ ID NO 230
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 230
auuaaaggag agguggcuc                                                      19

<210> SEQ ID NO 231
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 231
uuuaaaggag agguggcuc                                                      19

<210> SEQ ID NO 232
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 232
nuuaaaggag agguggcuc                                                      19

<210> SEQ ID NO 233
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 233
nuuaaaggag agguggcun                                                      19

<210> SEQ ID NO 234
<211> LENGTH: 19
<212> TYPE: RNA
<213> ORGANISM: Artificial sequence
<220> FEATURE:
<223> OTHER INFORMATION: RNAi agent antisense strand core 19-mer base
```

```
                        sequence

<400> SEQUENCE: 234
aauuaaagga gagguggcu                                                    19

<210> SEQ ID NO 235
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 235
uauuaaagga gagguggcu                                                    19

<210> SEQ ID NO 236
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 236
nauuaaagga gagguggcu                                                    19

<210> SEQ ID NO 237
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 237
nauuaaagga gagguggcn                                                    19

<210> SEQ ID NO 238
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 238
agaaauaaau uaaaggaga                                                    19

<210> SEQ ID NO 239
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 239
ugaaauaaau uaaaggaga                                                    19
```

```
<210> SEQ ID NO 240
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 240
ngaaauaaau uaaaggaga                                                   19

<210> SEQ ID NO 241
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 241
ngaaauaaau uaaaggagn                                                   19

<210> SEQ ID NO 242
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 242
agcccuauca ugaccaagg                                                   19

<210> SEQ ID NO 243
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 243
agcccuauca ugaccaaga                                                   19

<210> SEQ ID NO 244
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 244
agcccuauca ugaccaagn                                                   19

<210> SEQ ID NO 245
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 245
ngcccuauca ugaccaagn                                              19

<210> SEQ ID NO 246
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 246
ccuaucauga ccaaggagu                                              19

<210> SEQ ID NO 247
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 247
ccuaucauga ccaaggaga                                              19

<210> SEQ ID NO 248
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 248
ccuaucauga ccaaggagn                                              19

<210> SEQ ID NO 249
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 249
ncuaucauga ccaaggagn                                              19

<210> SEQ ID NO 250
<211> LENGTH: 19
<212> TYPE: RNA
```

```
<213> ORGANISM: Artificial sequence
<220> FEATURE:
<223> OTHER INFORMATION: RNAi agent sense strand core 19-mer base
      sequence

<400> SEQUENCE: 250
cuaucaugac caaggagua                                                    19

<210> SEQ ID NO 251
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 251
cuaucaugac caaggagun                                                    19

<210> SEQ ID NO 252
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 252
nuaucaugac caaggagun                                                    19

<210> SEQ ID NO 253
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 253
cuaucaugac caagganua                                                    19

<210> SEQ ID NO 254
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 17
<223> OTHER INFORMATION: n = hypoxanthine (inosine nucleotide)
<220> FEATURE:
<221> NAME/KEY: modified_base
<222> LOCATION: 19
<223> OTHER INFORMATION: n = any nucleobase

<400> SEQUENCE: 254
```
cuaucaugac caagganun                                              19

<210> SEQ ID NO 255
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine nucleotide)

<400> SEQUENCE: 255
nuaucaugac caagganun                                              19

<210> SEQ ID NO 256
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 17, 19
<223> OTHER INFORMATION: n = any nucleobase

<400> SEQUENCE: 256
nuaucaugac caagganun                                              19

<210> SEQ ID NO 257
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)

<400> SEQUENCE: 257
cuaucaugac caanganua                                              19

<210> SEQ ID NO 258
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)
<220> FEATURE:
<221> NAME/KEY: modified_base
<222> LOCATION: 19
<223> OTHER INFORMATION: n = any nucleobase

<400> SEQUENCE: 258
cuaucaugac caanganun                                              19

```
<210> SEQ ID NO 259
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14, 17
<223> OTHER INFORMATION: n = hypoxanthine (inosine nucleotide)

<400> SEQUENCE: 259
nuaucaugac caanganun                                                    19

<210> SEQ ID NO 260
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 14, 17, 19
<223> OTHER INFORMATION: n = any nucleobase

<400> SEQUENCE: 260
nuaucaugac caanganun                                                    19

<210> SEQ ID NO 261
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 261
uaucaugacc aaggaguau                                                    19

<210> SEQ ID NO 262
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 262
uaucaugacc aaggaguaa                                                    19

<210> SEQ ID NO 263
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 263
uaucaugacc aaggagun                                                     19
```

<210> SEQ ID NO 264
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 264
naucaugacc aaggaguan                                              19

<210> SEQ ID NO 265
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 265
aucaugacca aggaguauc                                              19

<210> SEQ ID NO 266
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 266
aucaugacca aggaguaua                                              19

<210> SEQ ID NO 267
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 267
aucaugacca aggaguaun                                              19

<210> SEQ ID NO 268
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 268
nucaugacca aggaguan                                               19

```
<210> SEQ ID NO 269
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 269
caugaccaag gaguaucaa                                                    19

<210> SEQ ID NO 270
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 270
caugaccaag gaguaucan                                                    19

<210> SEQ ID NO 271
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 271
naugaccaag gaguaucan                                                    19

<210> SEQ ID NO 272
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 272
ggagagugac caccaucag                                                    19

<210> SEQ ID NO 273
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 273
ggagagugac caccaucaa                                                    19

<210> SEQ ID NO 274
<211> LENGTH: 19
<212> TYPE: RNA
<213> ORGANISM: Artificial sequence
<220> FEATURE:
<223> OTHER INFORMATION: RNAi agent sense strand core 19-mer base
```

-continued

```
      sequence
<220> FEATURE:
<221> NAME/KEY: modified_base
<222> LOCATION: 19
<223> OTHER INFORMATION: n = any nucleobase

<400> SEQUENCE: 274
ggagagugac caccaucan                                                19

<210> SEQ ID NO 275
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 275
ngagagugac caccaucan                                                19

<210> SEQ ID NO 276
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 276
gagugaccac caucagcuc                                                19

<210> SEQ ID NO 277
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 277
gagugaccac caucagcua                                                19

<210> SEQ ID NO 278
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 278
gagugaccac caucagcun                                                19

<210> SEQ ID NO 279
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
```

```
<221> NAME/KEY: modified_base
<222> LOCATION: 1, 19
<223> OTHER INFORMATION: n = any nucleobase

<400> SEQUENCE: 279
nagugaccac caucagcun                                              19

<210> SEQ ID NO 280
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 280
caacuucaca gcgagcacg                                              19

<210> SEQ ID NO 281
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 281
caacuucaca gcgagcaca                                              19

<210> SEQ ID NO 282
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 282
caacuucaca gcgagcacn                                              19

<210> SEQ ID NO 283
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 283
naacuucaca gcgagcacn                                              19

<210> SEQ ID NO 284
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 284
```
agggaggcaa uugugggaag             19

<210> SEQ ID NO 285
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 285
agggaggcaa uugugggaaa             19

<210> SEQ ID NO 286
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 286
agggaggcaa uugugggaan             19

<210> SEQ ID NO 287
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 287
ngggaggcaa uugugggaan             19

<210> SEQ ID NO 288
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 288
ggaggcaaug ugggaagaa              19

<210> SEQ ID NO 289
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 289
ggaggcaaug ugggaagan              19

```
<210> SEQ ID NO 290
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 290
ngaggcaaug ugggaagan                                                  19

<210> SEQ ID NO 291
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 291 ggcaugugg gaagaaaga                                                   19

<210> SEQ ID NO 292
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 292 ggcaugugg gaagaaagn                                                   19

<210> SEQ ID NO 293
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 293 ngcaugugg gaagaaagn                                                   19

<210> SEQ ID NO 294
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 294
caauguggga agaaagaug                                                  19

<210> SEQ ID NO 295
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 295
caaugugggg agaaagaua                                                      19

<210> SEQ ID NO 296
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 296 caaugugggga agaaagaun                                                     19

<210> SEQ ID NO 297
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 297 naaugugggga agaaagaun                                                     19

<210> SEQ ID NO 298
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 7, 19
<223> OTHER INFORMATION: n = any nucleobase

<400> SEQUENCE: 298
naaugungga agaaagaun                                                      19

<210> SEQ ID NO 299
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 8, 19
<223> OTHER INFORMATION: n = any nucleobase

<400> SEQUENCE: 299
naaugugnga agaaagaun                                                      19
```

<210> SEQ ID NO 300
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 300 aauguggaa gaaagauga                                                19

<210> SEQ ID NO 301
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 301 aauguggaa gaaagaugn                                                19

<210> SEQ ID NO 302
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 302 nauguggaa gaaagaugn                                                19

<210> SEQ ID NO 303
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 6, 19
<223> OTHER INFORMATION: n = any nucleobase

<400> SEQUENCE: 303
naugunggaa gaaagaugn                                               19

<210> SEQ ID NO 304
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 304
gugggaagaa agaugaagu                                               19

<210> SEQ ID NO 305

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 305
gugggaagaa agaugaaga                                                       19

<210> SEQ ID NO 306
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 306
gugggaagaa agaugaagn                                                       19

<210> SEQ ID NO 307
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 307
nugggaagaa agaugaagn                                                       19

<210> SEQ ID NO 308
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 308
ggaagaaaga ugaagucgc                                                       19

<210> SEQ ID NO 309
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 309
ggaagaaaga ugaagucga                                                       19

<210> SEQ ID NO 310
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<220> FEATURE:
<221> NAME/KEY: modified_base
<222> LOCATION: 19
<223> OTHER INFORMATION: n = any nucleobase

<400> SEQUENCE: 310
ggaagaaaga ugaagucgn                                              19

<210> SEQ ID NO 311
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 311
ngaagaaaga ugaagucgn                                              19

<210> SEQ ID NO 312
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 312
gaagaaagau gaagucgcu                                              19

<210> SEQ ID NO 313
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 313
gaagaaagau gaagucgca                                              19

<210> SEQ ID NO 314
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 314
gaagaaagau gaagucgcn                                              19

<210> SEQ ID NO 315
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
```

```
<222> LOCATION: 1, 19
<223> OTHER INFORMATION: n = any nucleobase

<400> SEQUENCE: 315
naagaaagau gaagucgcn                                                    19

<210> SEQ ID NO 316
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 316
gaagaaagau gaagucncu                                                    19

<210> SEQ ID NO 317
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 317
gaagaaagau gaagucnca                                                    19

<210> SEQ ID NO 318
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 17
<223> OTHER INFORMATION: n = hypoxanthine (inosine nucleotide)
<220> FEATURE:
<221> NAME/KEY: modified_base
<222> LOCATION: 19
<223> OTHER INFORMATION: n = any nucleobase

<400> SEQUENCE: 318
gaagaaagau gaagucncn                                                    19

<210> SEQ ID NO 319
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine nucleotide)
```

```
<400> SEQUENCE: 319
naagaaagau gaagucncn                                           19

<210> SEQ ID NO 320
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 17, 19
<223> OTHER INFORMATION: n = any nucleobase

<400> SEQUENCE: 320
naagaaagau gaagucncn                                           19

<210> SEQ ID NO 321
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 321
ugcugcucca cgugaagca                                           19

<210> SEQ ID NO 322
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 322
ugcugcucca cgugaagcn                                           19

<210> SEQ ID NO 323
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 323
ngcugcucca cgugaagcn                                           19

<210> SEQ ID NO 324
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 324
```

-continued cugcuccacg ugaagcagu                                                19

<210> SEQ ID NO 325
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 325
cugcuccacg ugaagcaga                                                19

<210> SEQ ID NO 326
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 326
cugcuccacg ugaagcagn                                                19

<210> SEQ ID NO 327
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 327
nugcuccacg ugaagcagn                                                19

<210> SEQ ID NO 328
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 328
ugcuccacgu gaagcaguu                                                19

<210> SEQ ID NO 329
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 329
ugcuccacgu gaagcagua                                                19

<210> SEQ ID NO 330
<211> LENGTH: 19
<212> TYPE: RNA

```
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 330
ugcuccacgu gaagcagun                                                19

<210> SEQ ID NO 331
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 331
ngcuccacgu gaagcagun                                                19

<210> SEQ ID NO 332
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 332
gcuccacgug aagcaguuc                                                19

<210> SEQ ID NO 333
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 333
gcuccacgug aagcaguua                                                19

<210> SEQ ID NO 334
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 334
gcuccacgug aagcaguun                                                19

<210> SEQ ID NO 335
<211> LENGTH: 19
<212> TYPE: RNA
<213> ORGANISM: Artificial sequence
<220> FEATURE:
```

<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 335
ncuccacgug aagcaguun                                                        19

<210> SEQ ID NO 336
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 336
uccacgugaa gcaguucgu                                                        19

<210> SEQ ID NO 337
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 337
uccacgugaa gcaguucga                                                        19

<210> SEQ ID NO 338
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 338
uccacgugaa gcaguucgn                                                        19

<210> SEQ ID NO 339
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 339
nccacgugaa gcaguucgn                                                        19

<210> SEQ ID NO 340
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 340
gcuccagggc aauggcuca                                              19

<210> SEQ ID NO 341
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 341
gcuccagggc aauggcucn                                              19

<210> SEQ ID NO 342
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 342
ncuccagggc aauggcucn                                              19

<210> SEQ ID NO 343
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 343
cacgagcgca gcugcuacu                                              19

<210> SEQ ID NO 344
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 344
cacgagcgca gcugcuaca                                              19

<210> SEQ ID NO 345
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 345
cacgagcgca gcugcuacn                                                19

<210> SEQ ID NO 346
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 346
nacgagcgca gcugcuacn                                                19

<210> SEQ ID NO 347
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 347
agcgcagcug cuacugguu                                                19

<210> SEQ ID NO 348
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 348
agcgcagcug cuacuggua                                                19

<210> SEQ ID NO 349
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 349
agcgcagcug cuacuggun                                                19

<210> SEQ ID NO 350
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 350
ngcgcagcug cuacuggun                                                19

<210> SEQ ID NO 351
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 351
gcgcagcugc uacugguuc                                                    19

<210> SEQ ID NO 352
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 352
gcgcagcugc uacugguua                                                    19

<210> SEQ ID NO 353
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 353
gcgcagcugc uacugguun                                                    19

<210> SEQ ID NO 354
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 354
ncgcagcugc uacugguun                                                    19

<210> SEQ ID NO 355
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 355
gacgccgaca acuacugcc                                                    19

<210> SEQ ID NO 356
<211> LENGTH: 19
<212> TYPE: RNA
<213> ORGANISM: Artificial sequence

```
<220> FEATURE:
<223> OTHER INFORMATION: RNAi agent sense strand core 19-mer base
      sequence

<400> SEQUENCE: 356
gacgccgaca acuacugca                                              19

<210> SEQ ID NO 357
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 357
gacgccgaca acuacugcn                                              19

<210> SEQ ID NO 358
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 358
nacgccgaca acuacugcn                                              19

<210> SEQ ID NO 359
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 359
accugguggu ggucacguc                                              19

<210> SEQ ID NO 360
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 360
accugguggu ggucacgua                                              19

<210> SEQ ID NO 361
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
```

<223> OTHER INFORMATION: n = any nucleobase

<400> SEQUENCE: 361
accugguggu ggucacgun                                                    19

<210> SEQ ID NO 362
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 362
nccugguggu ggucacgun                                                    19

<210> SEQ ID NO 363
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 363
uggugguggu cacguccug                                                    19

<210> SEQ ID NO 364
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 364
uggugguggu cacguccua                                                    19

<210> SEQ ID NO 365
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 365
uggugguggu cacguccun                                                    19

<210> SEQ ID NO 366
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

```
<400> SEQUENCE: 366
nggugguggu cacguccun                                               19

<210> SEQ ID NO 367
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 367
aggagcagaa auugucca                                                19

<210> SEQ ID NO 368
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 368
aggagcagaa auuguccn                                                19

<210> SEQ ID NO 369
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 369
nggagcagaa auuguccn                                                19

<210> SEQ ID NO 370
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 370
gcagaaauuu guccagcac                                               19

<210> SEQ ID NO 371
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 371
gcagaaauuu guccagcaa                                               19

<210> SEQ ID NO 372
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 372
gcagaaauuu guccagcan                                               19

<210> SEQ ID NO 373
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 373
ncagaaauuu guccagcan                                               19

<210> SEQ ID NO 374
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 374
gccuccacga ccaaaacgg                                               19

<210> SEQ ID NO 375
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 375
gccuccacga ccaaaacga                                               19

<210> SEQ ID NO 376
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 376
gccuccacga ccaaaacgn                                               19

<210> SEQ ID NO 377
<211> LENGTH: 19
<212> TYPE: RNA
```

```
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 377
nccuccacga ccaaaacgn                                                 19

<210> SEQ ID NO 378
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 378
ggacgggacg gacuacgag                                                 19

<210> SEQ ID NO 379
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 379
ggacgggacg gacuacgaa                                                 19

<210> SEQ ID NO 380
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 380
ggacgggacg gacuacgan                                                 19

<210> SEQ ID NO 381
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 381
ngacgggacg gacuacgan                                                 19

<210> SEQ ID NO 382
<211> LENGTH: 19
<212> TYPE: RNA
<213> ORGANISM: Artificial sequence
<220> FEATURE:
```

```
<223> OTHER INFORMATION: RNAi agent sense strand core 19-mer base
      sequence

<400> SEQUENCE: 382
gacgggacgg acuacgaga                                                  19

<210> SEQ ID NO 383
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 383
gacgggacgg acuacgagn                                                  19

<210> SEQ ID NO 384
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 384
nacgggacgg acuacgagn                                                  19

<210> SEQ ID NO 385
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 385
acgggacgga cuacgagac                                                  19

<210> SEQ ID NO 386
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 386
acgggacgga cuacgagaa                                                  19

<210> SEQ ID NO 387
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase
```

<400> SEQUENCE: 387
acgggacgga cuacgagan                                            19

<210> SEQ ID NO 388
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 388
ncgggacgga cuacgagan                                            19

<210> SEQ ID NO 389
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 389
cagccggacg acugguacg                                            19

<210> SEQ ID NO 390
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 390
cagccggacg acugguaca                                            19

<210> SEQ ID NO 391
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 391
cagccggacg acugguacn                                            19

<210> SEQ ID NO 392
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 392
nagccggacg acugguacn						19

<210> SEQ ID NO 393
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 393
cgcuggaacg acgacgucu						19

<210> SEQ ID NO 394
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 394
cgcuggaacg acgacguca						19

<210> SEQ ID NO 395
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 395
cgcuggaacg acgacgucn						19

<210> SEQ ID NO 396
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 396
ngcuggaacg acgacgucn						19

<210> SEQ ID NO 397
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 15, 19
<223> OTHER INFORMATION: n = any nucleobase

<400> SEQUENCE: 397
ngcuggaacg acgangucn						19

-continued

```
<210> SEQ ID NO 398
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 398
ggucugcgag acagagcug                                                       19

<210> SEQ ID NO 399
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 399
ggucugcgag acagagcua                                                       19

<210> SEQ ID NO 400
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 400
ggucugcgag acagagcun                                                       19

<210> SEQ ID NO 401
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 401
ngucugcgag acagagcun                                                       19

<210> SEQ ID NO 402
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 402
ggagccaccu cuccuuuaa                                                       19

<210> SEQ ID NO 403
<211> LENGTH: 19
<212> TYPE: RNA
<213> ORGANISM: Artificial sequence
```

```
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 403
ggagccaccu cuccuuuan                                                   19

<210> SEQ ID NO 404
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 404
ngagccaccu cuccuuuan                                                   19

<210> SEQ ID NO 405
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 405
gagccaccuc uccuuuaau                                                   19

<210> SEQ ID NO 406
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 406
gagccaccuc uccuuuaaa                                                   19

<210> SEQ ID NO 407
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 407
gagccaccuc uccuuuaan                                                   19

<210> SEQ ID NO 408
<211> LENGTH: 19
<212> TYPE: RNA
<213> ORGANISM: Artificial sequence
<220> FEATURE:
<223> OTHER INFORMATION: RNAi agent sense strand core 19-mer base
```

-continued

```
      sequence
<220> FEATURE:
<221> NAME/KEY: modified_base
<222> LOCATION: 1, 19
<223> OTHER INFORMATION: n = any nucleobase

<400> SEQUENCE: 408
nagccaccuc uccuuuaan                                                    19

<210> SEQ ID NO 409
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 409
agccaccucu ccuuuaauu                                                    19

<210> SEQ ID NO 410
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 410
agccaccucu ccuuuaaua                                                    19

<210> SEQ ID NO 411
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 411
agccaccucu ccuuuaaun                                                    19

<210> SEQ ID NO 412
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 412
ngccaccucu ccuuuaaun                                                    19

<210> SEQ ID NO 413
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<400> SEQUENCE: 413
ucuccuuuaa uuuauuucu                                                  19

<210> SEQ ID NO 414
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 414
ucuccuuuaa uuuauuuca                                                  19

<210> SEQ ID NO 415
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 415
ucuccuuuaa uuuauuucn                                                  19

<210> SEQ ID NO 416
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 416
ncuccuuuaa uuuauuucn                                                  19

<210> SEQ ID NO 417
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 417
acuucaucuu ucuucccacu u                                               21

<210> SEQ ID NO 418
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 418
uagaaccagu agcagcugcu u                                               21

<210> SEQ ID NO 419
<211> LENGTH: 21
<212> TYPE: RNA
```

```
<213> ORGANISM: Artificial sequence
<220> FEATURE:
<223> OTHER INFORMATION: RNAi agent antisense strand modified sequence

<400> SEQUENCE: 419
acuucaucuu ucuucccaca u                                              21

<210> SEQ ID NO 420
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 420
acuucaucuu ucuucccaca u                                              21

<210> SEQ ID NO 421
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 421
acuucaucuu ucuucccaca u                                              21

<210> SEQ ID NO 422
<211> LENGTH: 23
<212> TYPE: RNA
<213> ORGANISM: Artificial sequence
<220> FEATURE:
<223> OTHER INFORMATION: RNAi agent antisense strand modified sequence

<400> SEQUENCE: 422
acuucaucuu ucuucccaca uug                                            23

<210> SEQ ID NO 423
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 423
ucuucaucuu ucuucccaca u                                              21

<210> SEQ ID NO 424
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 424
uacuccuugg ucaugauagg g                                              21

<210> SEQ ID NO 425
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 425
uacuccuugg ucaugauagg u                                              21
```

-continued

<210> SEQ ID NO 426
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 426
ucucguaguc cgucccgucc a                                              21

<210> SEQ ID NO 427
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 427
ucucguaguc cgucccgucu u                                              21

<210> SEQ ID NO 428
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 428
uuaaaggaga gguggcuccu g                                              21

<210> SEQ ID NO 429
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 429
uguagcagcu gcgcucgugc u                                              21

<210> SEQ ID NO 430
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 430
uguagcagcu gcgcucgugu u                                              21

<210> SEQ ID NO 431
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 431
ugugcucgcu gugaaguugc u                                              21

<210> SEQ ID NO 432
<211> LENGTH: 22
<212> TYPE: RNA
<213> ORGANISM: Artificial sequence
<220> FEATURE:

<223> OTHER INFORMATION: RNAi agent antisense strand modified sequence

<400> SEQUENCE: 432
ugugcucgcu gugaaguugc ug                                              22

<210> SEQ ID NO 433
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 433
uugauggugg ucacucuccu c                                               21

<210> SEQ ID NO 434
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 434
uugauggugg ucacucuccu u                                               21

<210> SEQ ID NO 435
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 435
ugacgucguc guuccagcgu u                                               21

<210> SEQ ID NO 436
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 436
agacgucguc guuccagcgu u                                               21

<210> SEQ ID NO 437
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 437
uagcugaugg uggucacucu c                                               21

<210> SEQ ID NO 438
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 438
uagcugaugg uggucacucu u                                               21

```
<210> SEQ ID NO 439
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 439
ugagccauug cccuggagcu u                                              21

<210> SEQ ID NO 440
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 440
uacgugacca ccaccagguu u                                              21

<210> SEQ ID NO 441
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 441
uacgugacca ccaccaggug c                                              21

<210> SEQ ID NO 442
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 442
ucugcuucac guggagcagu u                                              21

<210> SEQ ID NO 443
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 443
acuucaucuu ucuucccacu u                                              21

<210> SEQ ID NO 444
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 444
ucuucaucuu ucuucccacu u                                              21

<210> SEQ ID NO 445
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
```

```
<221> NAME/KEY: modified_base
<222> LOCATION: 1
<223> OTHER INFORMATION: n = 2-deoxyuridine-3-cyclopropyl-phosphonate

<400> SEQUENCE: 445
ncuucaucuu ucuucccacu u                                                    21

<210> SEQ ID NO 446
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 446
ucuucaucuu ucuucccacu u                                                    21

<210> SEQ ID NO 447
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 447
uacuccuugg ucaugauagg uu                                                   22

<210> SEQ ID NO 448
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 448
uacuccuugg ucaugauagg                                                      20

<210> SEQ ID NO 449
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 449
uacuccuugg ucaugauag                                                       19

<210> SEQ ID NO 450
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 450
uacuccuugg ucaugauagu u                                                    21

<210> SEQ ID NO 451
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 451
uacuccuugg ucaugauagg gc                                                   22
```

-continued

<210> SEQ ID NO 452
<211> LENGTH: 20
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 1
<223> OTHER INFORMATION: n = 2-deoxyuridine-3-cyclopropyl-phosphonate

<400> SEQUENCE: 452
nacuccuugg ucaugauagg                                              20

<210> SEQ ID NO 453
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 1
<223> OTHER INFORMATION: n = 2-deoxyuridine-3-cyclopropyl-phosphonate

<400> SEQUENCE: 453
nacuccuugg ucaugauagg u                                            21

<210> SEQ ID NO 454
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 454
uuaaaggaga gguggcuccu u                                            21

<210> SEQ ID NO 455
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 1
<223> OTHER INFORMATION: n = 2-deoxyuridine-3-cyclopropyl-phosphonate

<400> SEQUENCE: 455
nuaaaggaga gguggcuccu u                                            21

<210> SEQ ID NO 456
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 456
uuaaaggaga gguggcuccu u                                            21

<210> SEQ ID NO 457
<211> LENGTH: 21
<212> TYPE: RNA
<213> ORGANISM: Artificial sequence
<220> FEATURE:

<223> OTHER INFORMATION: RNAi agent antisense strand modified sequence

<400> SEQUENCE: 457
uuaaaggaga gguggcuccu u                                              21

<210> SEQ ID NO 458
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 458
uuaaaggaga gguggcuccu u                                              21

<210> SEQ ID NO 459
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 459
uuaaaggaga gguggcucc                                                 19

<210> SEQ ID NO 460
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 460
uuaaaggaga gguggcuccu gg                                             22

<210> SEQ ID NO 461
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 461
agacgucguc guuccagcgu u                                              21

<210> SEQ ID NO 462
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 462
ugacgucguc guuccagcgu u                                              21

<210> SEQ ID NO 463
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 463
ugacgucguc guuccagcgu u                                              21

```
<210> SEQ ID NO 464
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 464
ucucguaguc cgucccgucu u                                              21

<210> SEQ ID NO 465
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 465
ucucguaguc cgucccgucu u                                              21

<210> SEQ ID NO 466
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 466
acucguaguc cgucccgucu u                                              21

<210> SEQ ID NO 467
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 467
acucguaguc cgucccguc                                                 19

<210> SEQ ID NO 468
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 468
uacuccuugg ucaugauagg g                                              21

<210> SEQ ID NO 469
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 469
uacuccuugg ucaugauagg g                                              21

<210> SEQ ID NO 470
<211> LENGTH: 21
<212> TYPE: RNA
<213> ORGANISM: Artificial sequence
<220> FEATURE:
<223> OTHER INFORMATION: RNAi agent antisense strand modified sequence
```

-continued

<400> SEQUENCE: 470
uacuccuugg ucaugauagg g                                              21

<210> SEQ ID NO 471
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 471
uacuccuugg ucaugauagu u                                              21

<210> SEQ ID NO 472
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 472
uacuccuugg ucaugauagg g                                              21

<210> SEQ ID NO 473
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 473
ugcuucacgu ggagcagcag g                                              21

<210> SEQ ID NO 474
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 474 ucguuuggu cguggaggcc u                                               21

<210> SEQ ID NO 475
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 475
uuucccacau ugccucccug g                                              21

<210> SEQ ID NO 476
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 476
aaccaguagc agcugcgcuc g                                              21

<210> SEQ ID NO 477
<211> LENGTH: 21

```
<212> TYPE: RNA
<213> ORGANISM: Artificial sequence
<220> FEATURE:
<223> OTHER INFORMATION: RNAi agent antisense strand modified sequence

<400> SEQUENCE: 477
aaccaguagc agcugcgcuu u                                              21

<210> SEQ ID NO 478
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 478
ugcaguaguu gucggcguca g                                              21

<210> SEQ ID NO 479
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 479
uaggacguga ccaccaccag g                                              21

<210> SEQ ID NO 480
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 480
uugcuggaca aauuucugcu c                                              21

<210> SEQ ID NO 481
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 481
uucguagucc gucccgucca c                                              21

<210> SEQ ID NO 482
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 482
uucucguagu ccgucccguc u                                              21

<210> SEQ ID NO 483
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 483
```

-continued uguaccaguc guccggcugu u                                                21

<210> SEQ ID NO 484
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 484
agacgucguc guuccagcgu u                                                21

<210> SEQ ID NO 485
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 485
uaacugcuuc acguggagca g                                                21

<210> SEQ ID NO 486
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 486
uucuucccac auugccuccc u                                                21

<210> SEQ ID NO 487
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 487
uucuucccac auugccuccu u                                                21

<210> SEQ ID NO 488
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 488
ugcgacuuca ucuuucuucc c                                                21

<210> SEQ ID NO 489
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 489
agcgacuuca ucuuucuucc c                                                21

<210> SEQ ID NO 490
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 490
uuuaaaggag agguggcucc u					21

<210> SEQ ID NO 491
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 491
auuaaaggag agguggcucc u					21

<210> SEQ ID NO 492
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 492
aauuaaagga gagguggcuc c					21

<210> SEQ ID NO 493
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 493
aauuaaagga gagguggcuc c					21

<210> SEQ ID NO 494
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 494
uaaccaguag cagcugcgcu c					21

<210> SEQ ID NO 495
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 495
uagcucuguc ucgcagaccc a					21

<210> SEQ ID NO 496
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 496
ucuucaucaa acuucccacu u					21

<210> SEQ ID NO 497
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 497
uacuccuucc acaugauagg u                                              21

<210> SEQ ID NO 498
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 498
acuucaucuu ucuucccaca c                                              21

<210> SEQ ID NO 499
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 499
acuucaucuu ucuucccagg c                                              21

<210> SEQ ID NO 500
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 500
uacuccuugg ucaugauagg c                                              21

<210> SEQ ID NO 501
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 501
uacuccuugg ucaugauagc c                                              21

<210> SEQ ID NO 502
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 502
uacuccuugg ucaugauagg u                                              21

<210> SEQ ID NO 503
<211> LENGTH: 21
<212> TYPE: RNA
<213> ORGANISM: Artificial sequence
<220> FEATURE:
<223> OTHER INFORMATION: RNAi agent antisense strand modified sequence

```
<400> SEQUENCE: 503
uacuccuugg ucaugauagg u                                              21

<210> SEQ ID NO 504
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 504
aacuccuugg ucaugauagg u                                              21

<210> SEQ ID NO 505
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 505
ugcuucacgu ggagcagcau u                                              21

<210> SEQ ID NO 506
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 506
acuccuuggu caugauaggg c                                              21

<210> SEQ ID NO 507
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 507
uaucuuucuu cccacauugc c                                              21

<210> SEQ ID NO 508
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 508
ucgacuucau cuuucuuccc a                                              21

<210> SEQ ID NO 509
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 509
aacugcuuca cguggagcau u                                              21

<210> SEQ ID NO 510
```

```
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 510
acgaacugcu ucacguggau u                                              21

<210> SEQ ID NO 511
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 511
uggacaaauu ucugcuccuc c                                              21

<210> SEQ ID NO 512
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 512
uugauacucc uuggucauga u                                              21

<210> SEQ ID NO 513
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 513
ucuuucuucc cacauugccu c                                              21

<210> SEQ ID NO 514
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 514
ucaucuuucu ucccacauug c                                              21

<210> SEQ ID NO 515
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 515
ugaaauaaau uaaaggagcg g                                              21

<210> SEQ ID NO 516
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 516
```
agaaauaaau uaaaggagcg g                              21

<210> SEQ ID NO 517
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 517
ucuuggucau gauagggcug u                              21

<210> SEQ ID NO 518
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 518
acuccuuggu caugauaggg u                              21

<210> SEQ ID NO 519
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 519
auacuccuug gucaugauag c                              21

<210> SEQ ID NO 520
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 520
uauacuccuu ggucaugauc c                              21

<210> SEQ ID NO 521
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 521
uauacuccuu ggucaugaua c                              21

<210> SEQ ID NO 522
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 522
uacuccuugg ucaugauagg g                              21

<210> SEQ ID NO 523
<211> LENGTH: 21
<212> TYPE: RNA

```
<213> ORGANISM: Artificial sequence
<220> FEATURE:
<223> OTHER INFORMATION: RNAi agent antisense strand modified sequence

<400> SEQUENCE: 523
uacuccuugg ucaugauagg c                                              21

<210> SEQ ID NO 524
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 524
agcgacuuca ucuuucuucc c                                              21

<210> SEQ ID NO 525
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 525
agcgacuuca ucuuucuucc g                                              21

<210> SEQ ID NO 526
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 526
uuuaaaggag agguggcucu u                                              21

<210> SEQ ID NO 527
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 527
uuuaaaggag agguggcugu u                                              21

<210> SEQ ID NO 528
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 528
uugauacucc uuggucaugg u                                              21

<210> SEQ ID NO 529
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 529
uugauacucc uuggucauga g                                              21
```

<210> SEQ ID NO 530
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 530
uugauacucc uuggucaugg c                                              21

<210> SEQ ID NO 531
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 531
uaucuuucuu cccacauugc g                                              21

<210> SEQ ID NO 532
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 532
uaucuuucuu cccacauugg g                                              21

<210> SEQ ID NO 533
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 533
ucaucuuucu ucccacauug g                                              21

<210> SEQ ID NO 534
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 534
ucaucuuucu ucccacauuc g                                              21

<210> SEQ ID NO 535
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 535
ucaucuuucu ucccacaucg g                                              21

<210> SEQ ID NO 536
<211> LENGTH: 21
<212> TYPE: RNA
<213> ORGANISM: Artificial sequence
<220> FEATURE:

```
<223> OTHER INFORMATION: RNAi agent antisense strand modified sequence

<400> SEQUENCE: 536
ugaaauaaau uaaaggagag c                                              21

<210> SEQ ID NO 537
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 537
ugaaauaaau uaaaggaggg g                                              21

<210> SEQ ID NO 538
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 538
ugaaauaaau uaaaggaggg c                                              21

<210> SEQ ID NO 539
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 539
agcgacuuca ucuuucuucc c                                              21

<210> SEQ ID NO 540
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 540
agcgacuuca ucuuucuucc g                                              21

<210> SEQ ID NO 541
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 541
agcgacuuca ucuuucuucc g                                              21

<210> SEQ ID NO 542
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 542
agcgacuuca ucuuucuucc g                                              21
```

<210> SEQ ID NO 543
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 543
agcgacuuca ucuuucuucc u                                              21

<210> SEQ ID NO 544
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 544
agcgacuuca ucuuucuucu u                                              21

<210> SEQ ID NO 545
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 545
agcgacuuca ucuuucuucc a                                              21

<210> SEQ ID NO 546
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 546
agcgacuuca ucuuucuucg g                                              21

<210> SEQ ID NO 547
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 547
agcgacuuca ucuuucuucg c                                              21

<210> SEQ ID NO 548
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 548
agcgacuuca ucuuucuucc g                                              21

<210> SEQ ID NO 549
<211> LENGTH: 21
<212> TYPE: RNA
<213> ORGANISM: Artificial sequence
<220> FEATURE:
<223> OTHER INFORMATION: RNAi agent antisense strand modified sequence

```
<400> SEQUENCE: 549
uacuccuugg ucaugauagg u                                              21

<210> SEQ ID NO 550
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 550
uacuccuugg ucaugauagg u                                              21

<210> SEQ ID NO 551
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 551
agcgacuuca ucuuucuucc g                                              21

<210> SEQ ID NO 552
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 552
agcgacuuca ucuuucuucc g                                              21

<210> SEQ ID NO 553
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 553
agcgacuugu acuuucuucc g                                              21

<210> SEQ ID NO 554
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 554
uacuccuugg ucaugauagg u                                              21

<210> SEQ ID NO 555
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 555
uacuccuugg ucaugauagg u                                              21

<210> SEQ ID NO 556
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 556
gugggaagaa agaugaaguu u                                              21

<210> SEQ ID NO 557
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 557
gcagcugcua cugguucuau u                                              21

<210> SEQ ID NO 558
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 558
augugggaag aaagaugaag u                                              21

<210> SEQ ID NO 559
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 559
augugggaag aaagaugaag u                                              21

<210> SEQ ID NO 560
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 560
gugggaagaa agaugaagu                                                 19

<210> SEQ ID NO 561
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 561
gugggaagaa agaugaaguu u                                              21

<210> SEQ ID NO 562
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 562
``` auguggggaag aaagaugaag a                               21

<210> SEQ ID NO 563
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 563
cccuaucaug accaaggagu n                                21

<210> SEQ ID NO 564
<211> LENGTH: 20
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = inverted-2-deoxyadenosine (3'-3' linked)

<400> SEQUENCE: 564
ccuaucauga ccaaggagun                                  20

<210> SEQ ID NO 565
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 565
gacgggacgg acuacgagn                                   19

<210> SEQ ID NO 566
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 566
ggagccaccu cuccuuuan                                   19

<210> SEQ ID NO 567
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 567
caggagccac cucuccuuua n                                            21

<210> SEQ ID NO 568
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 568
cacgagcgca gcugcuacn                                               19

<210> SEQ ID NO 569
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 569
agcaacuuca cagcgagcac n                                            21

<210> SEQ ID NO 570
<211> LENGTH: 22
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 22
<223> OTHER INFORMATION: n = inverted-2-deoxyadenosine (3'-3' linked)

<400> SEQUENCE: 570
cagcaacuuc acagcgagca cn                                           22

<210> SEQ ID NO 571
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 571
gaggagagug accaccauca n                                            21

<210> SEQ ID NO 572
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 572
ggagagugac caccaucan                                                    19

<210> SEQ ID NO 573
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 573
gaggagagug accaccauca n                                                 21

<210> SEQ ID NO 574
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 574
cgcuggaacg acgacguca                                                    19

<210> SEQ ID NO 575
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 575
cgcuggaacg acgacgucu                                                    19

<210> SEQ ID NO 576
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 576
gagagugacc accaucagcu n                                                 21

<210> SEQ ID NO 577
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 577
gagugaccac caucagcun                                                    19

<210> SEQ ID NO 578
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 578
gcuccagggc aauggcucn                                              19

<210> SEQ ID NO 579
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 579
accugguggu ggucacgun                                              19

<210> SEQ ID NO 580
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 580
gcaccuggug guggucacgu n                                           21

<210> SEQ ID NO 581
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 581
cugcuccacg ugaagcagn                                              19

<210> SEQ ID NO 582
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 582

```
gugggaagaa agaugaagn                                                19
```

<210> SEQ ID NO 583
<211> LENGTH: 20
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = inverted-2-deoxyadenosine (3'-3' linked)

<400> SEQUENCE: 583

```
ccuaucauga ccaaggagun                                               20
```

<210> SEQ ID NO 584
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 584

```
cuaucaugac caaggagun                                                19
```

<210> SEQ ID NO 585
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 585

```
cccuaucaug accaaggagu n                                             21
```

<210> SEQ ID NO 586
<211> LENGTH: 22
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 22
<223> OTHER INFORMATION: n = inverted-2-deoxyadenosine (3'-3' linked)

<400> SEQUENCE: 586

```
gcccuaucau gaccaaggag un                                            22
```

<210> SEQ ID NO 587
<211> LENGTH: 22
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 22
<223> OTHER INFORMATION: n = inverted-2-deoxyadenosine (3'-3' linked)

<400> SEQUENCE: 587
gcccuaucau gaccaaggag un                                              22

<210> SEQ ID NO 588
<211> LENGTH: 20
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = inverted-2-deoxyadenosine (3'-3' linked)

<400> SEQUENCE: 588
ccuaucauga ccaaggagun                                                 20

<210> SEQ ID NO 589
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 589
gugggaagaa agaugaagu                                                  19

<210> SEQ ID NO 590
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 590
ggagccaccu cuccuuuan                                                  19

<210> SEQ ID NO 591
<211> LENGTH: 19
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = inverted-2-deoxyadenosine (3'-3' linked)

<400> SEQUENCE: 591
ggagccaccu cuccuuuan                                                  19

<210> SEQ ID NO 592
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 21
<223> OTHER INFORMATION: n = inverted-2-deoxyadenosine (3'-3' linked)

<400> SEQUENCE: 592
caggagccac cucuccuuua n                                               21

<210> SEQ ID NO 593
<211> LENGTH: 22
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 22
<223> OTHER INFORMATION: n = inverted-2-deoxyadenosine (3'-3' linked)

<400> SEQUENCE: 593
ccaggagcca ccucuccuuu an                                             22

<210> SEQ ID NO 594
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 594
gugggaagaa agaugaaga                                                 19

<210> SEQ ID NO 595
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 595
cgcuggaacg acgacgucu                                                 19

<210> SEQ ID NO 596
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 596
cgcuggaacg acgaugucu                                                 19

<210> SEQ ID NO 597
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 597
cgcuggaacg acgacguca                                                 19

<210> SEQ ID NO 598
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 598
gacgggacgg acuacgaga                                                 19

<210> SEQ ID NO 599
<211> LENGTH: 19

```
<212> TYPE: RNA
<213> ORGANISM: Artificial sequence
<220> FEATURE:
<223> OTHER INFORMATION: RNAi agent sense strand modified sequence

<400> SEQUENCE: 599
gacgggacgg acuacgagu                                                    19

<210> SEQ ID NO 600
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 600
gacgggacgg acuacgagau u                                                 21

<210> SEQ ID NO 601
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 601
cccuaucaug accaaggagu a                                                 21

<210> SEQ ID NO 602
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 602
accuaucaug accaaggagu a                                                 21

<210> SEQ ID NO 603
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 603
cuaucaugac caaggaguau u                                                 21

<210> SEQ ID NO 604
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 604
ccugcugcuc cacgugaagc a                                                 21

<210> SEQ ID NO 605
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 605
```
aggccuccac gaccaaaacg a        21

<210> SEQ ID NO 606
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 606
ccagggaggc aauggggaa a        21

<210> SEQ ID NO 607
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 607
cgagcgcagc ugcuacuggu u        21

<210> SEQ ID NO 608
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 608
agcgcagcug cuacugguuu u        21

<210> SEQ ID NO 609
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 609
cugacgccga caacuacugc a        21

<210> SEQ ID NO 610
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 610
ccugguggug gucacguccu a        21

<210> SEQ ID NO 611
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 611
gagcagaaau uuguccagca a        21

<210> SEQ ID NO 612
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 612
guggacggga cggacuacga a                                              21

<210> SEQ ID NO 613
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 613
agacgggacg gacuacgaga a                                              21

<210> SEQ ID NO 614
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 614
aacagccgga cgacugguac a                                              21

<210> SEQ ID NO 615
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 615
cgcuggaacg acgacgucuu u                                              21

<210> SEQ ID NO 616
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 616
cugcuccacg ugaagcaguu a                                              21

<210> SEQ ID NO 617
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 617
agggaggcaa uguggaaga a                                               21

<210> SEQ ID NO 618
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 618
ggaggcaaug ugggaagaau u                                              21
```

```
<210> SEQ ID NO 619
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 619
gggaagaaag augaagucgc a                                              21

<210> SEQ ID NO 620
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 620
gggaagaaag augaagucgc u                                              21

<210> SEQ ID NO 621
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 621
aggagccacc ucuccuuuaa a                                              21

<210> SEQ ID NO 622
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 622
aggagccacc ucuccuuuaa u                                              21

<210> SEQ ID NO 623
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 623
ggagccaccu cuccuuuaau u                                              21

<210> SEQ ID NO 624
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 624
ggagccaccu cuccuuuaau u                                              21

<210> SEQ ID NO 625
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 625
gagcgcagcu gcuacugguu a                                              21

<210> SEQ ID NO 626
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 626
ugggucugcg agacagagcu a                                              21

<210> SEQ ID NO 627
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 627
gugggaaguu ugaugaaga                                                 19

<210> SEQ ID NO 628
<211> LENGTH: 20
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = inverted-2-deoxyadenosine (3'-3' linked)

<400> SEQUENCE: 628
ccuaucaugu ggaaggagun                                                20

<210> SEQ ID NO 629
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 629
augugggaag aaagaugaag u                                              21

<210> SEQ ID NO 630
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 630
gugugggaag aaagaugaag u                                              21

<210> SEQ ID NO 631
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 631
```

```
gcgugggaag aaagaugaag u                                              21
```

-continued

```
gcgugggaag aaagaugaag u                                              21
```

<210> SEQ ID NO 632
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 632

```
gcgugggaag aaagaugaag u                                              21
```

<210> SEQ ID NO 633
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 633

```
gccugggaag aaagaugaag u                                              21
```

<210> SEQ ID NO 634
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 634

```
gccuaucaug accaaggagu a                                              21
```

<210> SEQ ID NO 635
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 635

```
ggcuaucaug accaaggagu a                                              21
```

<210> SEQ ID NO 636
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 636

```
accuaucaug accaagganu a                                              21
```

<210> SEQ ID NO 637
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 637
accuaucaug accaagnagu a                             21

<210> SEQ ID NO 638
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 638
accuaucaug accaangagu a                             21

<210> SEQ ID NO 639
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 639
accuaucaug accaanganu a                             21

<210> SEQ ID NO 640
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 640
accuaucaug accaaggagu u                             21

<210> SEQ ID NO 641
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 641
ugcugcucca cgugaagcau u                             21

<210> SEQ ID NO 642
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 642
ugcugcucca cgugaancau u                             21

<210> SEQ ID NO 643
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 643
ugcugcucca cgunaagcau u                                              21

<210> SEQ ID NO 644
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14, 17
<223> OTHER INFORMATION: n = 2'-O-methylinosine-3'-phosphate

<400> SEQUENCE: 644
ugcugcucca cgunaancau u                                              21

<210> SEQ ID NO 645
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 645
cggaagaaag augaagucnc u                                              21

<210> SEQ ID NO 646
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 646
cggaagaaag augaanucgc u                                              21

<210> SEQ ID NO 647
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 647
cggaagaaag augaanucnc u                                              21

<210> SEQ ID NO 648
<211> LENGTH: 21

```
<212> TYPE: RNA
<213> ORGANISM: Artificial sequence
<220> FEATURE:
<223> OTHER INFORMATION: RNAi agent sense strand modified sequence

<400> SEQUENCE: 648
cggaagaaag augaagucgc u                                              21

<210> SEQ ID NO 649
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 649
gcccuaucau gaccaaggag u                                              21

<210> SEQ ID NO 650
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 650
ggcaaugugg gaagaaagau a                                              21

<210> SEQ ID NO 651
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 651
ugggaagaaa gaugaagucg a                                              21

<210> SEQ ID NO 652
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 652
ugcuccacgu gaagcaguuu u                                              21

<210> SEQ ID NO 653
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 653
uccacgugaa gcaguucguu u                                              21

<210> SEQ ID NO 654
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 654
```

```
ggaggagcag aaauuugucc a                                          21

<210> SEQ ID NO 655
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 655
aucaugacca aggaguauca a                                          21

<210> SEQ ID NO 656
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 656
gaggcaaugu gggaagaaag a                                          21

<210> SEQ ID NO 657
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 657
gcaauguggg aagaaagaug a                                          21

<210> SEQ ID NO 658
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 658
ccucuccuuu aauuuauuuc a                                          21

<210> SEQ ID NO 659
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 659
ccgcuccuuu aauuuauuuc a                                          21

<210> SEQ ID NO 660
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 660
ccgcuccuuu aauuuauuuc u                                          21

<210> SEQ ID NO 661
<211> LENGTH: 21
<212> TYPE: RNA
<213> ORGANISM: Artificial sequence
```

```
<220> FEATURE:
<223> OTHER INFORMATION: RNAi agent sense strand modified sequence

<400> SEQUENCE: 661
acagcccuau caugaccaag a                                              21

<210> SEQ ID NO 662
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 662
acccuaucau gaccaaggag u                                              21

<210> SEQ ID NO 663
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 663
gcuaucauga ccaaggagua u                                              21

<210> SEQ ID NO 664
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 664
ggaucaugac caaggaguau a                                              21

<210> SEQ ID NO 665
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 665
guaucaugac caaggaguau a                                              21

<210> SEQ ID NO 666
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 666
accuaucaug accaaggagu a                                              21

<210> SEQ ID NO 667
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 667
cccuaucaug accaaggagu a                                              21
```

```
<210> SEQ ID NO 668
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 668
gccuaucaug accaaggagu a                                              21

<210> SEQ ID NO 669
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 669
gggaagaaag augaagucgc u                                              21

<210> SEQ ID NO 670
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 670
cggaagaaag augaagucgc u                                              21

<210> SEQ ID NO 671
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 671
gagccaccuc uccuuuaaau u                                              21

<210> SEQ ID NO 672
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 672
cagccaccuc uccuuuaaau u                                              21

<210> SEQ ID NO 673
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 673
gagccaccuc uccuuuaaau u                                              21

<210> SEQ ID NO 674
<211> LENGTH: 21
<212> TYPE: RNA
<213> ORGANISM: Artificial sequence
<220> FEATURE:
<223> OTHER INFORMATION: RNAi agent sense strand modified sequence
```

<400> SEQUENCE: 674
accuaucaug accaaggagu a                                          21

<210> SEQ ID NO 675
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 675
accuaucaug accaaggagu a                                          21

<210> SEQ ID NO 676
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2-aminopurine-2-O-methyl-3'-phosphate

<400> SEQUENCE: 676
cggaagaaag augaagucnc u                                          21

<210> SEQ ID NO 677
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 677
cggaagaaag augaagucac u                                          21

<210> SEQ ID NO 678
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 678
cggaagaaag augaagucuc u                                          21

<210> SEQ ID NO 679
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 679
cggaagaaag augaaguccc u                                          21

<210> SEQ ID NO 680
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19

<223> OTHER INFORMATION: n =

<400> SEQUENCE: 680
cggaagaaag augaagucnc u                                           21

<210> SEQ ID NO 681
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 681
cggaagaaag augaagucnc u                                           21

<210> SEQ ID NO 682
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 682
cggaagaaag aunaagucnc u                                           21

<210> SEQ ID NO 683
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 683
accaugacca aggaguauca a                                           21

<210> SEQ ID NO 684
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 684
cucaugacca aggaguauca a                                           21

<210> SEQ ID NO 685
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 685
gccaugacca aggaguauca a                                           21

```
<210> SEQ ID NO 686
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 686
cgcaaugugg gaagaaagau a                                              21

<210> SEQ ID NO 687
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methylinosine-3'-phosphate

<400> SEQUENCE: 687
cgcaaugugn gaagaaagau a                                              21

<210> SEQ ID NO 688
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 9
<223> OTHER INFORMATION: n = 2'-O-methylinosine-3'-phosphate

<400> SEQUENCE: 688
cgcaaugung gaagaaagau a                                              21

<210> SEQ ID NO 689
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 689
cccaaugugg gaagaaagau a                                              21

<210> SEQ ID NO 690
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 690
ccaauguggg aagaaagaug a                                              21

<210> SEQ ID NO 691
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 8
<223> OTHER INFORMATION: n = 2'-O-methylinosine-3'-phosphate
```

<400> SEQUENCE: 691
ccaaugungg aagaaagaug a                                              21

<210> SEQ ID NO 692
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 692
cgaaugUggg aagaaagaug a                                              21

<210> SEQ ID NO 693
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 693
ccgauguggg aagaaagaug a                                              21

<210> SEQ ID NO 694
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 694
gcucuccuuu aauuuauuuc a                                              21

<210> SEQ ID NO 695
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methyl-2'-aminoadenosine-3'-phosphate

<400> SEQUENCE: 695
gcucuccuuu aauuunuuuc a                                              21

<210> SEQ ID NO 696
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 12
<223> OTHER INFORMATION: n = 2'-O-methyl-2'-aminoadenosine-3'-phosphate

<400> SEQUENCE: 696
gcucuccuuu anuuuauuuc a                                              21

<210> SEQ ID NO 697
<211> LENGTH: 21
<212> TYPE: RNA
<213> ORGANISM: Artificial sequence
<220> FEATURE:
<223> OTHER INFORMATION: RNAi agent sense strand modified sequence

```
<400> SEQUENCE: 697
ccccuccuuu aauuuauuuc a                                              21

<210> SEQ ID NO 698
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 698
gcccuccuuu aauuuauuuc a                                              21

<210> SEQ ID NO 699
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 699
accuaucaug accaagganu a                                              21

<210> SEQ ID NO 700
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16, 19
<223> OTHER INFORMATION: n = 2'-O-methylinosine-3'-phosphate

<400> SEQUENCE: 700
accuaucaug accaanganu a                                              21

<210> SEQ ID NO 701
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate

<400> SEQUENCE: 701
cggaagaaag aunaagucgc u                                              21

<210> SEQ ID NO 702
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 702
cggaagaaag augaagucgc u                                              21

<210> SEQ ID NO 703
```

-continued

<210> SEQ ID NO 703 (implied)
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 703
aggaagaaag augaagucnc u                                              21

<210> SEQ ID NO 704
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate

<400> SEQUENCE: 704
cggaagaaag aunaagucgc u                                              21

<210> SEQ ID NO 705
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 705
gaagaaagau gaagucncuu u                                              21

<210> SEQ ID NO 706
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 706
uggaagaaag augaagucnc u                                              21

<210> SEQ ID NO 707
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 707
ccgaagaaag augaagucnc u                                              21

```
<210> SEQ ID NO 708
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 708
acgaagaaag augaagucnc u                                              21

<210> SEQ ID NO 709
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 709
gcgaagaaag augaagucnc u                                              21

<210> SEQ ID NO 710
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate

<400> SEQUENCE: 710
cggaagaaag aunaagucgc u                                              21

<210> SEQ ID NO 711
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 711
cggaagaaag augaagucgc u                                              21

<210> SEQ ID NO 712
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 712
cggaagaaag augaagucnc u                                              21

<210> SEQ ID NO 713
<211> LENGTH: 21
<212> TYPE: RNA
```

```
<213> ORGANISM: Artificial sequence
<220> FEATURE:
<223> OTHER INFORMATION: RNAi agent sense strand modified sequence

<400> SEQUENCE: 713
cggaagaaag augaagucgc u                                              21

<210> SEQ ID NO 714
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 714
cggaagaaag aunaagucnc u                                              21

<210> SEQ ID NO 715
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 715
cggaagaaag augaagucgc u                                              21

<210> SEQ ID NO 716
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 716
cggaagaaag atgaagucgc u                                              21

<210> SEQ ID NO 717
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxycytidine-3'-phosphate

<400> SEQUENCE: 717
accuaucaug acnaaggagu a                                              21

<210> SEQ ID NO 718
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxycytidine-3'-phosphate
```

```
<220> FEATURE:
<221> NAME/KEY: modified_base
<222> LOCATION: 19
<223> OTHER INFORMATION: n = 2'-O-methylinosine-3'-phosphate

<400> SEQUENCE: 718
accuaucaug acnaagganu a                                              21

<210> SEQ ID NO 719
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxycytidine-3'-phosphate

<400> SEQUENCE: 719
cggaagaaag uanaagucgc u                                              21

<210> SEQ ID NO 720
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-deoxyguanosine-3'-phosphate

<400> SEQUENCE: 720
cggaagaaag aunaagucgc u                                              21

<210> SEQ ID NO 721
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 721
acgaagaaag augaagucgc u                                              21

<210> SEQ ID NO 722
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 722
acuucaucuu ucuucccacu u                                              21

<210> SEQ ID NO 723
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 723
uagaaccagu agcagcugcu u                                              21
```

```
<210> SEQ ID NO 724
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 724
acuucaucuu ucuucccaca u                                            21

<210> SEQ ID NO 725
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 725
acuucaucuu ucuucccaca uug                                          23

<210> SEQ ID NO 726
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 726
ucuucaucuu ucuucccaca u                                            21

<210> SEQ ID NO 727
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 727
uacuccuugg ucaugauagg g                                            21

<210> SEQ ID NO 728
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 728
uacuccuugg ucaugauagg u                                            21

<210> SEQ ID NO 729
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 729
ucucguaguc cgucccgucc a                                            21
```

```
<210> SEQ ID NO 730
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 730
ucucguaguc cgucccgucu u                                              21

<210> SEQ ID NO 731
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 731
uuaaaggaga gguggcuccu g                                              21

<210> SEQ ID NO 732
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 732
uguagcagcu gcgcucgugc u                                              21

<210> SEQ ID NO 733
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 733
uguagcagcu gcgcucgugu u                                              21

<210> SEQ ID NO 734
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 734
ugugcucgcu gugaaguugc u                                              21

<210> SEQ ID NO 735
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 735
ugugcucgcu gugaaguugc ug                                             22

<210> SEQ ID NO 736
```

-continued

<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 736
uugauggugg ucacucuccu c                                              21

<210> SEQ ID NO 737
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 737
uugauggugg ucacucuccu u                                              21

<210> SEQ ID NO 738
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 738
ugacgucguc guuccagcgu u                                              21

<210> SEQ ID NO 739
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 739
agacgucguc guuccagcgu u                                              21

<210> SEQ ID NO 740
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 740
uagcugaugg uggucacucu c                                              21

<210> SEQ ID NO 741
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 741
uagcugaugg uggucacucu u                                              21

<210> SEQ ID NO 742
<211> LENGTH: 21

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 742
ugagccauug cccuggagcu u                                          21

<210> SEQ ID NO 743
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 743
uacgugacca ccaccagguu u                                          21

<210> SEQ ID NO 744
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 744
uacgugacca ccaccaggug c                                          21

<210> SEQ ID NO 745
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 745
ucugcuucac guggagcagu u                                          21

<210> SEQ ID NO 746
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 746
ucuucaucuu ucuucccacu u                                          21

<210> SEQ ID NO 747
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 747
uacuccuugg ucaugauagg uu                                         22

<210> SEQ ID NO 748
<211> LENGTH: 20
<212> TYPE: RNA
```

<213> ORGANISM: Artificial sequence
<220> FEATURE:
<223> OTHER INFORMATION: RNAi agent antisense strand underlying base
      sequence

<400> SEQUENCE: 748
uacuccuugg ucaugauagg                                              20

<210> SEQ ID NO 749
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 749
uacuccuugg ucaugauag                                               19

<210> SEQ ID NO 750
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 750
uacuccuugg ucaugauagu u                                            21

<210> SEQ ID NO 751
<211> LENGTH: 22
<212> TYPE: RNA
<213> ORGANISM: Artificial sequence
<220> FEATURE:
<223> OTHER INFORMATION: RNAi agent antisense strand underlying base
      sequence

<400> SEQUENCE: 751
uacuccuugg ucaugauagg gc                                           22

<210> SEQ ID NO 752
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 752
uuaaaggaga gguggcuccu u                                            21

<210> SEQ ID NO 753
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 753
uuaaaggaga gguggcucc                                               19

<210> SEQ ID NO 754
<211> LENGTH: 22
<212> TYPE: RNA
<213> ORGANISM: Artificial sequence

```
<220> FEATURE:
<223> OTHER INFORMATION: RNAi agent antisense strand underlying base
      sequence

<400> SEQUENCE: 754
uuaaaggaga gguggcuccu gg                                              22

<210> SEQ ID NO 755
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 755
acucguaguc cgucccgucu u                                               21

<210> SEQ ID NO 756
<211> LENGTH: 19
<212> TYPE: RNA
<213> ORGANISM: Artificial sequence
<220> FEATURE:
<223> OTHER INFORMATION: RNAi agent antisense strand underlying base
      sequence

<400> SEQUENCE: 756
acucguaguc cgucccguc                                                  19

<210> SEQ ID NO 757
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 757
ugcuucacgu ggagcagcag g                                               21

<210> SEQ ID NO 758
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 758
ucguuuuggu cguggaggcc u                                               21

<210> SEQ ID NO 759
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 759
uuucccacau ugccucccug g                                               21

<210> SEQ ID NO 760
<211> LENGTH: 21
<212> TYPE: RNA
<213> ORGANISM: Artificial sequence
<220> FEATURE:
```

-continued

```
<223> OTHER INFORMATION: RNAi agent antisense strand underlying base
      sequence

<400> SEQUENCE: 760
aaccaguagc agcugcgcuc g                                              21

<210> SEQ ID NO 761
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 761
aaccaguagc agcugcgcuu u                                              21

<210> SEQ ID NO 762
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 762
ugcaguaguu gucggcguca g                                              21

<210> SEQ ID NO 763
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 763
uaggacguga ccaccaccag g                                              21

<210> SEQ ID NO 764
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 764
uugcuggaca aauuucugcu c                                              21

<210> SEQ ID NO 765
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 765
uucguagucc gucccgucca c                                              21

<210> SEQ ID NO 766
<211> LENGTH: 21
<212> TYPE: RNA
<213> ORGANISM: Artificial sequence
<220> FEATURE:
<223> OTHER INFORMATION: RNAi agent antisense strand underlying base
```

-continued sequence

<400> SEQUENCE: 766
uucucguagu ccgucccguc u                                              21

<210> SEQ ID NO 767
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 767
uguaccaguc guccggcugu u                                              21

<210> SEQ ID NO 768
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 768
uaacugcuuc acguggagca g                                              21

<210> SEQ ID NO 769
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 769
uucuucccac auugccuccc u                                              21

<210> SEQ ID NO 770
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 770
uucuucccac auugccuccu u                                              21

<210> SEQ ID NO 771
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 771
ugcgacuuca ucuuucuucc c                                              21

<210> SEQ ID NO 772
<211> LENGTH: 21
<212> TYPE: RNA
<213> ORGANISM: Artificial sequence
<220> FEATURE:
<223> OTHER INFORMATION: RNAi agent antisense strand underlying base
      sequence -continued

<400> SEQUENCE: 772
agcgacuuca ucuuucuucc c                                              21

<210> SEQ ID NO 773
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 773
uuuaaaggag agguggcucc u                                              21

<210> SEQ ID NO 774
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 774
auuaaaggag agguggcucc u                                              21

<210> SEQ ID NO 775
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 775
aauuaaagga gagguggcuc c                                              21

<210> SEQ ID NO 776
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 776
uaaccaguag cagcugcgcu c                                              21

<210> SEQ ID NO 777
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 777
uagcucuguc ucgcagaccc a                                              21

<210> SEQ ID NO 778
<211> LENGTH: 21
<212> TYPE: RNA
<213> ORGANISM: Artificial sequence
<220> FEATURE:
<223> OTHER INFORMATION: RNAi agent antisense strand underlying base
      sequence

```
<400> SEQUENCE: 778
ucuucaucaa acuucccacu u                                             21

<210> SEQ ID NO 779
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 779
uacuccuucc acaugauagg u                                             21

<210> SEQ ID NO 780
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 780
acuucaucuu ucuucccaca c                                             21

<210> SEQ ID NO 781
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 781
acuucaucuu ucuucccagg c                                             21

<210> SEQ ID NO 782
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 782
uacuccuugg ucaugauagg c                                             21

<210> SEQ ID NO 783
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 783
uacuccuugg ucaugauagc c                                             21

<210> SEQ ID NO 784
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 784
```
aacuccuugg ucaugauagg u                                             21

<210> SEQ ID NO 785
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 785
ugcuucacgu ggagcagcau u                                             21

<210> SEQ ID NO 786
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 786
acuccuuggu caugauaggg c                                             21

<210> SEQ ID NO 787
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 787
uaucuuucuu cccacauugc c                                             21

<210> SEQ ID NO 788
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 788
ucgacuucau cuuucuuccc a                                             21

<210> SEQ ID NO 789
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 789
aacugcuuca cguggagcau u                                             21

<210> SEQ ID NO 790
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 790
acgaacugcu ucacguggau u                                              21

<210> SEQ ID NO 791
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 791
uggacaaauu ucugcuccuc c                                              21

<210> SEQ ID NO 792
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 792
uugauacucc uuggucauga u                                              21

<210> SEQ ID NO 793
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 793
ucuuucuucc cacauugccu c                                              21

<210> SEQ ID NO 794
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 794
ucaucuuucu ucccacauug c                                              21

<210> SEQ ID NO 795
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 795
ugaaauaaau uaaaggagcg g                                              21

<210> SEQ ID NO 796
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 796
agaaauaaau uaaaggagcg g                                              21

<210> SEQ ID NO 797
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 797
ucuuggucau gauagggcug u                                              21

<210> SEQ ID NO 798
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 798
acuccuuggu caugauaggg u                                              21

<210> SEQ ID NO 799
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 799
auacuccuug gucaugauag c                                              21

<210> SEQ ID NO 800
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 800
uauacuccuu ggucaugauc c                                              21

<210> SEQ ID NO 801
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 801
uauacuccuu ggucaugaua c                                              21

<210> SEQ ID NO 802
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 802
agcgacuuca ucuuucuucc g                                              21

```
<210> SEQ ID NO 803
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 803
uuuaaaggag agguggcucu u                                          21

<210> SEQ ID NO 804
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 804
uuuaaaggag agguggcugu u                                          21

<210> SEQ ID NO 805
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 805
uugauacucc uuggucaugg u                                          21

<210> SEQ ID NO 806
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 806
uugauacucc uuggucauga g                                          21

<210> SEQ ID NO 807
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 807
uugauacucc uuggucaugg c                                          21

<210> SEQ ID NO 808
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 808
uaucuuucuu cccacauugc g                                          21
```

```
<210> SEQ ID NO 809
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 809
uaucuuucuu cccacauugg g                                            21

<210> SEQ ID NO 810
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 810
ucaucuuucu ucccacauug g                                            21

<210> SEQ ID NO 811
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 811
ucaucuuucu ucccacauuc g                                            21

<210> SEQ ID NO 812
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 812
ucaucuuucu ucccacaucg g                                            21

<210> SEQ ID NO 813
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 813
ugaaauaaau uaaaggagag c                                            21

<210> SEQ ID NO 814
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 814
ugaaauaaau uaaaggaggg g                                            21

<210> SEQ ID NO 815
```

```
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 815
ugaaauaaau uaaaggaggg c                                            21

<210> SEQ ID NO 816
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 816
agcgacuuca ucuuucuucc u                                            21

<210> SEQ ID NO 817
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 817
agcgacuuca ucuuucuucu u                                            21

<210> SEQ ID NO 818
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 818
agcgacuuca ucuuucuucc a                                            21

<210> SEQ ID NO 819
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 819
agcgacuuca ucuuucuucg g                                            21

<210> SEQ ID NO 820
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 820
agcgacuuca ucuuucuucg c                                            21

<210> SEQ ID NO 821
<211> LENGTH: 21
```

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 821
agcgacuugu acuucuucc g                                              21

<210> SEQ ID NO 822
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 822
gugggaagaa agaugaaguu u                                             21

<210> SEQ ID NO 823
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 823
gcagcugcua cugguucuau u                                             21

<210> SEQ ID NO 824
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 824
augugggaag aaagaugaag u                                             21

<210> SEQ ID NO 825
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 825
gugggaagaa agaugaagu                                                19

<210> SEQ ID NO 826
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 826
augugggaag aaagaugaag a                                             21

<210> SEQ ID NO 827
<211> LENGTH: 21
<212> TYPE: RNA
```

<213> ORGANISM: Artificial sequence
<220> FEATURE:
<223> OTHER INFORMATION: RNAi agent sense strand underlying base
      sequence

<400> SEQUENCE: 827
cccuaucaug accaaggagu a                                              21

<210> SEQ ID NO 828
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 828
ccuaucauga ccaaggagua                                                20

<210> SEQ ID NO 829
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 829
gacgggacgg acuacgaga                                                 19

<210> SEQ ID NO 830
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 830
ggagccaccu cuccuuuaa                                                 19

<210> SEQ ID NO 831
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 831
caggagccac cucuccuuua a                                              21

<210> SEQ ID NO 832
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 832
cacgagcgca gcugcuaca                                                 19

<210> SEQ ID NO 833
<211> LENGTH: 21
<212> TYPE: RNA
<213> ORGANISM: Artificial sequence

```
<220> FEATURE:
<223> OTHER INFORMATION: RNAi agent sense strand underlying base
      sequence

<400> SEQUENCE: 833
agcaacuuca cagcgagcac a                                               21

<210> SEQ ID NO 834
<211> LENGTH: 22
<212> TYPE: RNA
<213> ORGANISM: Artificial sequence
<220> FEATURE:
<223> OTHER INFORMATION: RNAi agent sense strand underlying base
      sequence

<400> SEQUENCE: 834
cagcaacuuc acagcgagca ca                                              22

<210> SEQ ID NO 835
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 835
gaggagagug accaccauca a                                               21

<210> SEQ ID NO 836
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 836
ggagagugac caccaucaa                                                  19

<210> SEQ ID NO 837
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 837
cgcuggaacg acgacguca                                                  19

<210> SEQ ID NO 838
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 838
cgcuggaacg acgacgucu                                                  19

<210> SEQ ID NO 839
<211> LENGTH: 21
<212> TYPE: RNA
<213> ORGANISM: Artificial sequence
<220> FEATURE:
```

```
<223> OTHER INFORMATION: RNAi agent sense strand underlying base
      sequence

<400> SEQUENCE: 839
gagagugacc accaucagcu a                                              21

<210> SEQ ID NO 840
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 840
gagugaccac caucagcua                                                 19

<210> SEQ ID NO 841
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 841
gcuccagggc aauggcuca                                                 19

<210> SEQ ID NO 842
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 842
accugguggu ggucacgua                                                 19

<210> SEQ ID NO 843
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 843
gcaccuggug guggucacgu a                                              21

<210> SEQ ID NO 844
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 844
cugcuccacg ugaagcaga                                                 19

<210> SEQ ID NO 845
<211> LENGTH: 19
<212> TYPE: RNA
<213> ORGANISM: Artificial sequence
<220> FEATURE:
<223> OTHER INFORMATION: RNAi agent sense strand underlying base
``` sequence

<400> SEQUENCE: 845
gugggaagaa agaugaaga					19

<210> SEQ ID NO 846
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 846
cuaucaugac caaggagua					19

<210> SEQ ID NO 847
<211> LENGTH: 22
<212> TYPE: RNA
<213> ORGANISM: Artificial sequence
<220> FEATURE:
<223> OTHER INFORMATION: RNAi agent sense strand underlying base
      sequence

<400> SEQUENCE: 847
gcccuaucau gaccaaggag ua				22

<210> SEQ ID NO 848
<211> LENGTH: 22
<212> TYPE: RNA
<213> ORGANISM: Artificial sequence
<220> FEATURE:
<223> OTHER INFORMATION: RNAi agent sense strand underlying base
      sequence

<400> SEQUENCE: 848
ccaggagcca ccucuccuuu aa				22

<210> SEQ ID NO 849
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 849
cgcuggaacg acgaugucu					19

<210> SEQ ID NO 850
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 850
gacgggacgg acuacgagu					19

<210> SEQ ID NO 851
<211> LENGTH: 21
<212> TYPE: RNA
<213> ORGANISM: Artificial sequence
<220> FEATURE:
<223> OTHER INFORMATION: RNAi agent sense strand underlying base
      sequence -continued

<400> SEQUENCE: 851
gacgggacgg acuacgagau u                                              21

<210> SEQ ID NO 852
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)

<400> SEQUENCE: 852
gaagaaagau gaanucncu                                                 19

<210> SEQ ID NO 853
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 853
cuaucaugac caaggaguau u                                              21

<210> SEQ ID NO 854
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 854
ccugcugcuc cacgugaagc a                                              21

<210> SEQ ID NO 855
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 855
aggccuccac gaccaaaacg a                                              21

<210> SEQ ID NO 856
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 856
ccagggaggc aaugugggaa a                                              21

<210> SEQ ID NO 857
<211> LENGTH: 21
<212> TYPE: RNA
<213> ORGANISM: Artificial sequence

```
<220> FEATURE:
<223> OTHER INFORMATION: RNAi agent sense strand underlying base
      sequence

<400> SEQUENCE: 857
cgagcgcagc ugcuacuggu u                                              21

<210> SEQ ID NO 858
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 858
agcgcagcug cuacugguuu u                                              21

<210> SEQ ID NO 859
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 859
cugacgccga caacuacugc a                                              21

<210> SEQ ID NO 860
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 860
ccugguggug gucacguccu a                                              21

<210> SEQ ID NO 861
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 861
gagcagaaau uuguccagca a                                              21

<210> SEQ ID NO 862
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 862
guggacggga cggacuacga a                                              21

<210> SEQ ID NO 863
<211> LENGTH: 21
<212> TYPE: RNA
<213> ORGANISM: Artificial sequence
<220> FEATURE:
```

```
<223> OTHER INFORMATION: RNAi agent sense strand underlying base
      sequence

<400> SEQUENCE: 863
agacgggacg gacuacgaga a                                              21

<210> SEQ ID NO 864
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 864
aacagccgga cgacugguac a                                              21

<210> SEQ ID NO 865
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 865
cgcuggaacg acgacgucuu u                                              21

<210> SEQ ID NO 866
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 866
cugcuccacg ugaagcaguu a                                              21

<210> SEQ ID NO 867
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 867
agggaggcaa uguggaaga a                                               21

<210> SEQ ID NO 868
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 868
ggaggcaaug ugggaagaau u                                              21

<210> SEQ ID NO 869
<211> LENGTH: 21
<212> TYPE: RNA
<213> ORGANISM: Artificial sequence
<220> FEATURE:
<223> OTHER INFORMATION: RNAi agent sense strand underlying base
```

-continued

<400> SEQUENCE: 869
gggaagaaag augaagucgc a                          21

<210> SEQ ID NO 870
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 870
gggaagaaag augaagucgc u                          21

<210> SEQ ID NO 871
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 871
aggagccacc ucuccuuuaa a                          21

<210> SEQ ID NO 872
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 872
aggagccacc ucuccuuuaa u                          21

<210> SEQ ID NO 873
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 873
ggagccaccu cuccuuuaau u                          21

<210> SEQ ID NO 874
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 874
gagcgcagcu gcuacugguu a                          21

<210> SEQ ID NO 875
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 875
ugggucugcg agacagagcu a                                              21

<210> SEQ ID NO 876
<211> LENGTH: 19
<212> TYPE: RNA
<213> ORGANISM: Artificial sequence
<220> FEATURE:
<223> OTHER INFORMATION: RNAi agent sense strand underlying base
      sequence

<400> SEQUENCE: 876
gugggaaguu ugaugaaga                                                 19

<210> SEQ ID NO 877
<211> LENGTH: 20
<212> TYPE: RNA
<213> ORGANISM: Artificial sequence
<220> FEATURE:
<223> OTHER INFORMATION: RNAi agent sense strand underlying base
      sequence

<400> SEQUENCE: 877
ccuaucaugu ggaaggagua                                                20

<210> SEQ ID NO 878
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 878 guguggaag aaagaugaag u                                               21

<210> SEQ ID NO 879
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)

<400> SEQUENCE: 879
gaagaaagau gaanucnca                                                 19

<210> SEQ ID NO 880
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 880
gccugggaag aaagaugaag u                                              21

<210> SEQ ID NO 881
<211> LENGTH: 21
<212> TYPE: RNA
<213> ORGANISM: Artificial sequence

```
<220> FEATURE:
<223> OTHER INFORMATION: RNAi agent sense strand underlying base
      sequence

<400> SEQUENCE: 881
gccuaucaug accaaggagu a                                              21

<210> SEQ ID NO 882
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 882
ggcuaucaug accaaggagu a                                              21

<210> SEQ ID NO 883
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)
<220> FEATURE:
<221> NAME/KEY: modified_base
<222> LOCATION: 19
<223> OTHER INFORMATION: n = any nucleobase

<400> SEQUENCE: 883
gaagaaagau gaanucncn                                                 19

<210> SEQ ID NO 884
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 884
accuaucaug accaagnagu a                                              21

<210> SEQ ID NO 885
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = hypoxanthine (inosine nucleotide)

<400> SEQUENCE: 885
accuaucaug accaangagu a                                              21

<210> SEQ ID NO 886
<211> LENGTH: 19
```

```
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 14, 17
<223> OTHER INFORMATION: n = hypoxanthine (inosine nucleotide)
<220> FEATURE:
<221> NAME/KEY: modified_base
<222> LOCATION: 1, 19
<223> OTHER INFORMATION: n = any nucleobase

<400> SEQUENCE: 886
naagaaagau gaanucncn                                                    19

<210> SEQ ID NO 887
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 887
accuaucaug accaaggagu u                                                 21

<210> SEQ ID NO 888
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 888
ugcugcucca cgugaagcau u                                                 21

<210> SEQ ID NO 889
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 889
ugcugcucca cgugaancau u                                                 21

<210> SEQ ID NO 890
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14
<223> OTHER INFORMATION: n = hypoxanthine (inosine nucleotide)

<400> SEQUENCE: 890
ugcugcucca cgunaagcau u                                                 21
```

```
<210> SEQ ID NO 891
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14, 17
<223> OTHER INFORMATION: n = hypoxanthine (inosine nucleotide)

<400> SEQUENCE: 891
ugcugcucca cgunaancau u                                              21

<210> SEQ ID NO 892
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 14, 17, 19
<223> OTHER INFORMATION: n = any nucleobase

<400> SEQUENCE: 892
naagaaagau gaanucncn                                                 19

<210> SEQ ID NO 893
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = hypoxanthine (inosine nucleotide)

<400> SEQUENCE: 893
cggaagaaag augaanucgc u                                              21

<210> SEQ ID NO 894
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16, 19
<223> OTHER INFORMATION: n =

<400> SEQUENCE: 894
cggaagaaag augaanucnc u                                              21

<210> SEQ ID NO 895
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 895
cggaagaaag augaagucgc u                                              21
```

<210> SEQ ID NO 896
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 896
gcccuaucau gaccaaggag u                                              21

<210> SEQ ID NO 897
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 897
ggcaaugugg gaagaaagau a                                              21

<210> SEQ ID NO 898
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 898
ugggaagaaa gaugaagucg a                                              21

<210> SEQ ID NO 899
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 899
ugcuccacgu gaagcaguuu u                                              21

<210> SEQ ID NO 900
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 900
uccacgugaa gcaguucguu u                                              21

<210> SEQ ID NO 901
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 901
ggaggagcag aaauuugucc a                                              21

```
<210> SEQ ID NO 902
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 902
aucaugacca aggaguauca a                                              21

<210> SEQ ID NO 903
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 903
gaggcaaugu gggaagaaag a                                              21

<210> SEQ ID NO 904
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 904
gcaauguggg aagaaagaug a                                              21

<210> SEQ ID NO 905
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 905
ccucuccuuu aauuuauuuc a                                              21

<210> SEQ ID NO 906
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 906
ccgcuccuuu aauuuauuuc a                                              21

<210> SEQ ID NO 907
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 907
ccgcuccuuu aauuuauuuc u                                              21
```

-continued

<210> SEQ ID NO 908
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 908
acagcccuau caugaccaag a                                              21

<210> SEQ ID NO 909
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 909
acccuaucau gaccaaggag u                                              21

<210> SEQ ID NO 910
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 910
gcuaucauga ccaaggagua u                                              21

<210> SEQ ID NO 911
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 911
ggaucaugac caaggaguau a                                              21

<210> SEQ ID NO 912
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 912
guaucaugac caaggaguau a                                              21

<210> SEQ ID NO 913
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 913
gagccaccuc uccuuuaaau u                                              21

<210> SEQ ID NO 914

```
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 914
cagccaccuc uccuuuaaau u                                            21

<210> SEQ ID NO 915
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = 2-aminopurine

<400> SEQUENCE: 915
cggaagaaag augaagucnc u                                            21

<210> SEQ ID NO 916
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 916
cggaagaaag augaagucac u                                            21

<210> SEQ ID NO 917
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 917
cggaagaaag augaagucuc u                                            21

<210> SEQ ID NO 918
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 918
cggaagaaag augaaguccc u                                            21

<210> SEQ ID NO 919
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 919
accaugacca aggaguauca a                                            21
```

-continued

```
<210> SEQ ID NO 920
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 920
cucaugacca aggaguauca a                                              21

<210> SEQ ID NO 921
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 921
gccaugacca aggaguauca a                                              21

<210> SEQ ID NO 922
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 922
cgcaaugugg gaagaaagau a                                              21

<210> SEQ ID NO 923
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = hypoxanthine (inosine nucleotide)

<400> SEQUENCE: 923
cgcaaugugn gaagaaagau a                                              21

<210> SEQ ID NO 924
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 9
<223> OTHER INFORMATION: n = hypoxanthine (inosine nucleotide)

<400> SEQUENCE: 924
cgcaaugung gaagaaagau a                                              21

<210> SEQ ID NO 925
<211> LENGTH: 21
<212> TYPE: RNA
<213> ORGANISM: Artificial sequence
```

```
<220> FEATURE:
<223> OTHER INFORMATION: RNAi agent sense strand underlying base
      sequence

<400> SEQUENCE: 925
cccaaugugg gaagaaagau a                                              21

<210> SEQ ID NO 926
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 926
ccaauguggg aagaaagaug a                                              21

<210> SEQ ID NO 927
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 8
<223> OTHER INFORMATION: n = hypoxanthine (inosine nucleotide)

<400> SEQUENCE: 927
ccaaugungg aagaaagaug a                                              21

<210> SEQ ID NO 928
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 928
cgaauguggg aagaaagaug a                                              21

<210> SEQ ID NO 929
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 929
ccgauguggg aagaaagaug a                                              21

<210> SEQ ID NO 930
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 930
gcucuccuuu aauuuauuuc a                                              21

<210> SEQ ID NO 931
```

<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = 2-aminoadenine

<400> SEQUENCE: 931
gcucuccuuu aauuunuuuc a        21

<210> SEQ ID NO 932
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 12
<223> OTHER INFORMATION: n = 2-aminoadenine

<400> SEQUENCE: 932
gcucuccuuu anuuuauuuc a        21

<210> SEQ ID NO 933
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 933
ccccuccuuu aauuuauuuc a        21

<210> SEQ ID NO 934
<211> LENGTH: 21
<212> TYPE: RNA
<213> ORGANISM: Artificial sequence
<220> FEATURE:
<223> OTHER INFORMATION: RNAi agent sense strand underlying base
      sequence

```
<400> SEQUENCE: 934
gcccuccuuu aauuuauuuc a                                              21

<210> SEQ ID NO 935
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 935
aggaagaaag augaagucnc u                                              21

<210> SEQ ID NO 936
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = hypoxanthine (inosine nucleotide)

<400> SEQUENCE: 936
gaagaaagau gaagucncuu u                                              21

<210> SEQ ID NO 937
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 937
uggaagaaag augaagucnc u                                              21

<210> SEQ ID NO 938
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 938
ccgaagaaag augaagucnc u                                              21

<210> SEQ ID NO 939
<211> LENGTH: 21
<212> TYPE: RNA
<213> ORGANISM: Artificial sequence
<220> FEATURE:
<223> OTHER INFORMATION: RNAi agent sense strand underlying base
```

```
       sequence
<220> FEATURE:
<221> NAME/KEY: modified_base
<222> LOCATION: 19
<223> OTHER INFORMATION: n = hypoxanthine (inosine nucleotide)

<400> SEQUENCE: 939
acgaagaaag augaagucnc u                                              21

<210> SEQ ID NO 940
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = hypoxanthine (inosine nucleotide)

<400> SEQUENCE: 940
gcgaagaaag augaagucnc u                                              21

<210> SEQ ID NO 941
<211> LENGTH: 21
<212> TYPE: DNA
<213> ORGANISM: Artificial sequence
<220> FEATURE:
<223> OTHER INFORMATION: RNAi agent sense strand underlying base
      sequence

<400> SEQUENCE: 941
cggaagaaag atgaagucgc u                                              21

<210> SEQ ID NO 942
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 942
cggaagaaag uacaagucgc u                                              21

<210> SEQ ID NO 943
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 943
acgaagaaag augaagucgc u                                              21
```